US009290476B2

(12) United States Patent
Leonard et al.

(10) Patent No.: US 9,290,476 B2
(45) Date of Patent: *Mar. 22, 2016

(54) METHYLENE LINKED QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Joan Pierce, Raleigh, NC (US); Steven Goldberg, Encinitas, CA (US); Anne Fourie, San Diego, CA (US); Xiaohua Xue, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,653

(22) Filed: Oct. 15, 2013

(65) Prior Publication Data
US 2014/0107094 A1 Apr. 17, 2014

Related U.S. Application Data

(60) Provisional application No. 61/782,257, filed on Mar. 14, 2013, provisional application No. 61/725,528, filed on Nov. 13, 2012, provisional application No. 61/714,419, filed on Oct. 16, 2012.

(51) Int. Cl.
A61K 31/4709 (2006.01)
C07D 401/06 (2006.01)
A61K 45/06 (2006.01)
C07D 401/14 (2006.01)
C07D 417/14 (2006.01)
C07D 409/14 (2006.01)
C07D 413/14 (2006.01)

(52) U.S. Cl.
CPC .......... C07D 401/06 (2013.01); A61K 31/4709 (2013.01); A61K 45/06 (2013.01); C07D 401/14 (2013.01); C07D 409/14 (2013.01); C07D 413/14 (2013.01); C07D 417/14 (2013.01)

(58) Field of Classification Search
CPC . A61K 31/4709; A61K 45/06; C07D 401/06; C07D 401/14; C07D 409/14; C07D 413/14; C07D 417/14
USPC .......................................... 546/159; 514/312
See application file for complete search history.

(56) References Cited

U.S. PATENT DOCUMENTS

| 3,472,859 | A | 10/1969 | Lesher |
| 4,656,283 | A | 4/1987 | Doehner, Jr. |
| 4,710,507 | A | 12/1987 | Campbell et al. |
| 4,910,327 | A | 3/1990 | Doehner, Jr. |
| 4,927,926 | A | 5/1990 | Corominas et al. |
| 5,409,930 | A | 4/1995 | Spada et al. |
| 5,780,634 | A | 7/1998 | Inoue et al. |
| 6,248,739 | B1 | 6/2001 | Turner et al. |
| 6,451,812 | B1 * | 9/2002 | End et al. ...................... 514/312 |
| 6,624,159 | B2 | 9/2003 | Anderson et al. |

(Continued)

FOREIGN PATENT DOCUMENTS

| CN | 101143845 | 3/2008 |
| CN | 101899011 | 12/2010 |
| EP | 371564 A2 | 6/1990 |
| EP | 709377 A1 | 5/1996 |
| EP | 1106612 A1 | 6/2001 |
| EP | 2368886 A1 | 9/2011 |
| GB | 2095668 A | 10/1982 |
| JP | 48026772 | 4/1973 |
| JP | 2000169451 A | 6/2000 |
| WO | WO 9718208 A1 | 5/1997 |

(Continued)

OTHER PUBLICATIONS

Codarri, Nature Immunology, Jun. 2011, vol. 12(6), p. 560-568.*

(Continued)

Primary Examiner — D M Seaman
(74) Attorney, Agent, or Firm — Yuriy P. Stercho

(57) ABSTRACT

The present invention comprises compounds of Formula I.

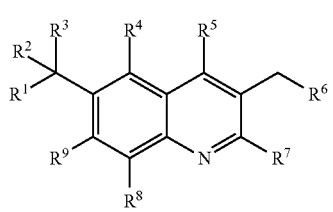

Formula I wherein:
$R^1$, $R^2$, $R^3$, $R^4$, $R^5$, $R^6$, $R^7$, $R^8$, and $R^9$ are defined in the specification.
The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

27 Claims, No Drawings

(56) References Cited

U.S. PATENT DOCUMENTS

| | | | |
|---|---|---|---|
| 6,686,356 B2 | 2/2004 | Strohbach et al. | |
| 6,743,805 B2 * | 6/2004 | End et al. | 514/312 |
| 7,053,105 B2 | 5/2006 | Angibaud et al. | |
| 7,652,014 B2 | 1/2010 | Mabire et al. | |
| 7,902,225 B2 | 3/2011 | Guillemont et al. | |
| 8,017,606 B2 | 9/2011 | Andries et al. | |
| 8,389,739 B1 | 3/2013 | Thacher et al. | |
| 2003/0166675 A1 | 9/2003 | Yang | |
| 2005/0131014 A1 | 6/2005 | Collini et al. | |
| 2007/0072844 A1 | 3/2007 | Jones et al. | |
| 2008/0188521 A1 | 8/2008 | Grimm et al. | |
| 2009/0197859 A1 | 8/2009 | Collantes et al. | |
| 2009/0286829 A1 | 11/2009 | Heidelbaugh et al. | |
| 2010/0311760 A1 | 12/2010 | de Vicente Fidalgo et al. | |
| 2011/0124870 A1 | 5/2011 | Guillemont et al. | |
| 2012/0322837 A1 | 12/2012 | Maeba et al. | |

FOREIGN PATENT DOCUMENTS

| | | |
|---|---|---|
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A1 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 0224687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 02070487 A1 | 9/2002 |
| WO | WO 02085364 A1 | 10/2002 |
| WO | WO 03/000705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075248 A1 | 8/2005 |
| WO | WO 2005075428 A1 | 8/2005 |
| WO | WO 2006003146 A1 | 1/2006 |
| WO | WO 2006013896 A1 | 2/2006 |
| WO | 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013061074 A1 | 5/2013 |
| WO | WO 2013064231 A1 | 5/2013 |
| WO | WO 2013079223 A1 | 6/2013 |

OTHER PUBLICATIONS

U.S. Appl. No. 14/053,797, filed Oct. 2013, Leonard et al.*
International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
U.S. Appl. No. 14/053,736.
U.S. Appl. No. 14/053,773.
U.S. Appl. No. 14/053,797.
U.S. Appl. No. 14/053,906.
U.S. Appl. No. 14/053,682.
U.S. Appl. No. 14/053,707.
Bink A, (A fungicidal piperazine-1-carboxamidine induces mitochondrial fission-dependent apoptosis in yeast), FEMS Yeast Research (2010), 10(7), 812-818.
Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.
Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.
Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.
Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.
Aghera V, (Synthesis, spectral and microbial studies of some novel quinoline derivatives via Vilsmeier-Haack reagent) Journal; (online computer file) URL: http://www.arkat-usa.org/get-file/25177/.
Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.
Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.
Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14,13-16.
Abdul-Ahad P, (Trends in dehydrogenase inhibitory potencies of some quinolones, using quantum chemical indices), European Journal of Medicinal Chemistry (1982), 17(4), 301-6.
Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.

(56) References Cited

OTHER PUBLICATIONS

Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.
Dong C, (Diversification of T-helper-cell lineages: finding the family root of IL-17-producing cells), Nat Rev Immunol (2006), 6(4), 329-333.
McKenzie B, (Understanding the IL-23-IL-17 immune pathway), Trends Immunol (2006), 27(1), 17-23.
Ivanov II B, (The orphan nuclear receptor RORgammat directs the differentiation program of proinflammatory IL-17+T helper cells), Cell (2006), 126(6), 1121-33.
Cua, D (Interleukin-23 rather than interleukin-12 is the critical cytokine for autoimmune inflammation of the brain), Nature (2003), 421(6924), 744-748.
Langrish C, (IL-23 drives a pathogenic T cell population that induces autoimmune inflammation), J Exp Med (2005), 201(2), 233-240.
Tonel G, (Cutting edge: A critical functional role for IL-23 in psoriasis), J Immunol (2010), 185(10), 5688-5691.
Barczyk A, (Interleukin-17 in sputum correlates with airway hyperresponsiveness to methacholine), Respir Med (2003), 97(6), 726-733.
Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Kappe T, (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4-Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.

International Search Report—PCT/US2013/065026, Feb. 21, 2014.
Yen D. (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 239-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Guy R, (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxymethyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel, P. (Preparation of Polyfunctional Ketones by a Cobalt (II) Mediated Carbonylation of Organozinc Reagents), Tetrahedron Letters (1995), 36(46), 8411-8414.
U.S. Appl. No. 14/513,426.
U.S. Appl. No. 14/513,455.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated 9/12/204.
U.S. Appl. No. 14/053,906, Notice of Allowance dated Mar. 23, 2015.
Dorwald F. A. "Slide Reactions in Organic Synthesis", 2005, Wiley: VCH, Weinheim p. IX of Preface pp. 1-15.
Venkatesh, et al. "Role of the Development Scientist in Compound Lead Selection and Optimization", J. Pharm. Sci. vol. 89, No. 2, pp. 145-154 2000.
STN Search Report Mar. 12, 2015, RN 1347913-41-0.

* cited by examiner

METHYLENE LINKED QUINOLINYL MODULATORS OF RORγT

CROSS-REFERENCE TO RELATED APPLICATIONS

This application claims priority from U.S. Application No. 61/714,419, filed on Oct. 16, 2012, U.S. Application No. 61/725,528, filed on Nov. 13, 2012, and U.S. Application No. 61/782,257, filed on Mar. 14, 2013, each of which is incorporated herein by reference.

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8. Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet. 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

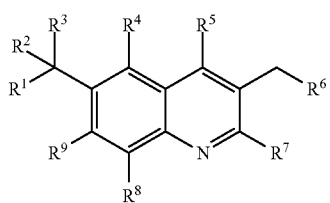

Formula I wherein:
$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is triazolyl, pyridyl, pyridyl-N-oxide, pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, or $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyrazolyl is optionally substituted with up to three $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, or 4-hydroxy-piperidinyl;

$R^6$ is phenyl, pyridyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl or said pyridyl is optionally substituted up to two times with $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, or $OCH_2CF_3$; wherein the selection of each optional substituent is independent; and wherein said pyrazolyl, triazolyl, imidazolyl, tetrazolyl, oxazolyl, and thiazolyl are optionally substituted with $CH_3$;

$R^7$ is H, Cl, —CN, $C_{(1-4)}$alkyl, $OC_{(1-4)}$alkylCF$_3$, $OCF_3$, $OCHF_2$, $OCH_2CH_2OC_{(1-4)}$alkyl, $CF_3$, $SCH_3$, $C_{(1-4)}$alkylN$A^1A^2$ (including $CH_2NA^1A^2$), $CH_2OC_{(2-3)}$alkylN$A^1A^2$, $NA^1A^2$, $C(O)NA^1A^2$, $CH_2NHC_{(2-3)}$alkylN$A^1A^2$, $CH_2N(CH_3)C_{(2-3)}$alkylN$A^1A^2$, $NHC_{(2-3)}$alkylN$A^1A^2$, $N(CH_3)C_{(2-4)}$alkylN$A^1A^2$, $OC_{(2-4)}$alkylN$A^1A^2$, $OC_{(1-4)}$alkyl, $OCH_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkylOC$_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

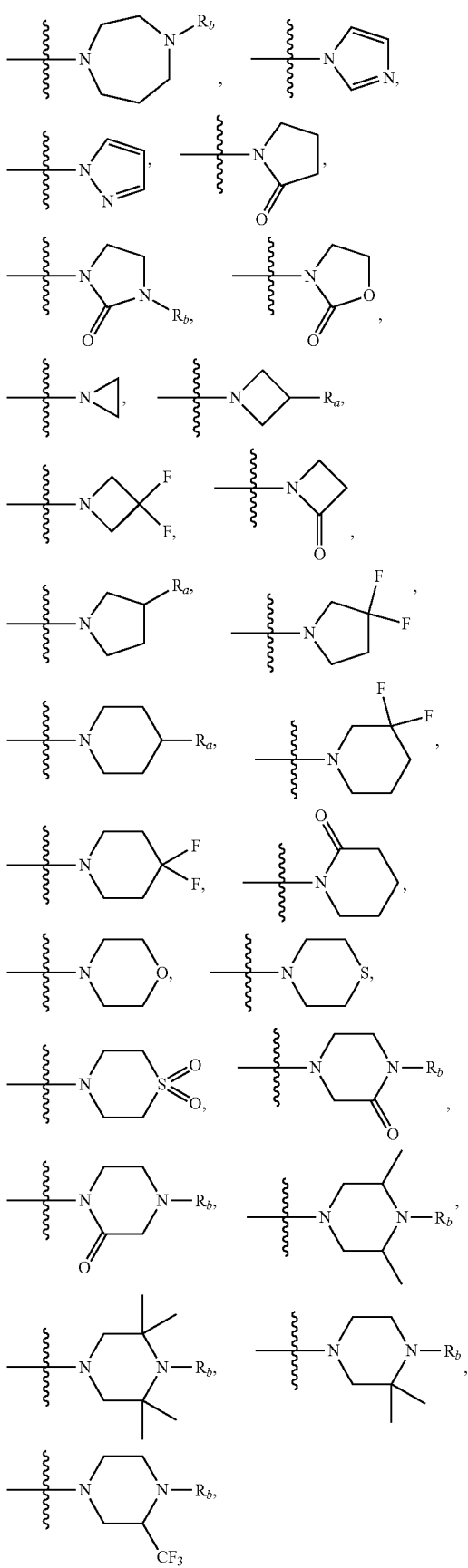

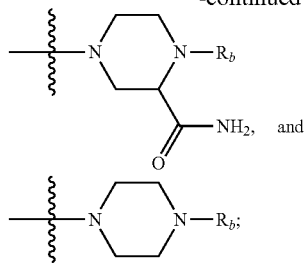

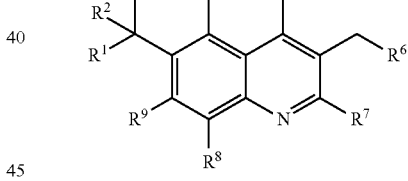

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl, (including $OCH_3$) $CF_3$, $NH_2$, $NHCH_3$, —CN, or F;

$R^9$ is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

DETAILED DESCRIPTION OF THE INVENTION

The present invention comprises compounds of Formula I.

Formula I wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$ alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is triazolyl, pyridyl, pyridyl-N-oxide, pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, or $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyrazolyl is optionally substituted with up to three $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, or 4-hydroxy-piperidinyl;

$R^6$ is phenyl, pyridyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl or said pyridyl is optionally substituted up to two times with $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, or $OCH_2CF_3$; wherein the selection of each optional substituent is independent; and wherein said pyrazolyl, triazolyl, imidazolyl, tetrazolyl, oxazolyl, and thiazolyl are optionally substituted with $CH_3$;

$R^7$ is H, Cl, —CN, $C_{(1-4)}$alkyl, $OC_{(1-4)}$alkylCF_3$, $OCF_3$, $OCHF_2$, $OCH_2CH_2OC_{(1-4)}$alkyl, $CF_3$, $SCH_3$, $C_{(1-4)}$alkyl$NA^1A^2$ (including $CH_2NA^1A^2$), $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$alkyl$NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

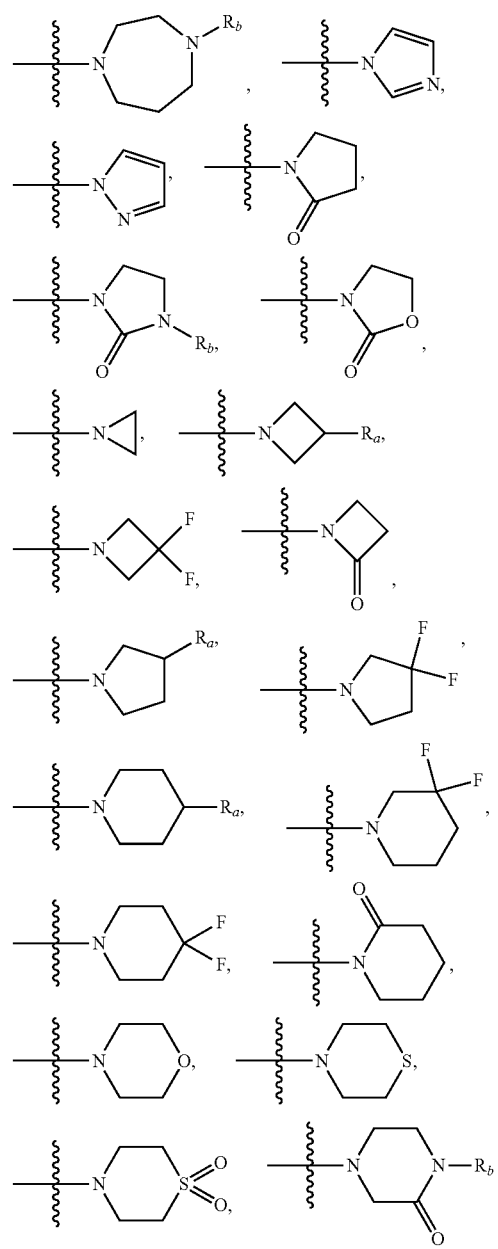

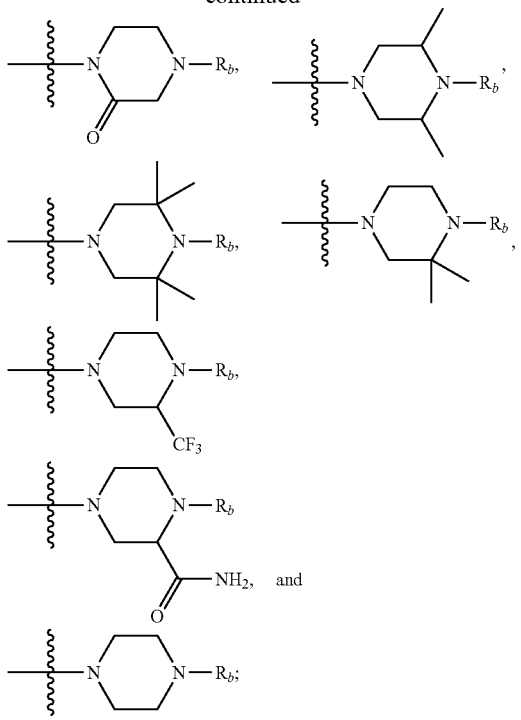

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl, (including $OCH_3$) $CF_3$, $NH_2$, $NHCH_3$, —CN, or F;

$R^9$ is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, imidazolyl, phenyl, thiophenyl, benzoxazolyl, pyrazolyl, pyridyl, pyridyl N-oxide, pyrazinyl, pyrimidinyl, pyridazyl, or quinolinyl are optionally substituted with $C(O)C_{(1-4)}$ alkyl, $C(O)NH_2$, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}$ $OCH_3$, $SCH_3$, $CF_3$, F, Cl, and $C_{(1-2)}$alkyl (including $CH_3$); and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$ alkyl, $CF_3$, F, Cl, and $C_{(1-4)}$alkyl;

$R^2$ is 1-methyl triazolyl, pyridyl, pyridyl-N-oxide, 1-methylpyrazolyl, pyrimidinyl, oxazolyl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-3)}$alkyl-piperidinyl (including N—$C_{(1-2)}$alkyl-piperidinyl), thiazolyl, pyridazyl, pyrazinyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional substituents independently selected from the group consisting of $C_{(1-2)}$alkyl (including $CH_3$), $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-2)}$alkyl (including $OCH_3$), $(CH_2)_{(2-3)}$ $OCH_3$, $SCH_3$, $CF_3$, F, Cl, and $C_{(1-2)}$alkyl (including $CH_3$); and said thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said 1-methylpyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$ alkyl$)_2$, or 4-hydroxy-piperidinyl;

$R^6$ is phenyl, pyridyl, benzothiophenyl, thiophenyl, pyrimidinyl, pyridazyl, or pyrazinyl; wherein said phenyl or said pyridyl is optionally substituted with $OCF_3$, $SO_2C_{(1-4)}$alkyl (including $SO_2CH_3$), $CF_3$, $CHF_2$, pyrazolyl, triazolyl, imidazolyl, tetrazolyl, oxazolyl, thiazolyl, $C_{(1-4)}$alkyl (including $CH_3$), $C_{(3-4)}$cycloalkyl, $OC_{(1-4)}$ alkyl (including $OCH_3$), $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl (including $NHCOCH_3$), $COC_{(1-2)}$alkyl (including $COCH_3$), or $SCH_3$;

$R^7$ is H, Cl, —CN, $C_{(1-4)}$alkyl, $OC_{(1-4)}$alkyl$CF_3$, $OCH_2CH_2OC_{(1-4)}$alkyl, $CF_3$, $SCH_3$, $CH_2NA^1A^2$, $CH_2OC_{(2-3)}$alkylNA$^1$A$^2$, NA$^1$A$^2$, C(O)NA$^1$A$^2$, N(CH$_3$) $C_{(2-4)}$alkylNA$^1$A$^2$, $OC_{(2-4)}$alkylNA$^1$A$^2$, $OC_{(1-4)}$alkyl, $OCH_2$-(1-methyl)-imidazol-2-yl, furyl, pyrazolyl, imidazolyl, pyridyl, pyridazyl, pyrazinyl, or pyrimidinyl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkylOC$_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

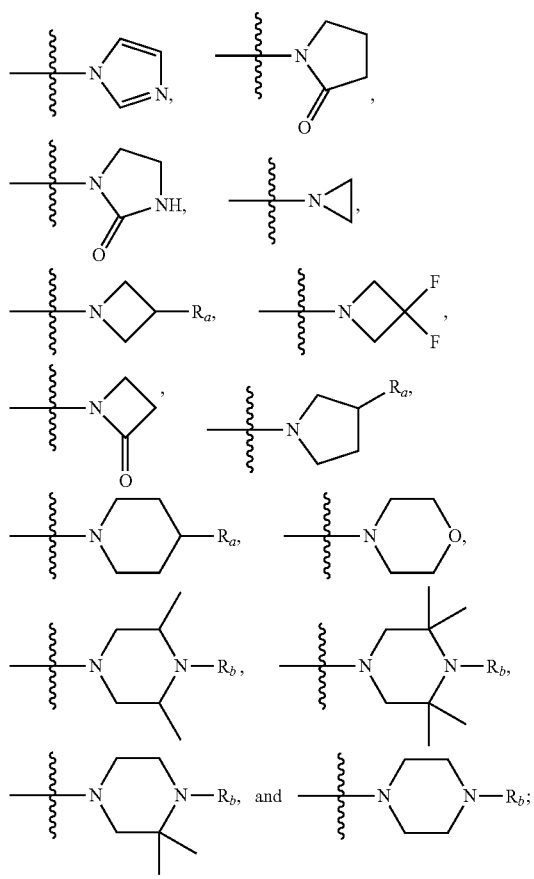

$R_a$ is H, $OC_{(1-4)}$alkyl, $CH_2OH$, $NH(CH_3)$, $N(CH_3)_2$, $NH_2$, $CH_3$, F, or OH;

$R_b$ is H, $CO_2C(CH_3)_3$, $C_{(1-4)}$alkyl, $C(O)C_{(1-4)}$alkyl (including $C(O)CH_3$), $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $CH_3$, $OCH_3$, or F;

$R^9$ is H, or F;

and pharmaceutically acceptable salts thereof;

provided that (4-chloro-2-methoxy-3-(4-(trifluoromethyl)benzyl)quinolin-6-yl)bis(1,2,5-trimethyl-1H-imidazol-4-yl)methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl)quinolin-6-yl)(1-methyl-1H-imidazol-5-yl)(6-(trifluoromethyl)pyridin-3-yl)methanol are excluded from the embodiment.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $C(O)C_{(1-4)}$alkyl (including $C(O)CH_3$), $C(O)NH_2$, $C_{(1-4)}$alkyl (including $CH_3$, and $CH_2CH_3$), $CF_3$, $CH_2CF_3$, Cl, F, —CN, $OC_{(1-4)}$alkyl (including $OCH_3$), $N(C_{(1-4)}$alkyl$)_2$ (including $N(CH_3)_2$), —$(CH_2)_3OCH_3$, $SC_{(1-4)}$alkyl (including $SCH_3$), OH, $CO_2H$, $CO_2C_{(1-4)}$alkyl (including $CO_2C(CH_3)_3$), $OCF_3$, $OCHF_2$, $SO_2CH_3$, $SO_2NH_2$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is 1-methyl triazolyl, pyridyl, pyridyl-N-oxide, 1-methylpyrazolyl, pyrimidinyl, pyrazinyl, oxazolyl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-2)}$alkyl-piperidinyl, thiazolyl, pyridazyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional $CH_3$ groups, or one substituent selected from the group consisting of $SCH_3$, and Cl; and said pyridyl, and pyridyl-N-oxide are optionally substituted with up to two substitutents independently selected from the group consisting of $SO_2CH_3$, $SO_2NH_2$, $C(O)NH_2$, —CN, $OCH_3$, $CF_3$, Cl, and $CH_3$; and said thiazolyl, oxazolyl and isoxazolyl are optionally substituted with up to two $CH_3$ groups; and said 1-methylpyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl (including $SCH_3$), $OC_{(1-4)}$alkyl, (including $OC_{(1-3)}$alkyl)OH, $C_{(1-4)}$alkyl, $N(CH_3)OCH_3$, $NH(C_{(1-4)}$alkyl) (including $NH(C_{(1-2)}$alkyl)), $N(C_{(1-4)}$alkyl$)_2$, (including $N(C_{(1-2)}$alkyl$)_2$), or 4-hydroxy-piperidinyl;

$R^6$ is phenyl, pyridyl, benzothiophenyl, thiophenyl, pyrimidinyl, pyridazyl, or pyrazinyl; wherein said phenyl or said pyridyl is optionally substituted with $OCF_3$, $SO_2CH_3$, $CF_3$, $CHF_2$, pyrazolyl, triazolyl, imidazolyl, tetrazolyl, oxazolyl, thiazolyl, $CH_3$, $OCH_3$, $N(CH_3)_2$, $SO_2NH_2$, $CONH_2$, Cl, F, —CN, $CO_2H$, OH, $CH_2OH$, $NHCOCH_3$, or $COCH_3$;

$R^7$ is H, Cl, —CN, $C_{(1-4)}$alkyl, $OC_{(1-4)}$alkylCF$_3$ (including $OCH_2CF_3$), $OCH_2CH_2OC_{(1-4)}$alkyl (including $OCH_2CH_2OCH_3$), $CF_3$, $SCH_3$, $NA^1A^2$, $C(O)NA^1A^2$ (including $C(O)NHCH_3$), $N(CH_3)C_{(2-4)}$alkyl$NA^1A^2$ (including $N(CH_3)CH_2CH_2NA^1A^2$), $OC_{(2-4)}$alkyl$NA^1A^2$ (including $OCH_2CH_2NA^1A^2$), $OC_{(1-4)}$alkyl (including $OC_{(1-3)}$alkyl), $OCH_2$-(1-methyl)-imidazol-2-yl, imidazolyl, furyl, pyrazolyl, pyridyl, or pyrimidinyl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkyl$OH$, $C(O)C_{(1-4)}$alkyl (including $C(O)C_{(1-2)}$alkyl), or $OC_{(1-4)}$alkyl (including $OCH_3$); or $A^1$ and $A^2$ may be taken together with their attached nitrogen to form a ring selected from the group consisting of:

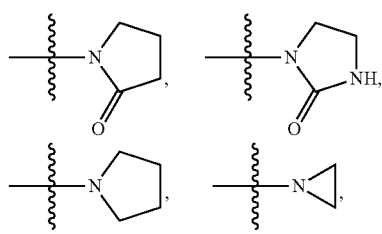

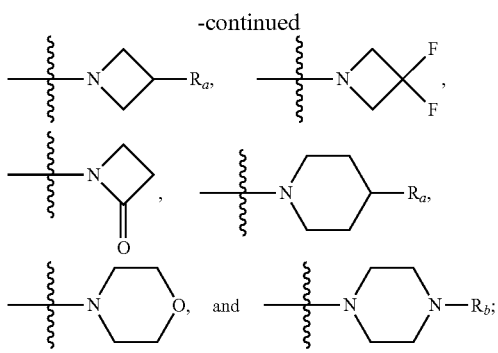

$R_a$ is H, F, $OC_{(1-4)}$alkyl (including $OCH_3$), or OH;
$R_b$ is $C_{(1-4)}$alkyl (including $CH_3$), $C(O)CH_3$, or phenyl;
$R^8$ is H, $CH_3$, $OCH_3$, or F;
$R^9$ is H, or F;
and pharmaceutically acceptable salts thereof;
provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:
$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;
$R^2$ is 1-methyl-1,2,3-triazolyl, pyridyl, pyridyl-N-oxide, 1-methylpyrazol-4-yl, pyrimidin-5-yl, pyridazyl, pyrazin-2-yl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-$C_{(1-2)}$alkyl imidazol-5-yl (including 1-ethyl imidazol-5-yl and 1-methyl imidazol-5-yl); wherein said 1-$C_{(1-2)}$alkyl imidazol-5-yl (including 1-methyl imidazol-5-yl) is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of C(O)$NH_2$, —CN, $OCH_3$, $CF_3$, Cl, and $CH_3$; and said thiazol-5-yl, and said isoxazolyl are optionally substituted with up to two $CH_3$ groups; and said 1-methylpyrazol-4-yl is optionally substituted with up to two additional $CH_3$ groups;
$R^3$ is H, OH, $OCH_3$, or $NH_2$;
$R^4$ is H, or F;

$R^5$ is H, Cl, —CN, $CF_3$, $SCH_3$, $OC_{(1-3)}$alkyl (including $OCH_3$), OH, $C_{(1-4)}$alkyl (including $CH_3$), $N(CH_3)OCH_3$, $NH(C_{(1-2)}$alkyl), $N(C_{(1-2)}$alkyl)$_2$, or 4-hydroxypiperidinyl;
$R^6$ is pyridyl, phenyl, benzothiophenyl, or thiophenyl; wherein said pyridyl or phenyl is optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;
$R^7$ is H, Cl, —CN, $C_{(1-4)}$alkyl (including $C_{(1-3)}$alkyl), $OCH_2CF_3$, $OCH_2CH_2OCH_3$, $CF_3$, $SCH_3$, $NA^1A^2$, $C(O)NHCH_3$, $N(CH_3)CH_2CH_2NA^1A^2$, $OCH_2CH_2NA^1A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; wherein said imidazolyl or pyrazolyl is optionally substituted with one $CH_3$ group;
$A^1$ is H, or $C_{(1-4)}$alkyl;
$A^2$ is H, $C_{(1-4)}$alkyl, $C_{(1-4)}$alkylO$C_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

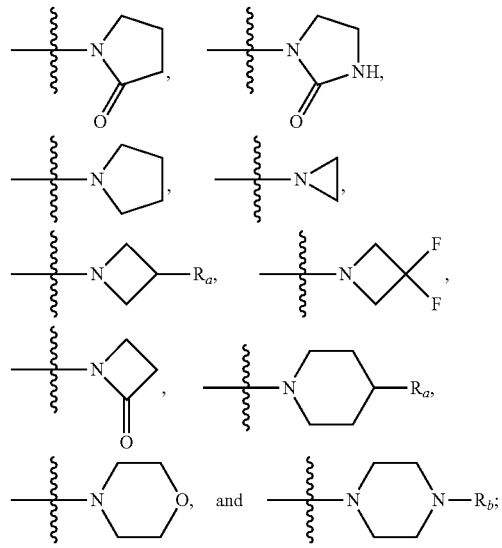

$R_a$ is H, F, $OCH_3$, or OH;
$R_b$ is $CH_3$, or phenyl;
$R^8$ is H, $CH_3$, $OCH_3$, or F;
$R^9$ is H, or F;
and pharmaceutically acceptable salts thereof;
provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:
$R^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with $SO_2CH_3$, $C(O)CH_3$, $CH_3$, $CF_3$, Cl, F, —CN, $OCH_3$, —$CF_3$, or $N(CH_3)_2$; and optionally substituted with up to one additional group independently selected from Cl, $OCH_3$, and $CH_3$; and wherein said triazolyl, oxazolyl, and thiazolyl are optionally substituted with one or two $CH_3$ groups;

$R^2$ is 1-methyl-1,2-3-triazol-5-yl, pyrid-3-yl, 1-methylpyrazol-4-yl, thiazol-5-yl, N-acetyl-piperidin-4-yl, N-acetyl-azetidin-3-yl, N-methylsulfonyl-azetidin-3-yl, N-Boc-azetidin-3-yl, 1,2-dimethyl imidazol-5-yl or 1-methyl imidazol-5-yl;

$R^3$ is OH, or $NH_2$;

$R^4$ is H;

$R^5$ is H, Cl, —CN, $CF_3$, $CH_3$, OH, $N(CH_3)OCH_3$, or $OCH_3$;

$R^6$ is pyridyl, phenyl, benzothiophenyl, or thiophenyl; wherein said pyridyl or phenyl is optionally substituted with pyrazol-1-yl, 1,2,4-triazol-1-yl, $CF_3$, $OCH_3$, $SO_2CH_3$, Cl, F, or —CN;

$R^7$ is Cl, —CN, $CF_3$, $C_{(1-4)}$alkyl, $NA^1A^2$, $C(O)NHCH_3$, $OCH_2CH_2OCH_3$, 1-methyl imidazol-2-yl, 1-methylpyrazol-4-yl, or $OC_{(1-2)}$alkyl;

$A^1$ is $C_{(1-2)}$alkyl;

$A^2$ is $C_{(1-2)}$alkyl, $CH_2CH_2OCH_3$, or $OCH_3$; or $A^1$ and $A^2$ may be taken together with their attached nitrogen to form a ring selected from the group consisting of:

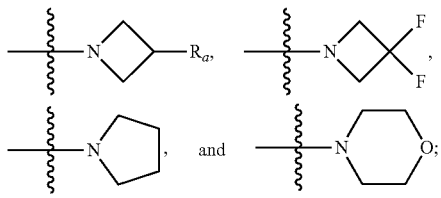

$R_a$ is OH, $OCH_3$, F, or H;

$R^8$ is H, $CH_3$, $OCH_3$, or F;

$R^9$ is H;

and pharmaceutically acceptable salts thereof.

In another embodiment of the invention:

$R^1$ is imidazolyl, triazolyl, thiazolyl, pyridyl, piperidinyl, phenyl, or oxazolyl; wherein said piperidinyl, pyridyl, imidazolyl, and phenyl are optionally substituted with $C(O)CH_3$, $CH_3$, $CF_3$, Cl, F, —CN, $OCH_3$, or $N(CH_3)_2$; and optionally substituted with up to one additional group independently selected from Cl, $OCH_3$, and $CH_3$; and wherein said triazolyl, oxazolyl, and thiazolyl are optionally substituted with one or two $CH_3$ groups;

$R^2$ is 1-methyl-1,2,3-triazol-5-yl, pyrid-3-yl, 1-methylpyrazol-4-yl, thiazol-5-yl, N-acetyl-piperidin-4-yl, 1,2-dimethyl imidazol-5-yl, or 1-methyl imidazol-5-yl;

$R^3$ is OH;

$R^4$ is H;

$R^5$ is H, Cl, —CN, $CF_3$, $CH_3$, or $OCH_3$;

$R^6$ is phenyl, thiophen-2-yl, or benzothiophen-2-yl; wherein said phenyl is optionally substituted with pyrazol-1-yl, 1,2,4-triazol-1-yl, $OCH_3$, $SO_2CH_3$, Cl, F, $CF_3$, or —CN;

$R^7$ is Cl, —CN, $CH_3$, $NA^1A^2$, $C(O)NHCH_3$, or $OC_{(1-2)}$alkyl;

$A^1$ is $C_{(1-2)}$alkyl;

$A^2$ is $C_{(1-2)}$alkyl, or $OCH_3$; or $A^1$ and $A^2$ may be taken together with their attached nitrogen to form a ring which is:

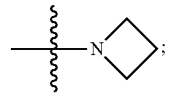

$R^8$ is H, $CH_3$, $OCH_3$, or F;

$R^9$ is H;

and pharmaceutically acceptable salts thereof.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is triazolyl, pyridyl, pyridyl-N-oxide, pyrazolyl, pyrimidinyl, oxazolyl, isoxazolyl, N-acetyl piperidinyl, 1-H-piperidinyl, N-Boc-piperidinyl, N—$C_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, or $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$ alkyl; and said thiadiazolyl and oxadiazolyl are optionally substituted with C$_{(1-2)}$alkyl; and said pyrazolyl is optionally substituted with up to three CH$_3$ groups;

R$^3$ is H, OH, OCH$_3$, or NH$_2$;

R$^4$ is H, or F;

R$^5$ is H, Cl, —CN, CF$_3$, SC$_{(1-4)}$alkyl, OC$_{(1-4)}$alkyl, OH, C$_{(1-4)}$alkyl, N(CH$_3$)OCH$_3$, NH(C$_{(1-4)}$alkyl), N(C$_{(1-4)}$alkyl)$_2$, or 4-hydroxy-piperidinyl;

R$^6$ is phenyl, pyridyl, benzothiophenyl, thiophenyl, pyrimidinyl, pyridazyl, or pyrazinyl; wherein said pyrimidinyl, pyridazyl, or pyrazinyl are optionally substituted with Cl, F, CH$_3$, SCH$_3$, OC$_{(1-4)}$alkyl, —CN, CONH$_2$, SO$_2$NH$_2$, or SO$_2$CH$_3$; and wherein said phenyl or said pyridyl is optionally substituted up to two times with OCF$_3$, SO$_2$C$_{(1-4)}$alkyl, CF$_3$, CHF$_2$, pyrazolyl, triazolyl, imidazolyl, tetrazolyl, oxazolyl, thiazolyl, C$_{(1-4)}$alkyl, C$_{(3-4)}$cycloalkyl, OC$_{(1-4)}$alkyl, N(CH$_3$)$_2$, SO$_2$NH$_2$, SO$_2$NHCH$_3$, SO$_2$N(CH$_3$)$_2$, CONH$_2$, CONHCH$_3$, CON(CH$_3$)$_2$, Cl, F, —CN, CO$_2$H, OH, CH$_2$OH, NHCOC$_{(1-2)}$alkyl, COC$_{(1-2)}$alkyl, SCH$_3$, CO$_2$C$_{(1-4)}$alkyl, NH$_2$, NHC$_{(1-2)}$alkyl, or OCH$_2$CF$_3$; wherein the selection of each optional substituent is independent; and wherein said pyrazolyl, triazolyl, imidazolyl, tetrazolyl, oxazolyl, and thiazolyl are optionally substituted with CH$_3$;

R$^7$ is H, Cl, —CN, C$_{(1-4)}$alkyl, OC$_{(1-4)}$alkylCF$_3$, OCF$_3$, OCHF$_2$, OCH$_2$CH$_2$OC$_{(1-4)}$alkyl, CF$_3$, SCH$_3$, C$_{(1-4)}$alkylNA$^1$A$^2$ (including CH$_2$NA$^1$A$^2$), CH$_2$OC$_{(2-3)}$alkylNA$^1$A$^2$, NA$^1$A$^2$, C(O)NA$^1$A$^2$, CH$_2$NHC$_{(2-3)}$alkylNA$^1$A$^2$, CH$_2$N(CH$_3$)C$_{(2-3)}$alkylNA$^1$A$^2$, NHC$_{(2-3)}$alkylNA$^1$A$^2$, N(CH$_3$)C$_{(2-4)}$alkylNA$^1$A$^2$, OC$_{(2-4)}$alkylNA$^1$A$^2$, OC$_{(1-4)}$alkyl, OCH$_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, CH$_3$, CF$_3$, and OCH$_3$;

A$^1$ is H, or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-4)}$alkyl, or OC$_{(1-4)}$alkyl; or A$^1$ and A$^2$ may be taken together with their attached nitrogen to form a ring selected from the group consisting of:

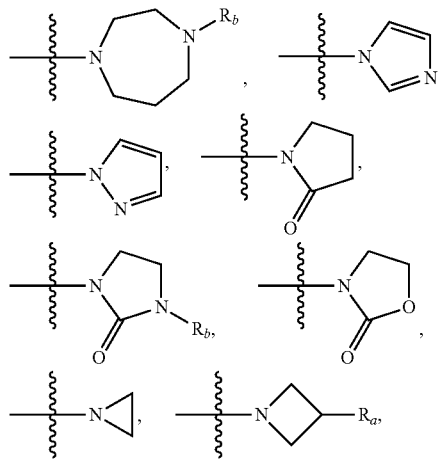

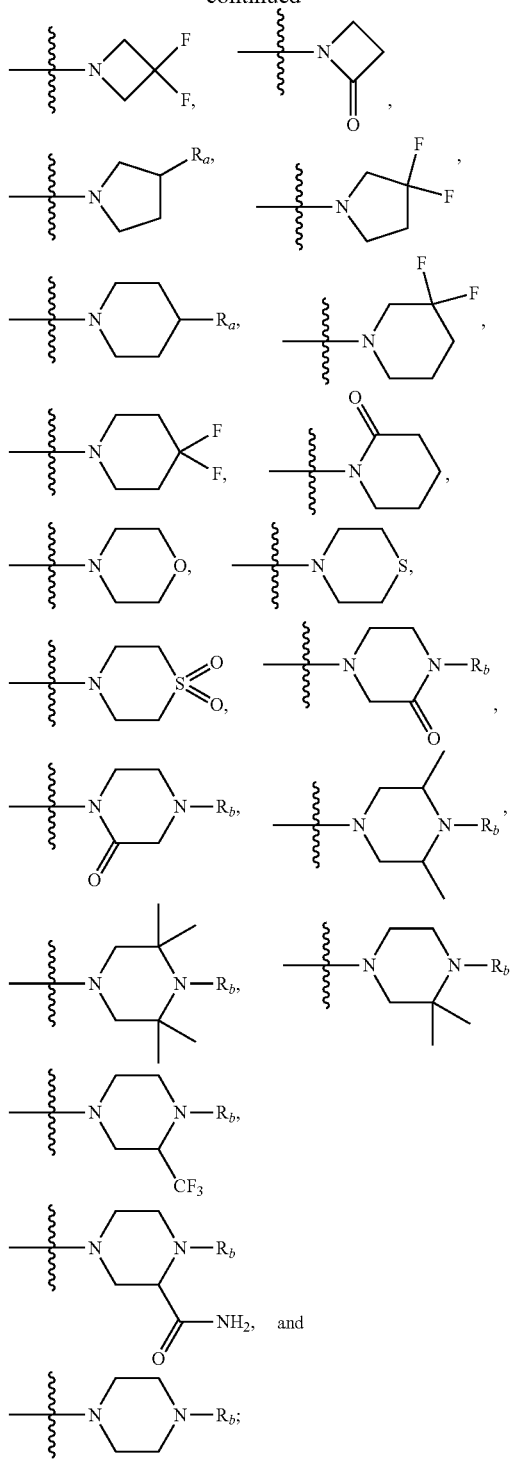

R$_a$ is H, OC$_{(1-4)}$alkyl, CH$_2$OH, NH(CH$_3$), N(CH$_3$)$_2$, NH$_2$, CH$_3$, F, CF$_3$, SO$_2$CH$_3$, or OH;

R$_b$ is H, CO$_2$C(CH$_3$)$_3$, C$_{(1-4)}$alkyl, C(O)C$_{(1-4)}$alkyl, SO$_2$C$_{(1-4)}$alkyl, CH$_2$CH$_2$CF$_3$, CH$_2$CF$_3$, CH$_2$-cyclopropyl, phenyl, CH$_2$-phenyl, or C$_{(3-6)}$cycloalkyl;

R$^8$ is H, C$_{(1-3)}$alkyl (including CH$_3$), OC$_{(1-3)}$alkyl, (including OCH$_3$) CF$_3$, NH$_2$, NHCH$_3$, —CN, or F;

R$^9$ is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, imidazolyl, phenyl, thiophenyl, benzoxazolyl, pyrazolyl, pyridyl, pyridyl N-oxide, pyrazinyl, pyrimidinyl, pyridazyl, or quinolinyl are optionally substituted with $C(O)C_{(1-4)}$ alkyl, $C(O)NH_2$, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$ alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}$ $OCH_3$, $SCH_3$, $CF_3$, F, Cl, and $C_{(1-2)}$alkyl (including $CH_3$); and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$ alkyl, $CF_3$, F, Cl, and $C_{(1-4)}$alkyl;

$R^2$ is 1-methyl triazolyl, pyridyl, pyridyl-N-oxide, 1-methylpyrazolyl, pyrimidinyl, oxazolyl, isoxazolyl, N-acetyl piperidinyl, 1-H-piperidinyl, N-Boc-piperidinyl, N—$C_{(1-3)}$alkyl-piperidinyl (including N—$C_{(1-2)}$alkyl-piperidinyl), thiazolyl, pyridazyl, pyrazinyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional substituents independently selected from the group consisting of $C_{(1-2)}$alkyl (including $CH_3$), $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-2)}$ alkyl (including $OCH_3$), $(CH_2)_{(2-3)}OCH_3$, $SCH_3$, $CF_3$, F, Cl, and $C_{(1-2)}$alkyl (including $CH_3$); and said thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said 1-methyl pyrazolyl is optionally substituted with up to two additional $CH_3$ groups;

$R^3$ is H, OH, $OCH_3$, or $NH_2$;
$R^4$ is H, or F;
$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$ alkyl$)_2$, or 4-hydroxy-piperidinyl;
$R^6$ is phenyl, pyridyl, benzothiophenyl, thiophenyl, pyrimidinyl, pyridazyl, or pyrazinyl; wherein said phenyl or said pyridyl is optionally substituted with $OCF_3$, $SO_2 C_{(1-4)}$alkyl (including $SO_2CH_3$), $CF_3$, $CHF_2$, pyrazolyl, triazolyl, imidazolyl, tetrazolyl, oxazolyl, thiazolyl, $C_{(1-4)}$alkyl (including $CH_3$), $C_{(3-4)}$cycloalkyl, $OC_{(1-4)}$ alkyl (including $OCH_3$), $N(CH_3)_2$, $SO_2NH_2$, $SO_2NHCH_3$, $SO_2N(CH_3)_2$, $CONH_2$, $CONHCH_3$, CON $(CH_3)_2$, Cl, F, —CN, $CO_2H$, OH, $CH_2OH$, NHCO $C_{(1-2)}$alkyl (including $NHCOCH_3$), $COC_{(1-2)}$alkyl (including $COCH_3$), or $SCH_3$;

$R^7$ is H, Cl, —CN, $C_{(1-4)}$alkyl, $OC_{(1-4)}$alkylCF_3$, $OCH_2CH_2OC_{(1-4)}$alkyl, $CF_3$, $SCH_3$, $CH_2NA^1A^2$, $CH_2OC_{(2-3)}$alkyl$NA^1A^2$, $NA^1A^2$, $C(O)NA^1A^2$, $N(CH_3)$ $C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, furyl, pyrazolyl, imidazolyl, pyridyl, pyridazyl, pyrazinyl, or pyrimidinyl; wherein said imidazolyl or pyrazolyl is optionally substituted with one $CH_3$ group;

$A^1$ is H, or $C_{(1-4)}$alkyl;
$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

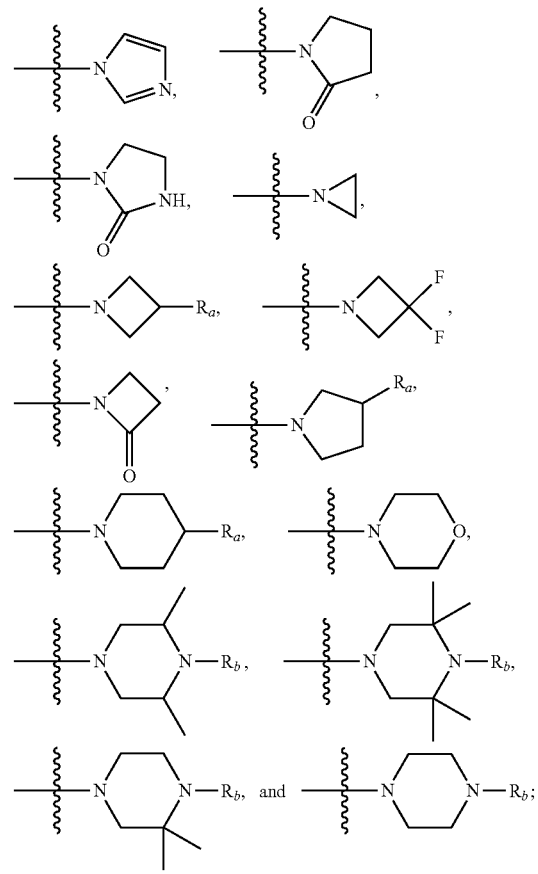

$R_a$ is H, $OC_{(1-4)}$alkyl, $CH_2OH$, $NH(CH_3)$, $N(CH_3)_2$, $NH_2$, $CH_3$, F, or OH;
$R_b$ is H, $CO_2C(CH_3)_3$, $C_{(1-4)}$alkyl, $C(O)C_{(1-4)}$alkyl (including $C(O)CH_3$), $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;
$R^8$ is H, $CH_3$, $OCH_3$, or F;
$R^9$ is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:
- $R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with C(O)$C_{(1-4)}$alkyl (including C(O)$CH_3$), C(O)$NH_2$, $C_{(1-4)}$alkyl (including $CH_3$, and $CH_2CH_3$), $CF_3$, $CH_2CF_3$, Cl, F, —CN, $OC_{(1-4)}$alkyl (including $OCH_3$), $N(C_{(1-4)}alkyl)_2$ (including $N(CH_3)_2$), —$(CH_2)_3OCH_3$, $SC_{(1-4)}$alkyl (including $SCH_3$), OH, $CO_2H$, $CO_2C_{(1-4)}$alkyl (including $CO_2C(CH_3)_3$), $OCF_3$, $OCHF_2$, $SO_2CH_3$, $SO_2NH_2$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;
- $R^2$ is 1-methyl triazolyl, pyridyl, pyridyl-N-oxide, 1-methylpyrazolyl, pyrimidinyl, pyrazinyl, oxazolyl, isoxazolyl, N-acetyl piperidinyl, 1-H-piperidinyl, N-Boc-piperidinyl, N—$C_{(1-2)}$alkyl-piperidinyl, thiazolyl, pyridazyl, 1-(3-methoxypropyl)-imidazolyl, or 1-$C_{(1-2)}$ alkyl imidazolyl; wherein said 1-$C_{(1-2)}$alkyl imidazolyl is optionally substituted with up to two additional $CH_3$ groups, or one substituent selected from the group consisting of $SCH_3$, and Cl; and said pyridyl, and pyridyl-N-oxide are optionally substituted with up to two substitutents independently selected from the group consisting of $SO_2CH_3$, $SO_2NH_2$, C(O)$NH_2$, —CN, $OCH_3$, $CF_3$, Cl, and $CH_3$; and said thiazolyl, oxazolyl and isoxazolyl are optionally substituted with up to two $CH_3$ groups; and said 1-methylpyrazolyl is optionally substituted with up to two additional $CH_3$ groups;
- $R^3$ is H, OH, $OCH_3$, or $NH_2$;
- $R^4$ is H, or F;
- $R^5$ is H, Cl, —CN, $CF_3$, $SC_{(1-4)}$alkyl (including $SCH_3$), $OC_{(1-4)}$alkyl, (including $OC_{(1-3)}$alkyl) OH, $C_{(1-4)}$alkyl, $N(CH_3)OCH_3$, $NH(C_{(1-4)}$alkyl) (including $NH(C_{(1-2)}$alkyl)), $N(C_{(1-4)}alkyl)_2$, (including $N(C_{(1-2)}alkyl)_2$), or 4-hydroxy-piperidinyl;
- $R^6$ is phenyl, pyridyl, benzothiophenyl, thiophenyl, pyrimidinyl, pyridazyl, or pyrazinyl; wherein said phenyl or said pyridyl is optionally substituted with $OCF_3$, $SO_2CH_3$, $CF_3$, $CHF_2$, pyrazolyl, triazolyl, imidazolyl, tetrazolyl, oxazolyl, thiazolyl, $CH_3$, $OCH_3$, $N(CH_3)_2$, $SO_2NH_2$, $CONH_2$, Cl, F, —CN, $CO_2H$, OH, $CH_2OH$, $NHCOCH_3$, or $COCH_3$;
- $R^7$ is H, Cl, —CN, $C_{(1-4)}$alkyl, $OC_{(1-4)}$alkyl$CF_3$ (including $OCH_2CF_3$), $OCH_2CH_2OC_{(1-4)}$alkyl (including $OCH_2CH_2OCH_3$), $CF_3$, $SCH_3$, $NA^1A^2$, C(O)$NA^1A^2$ (including C(O)$NHCH_3$), $N(CH_3)C_{(2-4)}$alkyl$NA^1A^2$ (including $N(CH_3)CH_2CH_2NA^1A^2$), $OC_{(2-4)}$alkyl$NA^1A^2$ (including $OCH_2CH_2NA^1A^2$), $OC_{(1-4)}$alkyl (including $OC_{(1-3)}$alkyl), $OCH_2$-(1-methyl)-imidazol-2-yl, imidazolyl, furyl, pyrazolyl, pyridyl, or pyrimidinyl; wherein said imidazolyl or pyrazolyl is optionally substituted with one $CH_3$ group;
- $A^1$ is H, or $C_{(1-4)}$alkyl;
- $A^2$ is H, $C_{(1-4)}$alkyl, $C_{(1-4)}$alkylO$C_{(1-4)}$alkyl, $C_{(1-4)}$alkylOH, C(O)$C_{(1-4)}$alkyl (including C(O)$C_{(1-2)}$alkyl), or $OC_{(1-4)}$alkyl (including $OCH_3$); or $A^1$ and $A^2$ may be taken together with their attached nitrogen to form a ring selected from the group consisting of:

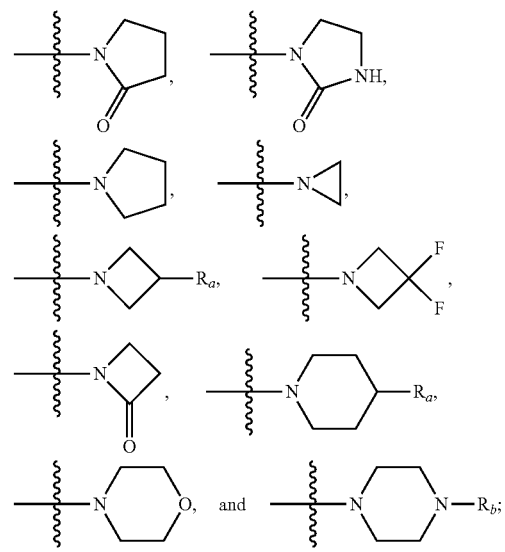

$R_a$ is H, F, $OC_{(1-4)}$alkyl (including $OCH_3$), or OH;
$R_b$ is $C_{(1-4)}$alkyl (including $CH_3$), C(O)$CH_3$, or phenyl;
$R^8$ is H, $CH_3$, $OCH_3$, or F;
$R^9$ is H, or F;
and pharmaceutically acceptable salts thereof;
provided that (4-chloro-2-methoxy-3-(4-(trifluoromethyl) benzyl)quinolin-6-yl)bis(1,2,5-trimethyl-1H-imidazol-4-yl) methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl) quinolin-6-yl)(1-methyl-1H-imidazol-5-yl)(6-(trifluoromethyl)pyridin-3-yl)methanol are excluded from the embodiment.

In another embodiment of the invention:
- $R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, C(O)$CH_3$, C(O)$NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;
- $R^2$ is 1-methyl-1,2,3-triazolyl, pyridyl, pyridyl-N-oxide, 1-methylpyrazol-4-yl, pyrimidin-5-yl, pyridazyl, pyrazin-2-yl, isoxazolyl, N-acetyl piperidinyl, 1-H-piperidinyl, N-Boc-piperidinyl, N—$C_{(1-2)}$alkyl-piperidinyl, thiazol-5-yl, 1-(3-methoxypropyl)-imidazol-5-yl, or 1-C$_{(1-2)}$alkyl imidazol-5-yl (including 1-ethyl imidazol-5-yl and 1-methyl imidazol-5-yl); wherein said 1-C$_{(1-2)}$alkyl imidazol-5-yl (including 1-methyl imidazol-5-yl) is optionally substituted with up to two additional CH$_3$ groups, or one substituent selected from the group consisting of SCH$_3$, and Cl; and said pyridyl, and pyridyl-N-oxide are optionally substituted with up to two substituents independently selected from the group consisting of C(O)NH$_2$, —CN, OCH$_3$, CF$_3$, Cl, and CH$_3$; and said thiazol-5-yl, and said isoxazolyl are optionally substituted with up to two CH$_3$ groups; and said 1-methylpyrazol-4-yl is optionally substituted with up to two additional CH$_3$ groups;

R$^3$ is H, OH, OCH$_3$, or NH$_2$;

R$^4$ is H, or F;

R$^5$ is H, Cl, —CN, CF$_3$, SCH$_3$, OC$_{(1-3)}$alkyl (including OCH$_3$), OH, C$_{(1-4)}$alkyl (including CH$_3$), N(CH$_3$)OCH$_3$, NH(C$_{(1-2)}$alkyl), N(C$_{(1-2)}$alkyl)$_2$, or 4-hydroxypiperidinyl;

R$^6$ is pyridyl, phenyl, benzothiophenyl, or thiophenyl; wherein said pyridyl or phenyl is optionally substituted with OCF$_3$, SO$_2$CH$_3$, CF$_3$, CHF$_2$, imidazol-1-yl, pyrazol-1-yl, 1,2,4-triazol-1-yl, CH$_3$, OCH$_3$, Cl, F, or —CN;

R$^7$ is H, Cl, —CN, C$_{(1-4)}$alkyl (including C$_{(1-3)}$alkyl), OCH$_2$CF$_3$, OCH$_2$CH$_2$OCH$_3$, CF$_3$, SCH$_3$, NA$^1$A$^2$, C(O)NHCH$_3$, N(CH$_3$)CH$_2$CH$_2$NA$^1$A$^2$, OCH$_2$CH$_2$NA$^1$A$^2$, OC$_{(1-3)}$alkyl, OCH$_2$-(1-methyl)-imidazol-2-yl, imidazol-2-yl, fur-2-yl, pyrazol-4-yl, pyrid-3-yl, or pyrimidin-5-yl; wherein said imidazolyl or pyrazolyl is optionally substituted with one CH$_3$ group;

A$^1$ is H, or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

R$_a$ is H, F, OCH$_3$, or OH;
R$_b$ is CH$_3$, or phenyl;
R$^8$ is H, CH$_3$, OCH$_3$, or F;
R$^9$ is H, or F;
and pharmaceutically acceptable salts thereof;
provided that (4-chloro-2-methoxy-3-(4-(trifluoromethyl)benzyl)quinolin-6-yl)bis(1,2,5-trimethyl-1H-imidazol-4-yl)methanol, N-(2-((3-(4-(1H-pyrazol-1-yl)benzyl)-6-((4-chlorophenyl)(hydroxy)(1-methyl-1H-imidazol-5-yl)methyl)-4-hydroxyquinolin-2-yl)oxy)ethyl)acetamide and (3-(4-(1H-pyrazol-1-yl)benzyl)-4-chloro-2-(4-methylpiperazin-1-yl)quinolin-6-yl)(1-methyl-1H-imidazol-5-yl)(6-(trifluoromethyl)pyridin-3-yl)methanol are excluded from the embodiment.

In another embodiment of the invention:
R$^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with SO$_2$CH$_3$, C(O)CH$_3$, CH$_3$, CF$_3$, Cl, F, —CN, OCH$_3$, or N(CH$_3$)$_2$; and optionally substituted with up to one additional group independently selected from Cl, OCH$_3$, and CH$_3$; and wherein said triazolyl, oxazolyl, and thiazolyl are optionally substituted with one or two CH$_3$ groups;

R$^2$ is 1-methyl-1,2-3-triazol-5-yl, pyrid-3-yl, 1-methylpyrazol-4-yl, thiazol-5-yl, N-acetyl-piperidin-4-yl, 1,2-dimethyl imidazol-5-yl or 1-methyl imidazol-5-yl;

R$^3$ is OH;

R$^4$ is H;

R$^5$ is H, Cl, —CN, CF$_3$, CH$_3$, OH, N(CH$_3$)OCH$_3$, or OCH$_3$;

R$^6$ is pyridyl, phenyl, benzothiophenyl, or thiophenyl; wherein said pyridyl or phenyl is optionally substituted with pyrazol-1-yl, 1,2,4-triazol-1-yl, CF$_3$, OCH$_3$, SO$_2$CH$_3$, Cl, F, or —CN;

R$^7$ is Cl, —CN, CF$_3$, C$_{(1-4)}$alkyl, NA$^1$A$^2$, C(O)NHCH$_3$, OCH$_2$CH$_2$OCH$_3$, 1-methyl imidazol-2-yl, 1-methylpyrazol-4-yl, or OC$_{(1-2)}$alkyl;

A$^1$ is C$_{(1-2)}$alkyl;

A$^2$ is C$_{(1-2)}$alkyl, CH$_2$CH$_2$OCH$_3$, or OCH$_3$; or A$^1$ and A$^2$ may be taken together with their attached nitrogen to form a ring selected from the group consisting of:

R$_a$ is OH, OCH$_3$, F;
R$^8$ is H, CH$_3$, OCH$_3$, or F;
R$^9$ is H;
and pharmaceutically acceptable salts thereof.

In another embodiment of the invention:
R$^1$ is imidazolyl, triazolyl, thiazolyl, pyridyl, piperidinyl, phenyl, or oxazolyl; wherein said piperidinyl, pyridyl, imidazolyl, and phenyl are optionally substituted with C(O)CH$_3$, CH$_3$, CF$_3$, Cl, F, —CN, OCH$_3$, or N(CH$_3$)$_2$; and optionally substituted with up to one additional group independently selected from Cl, OCH$_3$, and CH$_3$; and wherein said triazolyl, oxazolyl, and thiazolyl are optionally substituted with one or two CH$_3$ groups;

R$^2$ is 1-methyl-1,2,3-triazol-5-yl, pyrid-3-yl, 1-methylpyrazol-4-yl, thiazol-5-yl, N-acetyl-piperidin-4-yl, 1,2-dimethyl imidazol-5-yl, or 1-methyl imidazol-5-yl;

R$^3$ is OH;

R$^4$ is H;

R$^5$ is H, Cl, —CN, CF$_3$, CH$_3$, or OCH$_3$;

R$^6$ is phenyl, thiophen-2-yl, or benzothiophen-2-yl; wherein said phenyl is optionally substituted with pyrazol-1-yl, 1,2,4-triazol-1-yl, OCH$_3$, SO$_2$CH$_3$, Cl, F, CF$_3$, or —CN;

$R^7$ is Cl, —CN, $CH_3$, $NA^1A^2$, $C(O)NHCH_3$, or $OC_{(1-2)}$alkyl;
$A^1$ is $C_{(1-2)}$alkyl;
$A^2$ is $C_{(1-2)}$alkyl, or $OCH_3$; or $A^1$ and $A^2$ may be taken together with their attached nitrogen to form a ring which is:
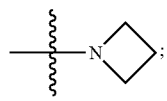 [SMILES: *N1CCC1]
$R^8$ is H, $CH_3$, $OCH_3$, or F;
$R^9$ is H;
and pharmaceutically acceptable salts thereof.
Another embodiment of the invention is a compound selected from the group consisting of:
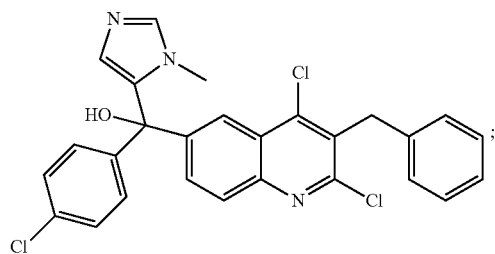
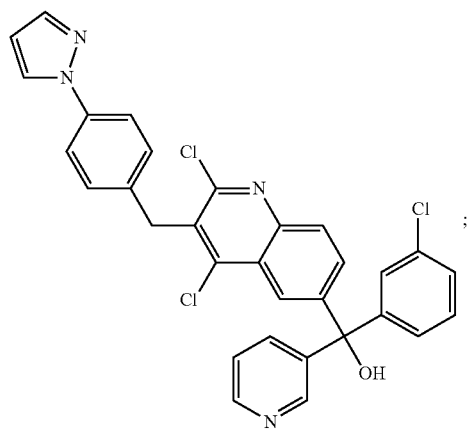
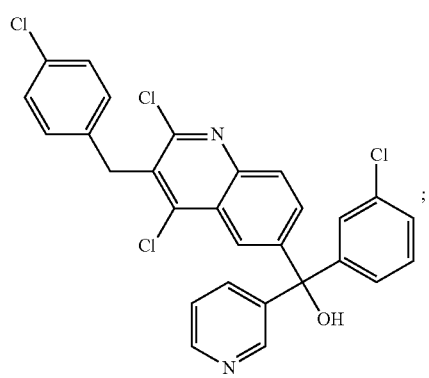
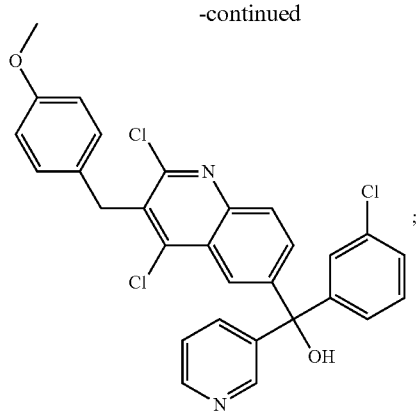
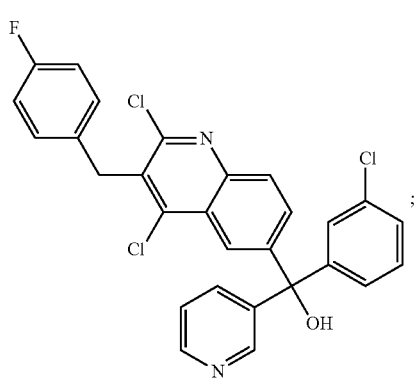
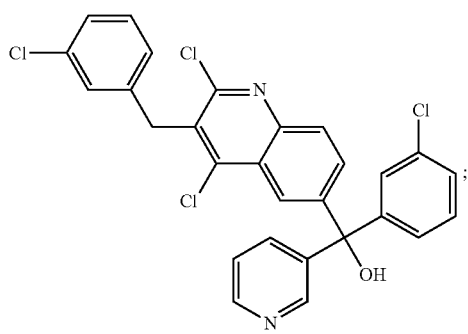

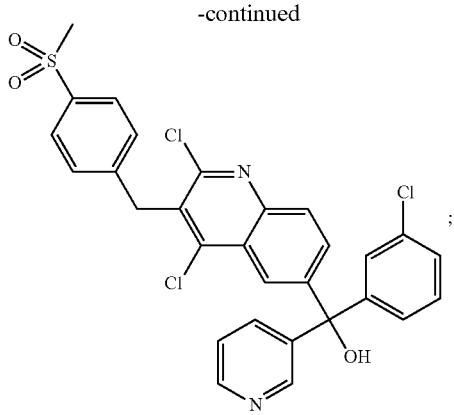
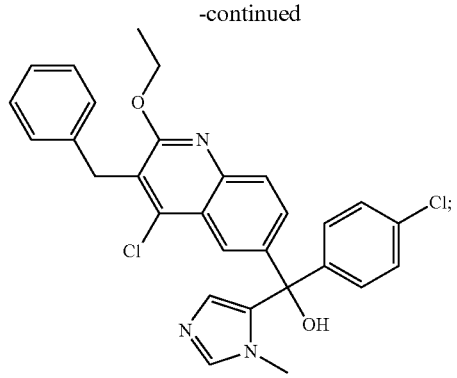
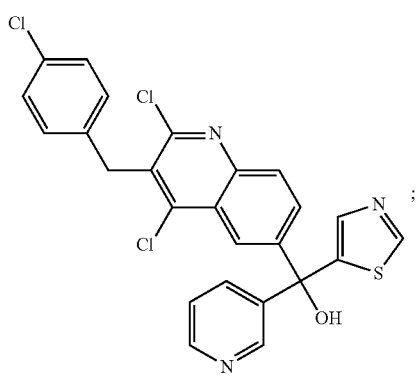
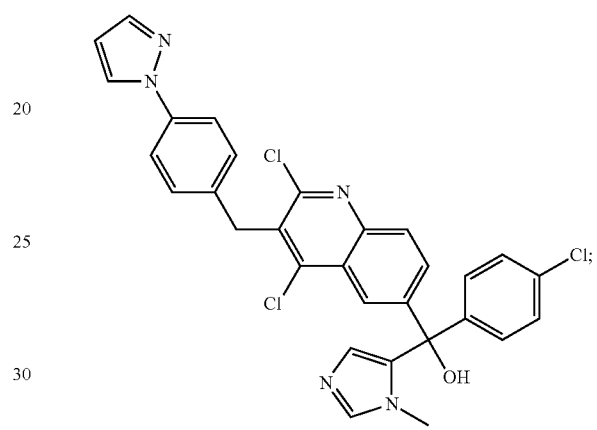
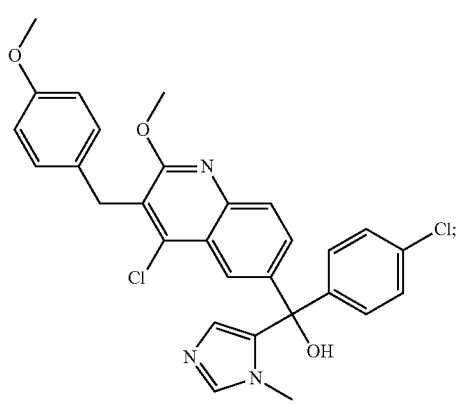
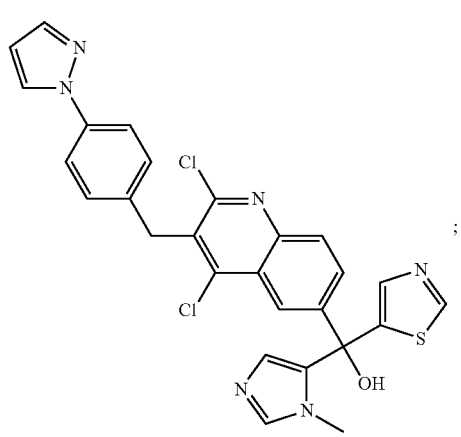
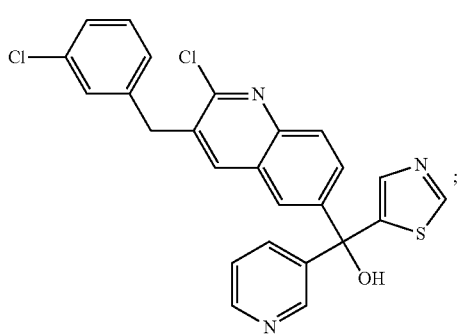
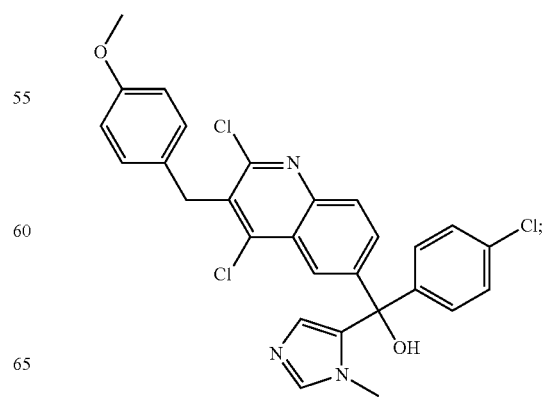

29
-continued
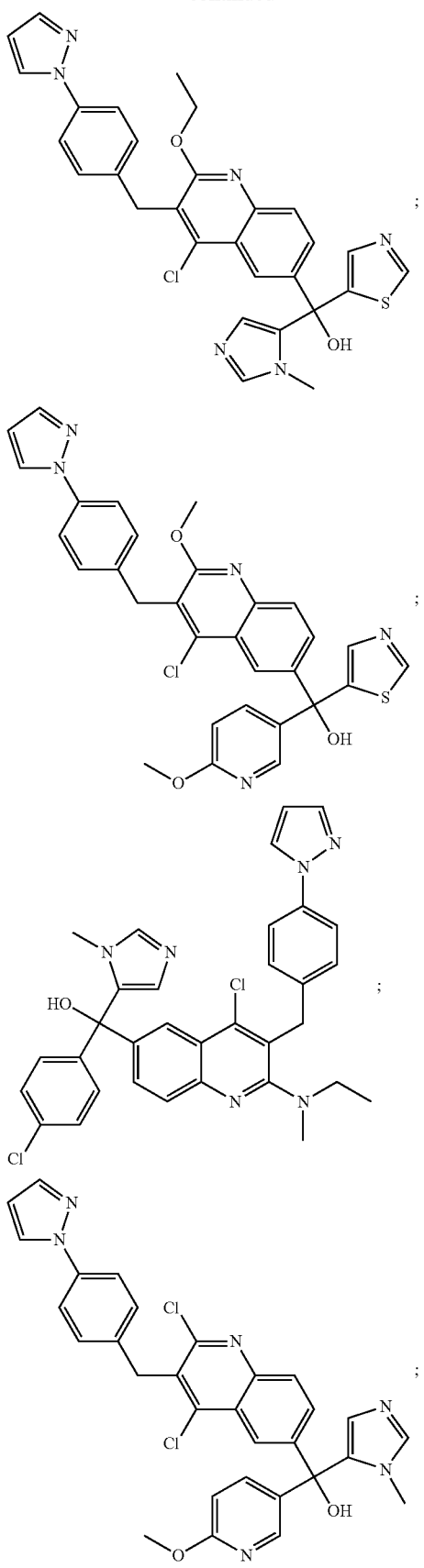
30
-continued
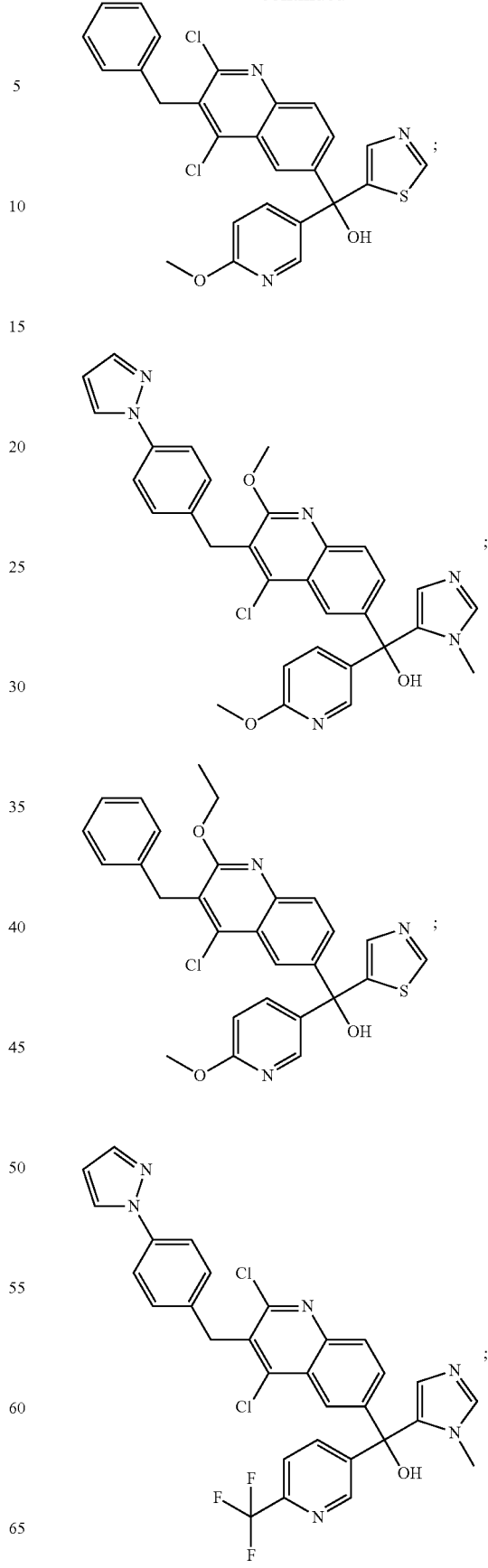

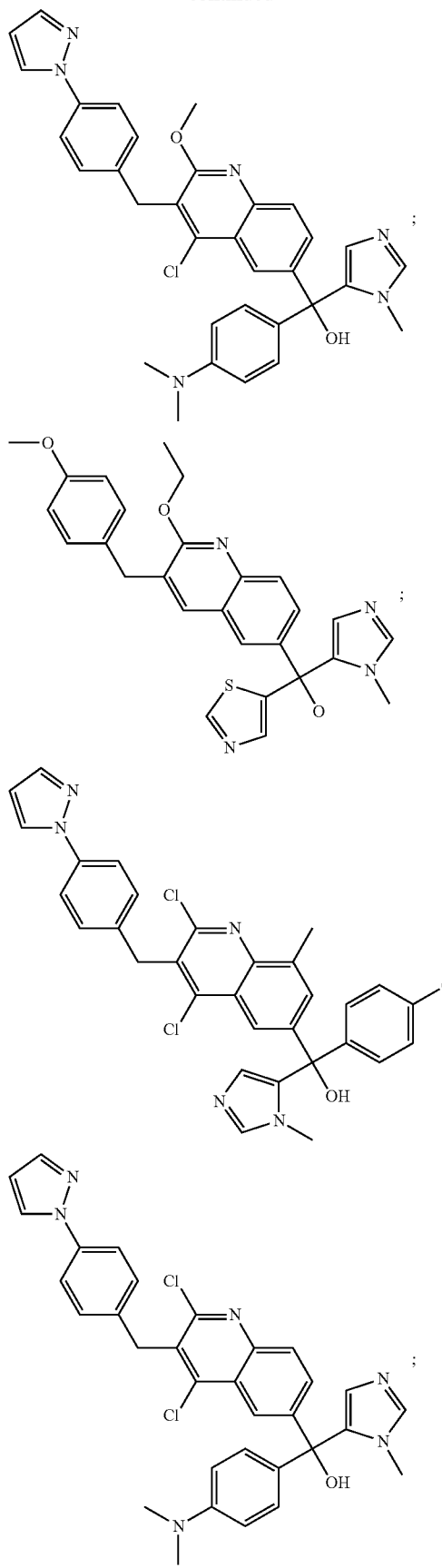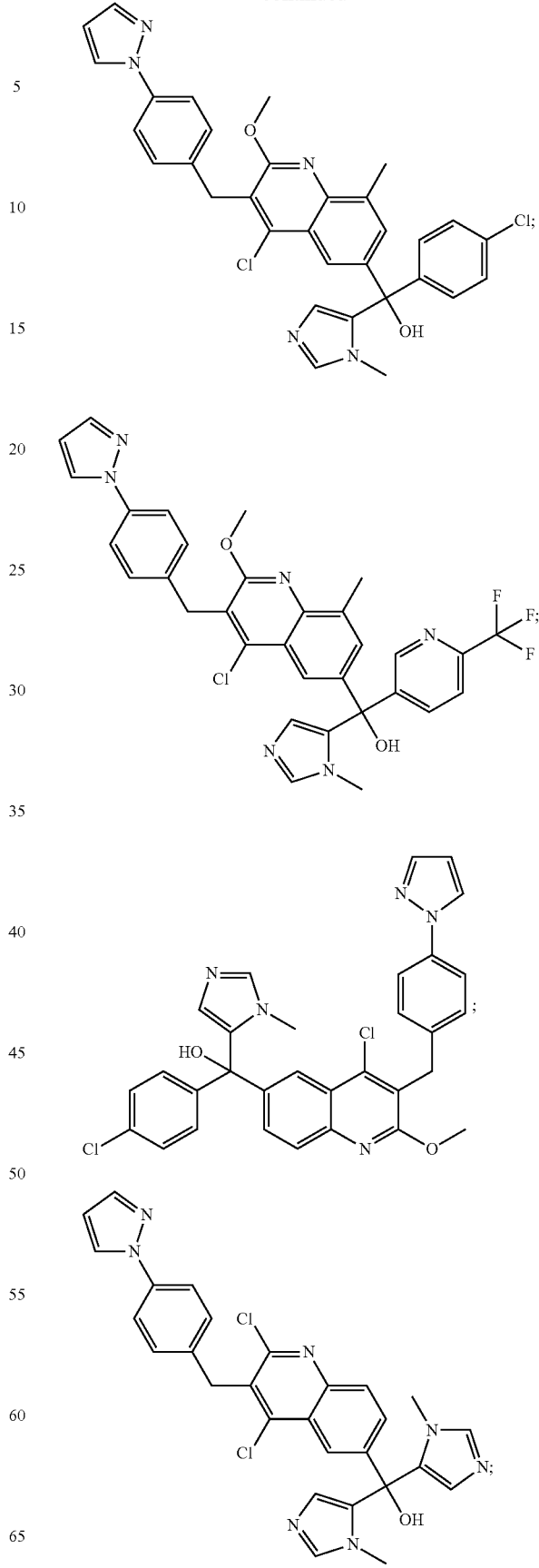

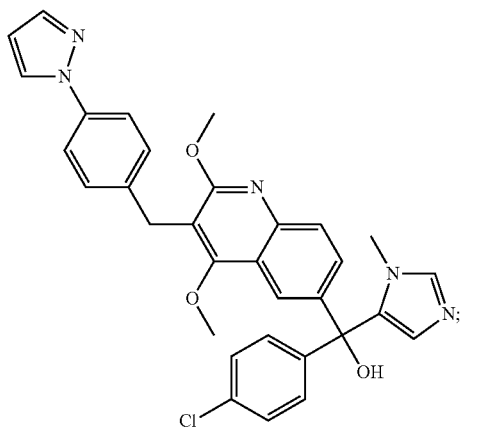
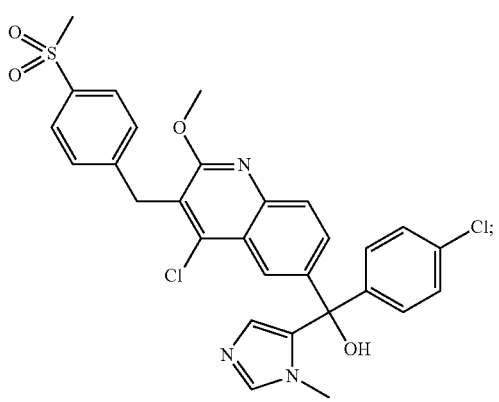
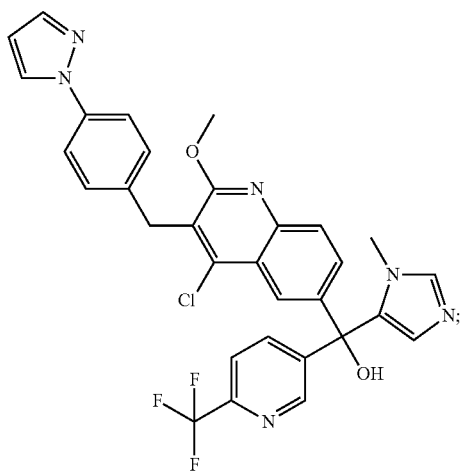
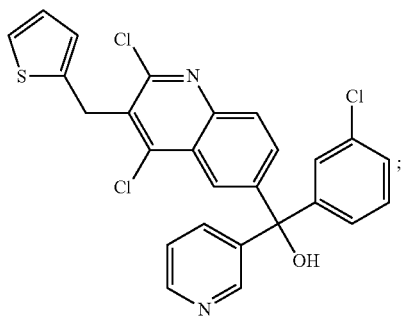
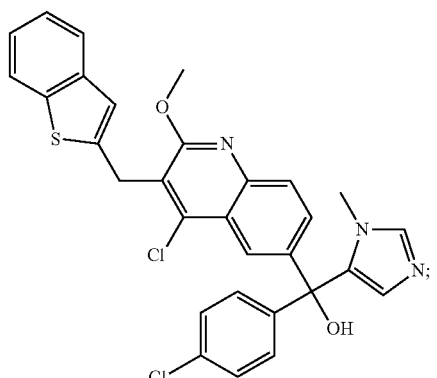
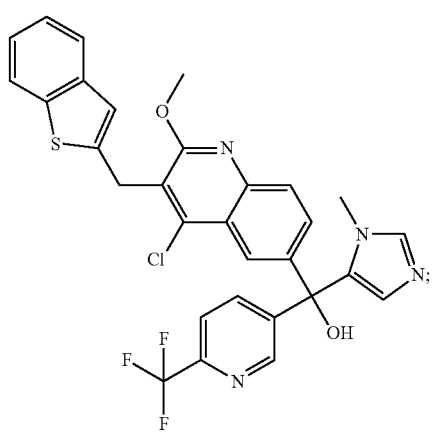
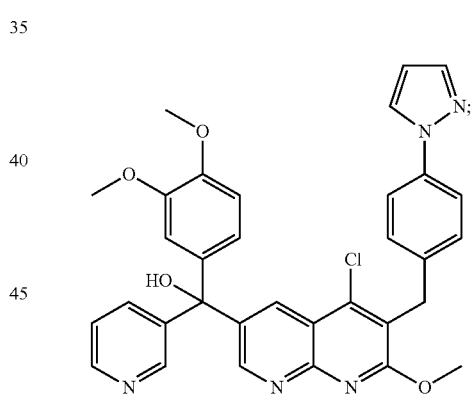
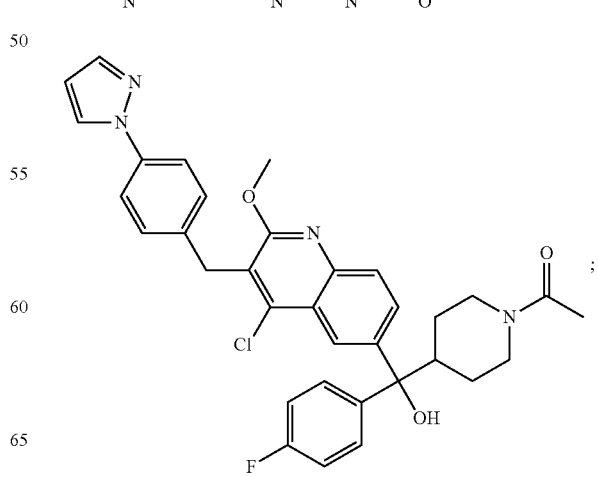

-continued
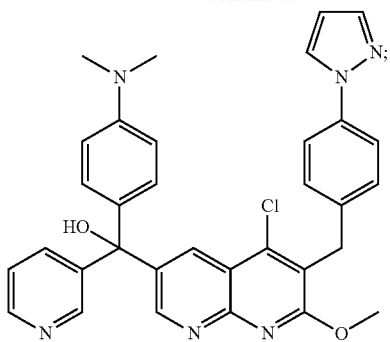
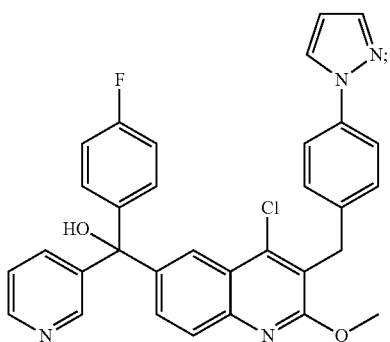
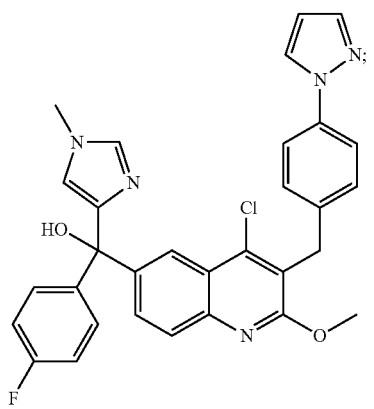
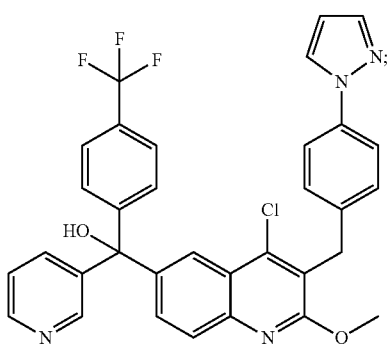
-continued
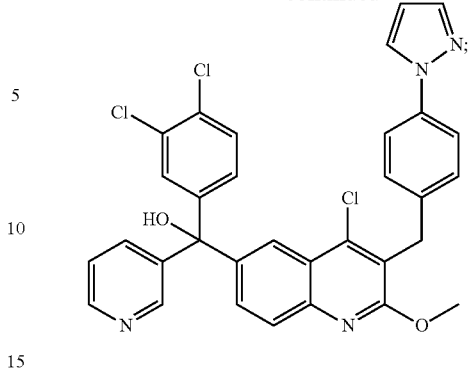
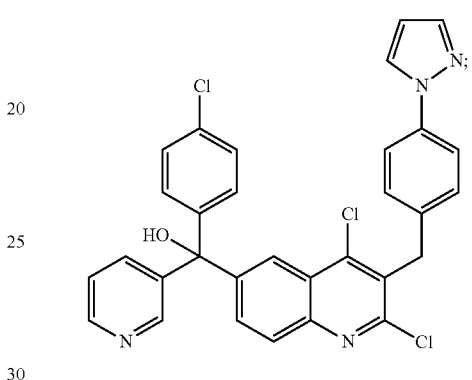
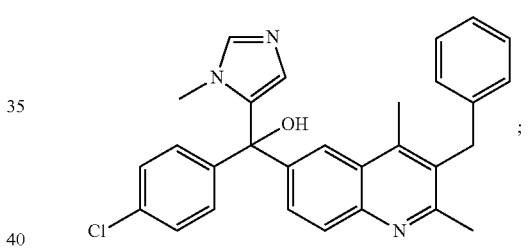
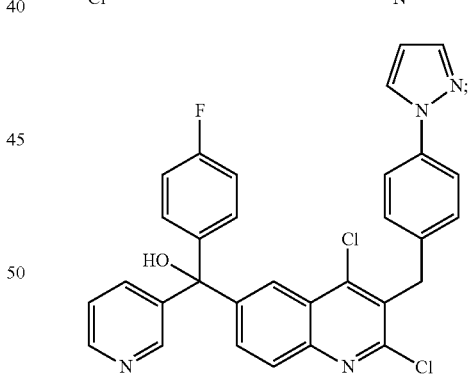
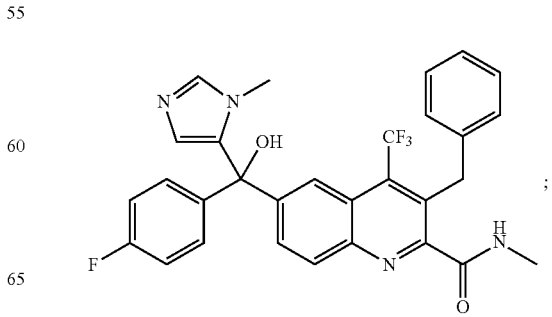

-continued
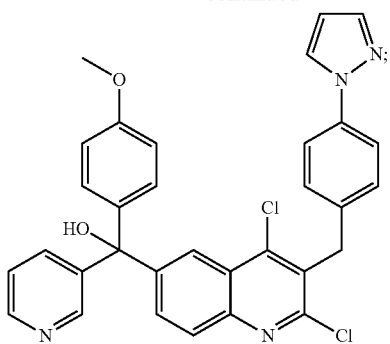
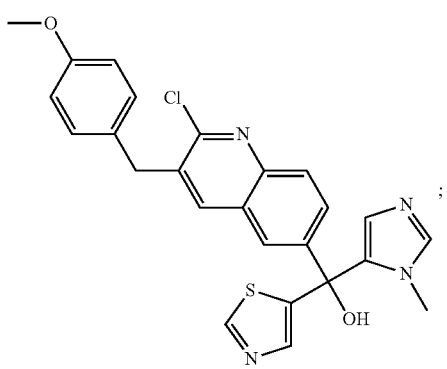
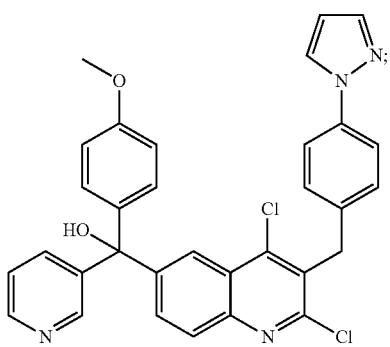
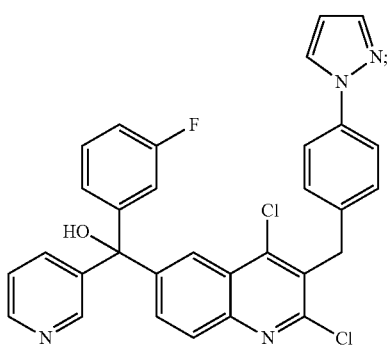
-continued
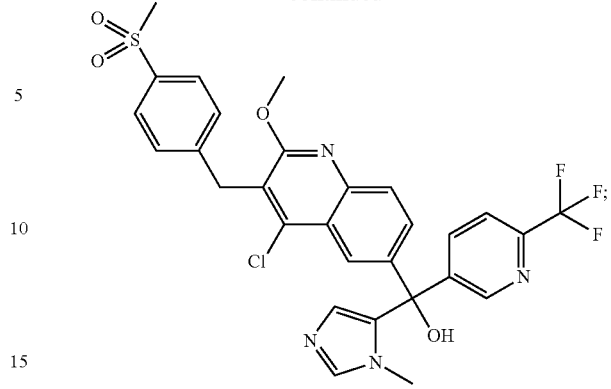
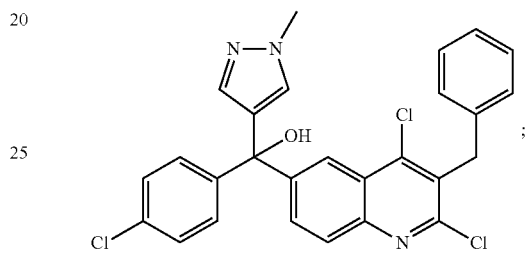
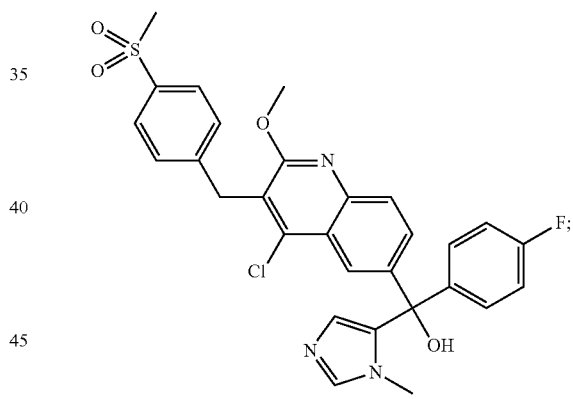
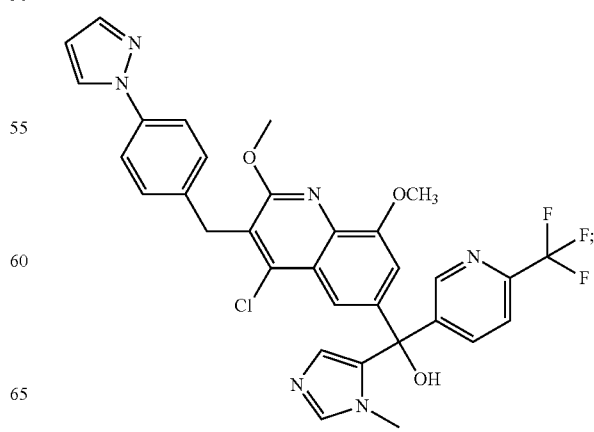

39
-continued
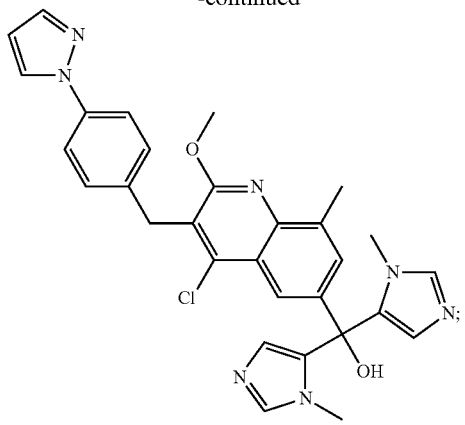
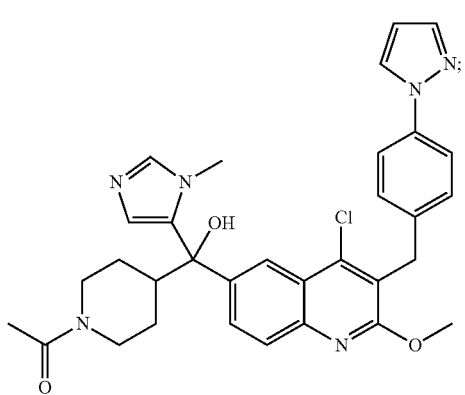
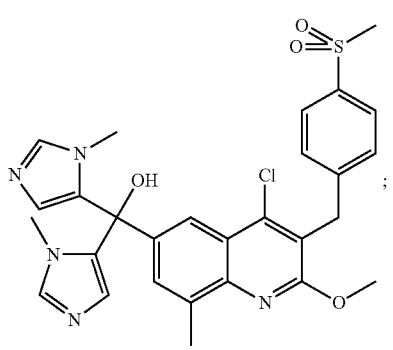
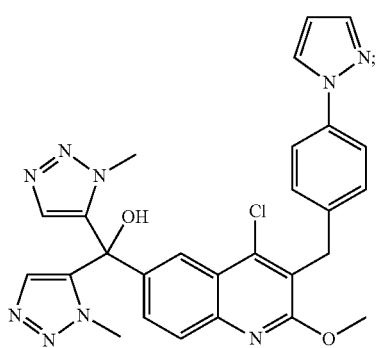
40
-continued
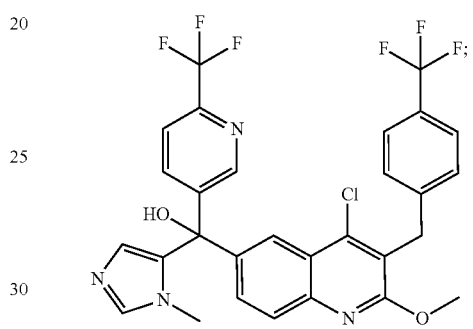
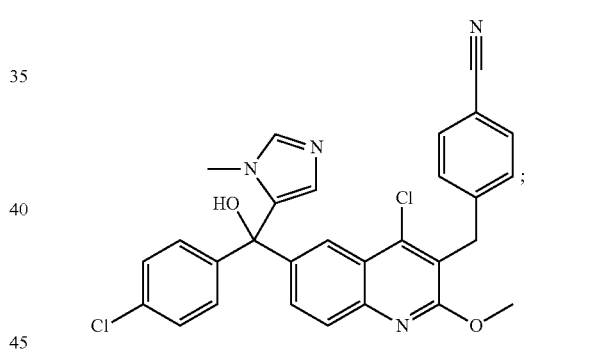
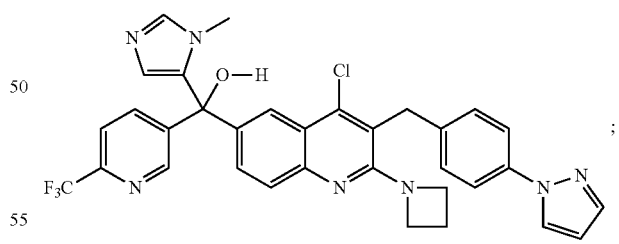
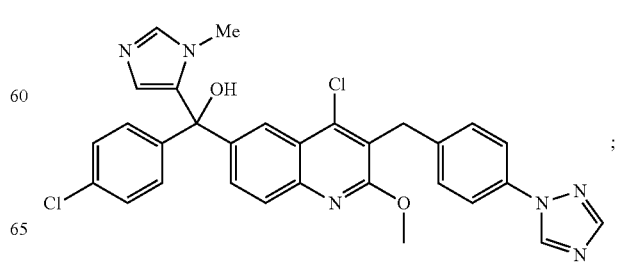

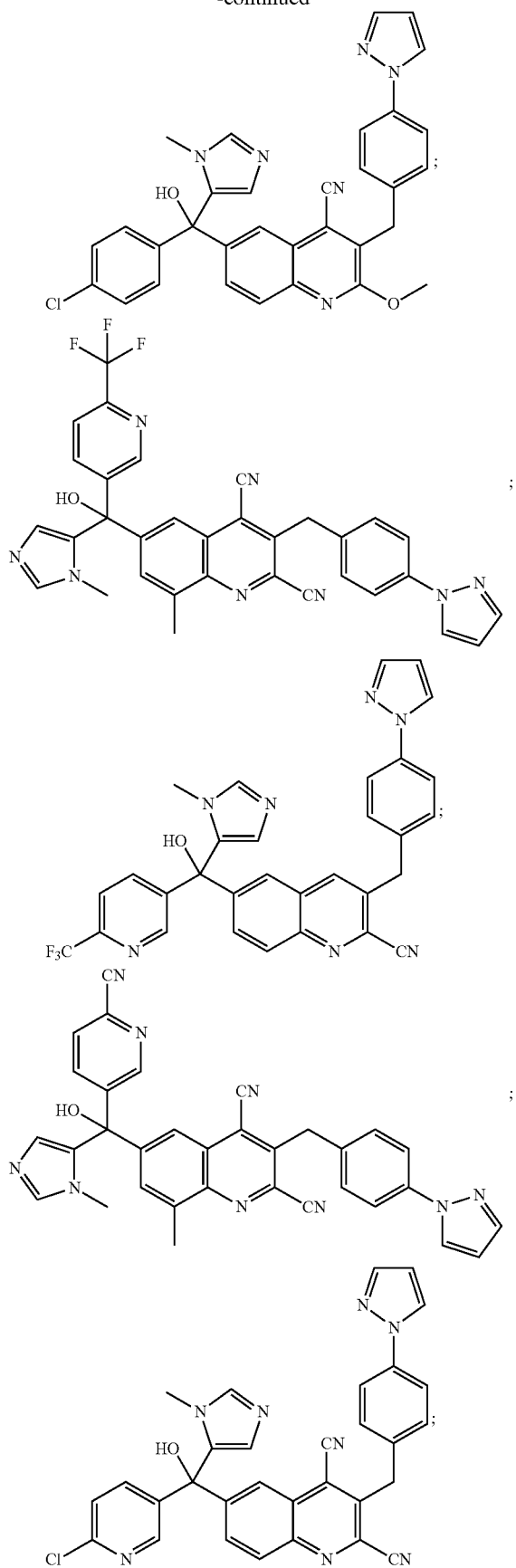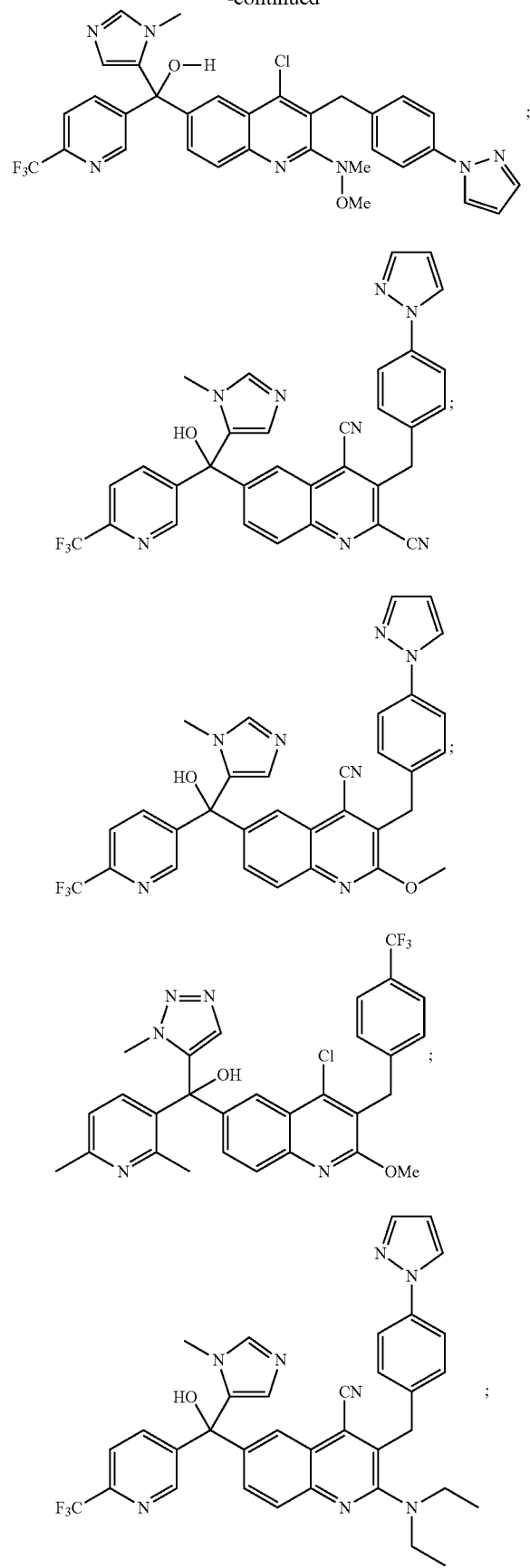

43
-continued
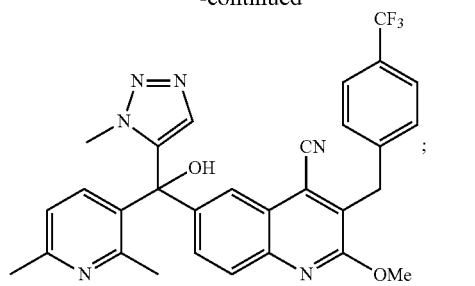
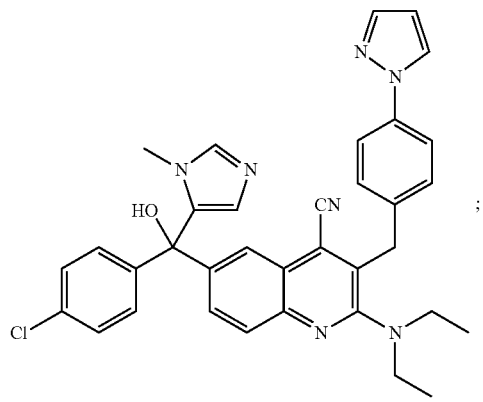
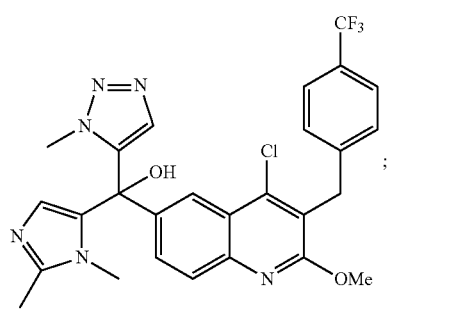
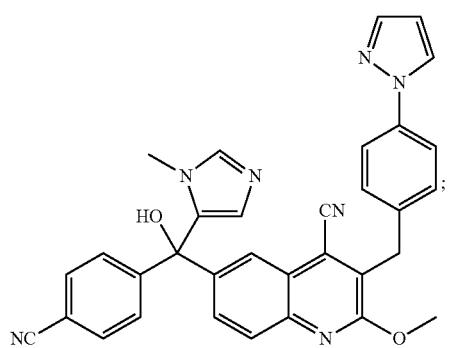
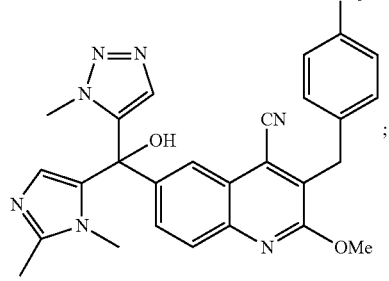
44
-continued
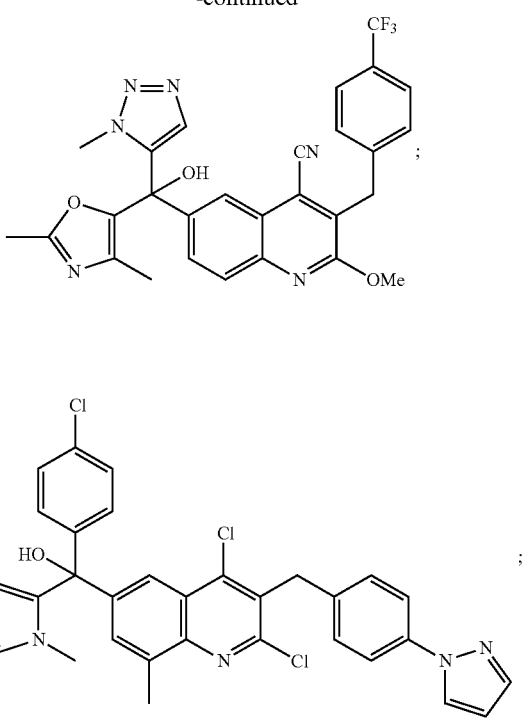
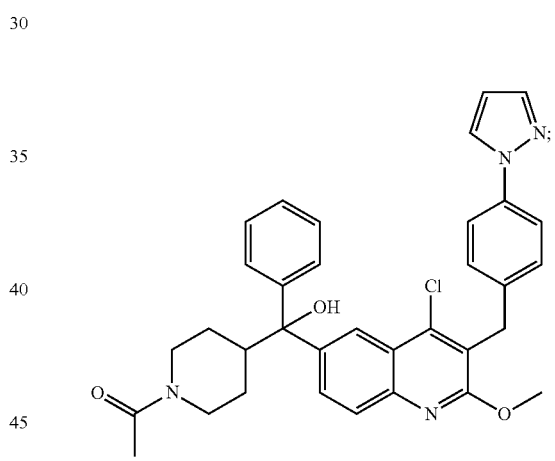
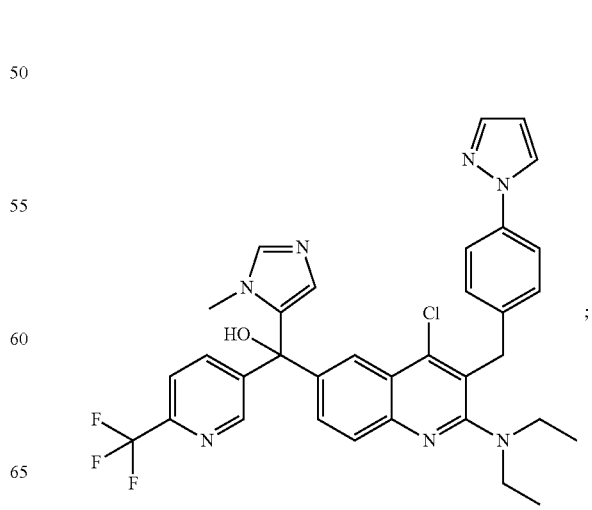

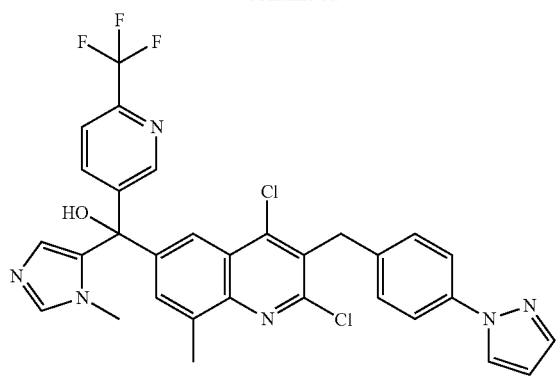
and pharmaceutically acceptable salts thereof.
Another embodiment of the invention is a compound selected from the group consisting of:
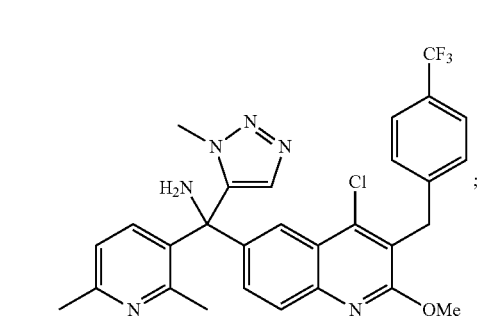
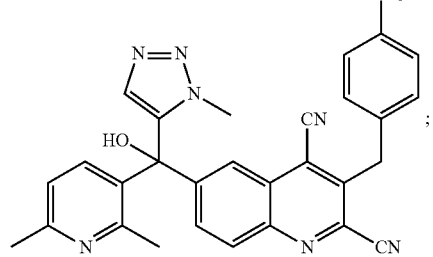
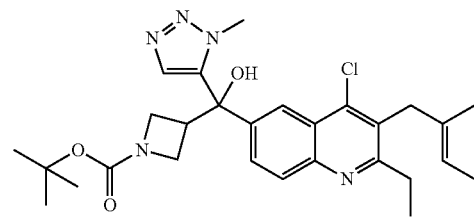
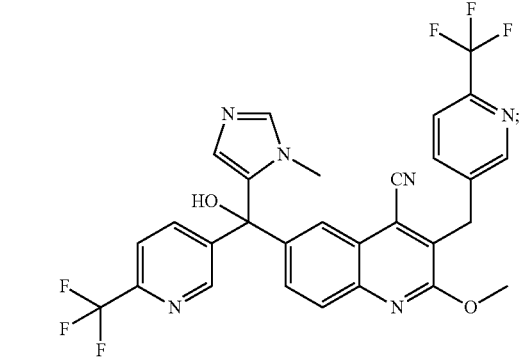
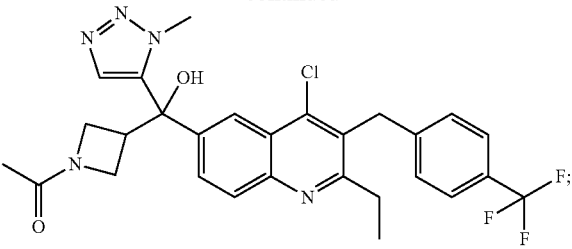
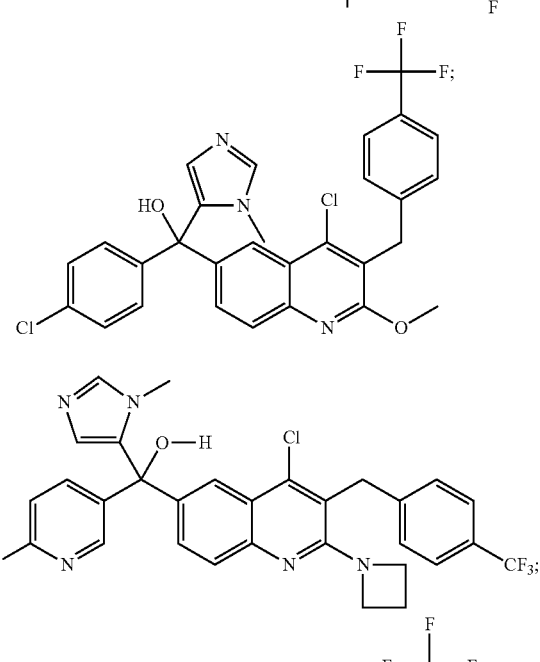
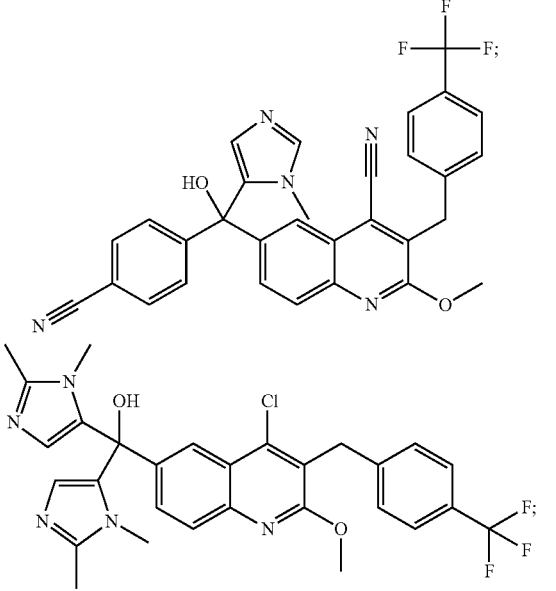

-continued

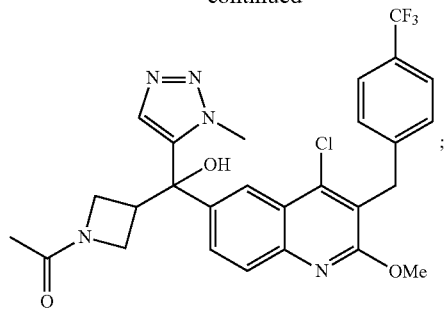

and pharmaceutically acceptable salts thereof.

Another embodiment of the invention is the combined sum of the preceeding two embodiments.

Another embodiment of the invention comprises a compound which is

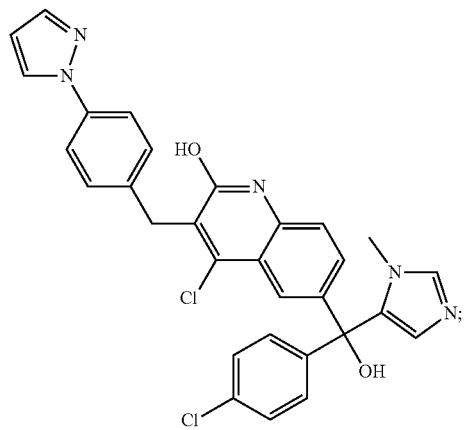 [SMILES: Cn1cncc1C(O)(c1ccc(Cl)cc1)c1ccc2nc(O)c(Cc3ccc(-n4cccn4)cc3)c(Cl)c2c1]

and pharmaceutically acceptable salts thereof.

Another embodiment of the invention is a compound selected from the group consisting of:

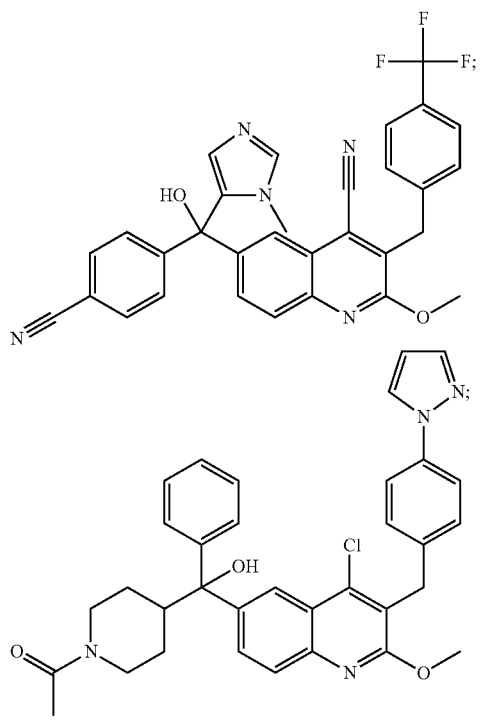

-continued

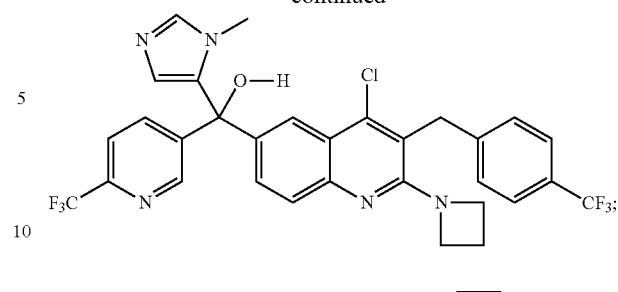

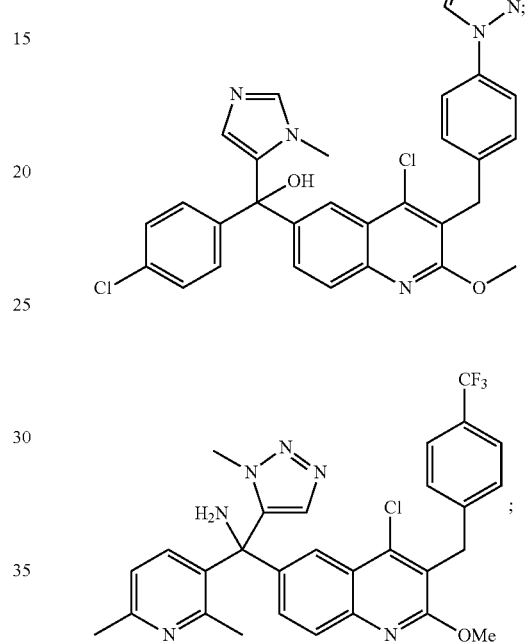

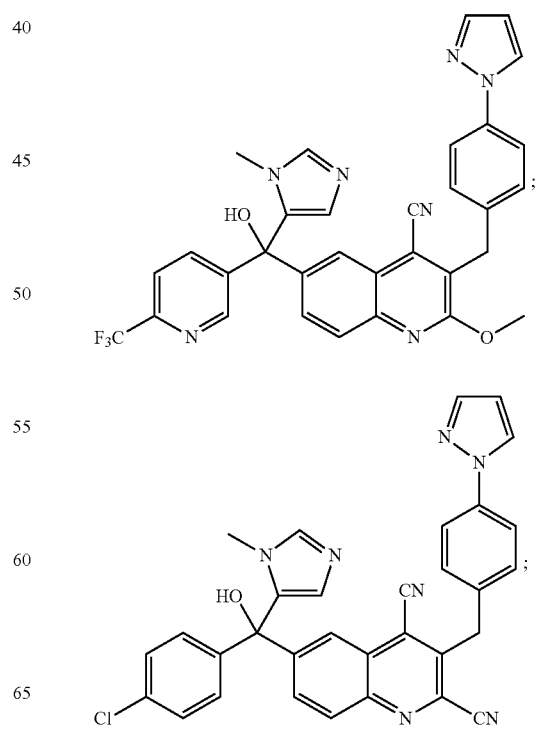

49
-continued
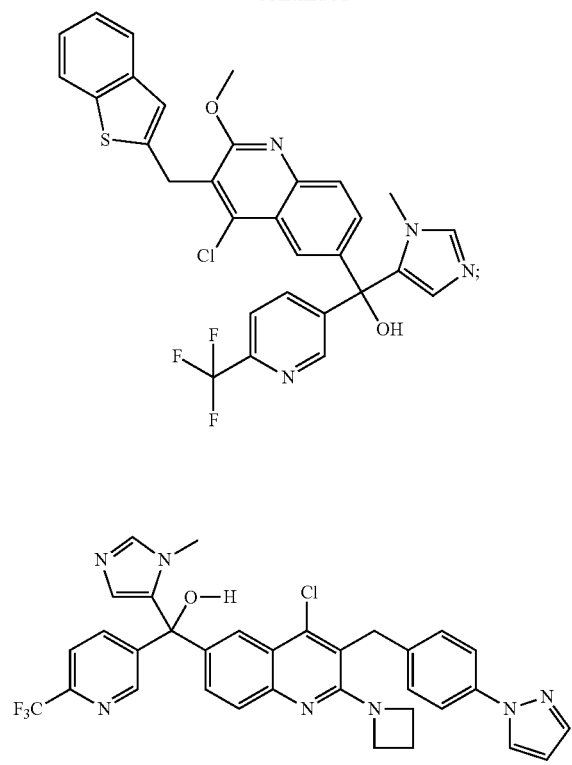
50
-continued
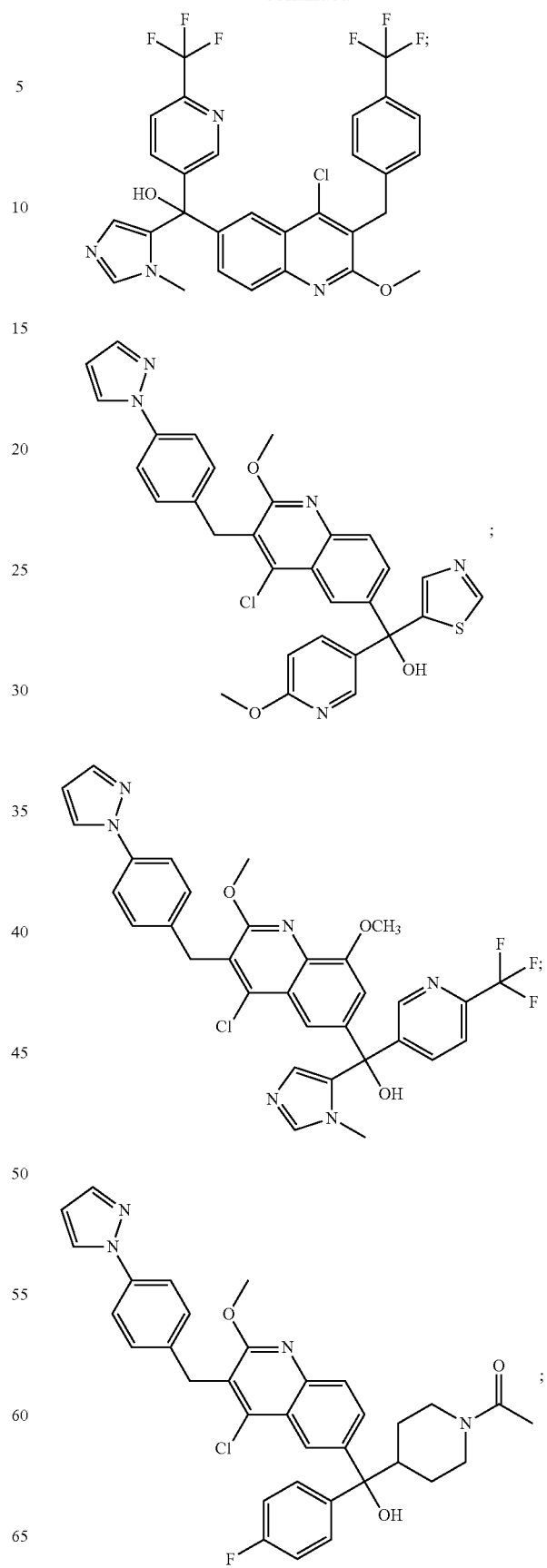

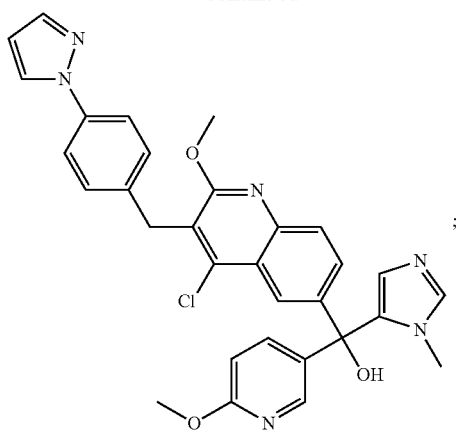
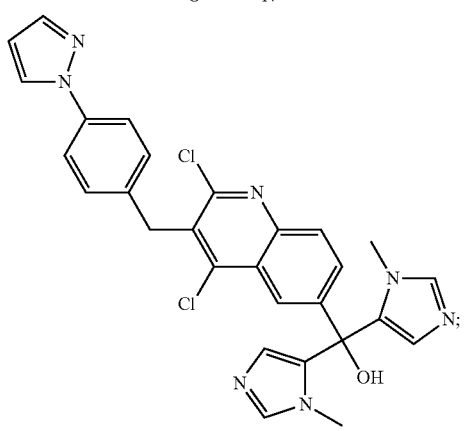
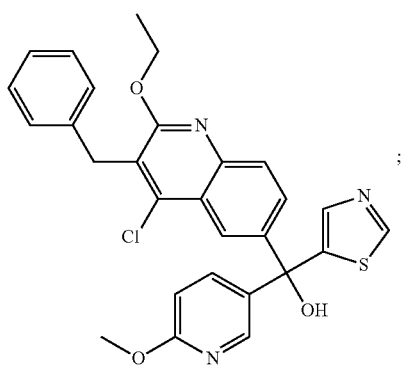
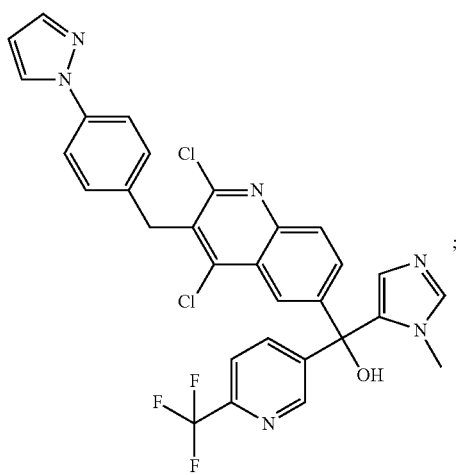
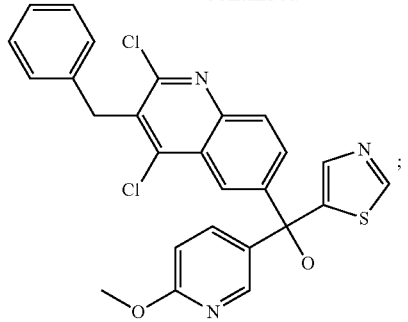
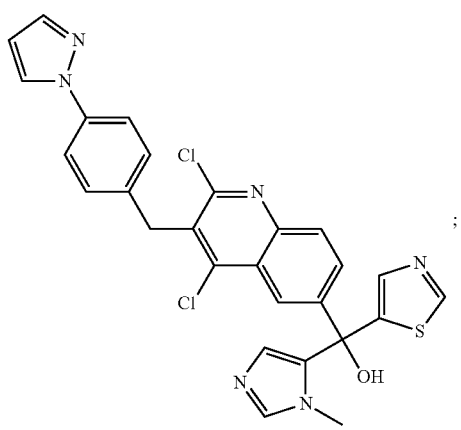
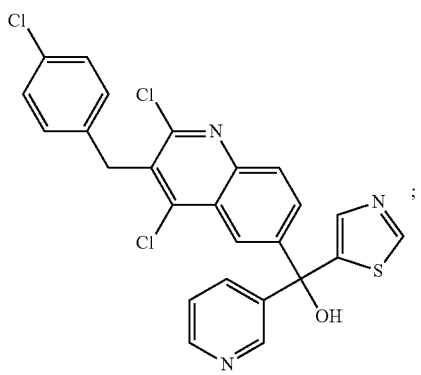
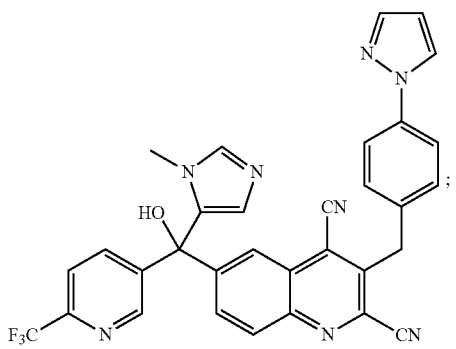

53
-continued
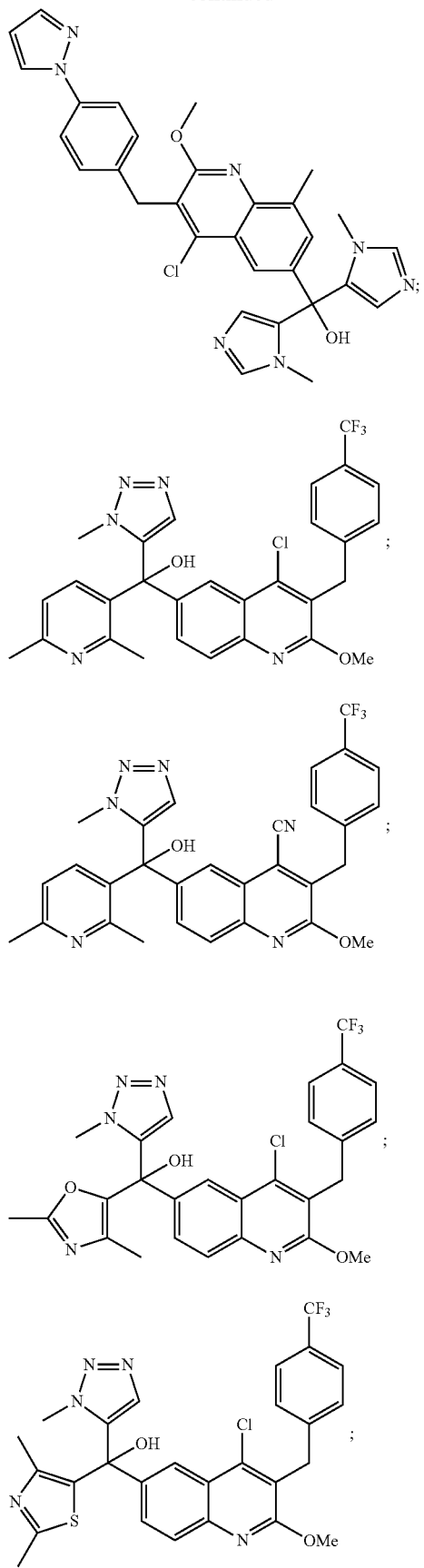
54
-continued
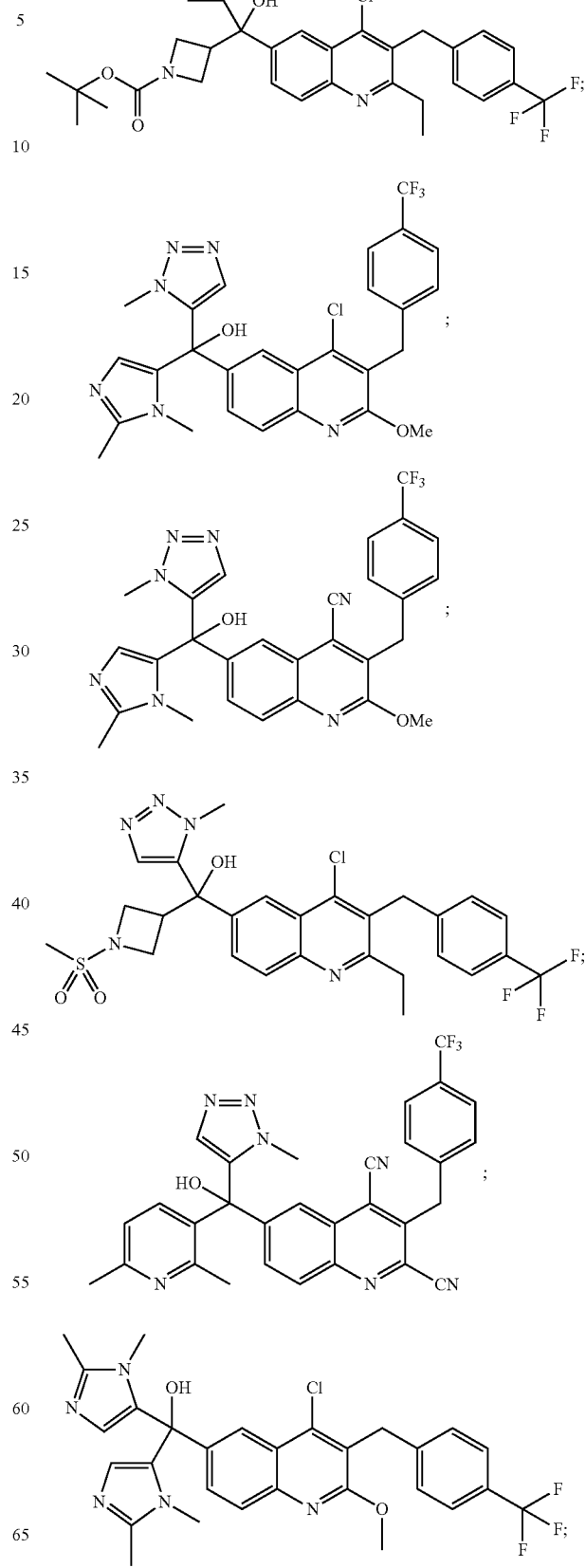

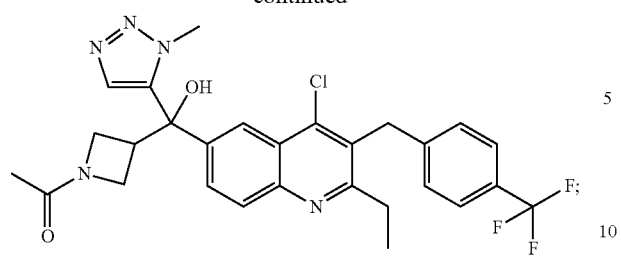
and pharmaceutically acceptable salts thereof.
Another embodiment of the invention is a compound selected from the group consisting of:
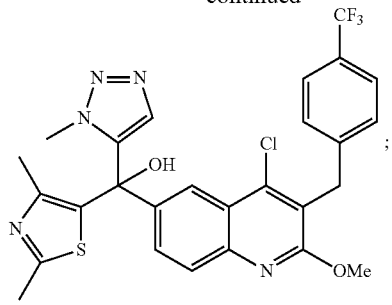
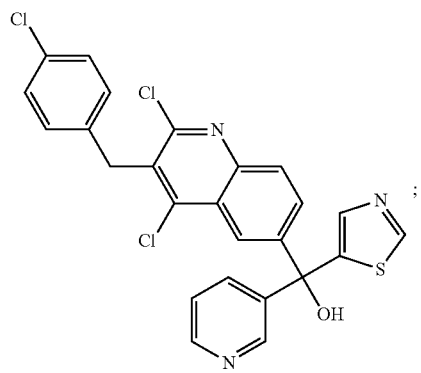
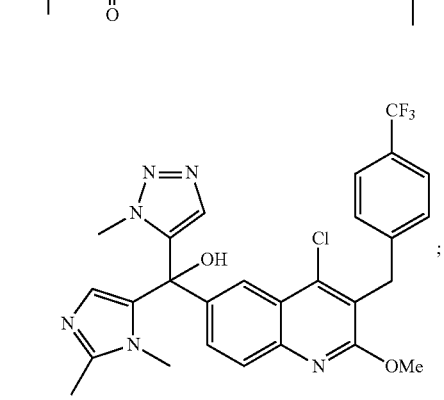
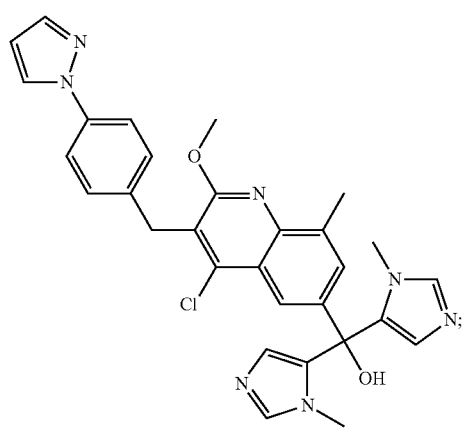
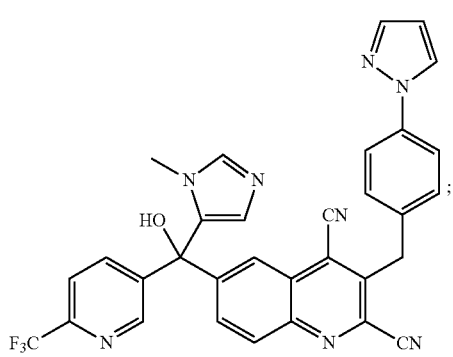
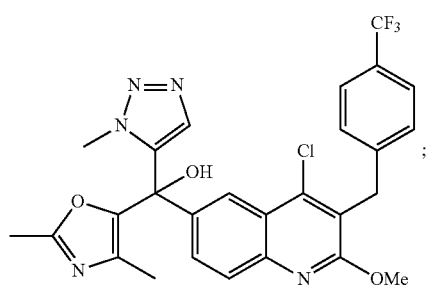
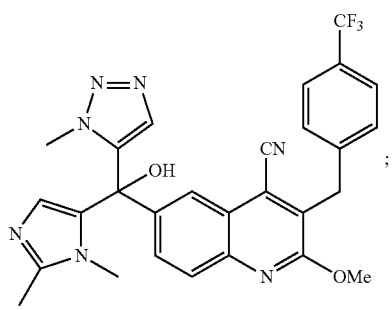

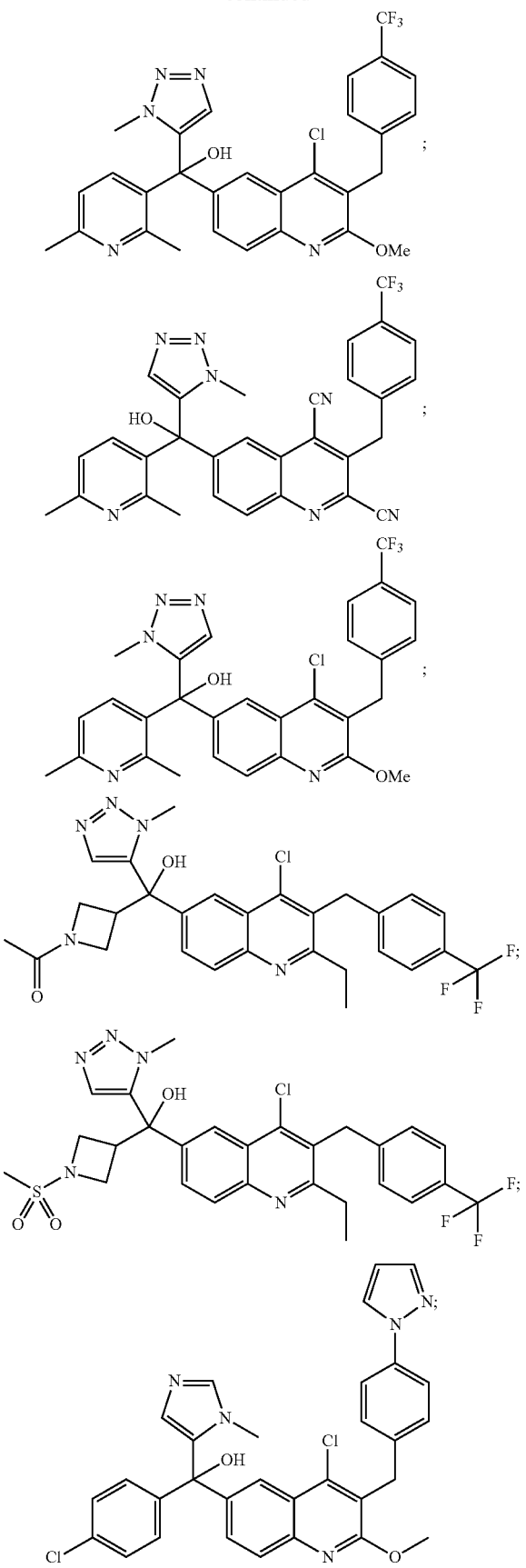

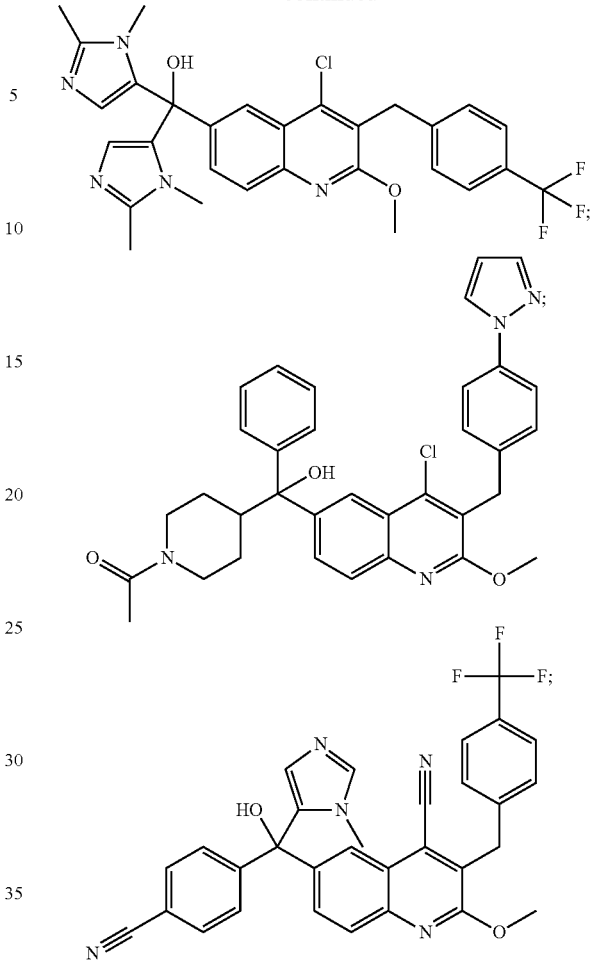

and pharmaceutically acceptable salts thereof.

In another embodiment of the invention:

$R^1$ is phenyl, pyridyl, 1-methyl-imidazol-5-yl, 1-methyl-1,2,3-triazol-5-yl, 2,4-dimethyl-oxazolyl, or thiazolyl, wherein said phenyl is optionally substituted with —CN, or Cl; wherein said pyridyl is optionally substituted with up to two $CH_3$ groups or one $CF_3$ group; wherein said 1-methyl-imidazol-5-yl is optionally substituted with an additional methyl group; and wherein said thiazolyl is optionally substituted with up to two $CH_3$ groups;

$R^2$ is N-acetyl piperidinyl, N-acetyl-azetidin-3-yl, N-methylsulfonyl-azetidin-3-yl, N-Boc-azetidin-3-yl, pyridyl, 1-methyl-1,2,3-triazol-5-yl, or 1-methyl-imidazol-5-yl, wherein said 1-methyl-imidazol-5-yl is optionally substituted with an additional methyl group;

$R^3$ is OH $R^4$ is H $R^5$ is Cl, —CN, or $OCH_3$;

$R^6$ is phenyl; wherein said phenyl is substituted with pyrazolyl, Cl, or $CF_3$;

$R^7$ is Cl, —CN, $CH_2CH_3$, or $OCH_3$;

$R^8$ is H, or $CH_3$;

$R^9$ is H;

and pharmaceutically acceptable salts thereof;

In another embodiment of the invention:

$R^1$ is phenyl, pyridyl, 1-methyl-imidazol-5-yl, 1-methyl-1,2,3-triazol-5-yl, 2,4-dimethyl-oxazolyl, or thiazolyl, wherein said phenyl is optionally substituted with —CN, or Cl; wherein said pyridyl is optionally substituted with up to two CH$_3$ groups or one CF$_3$ group; wherein said 1-methyl-imidazol-5-yl is optionally substituted with an additional methyl group; and wherein said thiazolyl is optionally substituted with up to two CH$_3$ groups;

R$^2$ is pyridyl, 1-methyl-1,2,3-triazol-5-yl, or 1-methyl-imidazol-5-yl, wherein said 1-methyl-imidazol-5-yl is optionally substituted with an additional methyl group;

R$^3$ is OH

R$^4$ is H

R$^5$ is Cl, —CN, or OCH$_3$;

R$^6$ is phenyl; wherein said phenyl is substituted with pyrazolyl, Cl, or CF$_3$;

R$^7$ is Cl, —CN, CH$_2$CH$_3$, or OCH$_3$;

R$^8$ is H, or CH$_3$;

R$^9$ is H;

and pharmaceutically acceptable salts thereof;

In another embodiment of the invention:

R$^1$ is phenyl, pyridyl, 1-methyl-imidazol-5-yl, 1-methyl-1,2,3-triazol-5-yl, 2,4-dimethyl-oxazolyl, or thiazolyl, wherein said phenyl is optionally substituted with —CN, or Cl; wherein said pyridyl is optionally substituted with up to two CH$_3$ groups or one CF$_3$ group; wherein said 1-methyl-imidazol-5-yl is optionally substituted with an additional methyl group; and wherein said thiazolyl is optionally substituted with up to two CH$_3$ groups;

R$^2$ is pyridyl, 1-methyl-1,2,3-triazol-5-yl, or 1-methyl-imidazol-5-yl, wherein said 1-methyl-imidazol-5-yl is optionally substituted with an additional methyl group;

R$^3$ is OH

R$^4$ is H

R$^5$ is Cl, —CN, or OCH$_3$;

R$^6$ is phenyl; wherein said phenyl is substituted with pyrazolyl, Cl, or CF$_3$;

R$^7$ is Cl, —CN, or CH$_2$CH$_3$;

R$^8$ is H, or CH$_3$;

R$^9$ is H;

and pharmaceutically acceptable salts thereof;

In another embodiment of the invention:

R$^1$ is phenyl, pyridyl, 1-methyl-imidazol-5-yl, 1-methyl-1,2,3-triazol-5-yl, 2,4-dimethyl-oxazolyl, or thiazolyl, wherein said phenyl is optionally substituted with —CN, or Cl; wherein said pyridyl is optionally substituted with up to two CH$_3$ groups or one CF$_3$ group; wherein said 1-methyl-imidazol-5-yl is optionally substituted with an additional methyl group; and wherein said thiazolyl is optionally substituted with up to two CH$_3$ groups;

R$^2$ is N-acetyl piperidinyl, N-acetyl-azetidin-3-yl, N-methylsulfonyl-azetidin-3-yl, or N-Boc-azetidin-3-yl;

R$^3$ is OH

R$^4$ is H

R$^5$ is Cl, —CN, or OCH$_3$;

R$^6$ is phenyl; wherein said phenyl is substituted with pyrazolyl, Cl, or CF$_3$;

R$^7$ is Cl, —CN, or CH$_2$CH$_3$;

R$^8$ is H, or CH$_3$;

R$^9$ is H;

and pharmaceutically acceptable salts thereof;

In another embodiment of the invention:

R$^1$ is phenyl, pyridyl, 1-methyl-imidazol-5-yl, 1-methyl-1,2,3-triazol-5-yl, 2,4-dimethyl-oxazolyl, or thiazolyl, wherein said phenyl is optionally substituted with —CN, or Cl; wherein said pyridyl is optionally substituted with up to two CH$_3$ groups or one CF$_3$ group; wherein said 1-methyl-imidazol-5-yl is optionally substituted with an additional methyl group; and wherein said thiazolyl is optionally substituted with up to two CH$_3$ groups;

R$^2$ is N-acetyl piperidinyl, N-acetyl-azetidin-3-yl, N-methylsulfonyl-azetidin-3-yl, or N-Boc-azetidin-3-yl;

R$^3$ is OH

R$^4$ is H

R$^5$ is Cl, —CN, or OCH$_3$;

R$^6$ is phenyl; wherein said phenyl is substituted with pyrazolyl, Cl, or CF$_3$;

R$^7$ is Cl, —CN, CH$_2$CH$_3$, or OCH$_3$;

R$^8$ is H, or CH$_3$;

R$^9$ is H;

and pharmaceutically acceptable salts thereof;

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is Crohn's disease comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel diseases, wherein said inflammatory bowel disease is ulcerative colitis comprising administering to a subject in need thereof an effective amount of a compound of Formula I or a form, composition or medicament thereof.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula (I), shall comprise all isotopes and isotopic mixtures of said element, either naturally occurring or synthetically produced, either with natural abundance or in an isotopically enriched form. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of 3H, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{3}H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.

Å angstrom
Ac acetyl
Ac$_2$O acetic anhydride
Boc tert-butyloxycarbonyl
BHT butylated hydroxytoluene
br broad
Bu butyl
n-BuLi n-butyl lithium d doublet
dba dibenzylideneacetone
DCM dichloromethane
Dess-Martin periodinane 1,1,1-tris(acetyloxy)-1,1-dihydro-1,2-benziodoxol-3-(1H)-one
DMA dimethylacetamide
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
EtMgBr ethylmagnesium bromide
ESI electrospray ionization
Et ethyl
Et$_2$O diethyl ether
EtOAc ethyl acetate
EtOH ethyl alcohol
Et$_3$SiCl chlorotriethylsilane
HATU O-(7-azabenzotriazol-1-yl)-N,N,N',N'-tetramethyluronium hexafluorophosphate
HPLC high pressure liquid chromatography
Hz hertz
iPr, i-Pr, iPr, or i-Pr isopropyl
i-PrOH isopropyl alcohol
KHMDS potassium hexamethyldisilazane
LCMS liquid chromatography-mass spectrometry
LDA lithium diisopropyl amine
m multiplet
M molar (moles/liter)
Me methyl
Meldrum's acid 2,2-dimethyl-1,3-dioxane-4,6-dione
MeOH methanol
MHz megahertz
min minutes
mL mililiters
MTBE methyl tertiary butyl ether
nBu, n-Bu, nBu, or n-Bu normal butyl
NaOiPr sodium isopropoxide
nm nanometers
NMR nuclear magnetic resonance
PdCl$_2$(dppf) [1,1'-bis(diphenylphosphino)ferrocene]dichloropalladium(II)
Pd$_2$(dba)$_3$ tris(dibenzylideneacetone)dipalladium(0)
Ph phenyl
ppm parts per million
Pr propyl
q quartet
RP-HPLC reverse phase high pressure liquid chromatography
s singlet
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1 describes the preparation of 6-bromo or 6-iodoquinolines of formula VI by various methods (path 1 to 5). As illustrated in path 1, the 2-substituted malonic acids IV (Q=H) can be prepared by addition of aromatic aldehydes to Meldrum's acid or dialkyl malonates as described by D. B. Ramachary et al. (*Tetrahedron Letters* 47 (2006) 651-656) followed by aqueous base hydrolysis under either microwave conditions or by heating at temperatures between 100 and 115° C., or treatment with an acid such as trifluoracetic acid in water at temperatures ranging from room temperature to 100° C. Haloanilines V (Z=Br or I) can be condensed with malonic acids IV (Q=H) in phosphorus oxychloride at temperatures between 80-120° C. affording 6-haloquinolines VI wherein R$^5$ and R$^7$ are Cl. Displacement of the 2-Cl of 2,4-dichloroquinoline VI with sodium alkoxides can be accomplished in an alcoholic solvent such as methanol, ethanol or isopropanol or at elevated temperatures in a non-polar solvent such as toluene (Alan Osborne et. al. *J. Chem. Soc. Perkin Trans.* 1 (1993) 181-184 and *J. Chem. Research* (S), 2002, 4) to provide substituted quinolines VI wherein R$^5$ is Cl and R$^7$ is Oalkyl. Alternatively, as shown in Path 2, the haloanilines V can be treated in one pot directly with Meldrum's acid then subsequently heated in the presence of Eaton's reagent as described in by W. T. Gao, et. al. (*Synthetic Communications* 40 (2010) 732) to form the 4-hydroxy-2(1H)-quinolinone XLI. Once treated with phosphorus oxychloride as previously described, the resulting 2,4-dichloroquinolines XLII can be deprotonated with a strong base such as lithium diisopropylamide and then added to substituted benzyl bromides to afford the intermediate quinolines VI (wherein R$^5$ and R$^7$ are chloro). In path 3, methyl 2-amino-5-halobenzoates VII can undergo acylation with acid chlorides VIII in the presence of a base such as triethylamine to form an amide intermediate, which can be further treated with a base, such as sodium ethoxide or potassium bis(trimethylsilyl)amide, affording 6-halo-4-hydroxyquinolin-2(1H)-ones IX. Conversion of hydroxyquinolin-2(1H)-ones IX to 2,4-dichloroquinolines VI can be carried out in phosphorus oxychloride at elevated temperatures. Displacement of the Cl of 2,4-dichloroquinolines VI with disubstituted amines, such as NHMe$_2$, NHEt$_2$, or NHMeEt, can be done in a hot polar solvent, such as MeOH, EtOH, or DMF to provide 2-N(alkyl)$_2$quinolines VI wherein R$^7$ is N(alkyl)$_2$. In path 4, amides XI can be generated from anilines V and acids X in the presence of an appropriate coupling agent such as EDCI or HATU and a base such as Et$_3$N. In-situ formylation under Vilsmeier-Haack conditions (POCl$_3$/DMF) followed by heating to promote ring cyclization as described in WO2007014940 can provide 2-chloroquinolines VI wherein R$^5$ is H and R$^7$ is Cl.

Scheme 1

PATH 1

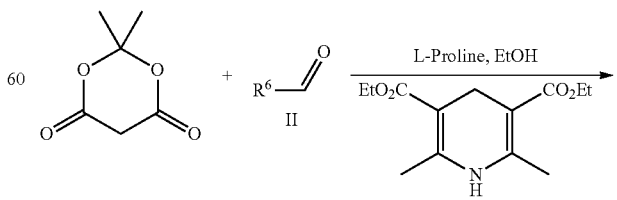

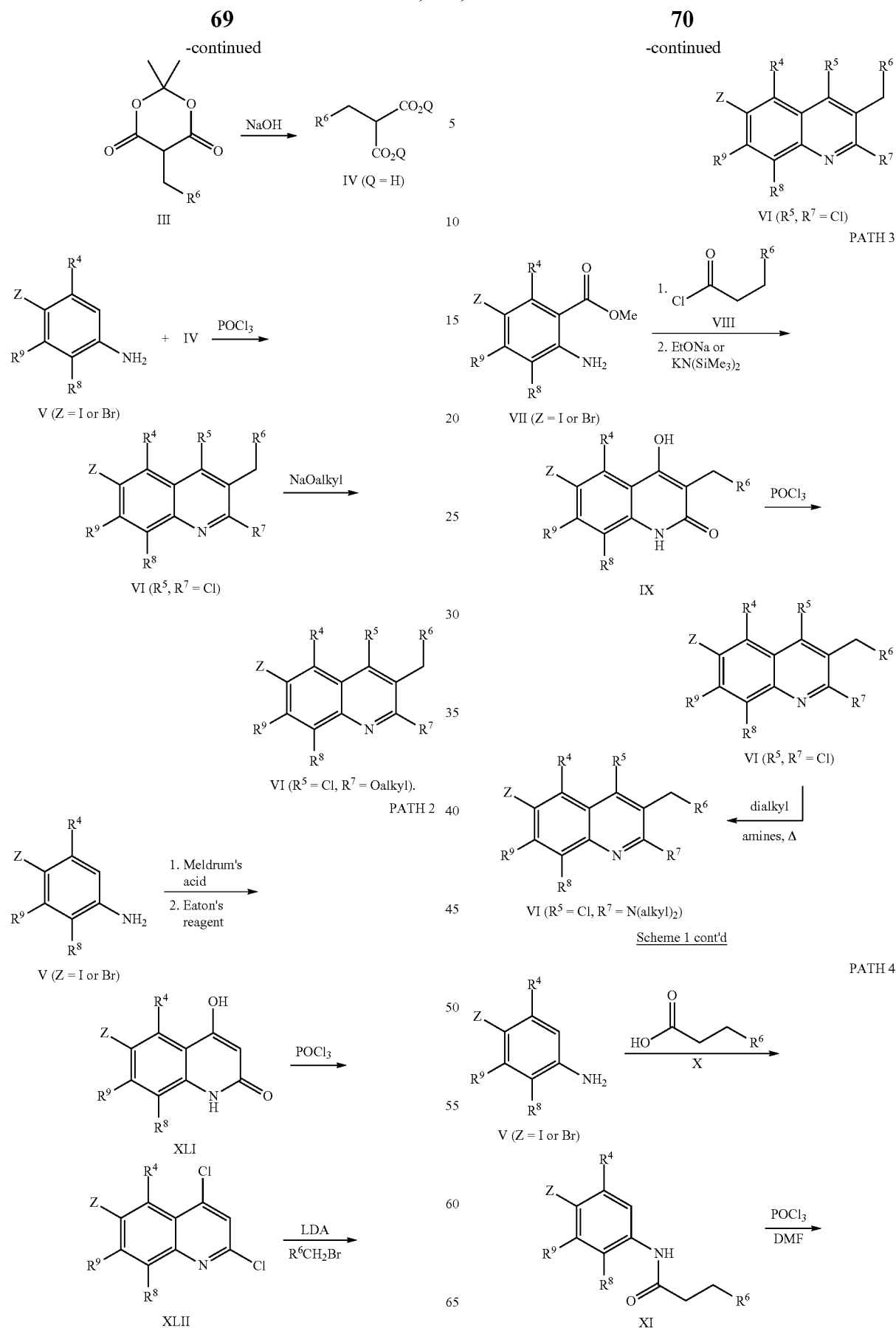

cyclization at elevated temperature affords 4-hydroxy quinolines VI, wherein $R^5$ is OH and $R^7$ is alkyl. The hydroxyl group could then be converted to a chloro group upon heating in acetonitrile with phosphorus oxychloride to provide 6-bromo or 6-iodoquinolines VI wherein $R^5$ is Cl and $R^7$ is alkyl.

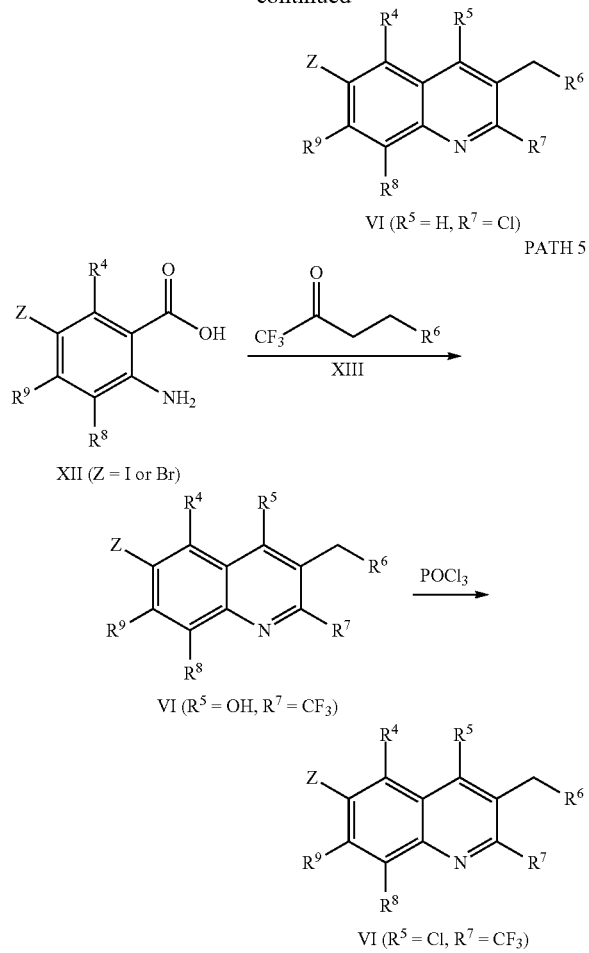

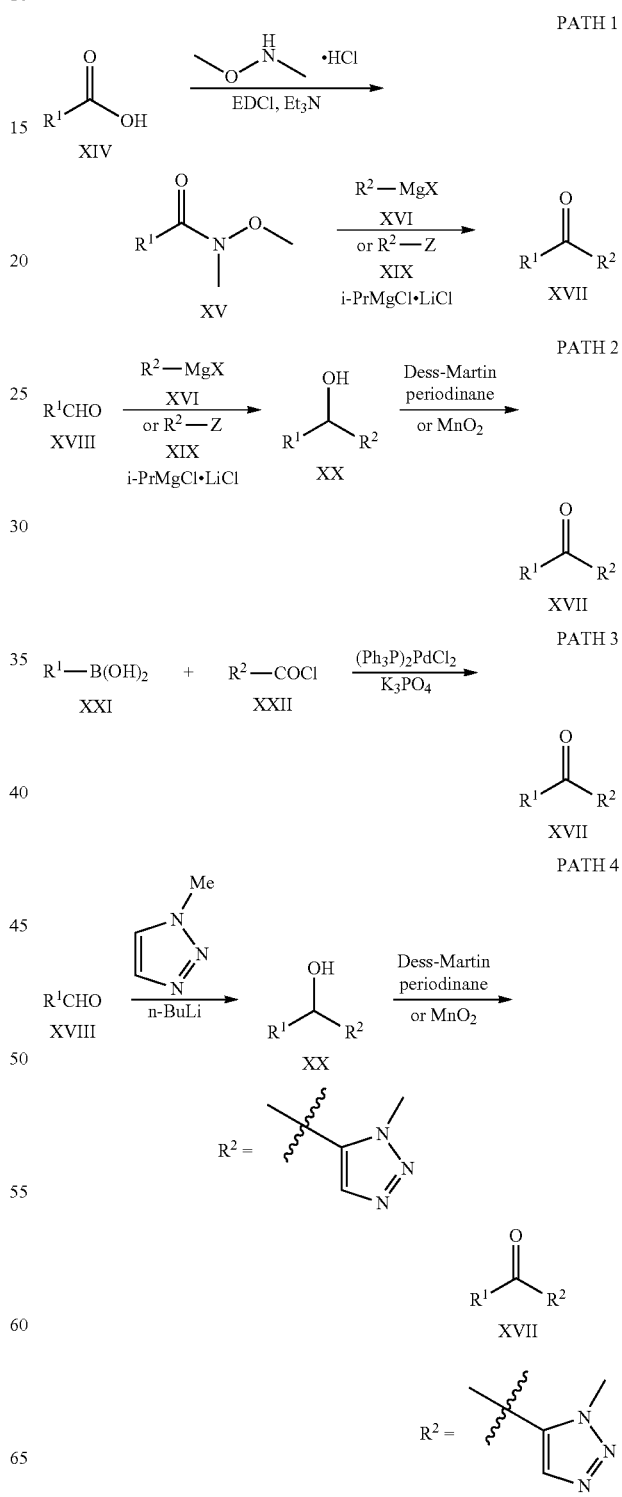

Compounds of formula VI wherein $R^7$ is trifluoromethyl, can be prepared starting from the 2-carboxyaniline XII as described in Path 5. One pot addition of 1,1,1-trifluoro-4-arylbutan-2-one XIII to 2-aminobenzoic acids XII and cyclization with Eaton's reagent at elevated temperatures yields 4-hydroxy-2-trifluoromethylquinolines VI, wherein $R^5$ is OH and $R^7$ is $CF_3$. The hydroxyl group could then be converted to chloro upon heating in phosphorus oxychloride to provide 6-bromo or 6-iodoquinolines VI wherein $R^5$ is Cl and $R^7$ is $CF_3$.

As shown in Path 6, compounds of formula VI can also be prepared from 4-hydroxy-2(1H)-quinolinones XLI by condensation with substituted aldehydes of the formula $R^6$CHO in the presence of a Hantzsch ester, such as diethyl 2,6-dimethyl-1,4-dihydropyridine-3,5-dicarboxylate, in solvents like ethanol and pyridine to afford 2,4-dihydroxyquinolines IX. Further treatment with phosphorus oxychloride as previously described, can provide quinolines of formula VI (wherein $R^5$ and $R^7$ are chloro).

Compounds of formula VI, wherein $R^7$ is alkyl, can be prepared as illustrated in Path 7. Intermediates of formula XLIV can be prepared by deprotonation of β-keto esters, such as ethyl 3-oxobutanoate or ethyl 3-oxopentanoate, with a base like sodium hydride followed by alkylation with substituted alkyl halides such as $R^6CH_2Br$ or $R^6CH_2I$. Condensation with 4-haloanilines (V) in the presence of an acid, such as para-toluenesulfonic acid (PTSA), in toluene as solvent with concomitant removal of water followed by intramolecular

PATH 5

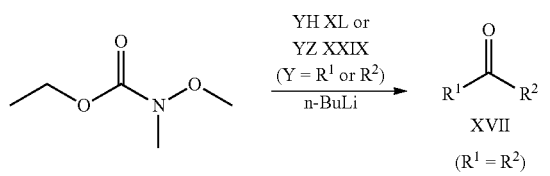

Scheme 2 outlines synthetic routes (path 1 to 5) to aryl ketones of formula XVII. In path 1, Weinreb amides XV can be prepared from carboxylic acids XIV and N,O-dimethylhydroxylamine hydrochloride in the presence of a base such as triethylamine or Hunig's base and a coupling reagent such as EDCI. The amides XV can be further treated with Grignard reagents such as $R^2MgX$ (X is Br or Cl) XVI that can be obtained commercially or preformed by treatment of $R^2Z$ XIX (Z=Br or I) with organometallic reagents such as i-PrMgCl or EtMgCl in THF or dichloromethane to afford the ketones XVII, wherein $R^1$ and $R^2$ are as defined above. As shown in path 2, aldehydes XVIII can also be treated with Grignard reagents, as described in path 1, to afford the intermediate alcohols XX. Subsequent oxidation with Dess-Martin periodinane or $MnO_2$ in a suitable solvent such as 1,4-dioxane or tetrahydrofuran at elevated temperatures can provide ketones XVII. Path 3, which employs palladium catalyzed cross-coupling of arylboronic acids XXI with acid chlorides XXII using $K_3PO_4$ as a base and $(Ph_3P)_2PdCl_2$ as a catalyst in a high boiling non-polar solvent such as toluene, can also be used to generate ketones XVII. In path 4, aryl ketones XVII, wherein $R^2$ is triazolyl, can be prepared by treatment of 1-methyl-1H-1,2,3-triazole, made according to PCT Int. Appl. 2008098104, with n-butyllithium followed by reaction with aldehydes XVIII to yield alcohols XX, which can undergo oxidation with Dess-Martin periodinane or $MnO_2$. Path 5 exemplifies the preparation of symmetrical ketones XVII, wherein $R^1$ and $R^2$ are the same. As illustrated, an aryl or heteroaryl group containing an acidic proton XL (Y=$R^1$ or $R^2$) can be deprotonated in the presence of a strong base such as n-butyllithium once solubilized in a preferred solvent such as tetrahydrofuran at temperatures between 0 and −78° C. then added in excess to ethyl methoxy(methyl) carbamate to provide aryl ketones XVII wherein $R^1$ and $R^2$ are the same. Aryl or heteroaryl bromide XXIX can also be lithiated through a lithium/halogen exchange with n-butyllithium before adding in excess to ethyl methoxy(methyl) carbamate as previously described to provide symmetrical ketones XVII.

Scheme 3

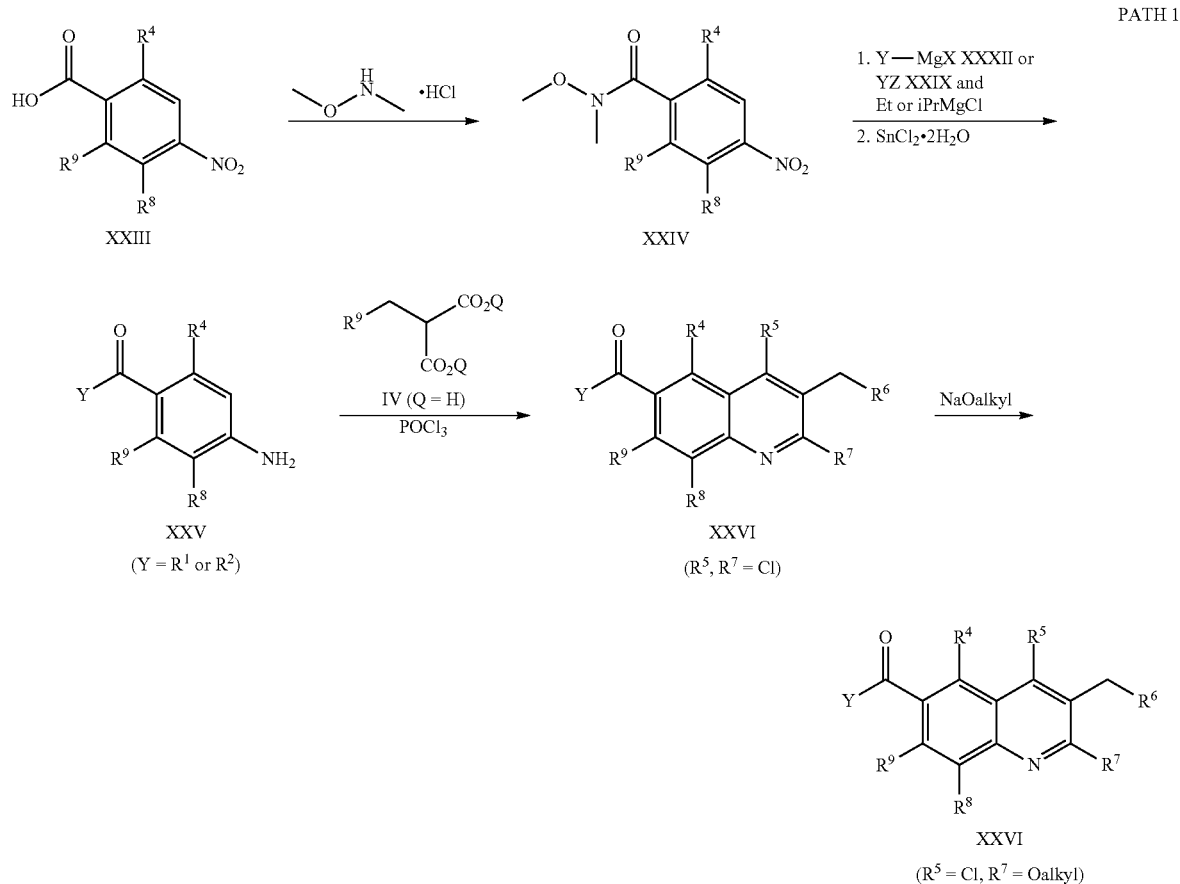

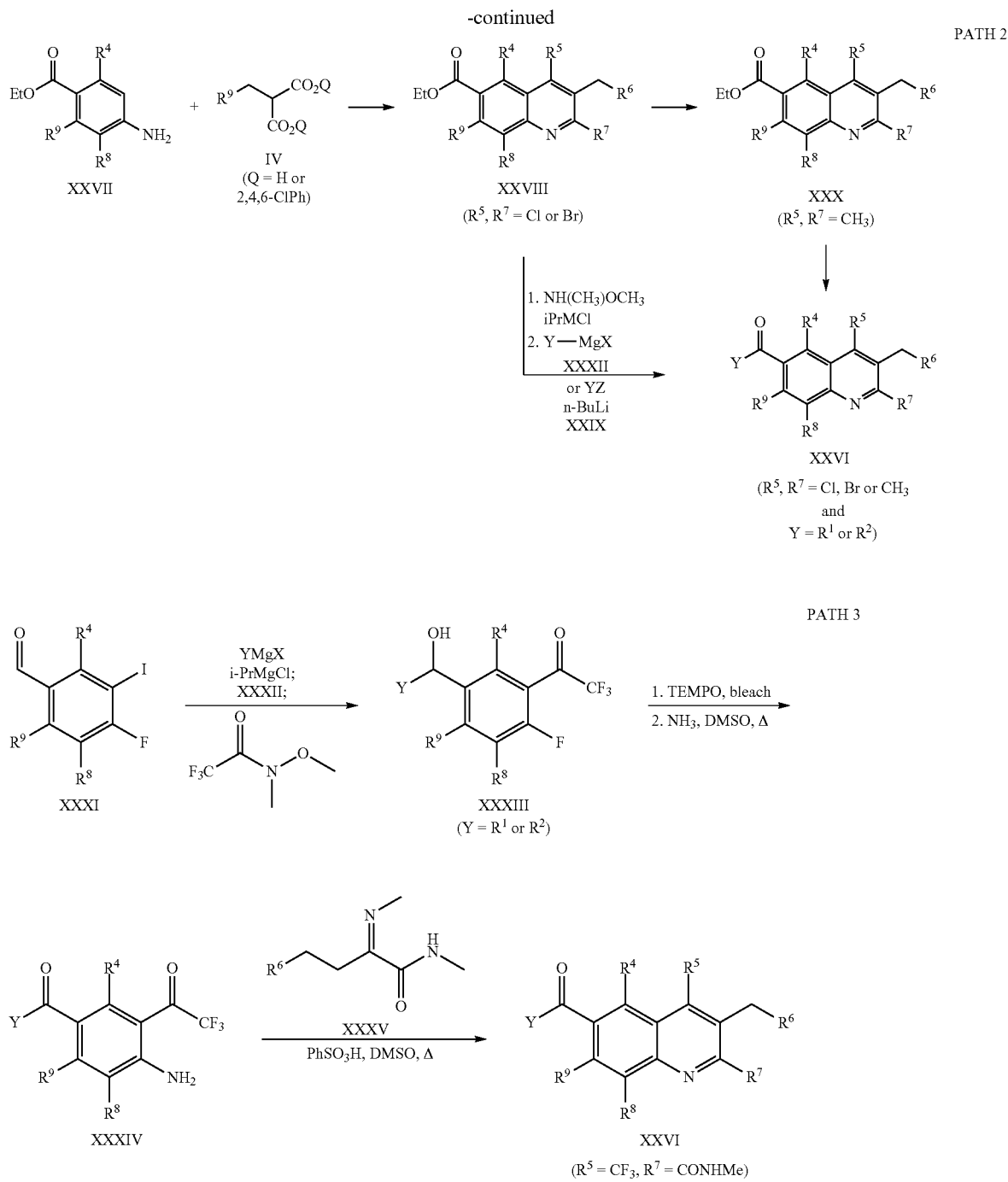

Scheme 3 shows examples of methods used to introduce either $R^1$ or $R^2$ to form ketoquinolines of formulas XXVI (path 1 to 3). As shown in path 1, Weinreb amides XXIV can be formed from 4-nitrobenzoic acids XXIII and N,O-dimethylhydroxylamine hydrochloride in the presence of a coupling reagent, for example, EDCI and a base such as triethylamine or Hunig's base in a chlorinated solvent at ambient temperature. Ketoanilines XXV can be prepared in two steps by reaction of the Weinreb amide XXIV with a Grignard reagent such as YMgX XXXII (X is bromide or chloride and Y is $R^1$ or $R^2$) or one that is pre-formed by combining YZ XXIX (Z=Br or I and Y is $R^1$ or $R^2$) with an organometallic reagent, such as EtMgCl or iPrMgCl, at 0° C. to ambient temperature to introduce ketone functionality followed by reduction of the nitro group by using an appropriate reducing agent such as $SnCl_2 \cdot 2H_2O$ in a polar solvent such as ethanol or THF at refluxing temperatures. The ketoanilines XXV can then be treated with malonic acids IV in phosphorus oxychloride at elevated temperatures to provide ketoquinolines XXVI wherein $R^5$ and $R^7$ are Cl and Y is $R^1$ or $R^2$. The 2-Cl group can be displaced with NaOalkyl in an appropriate hot alcoholic solvent such as methanol, ethanol or isopropanol or in a nonpolar solvent such as toluene at elevated temperatures to afford quinolines XXVI, wherein $R^5$ is Cl and $R^7$ is Oalkyl. Alternatively, as illustrated in Path 2, ethyl 4-aminobenzoates XXVII can be condensed with either malonic acid IV (Q=H) in phosphorus oxychloride at elevated temperatures or treated with activated malonic acid esters such as bis(2,4,6-trichlorophenyl)-2-benzyl malonates (Q=2,4,6-trichlorophenyl) at high temperatures in the microwave followed by heating in phosphoryl tribromide or phosphorus oxychloride to afford cyclized quinolines XXVIII wherein $R^5$ and $R^7$ are Cl or Br (Path 2). The 2,4-dibromoquinolines XXVIII can be further treated with trimethylboroxine under Suzuki reaction conditions to provide 2,4-dimethylquinolines XXX. The ethylester of quinolines XXVIII and XXX can then be either converted to the Weinreb amide using N,O-dimethylhydroxylamine hydrochloride and isopropylmagnesium chloride before addition of aryl magnesium bromide or chloride YMgX XXXII (Y=$R^1$ or $R^2$) as previously described or treated directly with arylhalides XXIX (Z=Br or I and Y=$R^1$ or $R^2$) and n-butyllithium at −78 to 0° C. to provide ketoquinolines XXVI, wherein $R^5$ and $R^7$ are Cl, Br or $CH_3$ and Y=$R^1$ or $R^2$ and are as defined above.

In path 3, one-pot reaction of aldehydes XXXI and Grignard reagents such as YMgX XXXII (X is bromide or chloride and Y is $R^1$ or $R^2$) followed by treatment with i-PrMgCl and addition of 2,2,2-trifluoro-N-methoxy-N-methylacetamide yields hydroxyl compounds XXXIII. The hydroxyl group can be oxidized using, for example, bleach and TEMPO. Fluoro displacement can then be achieved with ammonia in hot DMSO to provide anilines XXXIV. In the presence of benzenesulfonic acid, condensation of anilines XXXIV and N-methyl-2-(methylimino)-4-arylbutanamide XXXV in hot DMSO furnishes ketoquinolines XXVI wherein $R^5$ is $CF_3$, $R^7$ is CONHMe and Y is $R^1$ or $R^2$ and are as defined above.

Synthesis of the intermediate ketoquinolines XXVI may also be achieved via chemical routes shown in Scheme 4. In path 1, treatment of 6-bromo or 6-iodoquinolines VI with n-BuLi followed by addition of aldehydes XVIII, at temperatures between 0 and −78° C., provides secondary alcohol quinolines XXXVI. Final oxidation to ketoquinoline XXVI can be achieved with Dess-Martin periodinane or $MnO_2$, as previously described. Alternatively, 6-bromo or 6-iodoquinolines VI can be treated with n-BuLi at −78° C. then quenched with DMF to afford quinoline carboxaldehydes XXXVII. Ketoquinolines XXVI, wherein Y is $R^1$ or $R^2$, can then be obtained in a two-step process by addition of the aldehydes XXXVII to a reaction mixture of aryl halides XXIX (Y=$R^1$ or $R^2$ and Z=Br or I) and i-PrMgCl.LiCl followed by oxidation with $MnO_2$ (path 2).

Scheme 5

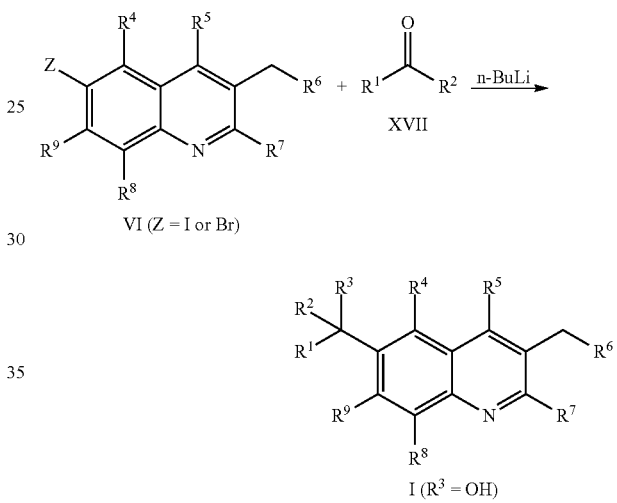

Scheme 4

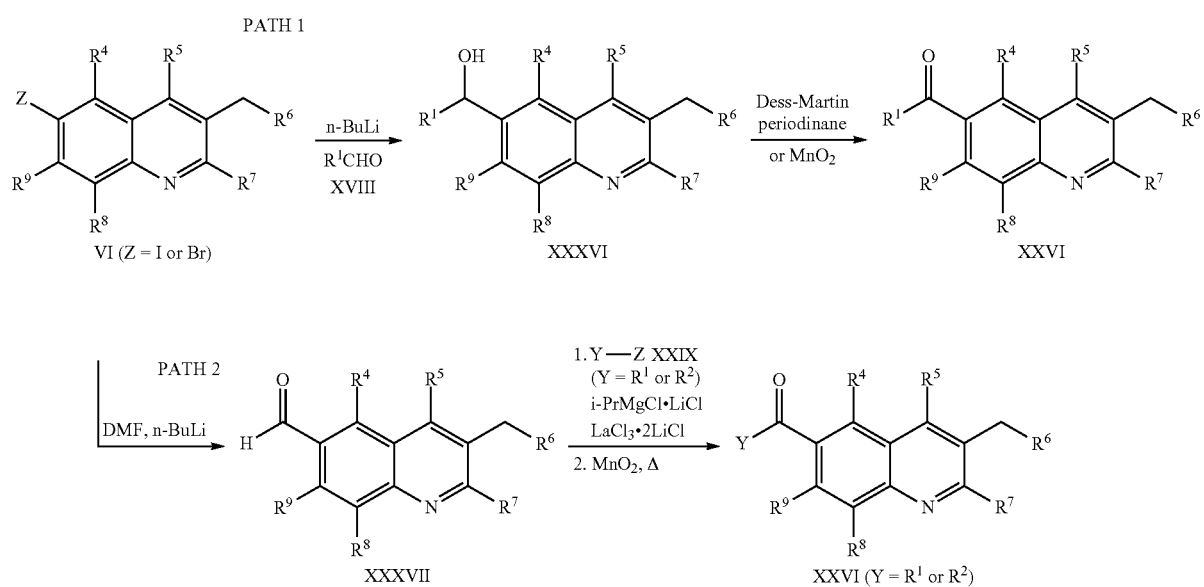

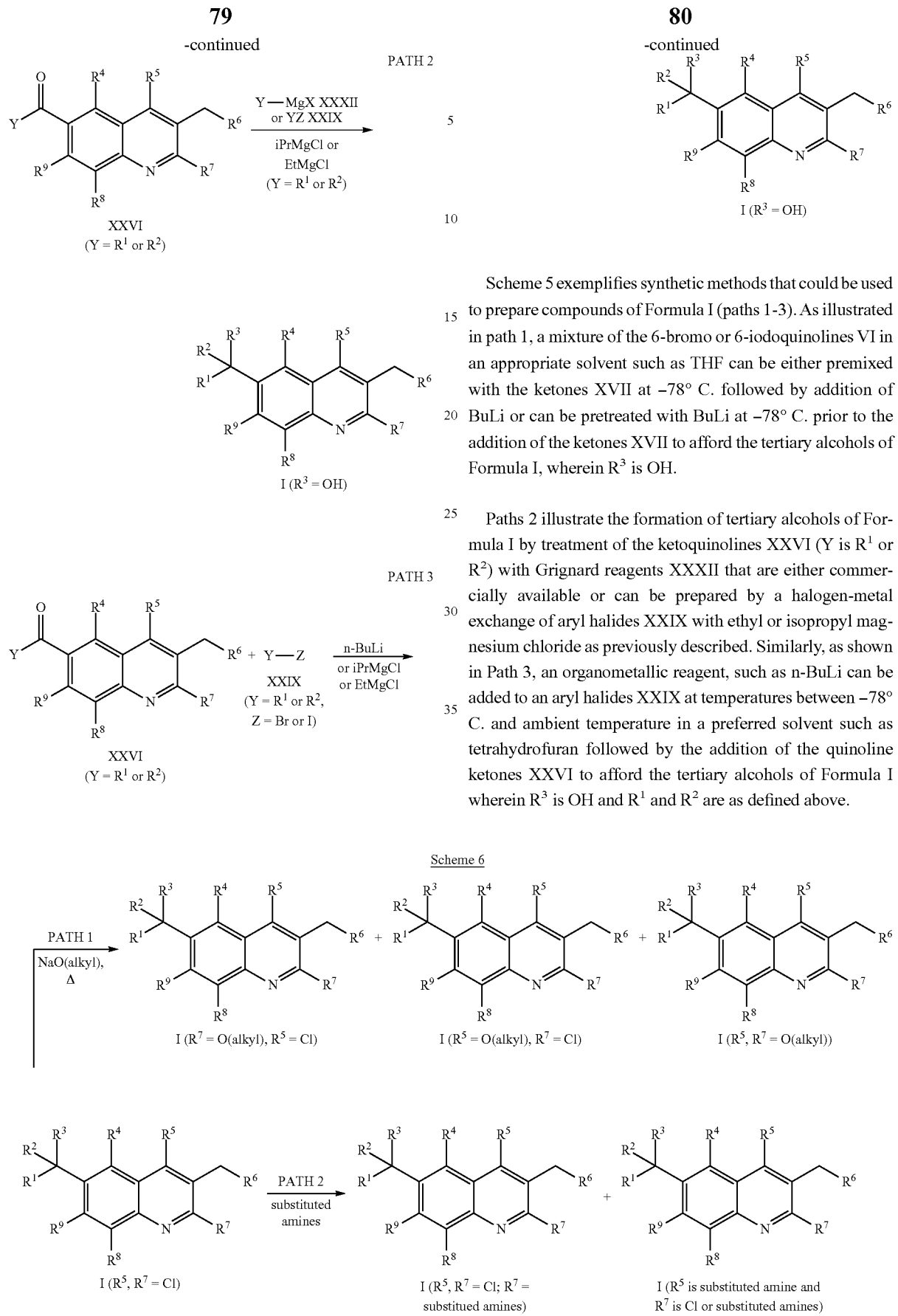

Scheme 5 exemplifies synthetic methods that could be used to prepare compounds of Formula I (paths 1-3). As illustrated in path 1, a mixture of the 6-bromo or 6-iodoquinolines VI in an appropriate solvent such as THF can be either premixed with the ketones XVII at −78° C. followed by addition of BuLi or can be pretreated with BuLi at −78° C. prior to the addition of the ketones XVII to afford the tertiary alcohols of Formula I, wherein $R^3$ is OH.

Paths 2 illustrate the formation of tertiary alcohols of Formula I by treatment of the ketoquinolines XXVI (Y is $R^1$ or $R^2$) with Grignard reagents XXXII that are either commercially available or can be prepared by a halogen-metal exchange of aryl halides XXIX with ethyl or isopropyl magnesium chloride as previously described. Similarly, as shown in Path 3, an organometallic reagent, such as n-BuLi can be added to an aryl halides XXIX at temperatures between −78° C. and ambient temperature in a preferred solvent such as tetrahydrofuran followed by the addition of the quinoline ketones XXVI to afford the tertiary alcohols of Formula I wherein $R^3$ is OH and $R^1$ and $R^2$ are as defined above.

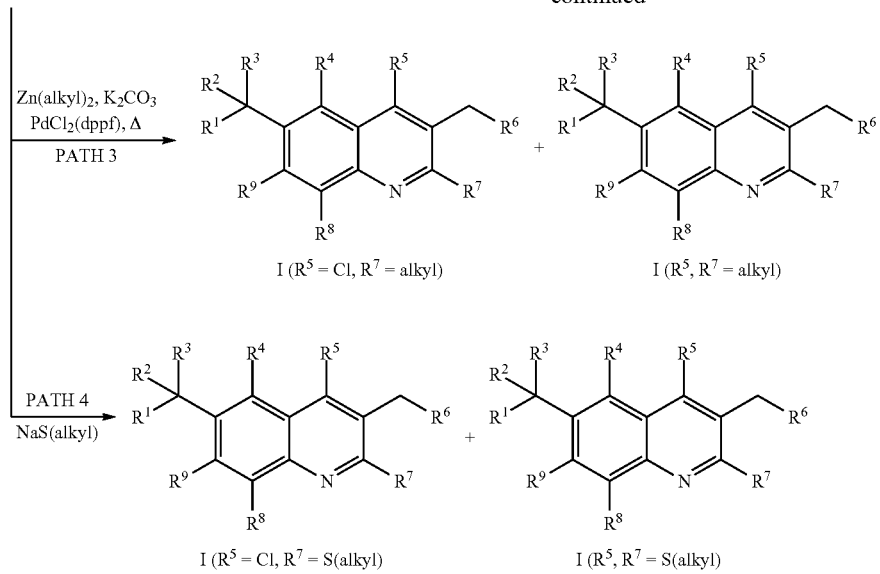

Scheme 6 illustrates methods used to synthesize compounds of Formula I wherein either the chlorine at $R^7$ or $R^5$ or at both $R^5$ and $R^7$ positions are replaced with nitrogen, oxygen, sulfur or alkyl groups. In path 1 and 4, nucleophilic displacement of 2,4-dichloroquinolines I ($R^5$ and $R^7$ are Cl) with NaO(alkyl), NaS(alkyl), such as NaOMe, NaSMe, NaOEt, or NaOiPr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene provides compounds of Formula I wherein $R^5$ is Cl and $R^7$ is O(alkyl), $O(CH_2)_2OCH_3$ or S(alkyl) and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocyclic amines, or N,O-dimethylhydroxylamine in polar solvents such as MeOH, EtOH, or $Et_2NCHO$, or DMF provides quinolines of Formula I (path 2) wherein $R^5$ is NH(alkyl), $N(alkyl)_2$, $N(CH_3)OCH_3$, or Cl, and $R^7$ is NH(alkyl), $N(alkyl)_2$, $N(CH_3)OCH_3$, $NA^1A^2$, $NHC_{(2-3)}$alkyl$NA^1A^2$ or $N(CH_3)C_{(2-4)}$alkyl$NA^1A^2$, wherein $A^1$ and $A^2$ are as defined above. Introduction of cyclic amides can be accomplished using Buchwald palladium catalyzed coupling conditions to provide compounds of Formula I, wherein $R^7$ are rings such as azetidin-2-ones or pyrrolidin-2-ones. Replacement of chlorine at positions 2 and 4 of quinolines I ($R^5$ and $R^7$ are Cl) with alkyl groups can be carried out using $Zn(alkyl)_2$ in the presence of $K_2CO_3$ and a palladium catalyst, such as $PdCl_2(dppf)$, to afford 2-alkyl and 2,4-dialkylquinolines of formula I (path 3).

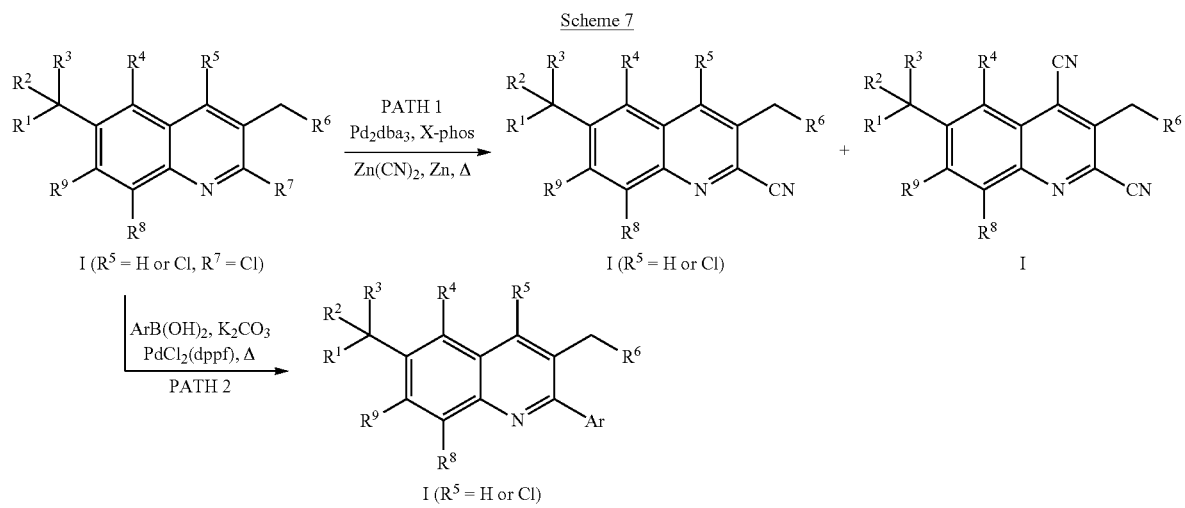

Synthetic routes to compounds of Formula I, wherein $R^5$ is H or Cl or CN, and $R^7$ is CN or aryl, are illustrated in Scheme 7. In path 1, cyanation of the 2,4-dichloroquinolines I with $Zn(CN)_2$ in the presence of Zn, a palladium catalyst, such as $Pd_2dba_3$, and a ligand, such as dppf or X-phos, at high temperatures can provide 2-CN and 2,4-diCN quinolines of Formula I. The 2,4-dichloroquinolines I can also undergo a Suzuki palladium catalyzed cross-coupling reaction with $ArB(OH)_2$ or $ArB(OR)_2$ with a palladium catalyst, such as $PdCl_2(dppf)$, yielding compounds of Formula I wherein $R^7$ is phenyl, substituted phenyl and five or six-membered heteroaryls such as furan, pyridine, pyridazine, pyrazine, pyrimidine, pyrrole, pyrazole, or imidazole (path 2).

Scheme 8

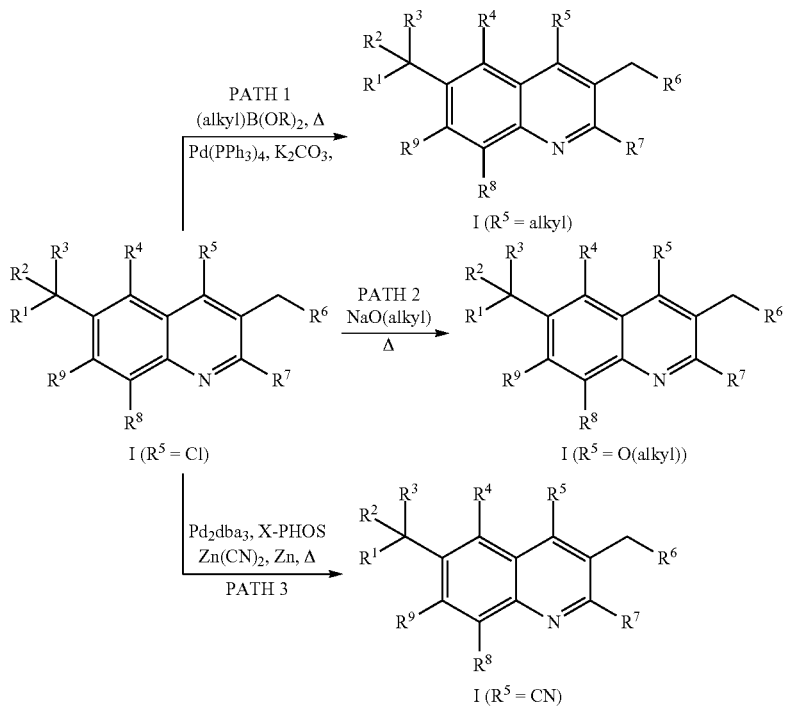

As illustrated in Scheme 8, compounds of Formula I prepared in Schemes 6 and 7 wherein only $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as defined above.

Scheme 9

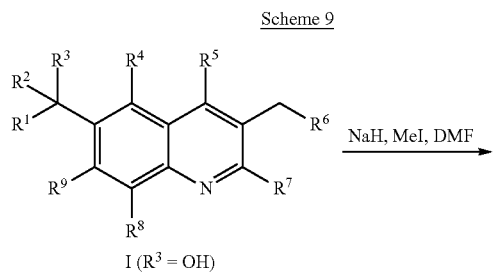

-continued

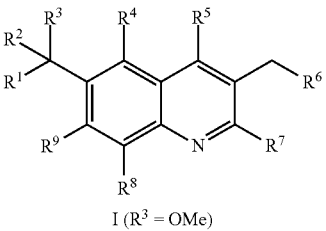

As shown in Scheme 9, tertiary alcohols of Formula I can be treated with base, such as NaH, and alkylated with MeI in DMF to provide compounds of Formula I wherein $R^3$ is OMe.

Scheme 10

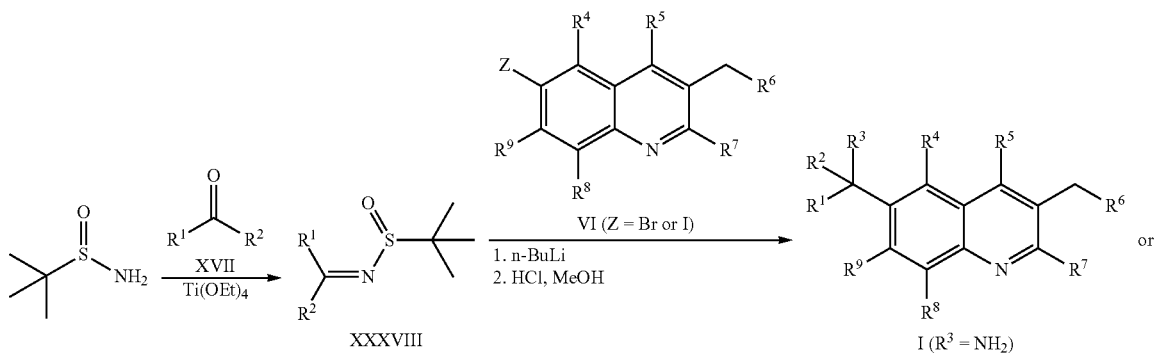

-continued

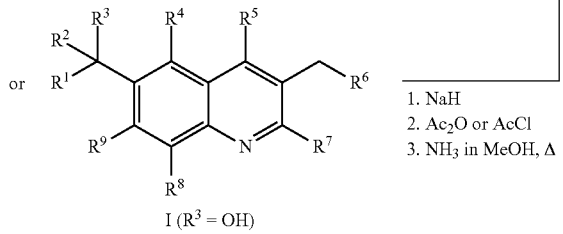

I ($R^3$ = OH)

1. NaH
2. Ac$_2$O or AcCl
3. NH$_3$ in MeOH, Δ

Synthetic routes to compounds of Formula I, wherein $R^3$ is NH$_2$, are illustrated in Scheme 10. Ketimines XXXVIII may be prepared by Ti(OEt)$_4$ mediated condensation of ketones XVII with 2-methylpropane-2-sulfinamide in refluxing THF. Addition of n-BuLi to the reaction mixture of ketimines XXXVIII and 6-bromo or 6-iodoquinolines VI at −78° C. followed by cleavage of the tert-butanesulfinyl group with HCl in MeOH liberates tertiary amines of Formula I.

Alternatively, compounds of Formula I, wherein $R^3$ is OH can be treated with sodium hydride followed by addition of acetic anhydride or acetyl chloride and stirred at room temperature over a 24 to 72 hr period to provide the intermediate acetate wherein $R^3$ is OAc. The acetate can then be combined with a solution of ammonia in methanol and heated at temperatures between 60 and 85° C. to provide compounds of Formula I, wherein $R^3$ is NH$_2$.

Scheme 11

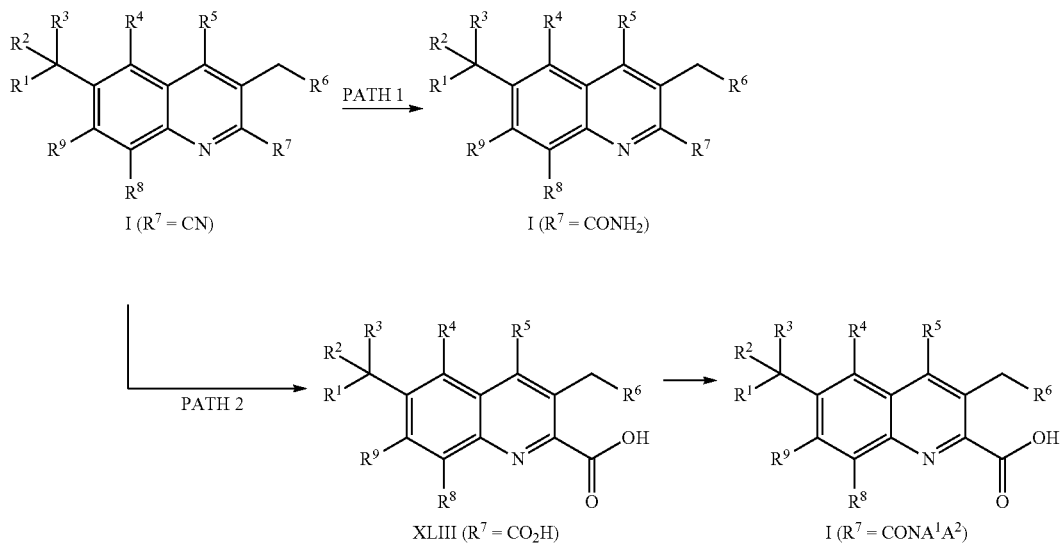

As shown in Scheme 11, the quinolines of Formula I wherein $R^7$ is CN can be hydrolyzed as described in US20080188521 by treatment with sodium carbonate and hydrogen peroxide to provide compounds of Formula I wherein $R^7$ is CONH$_2$ (Path 1) or can be treated with a strong acid like HCl to convert CN to a carboxylic acid XLIII (Path 2). Once formed the acid can be further coupled to substituted amines using appropriate coupling reagents such as EDCI or HATU in the presence of a base like triethylamine or Hunig's base to provide compounds of Formula I wherein $R^7$ is CONA$^1$A$^2$.

Scheme 12

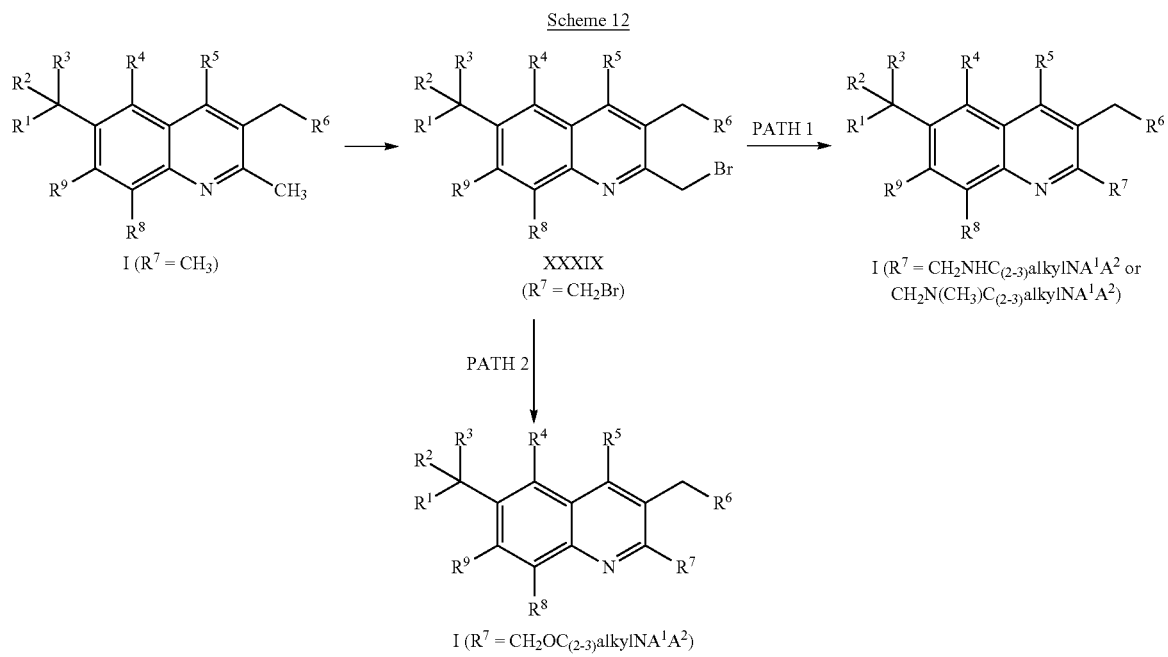

Synthesis of compounds of Formula I, wherein $R^7$ is an aminoalkylaminomethylene or an aminoalkoxymethylene can be prepared from 2-methylquinolines as shown in Scheme 12. Bromination of 2-methylquinolines of Formula I can accomplished with N-bromosuccinamide in acetic acid at elevated temperatures as described in WO2010151740, to provide the methylbromide intermediate XXXIX. Nucleophilic displacement of the bromide under basic conditions using procedures known in the art could afford compounds of Formula I wherein $R^7$ is —$CH_2NHC_{(2-3)}$alkylN$A^1A^2$ or —$CH_2N(CH_3)C_{(2-3)}$alkylN$A^1A^2$ (Path 1) or $CH_2OC_{(2-3)}$alkylN$A^1A^2$ (Path 2) and $A^1$ and $A^2$ are defined above.

Compounds of Formula I wherein $R^1$, $R^2$ or $R^6$ are pyridyl can be treated with m-chloroperbenzoic acid in a chlorinated solvent at ambient to 40° C. to form the pyridyl-N-oxides of Formula I.

Scheme 13

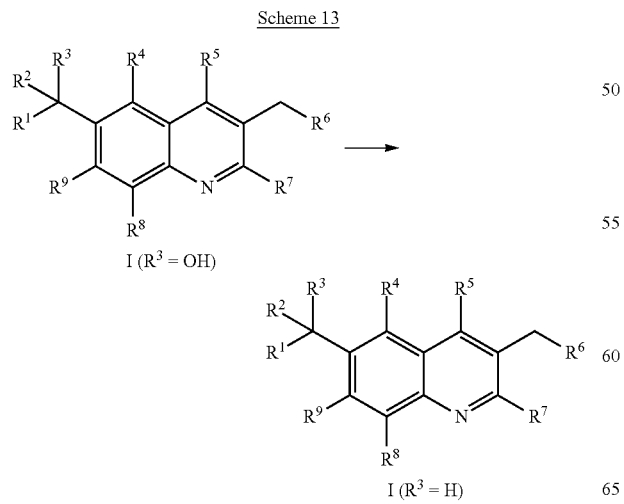

As shown in Scheme 13, compounds of the Formula I wherein $R^3$ is H can be prepared by treating compounds of Formula I wherein $R^3$ is OH with an acid such as trifluoroacetic acid in a solvent such as dichloromethane at room temperature or with heating (WO2009091735).

Scheme 14

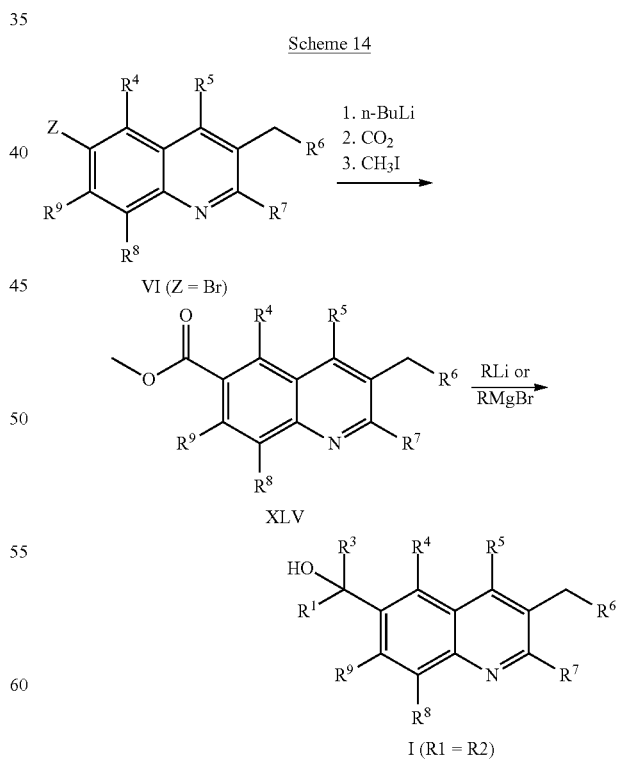

Compounds of Formula I, wherein $R^1$ and $R^2$ are the same, can also be prepared as described in Scheme 14. The starting 6 bromoquinolines can be treated with butyl lithium, quenched with carbondioxide then subsequently treated with methyl iodide as described in U.S. Pat. No. 4,710,507 A1, 1987 to provide the intermediate quinoline methylester XLV. Further treatment of the methyl ester with excess R¹Li, R²Li, R¹MgBr or R²MgBr, in the presence or absence or lanthanum chloride, can afford the symmetrical compounds of Formula I.

EXAMPLES

Compounds of the present invention can be prepared by methods known to those who are skilled in the art. The following examples are only meant to represent examples of the invention and are in no way meant to be a limit of the invention.

Intermediate 1: Step a

4-Chloro-N-methoxy-N-methylbenzamide

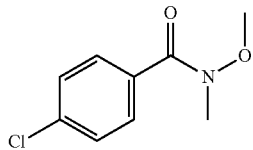

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration, washing with DCM. The filtrate was washed with 1 N aqueous HCl followed by water. The organic phase was dried (Na$_2$SO$_4$), filtered, and concentrated, affording the crude title compound as a colorless liquid which was used without purification in the next step.

Intermediate 1: Step b (4-Chlorophenyl)(1-methyl-1H-imidazol-5-yl)methanone

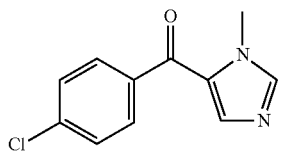

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 minutes, then was again cooled in an ice bath before addition of 4-chloro-N-methoxy-N-methylbenzamide (10.7 g, 53.6 mmol, Intermediate 1: step a). The resulting white suspension was stirred overnight at room temperature. The reaction was quenched by addition of saturated aqueous NH$_4$Cl and diluted with water. The mixture was partially concentrated to remove THF and was diluted with DCM. The mixture was acidified to pH 1 with 1 N aqueous HCl, then neutralized with saturated aqueous NaHCO$_3$. The phases were separated and the aqueous phase was further extracted with DCM. The organic extracts were washed with water, then were dried (Na$_2$SO$_4$), filtered, and concentrated, affording a white solid. The crude product was triturated with a mixture of EtOAc:heptanes (1:1, 150 mL). The precipitated solid was collected by vacuum filtration, washing with heptanes, to afford the title compound.

Intermediate 2: Step a

Methyl 5-bromo-2-(3-phenylpropanamido)benzoate

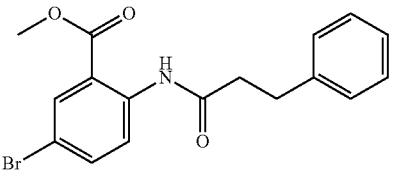 [SMILES: COC(=O)c1cc(Br)ccc1NC(=O)CCc1ccccc1]

Into a 100-mL round-bottom flask, was placed a solution of methyl 2-amino-5-bromobenzoate (5.0 g, 21.73 mmol), triethylamine (4.39 g, 43.38 mmol), 3-phenylpropanoyl chloride (3.67 g, 21.76 mmol) in dichloromethane (50 mL). The resulting mixture was stirred for 12 hours at room temperature. The reaction was then quenched by the addition of 50 mL of water. The resulting mixture was extracted with 3×50 mL of dichloromethane. The combined organic layer was dried over anhydrous sodium sulfate, filtered and concentrated under vacuum. The residue was purified by chromatography over a silica gel column with ethyl acetate/petroleum ether (2:1) to give the title compound as a white solid.

Intermediate 2: Step b

3-Benzyl-6-bromo-4-hydroxy-1,2-dihydroquinolin-2-one

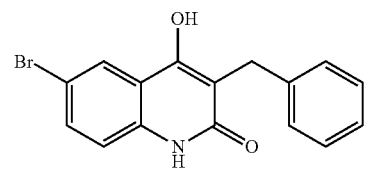 [SMILES: O=c1[nH]c2ccc(Br)cc2c(O)c1Cc1ccccc1]

Into a 50-mL round-bottom flask purged and maintained with an inert atmosphere of nitrogen, was placed a solution of methyl 5-bromo-2-(3-phenylpropanamido)benzoate (2.8 g, 7.8 mmol, Intermediate 2: step a), KHMDS (47 mL, 15% in toluene) in tetrahydrofuran (50 mL). The resulting solution was stirred for 12 hours at room temperature. The reaction was then quenched by the addition of 2 mL of methanol and 10 mL of aqueous HCl (1M). The resulting solution was extracted with 2×100 mL of ethyl acetate. The combined organic layers were dried over anhydrous sodium sulfate, filtered and concentrated under vacuum. The crude product was purified by re-crystallization from ethyl acetate to give the title compound as a white solid.

Intermediate 2: Step c

3-Benzyl-6-bromo-2,4-dichloroquinoline

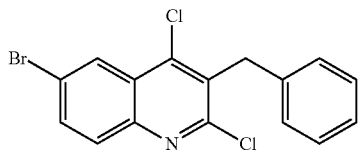 [SMILES: Clc1nc2ccc(Br)cc2c(Cl)c1Cc1ccccc1]

Into a 100-mL round-bottom flask, was placed a solution of 3-benzyl-6-bromo-4-hydroxy-1,2-dihydroquinolin-2-one (2.9 g, 8.78 mmol, Intermediate 2: step b) in $POCl_3$ (20 mL). The resulting solution was stirred for 1 hour at 110° C. The reaction was then quenched by the addition of 50 mL of water/ice. The pH value of the solution was adjusted to 7-8 with aqueous ammonia. The resulting solution was extracted with 3×50 mL of ethyl acetate. The combined organic layers were dried over anhydrous sodium sulfate, filtered and concentrated under vacuum. The residue was purified by chromatography over a silica gel column with ethyl acetate/petroleum ether (2:1) to give the title compound as a white solid.

Intermediate 3: Step a 5-(4-Chlorobenzyl)-2,2-dimethyl-1,3-dioxane-4,6-dione

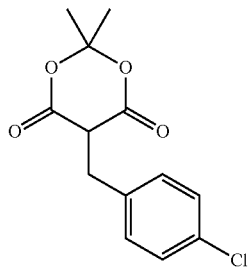 [SMILES: CC1(C)OC(=O)C(Cc2ccc(Cl)cc2)C(=O)O1]

Proline (0.165 g, 1.42 mmol) was added to a solution of 4-chlorobenzaldehyde (1.00 g, 7.11 mmol) and Meldrum's acid (1.03 g, 7.11 mmol) in EtOH (10 mL). The mixture was stirred at room temperature for 1 hour and diethyl 1,4-dihydro-2,6-dimethyl-3,5-pyridinedicarboxylate (1.80 g, 7.11 mmol) was added. Stirring was continued for 3 hours and EtOH removed under reduced pressure. The residue was diluted with i-PrOH and filtered to provide the desired compound as a white solid.

Intermediate 3: Step b 2-(4-Chlorobenzyl)malonic acid

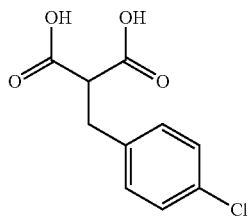 [SMILES: O=C(O)C(Cc1ccc(Cl)cc1)C(=O)O]

A solution of 5-(4-chlorobenzyl)-2,2-dimethyl-1,3-dioxane-4,6-dione (1.50 g, 5.58 mmol, Intermediate 3: step a) and 3 M aqueous NaOH (16 mL) was heated in the microwave at 75 W for 20 minutes at 120° C. The aqueous mixture was extracted with EtOAc (1×) then acidified to pH 1 with concentrated aqueous HCl and extracted with EtOAc (2×). The combined EtOAc extract was washed with $H_2O$, brine and dried over $Na_2SO_4$, filtered. Solvents were removed under reduced pressure to afford the title compound as a white solid.

Intermediate 3: Step c

6-Bromo-2,4-dichloro-3-(4-chlorobenzyl)quinoline

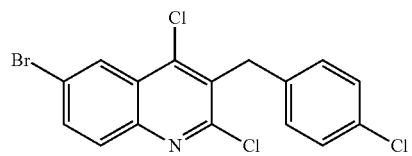 [SMILES: Clc1ccc(Cc2c(Cl)nc3ccc(Br)cc3c2Cl)cc1]

A mixture of 2-(4-chlorobenzyl)malonic acid (1.16 g, 5.07 mmol, Intermediate 3: step b) and 4-bromoaniline (0.872 g, 5.07 mmol) in $POCl_3$ (4.72 mL, 50.7 mmol) was heated at 80° C. for 5 hours, cooled to room temperature and evaporated in vacuo to remove excess $POCl_3$. The residue was poured into ice $H_2O$, and treated with aqueous $NH_4OH$ to pH 8-9. The aqueous mixture was extracted with EtOAc (2×). The combined organic extract was washed with $H_2O$, brine, dried over $Na_2SO_4$, filtered and evaporated in vacuo. The title compound was precipitated from $Et_2O$, collected by filtration and dried to provide a pale yellow solid.

Intermediate 4: Step a 5-(4-Fluorobenzyl)-2,2-dimethyl-1,3-dioxane-4,6-dione

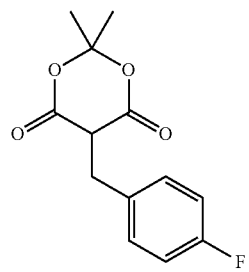 [SMILES: CC1(C)OC(=O)C(Cc2ccc(F)cc2)C(=O)O1]

The title compound was prepared using 4-fluorobenzaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 4: Step b 2-(4-Fluorobenzyl)malonic acid

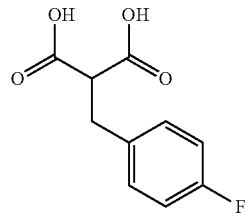 [SMILES: O=C(O)C(Cc1ccc(F)cc1)C(=O)O]

The title compound was prepared by substituting 5-(4-chlorobenzyl)-2,2-dimethyl-1,3-dioxane-4,6-dione (Intermediate 3: step a) with 5-(4-fluorobenzyl)-2,2-dimethyl-1,3-dioxane-4,6-dione (Intermediate 4: step a) then following the procedure described for the preparation of 2-(4-chlorobenzyl)malonic acid (Intermediate 3: step b).

Intermediate 4: Step c

6-Bromo-2,4-dichloro-3-(4-fluorobenzyl)quinoline

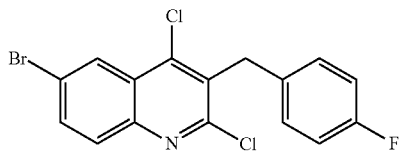 [SMILES: Fc1ccc(Cc2c(Cl)nc3ccc(Br)cc3c2Cl)cc1]

The title compound was prepared by substituting 2-(4-chlorobenzyl)malonic acid (Intermediate 3: step b) with 2-(4-fluorobenzyl)malonic acid (Intermediate 4: step b) then following the procedure described for the preparation of 6-bromo-2,4-dichloro-3-(4-chlorobenzyl)quinoline (Intermediate 3: step c).

Intermediate 4: Step d

6-Bromo-4-chloro-3-(4-fluorobenzyl)-2-methoxyquinoline

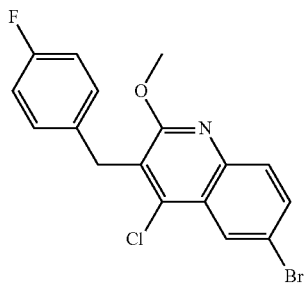 [SMILES: COc1nc2ccc(Br)cc2c(Cl)c1Cc1ccc(F)cc1]

A mixture of 6-bromo-2,4-dichloro-3-(4-fluorobenzyl)quinoline (0.350 g, 0.909 mmol, Intermediate 4: step c) and a 0.5 M sodium methoxide in methanol solution (9.09 mL. 4.55 mmol) was stirred at reflux for 16 hours. The mixture was poured into ice water and extracted with EtOAc (2×). The combined EtOAc extract was dried (Na$_2$SO$_4$), filtered and evaporated in vacuo and purified by column chromatography with silica gel (heptane/CH$_2$Cl$_2$) to provide the title compound as a white solid.

Intermediate 5: Step a 5-(3-Chlorobenzyl)-2,2-dimethyl-1,3-dioxane-4,6-dione

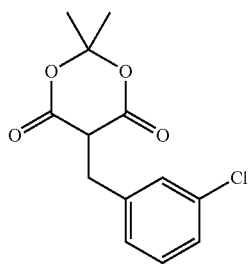 [SMILES: CC1(C)OC(=O)C(Cc2cccc(Cl)c2)C(=O)O1]

The title compound was prepared using 3-chlorobenzaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 5: Step b 2-(3-Chlorobenzyl)malonic acid

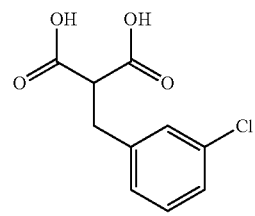 [SMILES: O=C(O)C(Cc1cccc(Cl)c1)C(=O)O]

The title compound was prepared by substituting 5-(4-chlorobenzyl)-2,2-dimethyl-1,3-dioxane-4,6-dione (Intermediate 3: step a) with 5-(3-chlorobenzyl)-2,2-dimethyl-1,3-dioxane-4,6-dione (Intermediate 5: step a) then following the procedure described for the preparation of 2-(4-chlorobenzyl)malonic acid (Intermediate 3: step b).

Intermediate 5: Step c

6-Bromo-2,4-dichloro-3-(3-chlorobenzyl)quinoline

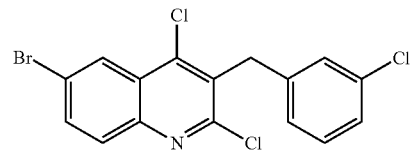 [SMILES: Clc1cccc(Cc2c(Cl)nc3ccc(Br)cc3c2Cl)c1]

The title compound was prepared by substituting 2-(4-chlorobenzyl)malonic acid (Intermediate 3: step b) with 2-(3-chlorobenzyl)malonic acid (Intermediate 5: step b) then following the procedure described for the preparation of 6-bromo-2,4-dichloro-3-(4-chlorobenzyl)quinoline (Intermediate 3: step c).

Intermediate 6: Step a 5-(4-(1H-Pyrazol-1-yl)benzyl)-2,2-dimethyl-1,3-dioxane-4,6-dione

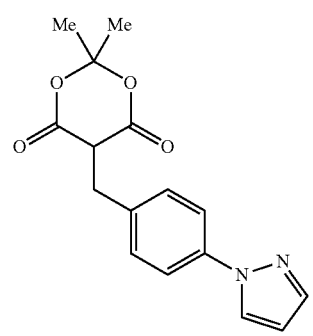 [SMILES: CC1(C)OC(=O)C(Cc2ccc(-n3cccn3)cc2)C(=O)O1]

L-Proline (4.07 g, 35.0 mmol) was added to a semi-heterogeneous mixture of 4-(1H-pyrazol-1-yl)benzaldehyde (30.0 g, 174 mmol) and 2,2-dimethyl-1,3-dioxane-4,6-dione (25.6 g, 174 mmol) in ethanol (996 mL) at room temperature. After 40 minutes, diethyl 1,4-dihydro-2,6-dimethyl-3,5-pyridinedicarboxylate (44.1 g, 174 mmol) was added in one portion followed by ethanol (125 mL). After overnight stirring, the mixture was concentrated under reduced pressure to afford a yellow solid. Isopropanol (300 mL) was added and the heterogeneous mixture was sonicated for 30 minutes. The mixture was filtered and the filter cake was washed with isopropanol. The solids were collected and dried under vacuum to provide the title compound as a white solid.

Intermediate 6: Step b 2-(4-(1H-Pyrazol-1-yl)benzyl)malonic acid

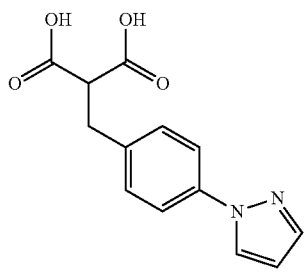 [SMILES: O=C(O)C(Cc1ccc(-n2cccn2)cc1)C(=O)O]

A mixture of 5-(4-(1H-pyrazol-1-yl)benzyl)-2,2-dimethyl-1,3-dioxane-4,6-dione (41.4 g, 137 mmol, Intermediate 6: step a) and 3 M aqueous NaOH solution (300 mL, 900 mmol) was heated for 48 hours at 110° C. The mixture was cooled to room temperature, diluted with water (200 mL) and extracted with EtOAc (1×100 mL) and then acidified to pH 1 with concentrated aqueous HCl at 0° C. The resulting mixture was stirred at 0° C. for 1.5 hours, filtered and the filter cake was washed with water. The solids were collected and dried under vacuum at 40° C. to provide the title compound as a white solid.

Intermediate 6: Step c 3-(4-(1H-Pyrazol-1-yl)benzyl)-6-bromo-2,4-dichloroquinoline

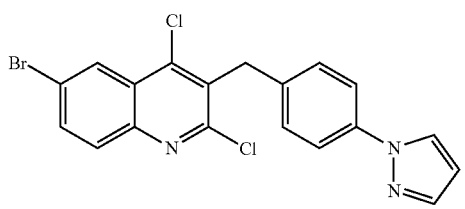 [SMILES: Clc1nc2ccc(Br)cc2c(Cl)c1Cc1ccc(-n2cccn2)cc1]

A mixture of 2-(4-(1H-pyrazol-1-yl)benzyl)malonic acid (3.37 g, 19.6 mmol, Intermediate 6: step b) and 4-bromoaniline (5.10 g, 19.6 mmol) in POCl$_3$ (18 mL) was heated at 105° C. for 3 hours, cooled to room temperature and evaporated in vacuo to remove excess POCl$_3$. The residue was poured into ice H$_2$O and treated with aqueous NH$_4$OH to pH 8-9 (temperature of the aqueous mixture was kept cold during addition). The precipitates were collected, rinsed with H$_2$O and dried under reduced pressure. After drying the resulting crude pale yellow solid was washed several times with Et$_2$O then acetonitrile and dried to provide the title compound as a pale yellow solid.

Intermediate 7: Step a 5-(4-Methoxybenzyl)-2,2-dimethyl-1,3-dioxane-4,6-dione

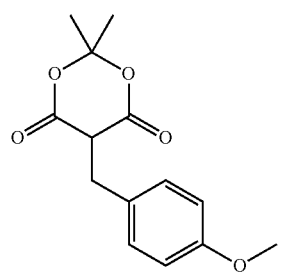 [SMILES: COc1ccc(CC2C(=O)OC(C)(C)OC2=O)cc1]

The title compound was prepared using 4-methoxybenzaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 7: Step b 2-(4-Methoxybenzyl)malonic acid

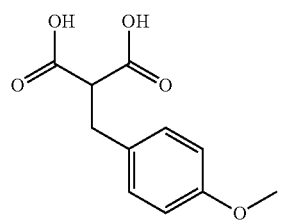 [SMILES: COc1ccc(CC(C(=O)O)C(=O)O)cc1]

The title compound was prepared by substituting 5-(4-chlorobenzyl)-2,2-dimethyl-1,3-dioxane-4,6-dione (Intermediate 3: step a) with 5-(4-methoxybenzyl)-2,2-dimethyl-1,3-dioxane-4,6-dione (Intermediate 7: step a) then following the procedure described for the preparation of 2-(4-chlorobenzyl)malonic acid (Intermediate 3: step b).

Intermediate 7: Step c

6-Bromo-2,4-dichloro-3-(4-methoxybenzyl)quinoline

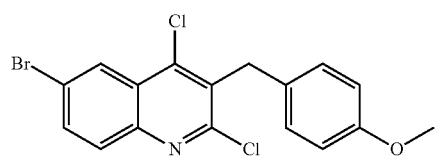 [SMILES: COc1ccc(Cc2c(Cl)nc3ccc(Br)cc3c2Cl)cc1]

The title compound was prepared by substituting 2-(4-chlorobenzyl)malonic acid (Intermediate 3: step b) with 2-(4-methoxybenzyl)malonic acid (Intermediate 7: step b) then following the procedure described for the preparation of 6-bromo-2,4-dichloro-3-(4-chlorobenzyl)quinoline (Intermediate 3: step c).

Intermediate 8: Step a 5-(4-Methylsulfonylbenzyl)-2,2-dimethyl-1,3-dioxane-4,6-dione

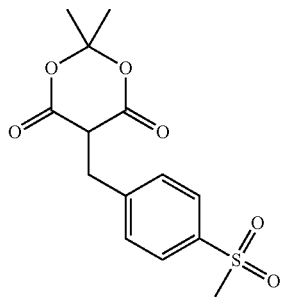 [SMILES: CC1(C)OC(=O)C(Cc2ccc(S(C)(=O)=O)cc2)C(=O)O1]

The title compound was prepared using 4-(methylsulfonyl)benzaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 8: Step b 2-(4-Methylsulfonylbenzyl)malonic acid

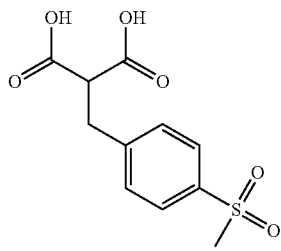 [SMILES: CS(=O)(=O)c1ccc(CC(C(=O)O)C(=O)O)cc1]

The title compound was prepared by substituting 5-(4-chlorobenzyl)-2,2-dimethyl-1,3-dioxane-4,6-dione (Intermediate 3: step a) with 5-(4-methylsulfonylbenzyl)-2,2-dimethyl-1,3-dioxane-4,6-dione (Intermediate 8: step a) then following the procedure described for the preparation of 2-(4-chlorobenzyl)malonic acid (Intermediate 3: step b).

Intermediate 8: Step c

6-Bromo-2,4-dichloro-3-(4-(methylsulfonyl)benzyl)quinoline

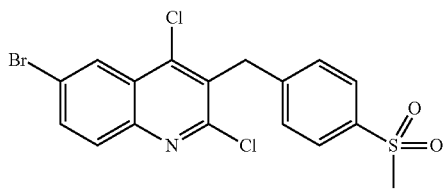 [SMILES: CS(=O)(=O)c1ccc(Cc2c(Cl)nc3ccc(Br)cc3c2Cl)cc1]

The title compound was prepared by substituting 2-(4-chlorobenzyl)malonic acid (Intermediate 3: step b) with 2-(4-methylsulfonylbenzyl)malonic acid (Intermediate 8: step b) then following the procedure described for the preparation of 6-bromo-2,4-dichloro-3-(4-chlorobenzyl)quinoline (Intermediate 3: step c).

Intermediate 9: Step a 2,2-Dimethyl-5-(thiophen-2-ylmethyl)-1,3-dioxane-4,6-dione

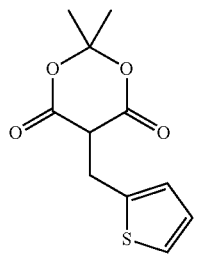 [SMILES: CC1(C)OC(=O)C(Cc2cccs2)C(=O)O1]

The title compound was prepared using thiophene-2-carbaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 9: Step b 2-(Thiophen-2-ylmethyl)malonic acid

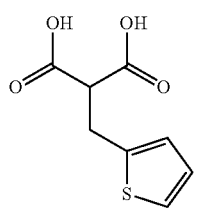 [SMILES: O=C(O)C(Cc1cccs1)C(=O)O]

The title compound was prepared by substituting 5-(4-chlorobenzyl)-2,2-dimethyl-1,3-dioxane-4,6-dione (Intermediate 3: step a) with 2,2-dimethyl-5-(thiophen-2-ylmethyl)-1,3-dioxane-4,6-dione (Intermediate 9: step a) then following the procedure described for the preparation of 2-(4-chlorobenzyl)malonic acid (Intermediate 3: step b).

Intermediate 9: Step c

6-Bromo-2,4-dichloro-3-(thiophen-2-ylmethyl)quinoline

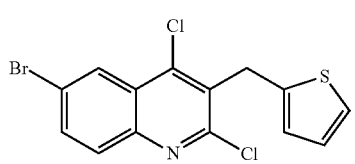 [SMILES: Clc1nc2ccc(Br)cc2c(Cl)c1Cc1cccs1]

The title compound was prepared by substituting 2-(4-chlorobenzyl)malonic acid (Intermediate 3: step b) with 2-(thiophen-2-ylmethyl)malonic acid (Intermediate 9: step b)

then following the procedure described for the preparation of 6-bromo-2,4-dichloro-3-(4-chlorobenzyl)quinoline (Intermediate 3: step c).

Intermediate 10: Step a 5-(Benzo[b]thiophen-2-ylmethyl)-2,2-dimethyl-1,3-dioxane-4,6-dione

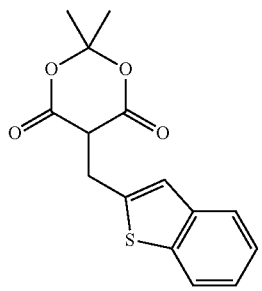 [SMILES: CC1(C)OC(=O)C(Cc2cc3ccccc3s2)C(=O)O1]

The title compound was prepared using benzo[b]thiophene-2-carbaldehyde in place of 4-chlorobenzaldehyde using the procedure described for the preparation of 5-(4-chlorobenzyl)-2,2-dimethyl-1,3-dioxane-4,6-dione (Intermediate 3: step a).

Intermediate 10: Step b 2-(Benzo[b]thiophen-2-ylmethyl)malonic acid

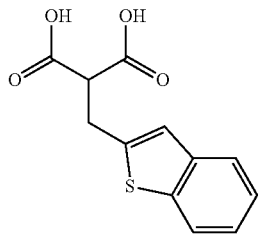 [SMILES: O=C(O)C(Cc1cc2ccccc2s1)C(=O)O]

The title compound was prepared by substituting 5-(4-chlorobenzyl)-2,2-dimethyl-1,3-dioxane-4,6-dione (Intermediate 3: step a) with 5-(benzo[b]thiophen-2-ylmethyl)-2,2-dimethyl-1,3-dioxane-4,6-dione (Intermediate 10: step a) then following the procedure described for the preparation of 2-(4-chlorobenzyl)malonic acid (Intermediate 3: step b).

Intermediate 10: Step c 3-(Benzo[b]thiophen-2-ylmethyl)-6-bromo-2,4-dichloroquinoline

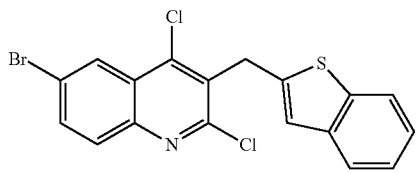 [SMILES: Clc1nc2ccc(Br)cc2c(Cl)c1Cc1cc2ccccc2s1]

The title compound was prepared by substituting 2-(4-chlorobenzyl)malonic acid (Intermediate 3: step b) with 2-(benzo[b]thiophen-2-ylmethyl)malonic acid (Intermediate 10: step b) then following the procedure described for the preparation of 6-bromo-2,4-dichloro-3-(4-chlorobenzyl)quinoline (Intermediate 3: step c).

Intermediate 11: Step a

N-Methoxy-N-methylthiazole-5-carboxamide

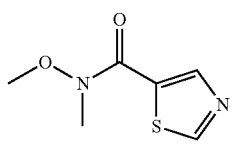

Triethylamine (2.77 mL, 19.9 mmol) was added slowly to a mixture of commercially available thiazole-5-carboxylic acid (1.03 g, 7.98 mmol), N,O-dimethylhydroxylamine hydrochloride (0.778 g, 7.98 mmol), and EDCI (1.83 g, 9.57 mmol) in $CH_2Cl_2$ (10 mL). The mixture was stirred at room temperature for 72 hours then quenched with saturated aqueous $NaHCO_3$. Water (50 mL) was added followed by additional $CH_2Cl_2$. The mixture as stirred for 10 minutes and layers were separated. The $CH_2Cl_2$ layer was dried over $Na_2SO_4$, then filtered. The solvent was removed under reduced pressure and the residual oil chromatographed ($CH_2Cl_2$/EtOAc) to provide the title compound as a white solid.

Intermediate 11: Step b

Pyridin-3-yl(thiazol-5-yl)methanone

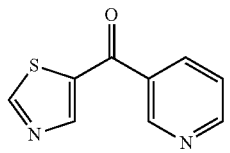 [SMILES: O=C(c1cccnc1)c1cncs1]

A n-BuLi solution (2.37 mL, 3.80 mmol, 1.6 M solution in hexane) was slowly added to a −78° C. to a solution of 3-bromopyridine (0.600 g, 3.80 mmol) in $Et_2O$ (10 mL). After addition, stirring was continued for an additional 40 minutes and N-methoxy-N-methylthiazole-5-carboxamide (0.752 g, 4.37 mmol, Intermediate 11: step a) dissolved in $Et_2O$ (10 mL) was slowly added. The mixture was stirred at −78° C. for 10 minutes then warmed to 0° C. and stirred for 1 hour. The cold solution was quenched with saturated aqueous $NH_4Cl$ and warmed to room temperature. $H_2O$ was added and layers were separated. The aqueous layer was extracted with EtOAc and the combined organic extracts washed with brine, dried over $Na_2SO_4$, filtered, evaporated in vacuo and chromatographed ($CH_2Cl_2$/EtOAc) to provide the title compound as a yellow solid (precipitated from $Et_2O$ and dried under reduced pressure).

Intermediate 12: Step a

N-(4-Bromophenyl)-3-(3-chlorophenyl)propanamide

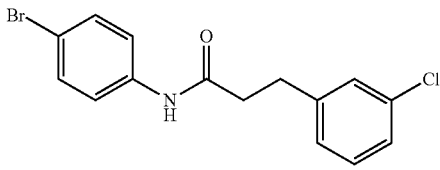 [SMILES: O=C(CCc1cccc(Cl)c1)Nc1ccc(Br)cc1]

Triethylamine (1.01 mL, 7.27 mmol) was added slowly to a mixture of 4-bromoaniline (0.500 g, 2.91 mmol), 3-(3-chlorophenyl)propanoic acid (0.643 g, 2.91 mmol), and EDCI (0.669 g, 3.49 mmol) in $CH_2Cl_2$ (20 mL). The mixture was stirred at room temperature for 48 hours and saturated aqueous $NaHCO_3$ was added. Water (50 mL) was added followed by additional $CH_2Cl_2$. The mixture as stirred for 10 minutes and layers were separated. The $CH_2Cl_2$ layer was dried over $Na_2SO_4$, then filtered. The solvent was removed under reduced pressure and the residual oil chromatographed ($CH_2Cl_2$/EtOAc) to provide the title compound as a white fluffy solid.

Intermediate 12: Step b

6-Bromo-2-chloro-3-(3-chlorobenzyl)quinoline

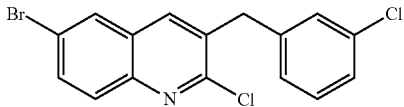 [SMILES: Clc1cccc(Cc2cc3cc(Br)ccc3nc2Cl)c1]

Phosphorus (V) oxychloride (1.69 mL, 18.2 mmol) was added to a cold (ice bath) DMF (0.60 mL, 7.8 mmol) solution. The mixture was warmed to room temperature and N-(4-bromophenyl)-3-(3-chlorophenyl)propanamide (0.879 g, 2.60 mmol, Intermediate 12: step a) was added. The resulting mixture was heated in an 80° C. oil bath overnight, poured over ice and extracted with $CH_2Cl_2$ (2×). The $CH_2Cl_2$ extracts were dried ($Na_2SO_4$), filtered, evaporated in vacuo and chromatographed (EtOAc/Heptane) to provide the title compound as a white solid.

Intermediate 13

(1-Methyl-1H-imidazol-5-yl)(thiazol-5-yl)methanone

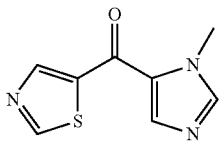

To a solution of 5-bromo-1-methyl-1H-imidazole (1.14 g, 7.11 mmol) in DCM was added ethyl magnesium bromide (2.34 mL, 7.11 mmol; 3.0 M in diethyl ether) dropwise over a 10 minute period. The resulting pale yellow solution was stirred at room temperature for 15 minutes, cooled in an ice bath to 0° C. and N-methoxy-N-methylthiazole-5-carboxamide (1.02 g, 5.92 mmol, Intermediate 11: step a) dissolved in DCM (3 mL) was added dropwise. The cold bath was removed and the reaction mixture stirred at room temperature for 48 hours. To the resulting yellow suspension was added water followed by 6 M aqueous HCl to a neutral pH (pH=6-7). The aqueous mixture was extracted with DCM, dried over $Na_2SO_4$, filtered and concentrated. $Et_2O$ was added and the mixture sonicated. The precipitate was collected by filtration and dried to provide the title compound as a tan solid.

Intermediate 14

3-(4-(1H-Pyrazol-1-yl)benzyl)-6-bromo-4-chloro-N-ethyl-N-methylquinolin-2-amine

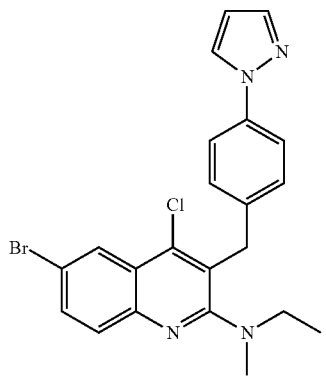 [SMILES: CCN(C)c1nc2ccc(Br)cc2c(Cl)c1Cc1ccc(-n2cccn2)cc1]

A mixture of 3-(4-(1H-pyrazol-1-yl)benzyl)-6-bromo-2,4-dichloroquinoline (Intermediate 6: step c, 0.100 g, 0.231 mmol), N-ethylmethylamine (1.5 mL) and DMF (0.5 mL) were heated in a sealed tube at 80° C. for 8 hours, cooled to room temperature, evaporated in vacuo, diluted with acetonitrile and filtered. The filtrate was evaporated in vacuo and chromatographed (EtOAc/Heptane) to provide the title compound.

Intermediate 15

(6-Methoxypyridin-3-yl)(thiazol-5-yl)methanone

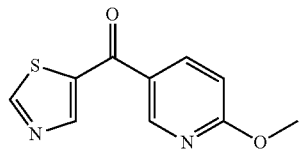

A n-BuLi solution (1.89 mL, 3.03 mmol, 1.6 M solution in hexane) was slowly added to a −78° C. solution of 5-bromo-2-methoxypyridine (0.392 mL, 3.03 mmol) in dry THF (10 mL). After addition, stirring was continued for an additional 40 minutes and N-methoxy-N-methylthiazole-5-carboxamide (0.600 g, 3.48 mmol, Intermediate 11: step a) dissolved in THF (10 mL) was slowly added. The mixture was stirred at −78° C. for 10 minutes then warmed to 0° C. and stirred for 1 hour. The cold solution was quenched with saturated aqueous $NH_4Cl$ and warmed to room temperature. $H_2O$ was added and layers were separated. The aqueous layer was extracted with EtOAc (3×) and the combined organic extracts washed with brine, dried ($Na_2SO_4$), filtered, evaporated in vacuo, preabsorbed onto silica gel and chromatographed ($CH_2Cl_2$/EtOAc) to provide product. The pure white solid title compound was precipitated from MeOH, filtered and dried under reduced pressure.

Intermediate 16

3-(4-(1H-Pyrazol-1-yl)benzyl)-6-bromo-4-chloro-2-methoxyquinoline

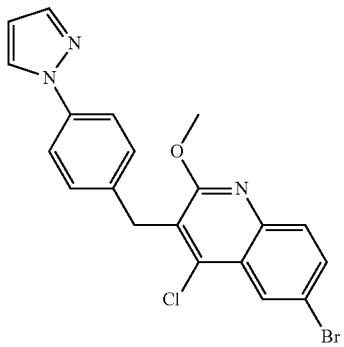 [SMILES: COc1nc2ccc(Br)cc2c(Cl)c1Cc1ccc(-n2cccn2)cc1]

A heterogeneous mixture of 3-(4-(1H-pyrazol-1-yl)benzyl)-6-bromo-2,4-dichloroquinoline (13.0 g, 30.0 mmol, Intermediate 6: step c), sodium methoxide (9.73 g, 180 mmol), and toluene (120 mL) was heated at 110° C. After 5.5 hours, the mixture was cooled to room temperature then filtered through Celite® rinsing with dichloromethane. The filtrate was concentrated to provide a crude yellow solid. The crude solid was purified by flash column chromatography (silica gel, 50% dichloromethane-hexanes initially, grading to 100% dichloromethane) to provide the title compound as a white solid.

Intermediate 17: Step a

N-(4-bromophenyl)-3-(4-methoxyphenyl)propanamide

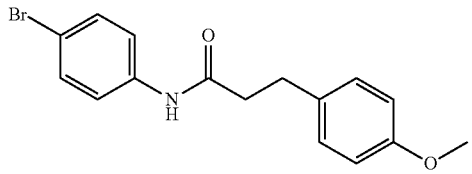 [SMILES: COc1ccc(CCC(=O)Nc2ccc(Br)cc2)cc1]

The title compound was prepared by substituting 3-(3-chlorophenyl)propanoic acid with 3-(4-methoxyphenyl)propanoic acid then following the procedure described in Intermediate 12: step a.

Intermediate 17: Step b

6-Bromo-2-chloro-3-(4-methoxybenzyl)quinoline

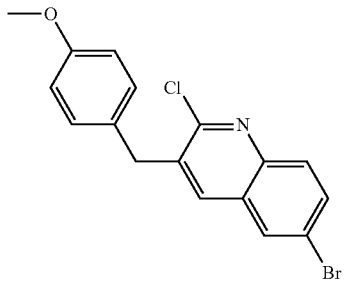 [SMILES: COc1ccc(Cc2cc3cc(Br)ccc3nc2Cl)cc1]

The title compound was prepared by substituting N-(4-bromophenyl)-3-(3-chlorophenyl)propanamide (Intermediate 12: step a) with N-(4-bromophenyl)-3-(4-methoxyphenyl)propanamide (Intermediate 17: step a) then following the procedure described for the preparation of Intermediate 12: step b.

Intermediate 18

(4-(Dimethylamino)phenyl)(1-methyl-1H-imidazol-5-yl)methanone

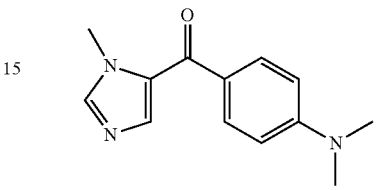

The title compound was prepared by substituting N-methoxy-N-methylthiazole-5-carboxamide (Intermediate 11: step a) with 4-(dimethylamino)-N-methoxy-N-methylbenzamide then following the procedure described for the preparation of (1-methyl-1H-imidazol-5-yl)(thiazol-5-yl)methanone (Intermediate 13).

Intermediate 19: Step a 3-(4-(1H-Pyrazol-1-yl)benzyl)-6-bromo-2,4-dichloro-8-methylquinoline

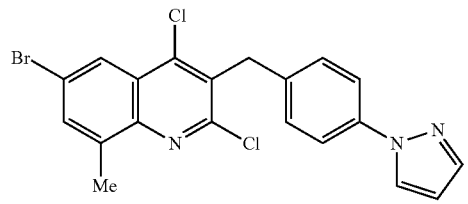 [SMILES: Cc1cc(Br)cc2c(Cl)c(Cc3ccc(-n4cccn4)cc3)c(Cl)nc12]

A mixture of 2-(4-(1H-pyrazol-1-yl)benzyl)malonic acid (20.0 g, 71.5 mmol, Intermediate 6, step b) and 4-bromo-2-methylaniline (13.3 g, 71.5 mmol) in phosphorus oxychloride (66.8 mL, 712 mmol) was heated at 105° C. After 5 hours, the mixture was cooled to room temperature and added to water (600 mL) with cooling so that the internal temperature did not exceed 35° C. The pH of the mixture was adjusted to 8-9 by the slow addition of saturated aqueous ammonia solution such that the internal temperature did not exceed 35° C. After 30 minutes of stirring at room temperature, the mixture was filtered and the solid material was suspended in acetonitrile (200 mL), sonicated and filtered. The solid material was collected and suspended in DCM (80 mL), sonicated and filtered and washed with ether (40 mL). The filtrate was concentrated, suspended in DCM (40 mL), sonicated and filtered to provide more of the desired product. To 5 g of the isolated solid, DCM (300 mL) and aqueous saturated NaHCO$_3$ (100 mL) were added and the mixture was transferred to a separatory funnel, and the layers were separated. The DCM layer was further washed with brine (100 mL), dried (MgSO$_4$), filtered and the solvents were removed under reduced pressure. The crude material was purified using flash-column chromatography on silica gel eluting with DCM to provide 3-(4-(1H-pyrazol-1-yl)benzyl)-6-bromo-2,4-dichloro-8-methylquinoline as an off-white solid.

Intermediate 19: Step b 3-(4-(1H-Pyrazol-1-yl)benzyl)-6-bromo-4-chloro-2-methoxy-8-methylquinoline

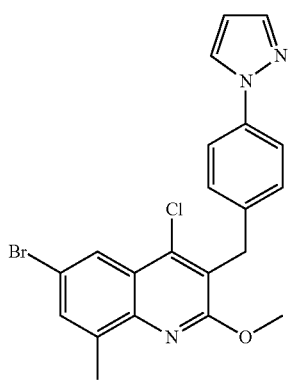 [SMILES: COc1nc2c(C)cc(Br)cc2c(Cl)c1Cc1ccc(-n2cccn2)cc1]

The title compound was prepared by using 3-(4-(1H-pyrazol-1-yl)benzyl)-6-bromo-2,4-dichloro-8-methylquinoline (Intermediate 19: step a) in place of 3-(4-(1H-pyrazol-1-yl)benzyl)-6-bromo-2,4-dichloroquinoline (Intermediate 6: step c) then following the procedure described for the preparation of 3-(4-(1H-pyrazol-1-yl)benzyl)-6-bromo-4-chloro-2-methoxyquinoline (Intermediate 16).

Intermediate 20: Step a

N-Methoxy-N-methyl-4-nitrobenzamide

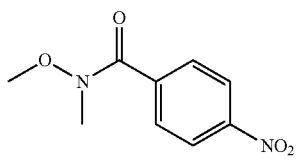

The title compound was prepared by substituting thiazole-5-carboxylic acid with 4-nitrobenzoic acid then following the procedure described for the preparation of N-methoxy-N-methylthiazole-5-carboxamide (Intermediate 11: step a).

Intermediate 20: Step b (1-Methyl-1H-imidazol-5-yl)(4-nitrophenyl)methanone

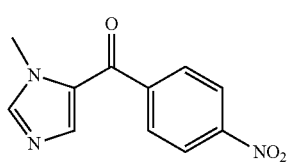

The title compound was prepared by substituting N-methoxy-N-methylthiazole-5-carboxamide (Intermediate 11: step a) with N-methoxy-N-methyl-4-nitrobenzamide (Intermediate 20: step a) then following the procedure described for the preparation of (1-methyl-1H-imidazol-5-yl)(thiazol-5-yl)methanone (Intermediate 13).

Intermediate 20: Step c (4-Aminophenyl)(1-methyl-1H-imidazol-5-yl)methanone

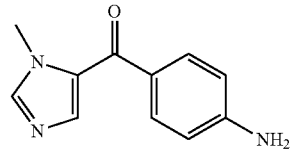

A mixture of (1-methyl-1H-imidazol-5-yl)(4-nitrophenyl)methanone (1.30 g, 5.62 mmol, Intermediate 20, step b) and tin(II)chloride dihydrate (6.54 g, 28.1 mmol) in EtOH (35 mL) was stirred at reflux for 1 hour, cooled to room temperature and evaporated in vacuo to remove most of the EtOH. The residue was poured into a 3 M aqueous NaOH/ice solution rinsing with EtOAc. The mixture was stirred at room temperature for 15 minutes then layers were separated. The aqueous layer was again extracted with EtOAc. The combined EtOAc extracts was washed with brine, dried ($Na_2SO_4$), filtered and evaporated in vacuo to provide the title compound as a yellow solid.

Intermediate 20: Step d (3-(4-(1H-Pyrazol-1-yl)benzyl)-2,4-dichloroquinolin-6-yl)(1-methyl-1H-imidazol-5-yl)methanone

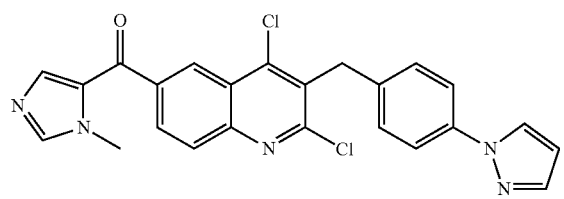 [SMILES: Cn1cncc1C(=O)c1ccc2nc(Cl)c(Cc3ccc(-n4cccn4)cc3)c(Cl)c2c1]

A mixture of (4-aminophenyl)(1-methyl-1H-imidazol-5-yl)methanone (0.160 g, 0.795 mmol, Intermediate 20: step c) and 2-(4-(1H-pyrazol-1-yl)benzyl)malonic acid (0.207 g, 0.795 mmol, Intermediate 6: step b), in $POCl_3$ (3 mL) was heated at 105° C. for 4 hours, cooled to room temperature and concentrated to remove excess $POCl_3$. The residue was poured into ice $H_2O$ and treated with aqueous $NH_4OH$ to pH 8-9 (temperature of the aqueous mixture was kept cold during addition). The aqueous mixture was extracted with DCM (2×). The combined dichloromethane extracts was dried over $Na_2SO_4$, filtered, evaporated to dryness under reduced pressure and chromatographed (0-5% MeOH in $CH_2Cl_2$) to provide the title compound as a yellow solid.

Intermediate 21: Step a (4-Chlorophenyl)(4-nitrophenyl)methanone

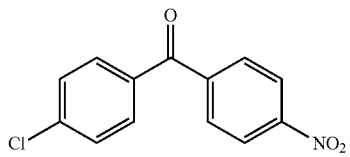

A mixture of (4-chlorophenyl)boronic acid (1.50 g, 9.59 mmol), 4-nitrobenzoyl chloride (1.78 g 9.59 mmol), bis(triphenylphosphine)palladium(II) chloride (0.137 g, 0.192 mmol) and $K_3PO_4$ (3.34 g, 19.2 mmol) in toluene (30 mL) was treated as described in WO 2010/015355 to provide the title compound.

Intermediate 21: Step b (4-Aminophenyl)(4-chlorophenyl)methanone

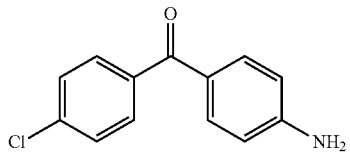 [SMILES: O=C(c1ccc(Cl)cc1)c1ccc([N+](=O)[O-])cc1]

The title compound was prepared by using (4-chlorophenyl)(4-nitrophenyl)methanone, (Intermediate 21: step a) in place of (1-methyl-1H-imidazol-5-yl)(4-nitrophenyl)methanone, (Intermediate 20: step b) then following the procedure described for the preparation of (4-aminophenyl)(1-methyl-1H-imidazol-5-yl)methanone (Intermediate 20: step c).

Intermediate 22: Step a (4-Chlorophenyl)(2,4-dichloro-3-(4-(methylsulfonyl)benzyl)quinolin-6-yl)methanone

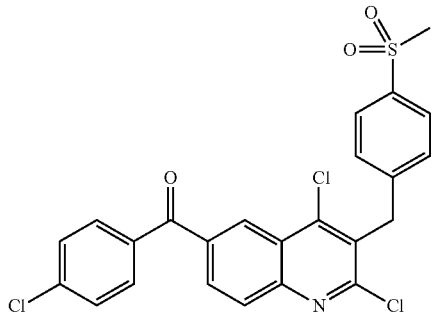 [SMILES: CS(=O)(=O)c1ccc(Cc2c(Cl)nc3ccc(C(=O)c4ccc(Cl)cc4)cc3c2Cl)cc1]

A mixture of (4-aminophenyl)(4-chlorophenyl)methanone (0.351 g, 1.52 mmol, Intermediate 21: step b) and 2-(4-(methylsulfonyl)benzyl)malonic acid (0.413 g, 1.52 mmol, Intermediate 8: step b), in $POCl_3$ (4 mL) was heated at 105° C. for 4 hours, cooled to room temperature and concentrated to remove excess $POCl_3$. The residue was poured into ice $H_2O$ and treated with aqueous $NH_4OH$ to pH 8-9 (temperature of the aqueous mixture was kept cold during addition). The solid precipitates were isolated by filtration rinsing further with $H_2O$ and dried to provide the title compound as a tan solid.

Intermediate 22: Step b (4-Chloro-2-methoxy-3-(4-(methylsulfonyl)benzyl)quinolin-6-yl)(4-chlorophenyl)methanone

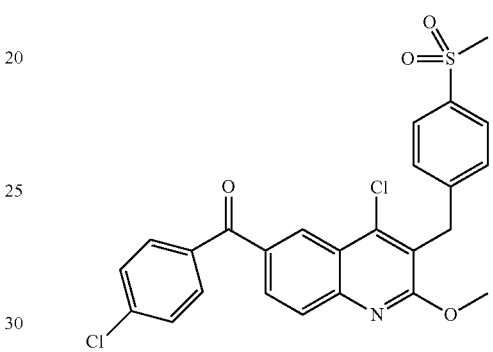

The title compound was prepared by substituting 3-(4-(1H-pyrazol-1-yl)benzyl)-6-bromo-2,4-dichloroquinoline (Intermediate 6: step c) with (4-chlorophenyl)(2,4-dichloro-3-(4-(methylsulfonyl)benzyl)quinolin-6-yl)methanone (Intermediate 22: step a) then following the procedure described for the preparation of 3-(4-(1H-pyrazol-1-yl)benzyl)-6-bromo-4-chloro-2-methoxyquinoline (Intermediate 16).

Intermediate 23

3-(Benzo[b]thiophen-2-ylmethyl)-6-bromo-4-chloro-2-methoxyquinoline

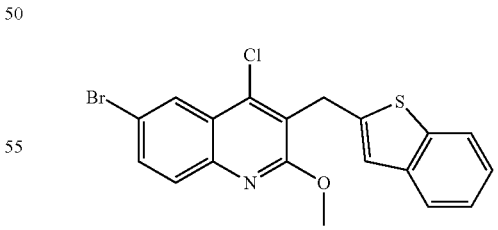

The title compound was prepared by substituting 3-(4-(1H-pyrazol-1-yl)benzyl)-6-bromo-2,4-dichloroquinoline (Intermediate 6: step c) with 3-(benzo[b]thiophen-2-ylmethyl)-6-bromo-2,4-dichloroquinoline (Intermediate 10: step c) then following the procedure described for the preparation of 3-(4-(1H-pyrazol-1-yl)benzyl)-6-bromo-4-chloro-2-methoxyquinoline (Intermediate 16).

Intermediate 24

1-(4-(4-Fluorobenzoyl)piperidin-1-yl)ethanone

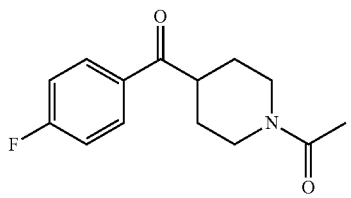 [SMILES: CC(=O)N1CCC(C(=O)c2ccc(F)cc2)CC1]

Acetic anhydride (2.32 g, 24.6 mmol) was added dropwise to a cold (0° C.) solution of (4-fluorophenyl)(piperidin-4-yl)methanone (5.00 g, 20.5 mmol) in DCM (33 mL) and triethylamine (10.0 mL, 71.8 mmol). The resulting mixture was removed from the ice bath after 5 minutes and stirred at room temperature for 2 hours. The reaction was then added to a mixture of 1 M aqueous $K_3PO_4$ (100 mL), $H_2O$, and DCM was added. The layers were separated and the aqueous layer again extracted with DCM. The combined organic layers was dried ($Na_2SO_4$), filtered, concentrated under reduced pressure and chromatographed ($CH_2Cl_2$/EtOAc) to provide the title compound as a clear oil.

Intermediate 25: Step a (1-Methyl-1H-imidazol-5-yl)(pyridin-2-yl)methanol

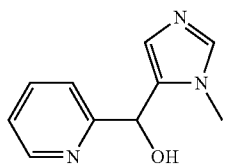

A solution of isopropylmagnesium chloride/lithium chloride complex (1.3 M in THF, 19.5 mL, 25.35 mmol) was added dropwise by syringe to a solution of 5-bromo-1-methyl-1H-imidazole (4.12 g, 25.58 mmol) in dry THF (130 mL) at 0° C. After 15 minutes, the Grignard solution was added via cannulation to a solution of picolinaldehyde (2.0 ml, 20.93 mmol) in dry THF (55 mL) at 0° C. The reaction mixture was stirred for 5 minutes at 0° C., then warmed to room temperature for 1 hour. The reaction mixture was then cooled in an ice bath and quenched with saturated aqueous ammonium chloride. The mixture was partitioned between brine and ethyl acetate. The separated aqueous phase was further extracted with ethyl acetate. The organic phase was dried ($Na_2SO_4$), filtered, and concentrated. The crude product was purified by flash column chromatography (silica gel, 0-5% MeOH-DCM) to provide the title compound as a white solid.

Intermediate 25: Step b (1-Methyl-1H-imidazol-5-yl)(pyridin-2-yl)methanone

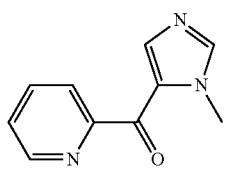

A heterogenous mixture of (1-methyl-1H-imidazol-5-yl)(pyridin-2-yl)methanol (1.41 g, 7.45 mmol, Intermediate 25: step a) and manganese dioxide (3.24 g, 37.27 mmol) in 1,4-dioxane (52 mL) was stirred at 100° C. for 2 hours. The reaction mixture was then cooled to room temperature, filtered through Celite®, washed with DCM, and concentrated to provide the title compound as an off-white solid.

Intermediate 26: Step a

Pyridin-3-yl(4-(trifluoromethyl)phenyl)methanol

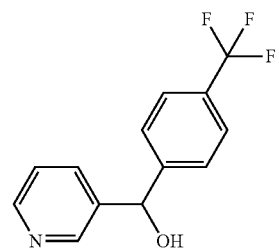 [SMILES: OC(c1ccc(C(F)(F)F)cc1)c1cccnc1]

The title compound was prepared analogously to the method in Intermediate 25: step a using 3-bromopyridine and 4-(trifluoromethyl)benzaldehyde in place of 5-bromo-1-methyl-1H-imidazole and picolinaldehyde, respectively.

Intermediate 26: Step b

Pyridin-3-yl(4-(trifluoromethyl)phenyl)methanone

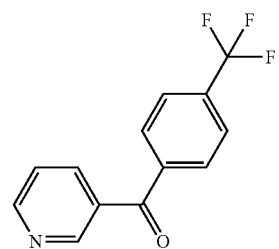 [SMILES: O=C(c1ccc(C(F)(F)F)cc1)c1cccnc1]

The title compound was prepared analogously to the method in Intermediate 25: step b using pyridin-3-yl(4-(trifluoromethyl)phenyl)methanol (Intermediate 26: step a) in place of (1-methyl-1H-imidazol-5-yl)(pyridin-2-yl)methanol.

Intermediate 27: Step a (3,4-Dimethoxyphenyl)(pyridin-3-yl)methanol

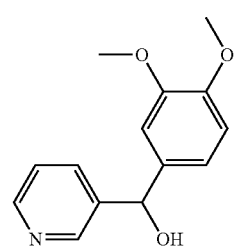 [SMILES: COc1ccc(C(O)c2cccnc2)cc1OC]

(3,4-dimethoxyphenyl)magnesium bromide (0.5 M in THF, 9.5 mL, 4.75 mmol) was added dropwise by syringe to a solution of nicotinaldehyde (0.88 mL, 9.37 mmol) in dry THF (20 mL) at 0° C. The reaction mixture was stirred for 30 minutes at 0° C., then quenched with saturated aqueous ammonium chloride solution. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 0-60% EtOAc-hexanes) to provide the title compound as a brown oil.

Intermediate 27: Step b (3,4-Dimethoxyphenyl)(pyridin-3-yl)methanone

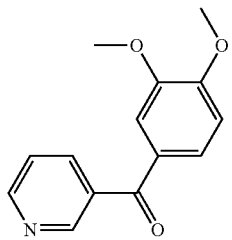 [SMILES: COc1ccc(C(=O)c2cccnc2)cc1OC]

The title compound was prepared analogously to the method in Intermediate 25: step b using (3,4-dimethoxyphenyl)(pyridin-3-yl)methanol (Intermediate 27: step a) in place of (1-methyl-1H-imidazol-5-yl)(pyridin-2-yl)methanol.

Intermediate 28: Step a (4-(Dimethylamino)phenyl)(pyridin-3-yl)methanol

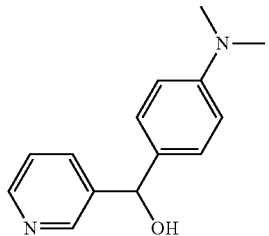 [SMILES: CN(C)c1ccc(C(O)c2cccnc2)cc1]

The title compound was prepared analogously to the method in Intermediate 27: step a using (4-(dimethylamino)phenyl)magnesium bromide in place of (3,4-dimethoxyphenyl)magnesium bromide.

Intermediate 28: Step b (4-(Dimethylamino)phenyl)(pyridin-3-yl)methanone

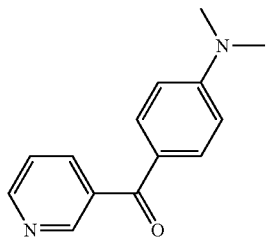 [SMILES: CN(C)c1ccc(C(=O)c2cccnc2)cc1]

The title compound was prepared analogously to the method in Intermediate 25: step b using (4-(dimethylamino)phenyl)(pyridin-3-yl)methanol (Intermediate 28: step a) in place of (1-methyl-1H-imidazol-5-yl)(pyridin-2-yl)methanol.

Intermediate 29: Step a (4-Fluorophenyl)(1-methyl-1H-imidazol-5-yl)methanol

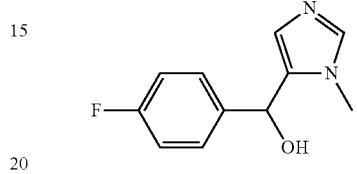

The title compound was prepared analogously to the method in Intermediate 27: step a using (4-fluorophenyl)magnesium bromide and 1-methyl-1H-imidazole-5-carbaldehyde in place of (3,4-dimethoxyphenyl)magnesium bromide and nicotinaldehyde, respectively.

Intermediate 29: Step b (4-Fluorophenyl)(1-methyl-1H-imidazol-5-yl)methanone

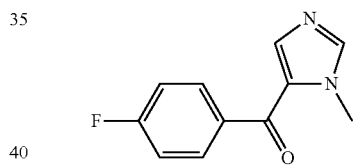

The title compound was prepared analogously to the method in Intermediate 25: step b using (4-fluorophenyl)(1-methyl-1H-imidazol-5-yl)methanol (Intermediate 29: step a) in place of (1-methyl-1H-imidazol-5-yl)(pyridin-2-yl)methanol.

Intermediate 30: Step a (3,4-Dichlorophenyl)(pyridin-3-yl)methanol

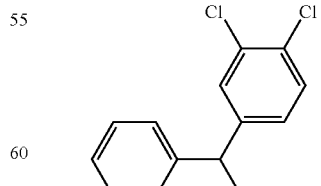

The title compound was prepared analogously to the method in Intermediate 27: step a using (3,4-dichlorophenyl)magnesium bromide in place of (3,4-dimethoxyphenyl)magnesium bromide.

Intermediate 30: Step b (3,4-Dichlorophenyl)(pyridin-3-yl)methanone

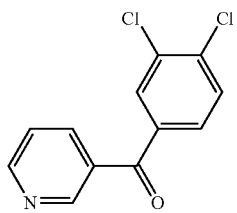 [SMILES: O=C(c1cccnc1)c1ccc(Cl)c(Cl)c1]

The title compound was prepared analogously to the method in Intermediate 25: step b using 3,4-dichlorophenyl)(pyridin-3-yl)methanol (Intermediate 30: step a) in place of (1-methyl-1H-imidazol-5-yl)(pyridin-2-yl)methanol.

Intermediate 31: Step a (4-Methoxyphenyl)(pyridin-3-yl)methanol

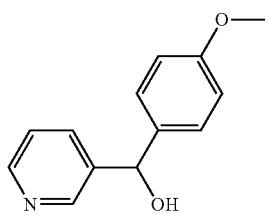 [SMILES: COc1ccc(C(O)c2cccnc2)cc1]

The title compound was prepared analogously to the method in Intermediate 27: step a using (4-methoxyphenyl)magnesium bromide in place of (3,4-dimethoxyphenyl)magnesium bromide.

Intermediate 31: Step b (4-Methoxyphenyl)(pyridin-3-yl)methanone

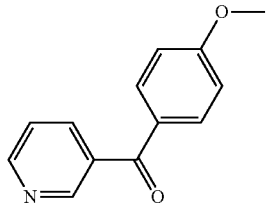 [SMILES: COc1ccc(C(=O)c2cccnc2)cc1]

The title compound was prepared analogously to the method in Intermediate 25: step b using (4-methoxyphenyl)(pyridin-3-yl)methanol (Intermediate 31: step a) in place of (1-methyl-1H-imidazol-5-yl)(pyridin-2-yl)methanol.

Intermediate 32: Step a (3-Fluorophenyl)(pyridin-3-yl)methanol

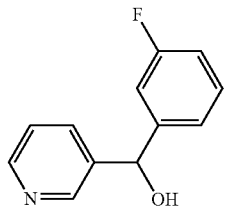 [SMILES: OC(c1cccnc1)c1cccc(F)c1]

The title compound was prepared analogously to the method in Intermediate 27: step a using (3-fluorophenyl)magnesium bromide in place of (3,4-dimethoxyphenyl)magnesium bromide.

Intermediate 32: Step b (3-Fluorophenyl)(pyridin-3-yl)methanone

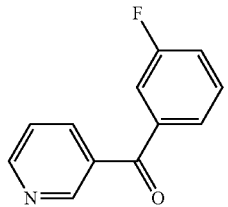 [SMILES: O=C(c1cccnc1)c1cccc(F)c1]

The title compound was prepared analogously to the method in Intermediate 25: step b using (3-fluorophenyl)(pyridin-3-yl)methanol (Intermediate 32: step a) in place of (1-methyl-1H-imidazol-5-yl)(pyridin-2-yl)methanol.

Intermediate 33: Step a

Bis(2,4,6-Trichlorophenyl) 2-benzylmalonate

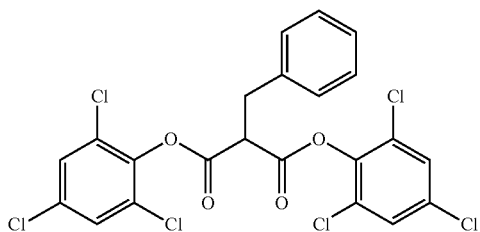 [SMILES: O=C(Oc1c(Cl)cc(Cl)cc1Cl)C(Cc1ccccc1)C(=O)Oc1c(Cl)cc(Cl)cc1Cl]

A mixture of 2-benzylmalonic acid (10.0 g, 51.5 mmol), 2,4,6-trichlorophenol (20.3 g, 103 mmol), and $POCl_3$ (12.0 mL, 129 mmol) was stirred under air at 105° C. for 2 hours. The reaction was then cooled to room temperature, poured on 150 mL ice, and extracted with 4:1 ether/DCM (3×150 mL). The combined organic layers were washed with water (1×400 mL) and 4 M aqueous NaCl (1×100 mL), and the yellow organic layer was dried ($Na_2SO_4$), filtered, and concentrated by rotary evaporation at <40° C. to provide the title compound as a tan thick oil that became a beige solid upon standing.

Intermediate 33: Step b

Ethyl 3-benzyl-4-hydroxy-2-oxo-1,2-dihydroquinoline-6-carboxylate

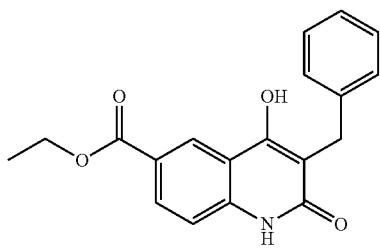 [SMILES: CCOC(=O)c1ccc2[nH]c(=O)c(Cc3ccccc3)c(O)c2c1]

A mixture of ethyl 4-aminobenzoate (2.85 g, 17.2 mmol) and bis(2,4,6-trichlorophenyl) 2-benzylmalonate (11.4 g, 20.7 mmol, Intermediate 33: step a) was microwaved at 250° C. for 15 minutes (Biotage Initiator). The reaction was then allowed to cool to room temperature, and the resulting tan semisolid was dispersed in ether (15 mL) and filtered. The beige filter cake was washed with ether (1×15 mL) and dried at 100° C. to provide the title compound as a light beige powder.

Intermediate 33: Step c

Ethyl 3-benzyl-2,4-dichloroquinoline-6-carboxylate

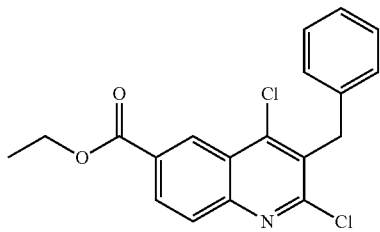 [SMILES: CCOC(=O)c1ccc2nc(Cl)c(Cc3ccccc3)c(Cl)c2c1]

A mixture of ethyl 3-benzyl-4-hydroxy-2-oxo-1,2-dihydroquinoline-6-carboxylate (0.746 g, 2.31 mmol, Intermediate 33: step b) in POCl$_3$ (4.29 mL, 46.1 mmol) was stirred at reflux (130° C. aluminum block temperature) for 30 minutes. The clear yellow solution was cooled to room temperature, diluted with ice (50 mL), and quenched with concentrated aqueous NH$_4$OH (1×12 mL) on ice. The mixture was extracted with DCM (2×50 mL), dried (Na$_2$SO$_4$), filtered, and concentrated to provide the title compound as a yellow solid.

Intermediate 33: Step d (3-Benzyl-2,4-dichloroquinolin-6-yl)(4-chlorophenyl)methanone

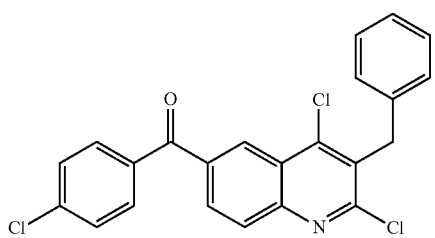 [SMILES: O=C(c1ccc(Cl)cc1)c1ccc2nc(Cl)c(Cc3ccccc3)c(Cl)c2c1]

A solution of 1-chloro-4-iodobenzene (146 mg, 0.611 mmol) in THF (0.8 mL) was added dropwise under argon to a −72° C. solution of n-BuLi (2.59 M in hexane, 0.236 mL, 0.611 mmol) in THF (1.5 mL). The resulting clear yellow solution was stirred at −72° C. for 25 minutes, and was then treated dropwise with a solution of ethyl 3-benzyl-2,4-dichloroquinoline-6-carboxylate (200 mg, 0.555 mmol, Intermediate 33: step c) in THF (0.8 mL). The resulting dark solution was stirred at −72° C. for 30 minutes, and was then allowed to warm to 0° C. over 15 minutes and then quenched with 5 M aqueous NH$_4$Cl (3 mL). The mixture was diluted with diethyl ether (5 mL), and the aqueous layer was extracted with ether (1×5 mL). The combined organic layers were dried (Na$_2$SO$_4$), filtered, and concentrated to provide a residue that was flash chromatographed with a heptane to 30% EtOAc/heptane gradient to provide a ~1:1 mol ratio of the title compound and recovered ethyl 3-benzyl-2,4-dichloroquinoline-6-carboxylate.

Intermediate 34: Step a

Ethyl 3-benzyl-2,4-dibromoquinoline-6-carboxylate

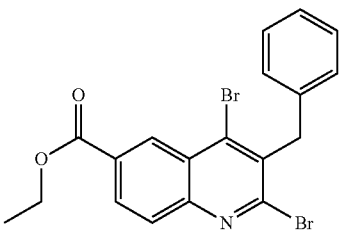 [SMILES: CCOC(=O)c1ccc2nc(Br)c(Cc3ccccc3)c(Br)c2c1]

A mixture of ethyl 3-benzyl-4-hydroxy-2-oxo-1,2-dihydroquinoline-6-carboxylate (0.749 g, 2.32 mmol, Intermediate 33: step b) in POBr$_3$ (13.3 g, 46.3 mmol) was stirred at 130° C. for 30 minutes, and was then allowed to cool to room temperature overnight at which point it solidified. This was partitioned with 50 mL DCM and 50 mL ice, and the aqueous layer was extracted with DCM (1×50 mL). The combined cloudy organic layers were filtered and the clear yellow filtrate was concentrated to provide a yellow solid that was triturated in 50 mL hot toluene. The mixture was allowed to cool to room temperature and filtered to provide the title compound as a beige powder.

Intermediate 34: Step b

Ethyl 3-benzyl-2,4-dimethylquinoline-6-carboxylate

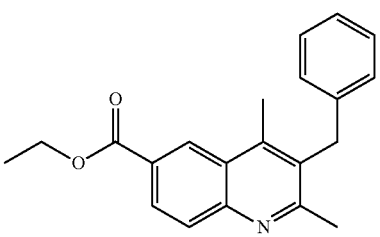 [SMILES: CCOC(=O)c1ccc2nc(C)c(Cc3ccccc3)c(C)c2c1]

A mixture of ethyl 3-benzyl-2,4-dibromoquinoline-6-carboxylate (0.245 g, 0.545 mmol, Intermediate 34: step a), 2,4,6-trimethyl-1,3,5,2,4,6-trioxatriborinane (0.229 mL, 1.64 mmol), and 5 M aqueous $K_2CO_3$ (0.436 mL, 2.18 mmol) was treated with $Pd(PPh_3)_4$ (63 mg, 0.055 mmol) and dioxane (3 mL). This was microwaved under argon at 140° C. for 15 minutes (Biotage Initiator). The reaction was diluted with 1:1 heptane/EtOAc (5 mL), filtered, and the organic layer was dried ($Na_2SO_4$), filtered, and concentrated. The residue was flash chromatographed with a heptane to 70% EtOAc/heptane gradient to provide the title compound as a clear amber oil that crystallized upon standing.

Intermediate 34: Step c

3-Benzyl-N-methoxy-N,2,4-trimethylquinoline-6-carboxamide

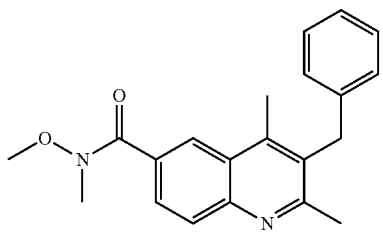 [SMILES: CON(C)C(=O)c1ccc2nc(C)c(Cc3ccccc3)c(C)c2c1]

A slurry of ethyl 3-benzyl-2,4-dimethylquinoline-6-carboxylate (99.5 mg, 0.312 mmol, Intermediate 34: step b) and N,O-dimethylhydroxylamine.HCl (42.2 mg, 0.433 mmol) in THF (1 mL) was stirred at 0° C. under argon while iPrMgCl (2.01 M in THF, 0.43 mL, 0.864 mmol) was added dropwise. The resulting dark solution was stirred at 0° C. overnight while the ice bath expired. It was then quenched with 5 M aqueous $NH_4Cl$ (4 mL) and extracted with EtOAc (2×3 mL). The combined organic layers were dried ($Na_2SO_4$), filtered, and concentrated, and the residue was flash chromatographed with a heptane to 100% EtOAc gradient to yield the title compound as an amber oil.

Intermediate 34: Step d (3-Benzyl-2,4-dimethylquinolin-6-yl)(1-methyl-1H-imidazol-5-yl)methanone

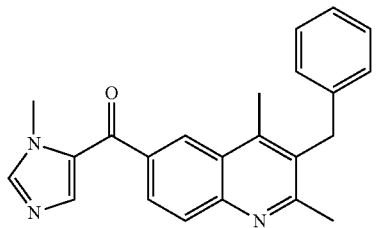 [SMILES: Cc1nc2ccc(C(=O)c3cncn3C)cc2c(C)c1Cc1ccccc1]

A translucent solution of 5-iodo-1-methyl-1H-imidazole (197 mg, 0.946 mmol) in THF (1.5 mL) was stirred at 0° C. while iPrMgCl (2.01 M in THF, 0.43 mL, 0.864 mmol) was added dropwise under argon. The ice bath was immediately removed and the white mixture was stirred at room temperature for 15 minutes, and was then added rapidly dropwise to a solution of 3-benzyl-N-methoxy-N,2,4-trimethylquinoline-6-carboxamide (71.9 mg, 0.215 mmol, Intermediate 34: step c) in THF (0.5 mL) at room temperature. The resulting milky opaque mixture was stirred at room temperature for 1.5 hours, and was then quenched with 1 M aqueous $NaHCO_3$ (6 mL) and extracted with EtOAc (2×6 mL). The combined organic layers were shown by LCMS to be a mixture of title compound and starting material, so the material was concentrated from THF (3×) and re-subjected to the above conditions but with reaction at 50° C. for 2 hours. The reaction was then worked up as described above, and the residue was flash chromatographed with a heptane to 100% EtOAc gradient to provide a 1:4 mol ratio of the title compound and N-methylimidazole.

Intermediate 35: Step a

4-Fluoro-3-iodobenzaldehyde

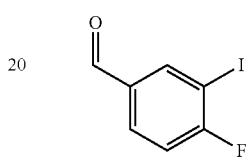

A mixture of $NaIO_4$ (61.6 g, 288 mmol) in $Ac_2O$ (120 mL, 1.27 mol) was treated with KI (63.8 g, 384 mmol) under air at room temperature with overhead stirring, and the resulting tan mixture was stirred on a dry ice-$CH_3CN$ bath while $H_2SO_4$ was added dropwise over 20 minutes, keeping the internal temperature below 20° C. Immediately following completion of $H_2SO_4$ addition, the dark brown reaction was stirred on a room temperature water bath for 5 minutes, and was then treated with 4-fluorobenzaldehyde (59.1 mL, 560 mmol) in one portion over ~30 seconds followed by BHT (617 mg, 2.8 mmol), and the resulting purplish-brown reaction was stirred at room temperature for 21 hours, keeping the internal temp below 30° C. with intermittent ice bath stirring for the first few hours until the mild exotherm had ceased. The resulting light yellow opaque slurry was then stirred on an ice bath and treated with 12 N aqueous HCl (40 mL) rapidly dropwise over 1.5 minutes. After stirring for an additional 5 minutes, the yellow slurry was treated with $CHCl_3$ (200 mL), BHT (600 mg), and ice water (200 mL) and stirred for 5 minutes. The orange mixture was then partitioned with $CHCl_3$ (200 mL) and water (800 mL). The yellow organic layer was washed with water (1×1 L; pH~2) and 2 M aqueous $K_2CO_3$/0.5 M aqueous $Na_2S_2O_3$ (1×500 mL; pH>11), and the clear yellow organic layer was dried ($Na_2SO_4$), filtered, and concentrated by rotary evaporation at room temperature to provide a yellow solid. This was taken up in heptane (250 mL) and concentrated again below 40° C. to the crude title compound as a yellow solid. This was recrystallized from heptane (600 mL) and BHT (600 mg) to provide, after washing the crystalline filter cake with heptane (1×80 mL), the title compound as an off-white powder.

Intermediate 35: Step b 2,2,2-Trifluoro-1-(2-fluoro-5-((4-fluorophenyl)(hydroxy)methyl)phenyl)ethanone

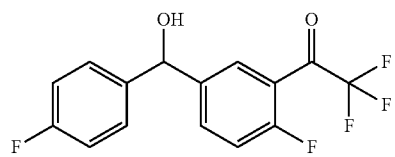 [SMILES: O=C(c1cc(C(O)c2ccc(F)cc2)ccc1F)C(F)(F)F]

A solution of 4-fluorophenylmagnesium bromide (3.64 mL, 1.1 M in THF, 4.0 mmol) in THF (3.6 mL) was stirred on a dry ice/acetone bath under argon while a solution of 4-fluoro-3-iodobenzaldehyde (1.00 g, 4.00 mmol, Intermediate 35: step a) in THF (6.4 mL) was added rapidly dropwise over 1.5 minutes, and the reaction was then immediately transferred to a room temperature water bath and stirred for 5 minutes. The clear, ~colorless reaction was then cooled in the dry ice/acetone bath and treated with iPrMgCl (2.04 mL, 2.06 M in THF, 4.20 mmol) rapidly dropwise over 2.5 minutes. The yellow reaction was stirred for 30 minutes, and was then treated with 2,2,2-trifluoro-N-methoxy-N-methylacetamide dropwise over ~30 seconds. The homogeneous yellow reaction was then immediately removed from the cold bath and allowed to warm to room temperature with stirring. After 2.5 hours, the dark yellow homogeneous reaction was chilled in a dry ice/acetone bath and quenched with 1 M aqueous $NaH_2PO_4$ (10 mL) in one portion. The reaction was warmed to room temperature and extracted with MTBE (1×10 mL, 1×5 mL), and the combined organic layers were washed with 5 M NaCl (1×3 mL), dried ($Na_2SO_4$), filtered, and concentrated twice from DCM to provide the crude title compound as a clear yellow oil.

Intermediate 35: Step c 2,2,2-Trifluoro-1-(2-fluoro-5-(4-fluorobenzoyl)phenyl)ethanone

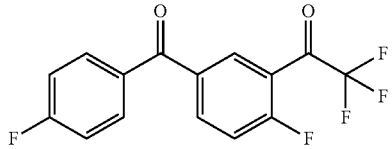 [SMILES: O=C(c1ccc(F)cc1)c1ccc(F)c(C(=O)C(F)(F)F)c1]

A homogeneous yellow solution of crude 2,2,2-trifluoro-1-(2-fluoro-5-((4-fluorophenyl)(hydroxy)methyl)phenyl)ethanone (1.15 g, 3.64 mmol, Intermediate 35: step b) and TEMPO (18.4 mg, 0.118 mmol) in DCM (7.3 mL) was stirred on an ice bath while a solution of aqueous KBr (43 mg, 0.36 mmol) in 1 M aqueous $NaHCO_3$ (1.27 mL, 1.27 mmol) was added in one portion. NaOCl [4.6 mL, 0.89 M (6.15% w/w Clorox bleach), 4.1 mmol] was then added dropwise over 5 minutes to the homogeneous bilayer. After 20 minutes stirring on the ice bath, the clear yellow organic layer was collected, and the aqueous layer extracted with DCM (1×6 mL). The combined organic layers were washed with 5 M aqueous NaCl (1×3 mL), dried ($Na_2SO_4$), filtered, and concentrated to provide the crude title compound as a clear yellow oil.

Intermediate 35: Step d 1-(2-Amino-5-(4-fluorobenzoyl)phenyl)-2,2,2-trifluoroethanone

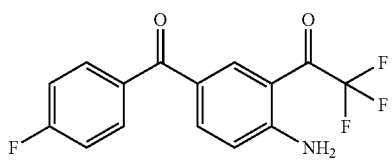 [SMILES: Nc1ccc(C(=O)c2ccc(F)cc2)cc1C(=O)C(F)(F)F]

A solution of crude 2,2,2-trifluoro-1-(2-fluoro-5-(4-fluorobenzoyl)phenyl)ethanone (1.09 g, 3.47 mmol, Intermediate 35: step c) in DMSO (1 mL) was bubbled with $NH_3$ gas for 1 minute in a 200 mL capacity round bottomed pressure flask, and was then sealed under air. The reaction was stirred at 100° C. for 2 hours, and was then allowed to cool to room temperature. The reaction was partitioned between MTBE (6 mL) and 1 M aqueous $NaHCO_3$ (10 mL), the aqueous layer was extracted with MTBE (2×6 mL), and the combined organic layers were dried ($Na_2SO_4$), filtered, concentrated. The residue was flash chromatographed with a heptane to 40% acetone/heptane gradient to provide the title compound as a yellow solid.

Intermediate 35: Step e

N-Methyl-2-(methylimino)-4-phenylbutanamide

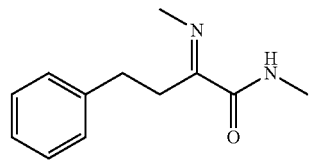

Methylamine (1.9 mL, 7.8 M in EtOH, 15 mmol) was added to ethyl 2-oxo-4-phenylbutanoate (1.02 g, 4.94 mmol) in one portion at room temperature, and upon stirring at room temperature the solution spontaneously warmed and became a solid off-white paste within 10 seconds. After sitting for ~1 minute, the reaction was diluted with ether (10 mL) and filtered. The white filter cake was washed with ether (2×3 mL) and dried under vacuum to provide the title compound as a white solid.

Intermediate 35: Step f

3-Benzyl-6-(4-fluorobenzoyl)-N-methyl-4-(trifluoromethyl)quinoline-2-carboxamide

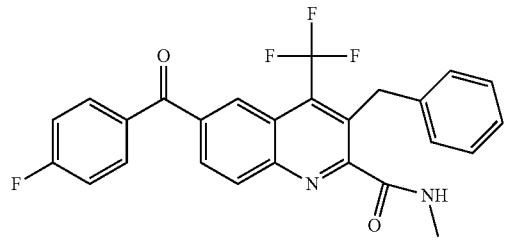 [SMILES: CNC(=O)c1nc2ccc(C(=O)c3ccc(F)cc3)cc2c(C(F)(F)F)c1Cc1ccccc1]

A mixture of 1-(2-amino-5-(4-fluorobenzoyl)phenyl)-2,2,2-trifluoroethanone (107 mg, 0.345 mmol, Intermediate 35: step d), N-methyl-2-(methylimino)-4-phenylbutanamide (85.5 mg, 0.418 mmol, Intermediate 35: step e), and DMSO (0.17 mL) was stirred at 100° C. for ~1 minute to form a clear yellow solution. Benzenesulfonic acid (216 mg, 1.37 mmol) was added at room temperature, and the mixture was stirred at 130° C. for 3 hours. The orange thick solution was cooled to room temperature, partitioned between 2 M aqueous $K_2CO_3$ (3 mL) and EtOAc (4 mL), and the organic layer was washed with 5 M aqueous NaCl (1×4 mL), dried ($Na_2SO_4$), filtered, and concentrated. The residue was flash chromatographed with isocratic DCM followed by a DCM to 40% EtOAc/DCM gradient to provide the title compound as a yellow crystalline solid.

Intermediate 36: Step a 6-(Trifluoromethyl)nicotinoyl chloride

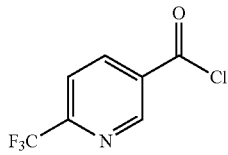

To a 1 L 3-neck flask equipped with an overhead stirrer, Claisen adaptor, nitrogen bubbler, 60 mL addition funnel, and thermocouple was added 6-(trifluoromethyl)nicotinic acid (45 g, 235.5 mmol), dichloromethane (540 mL) and DMF (0.910 mL, 11.77 mmol) via syringe. To this solution was added oxalyl chloride (24.51 mL, 282.56 mmol) and the reaction was allowed to stir at ambient temperature overnight. The reaction was then filtered and the clear filtrate was condensed in vacuo to afford the title compound as a brownish semisolid.

Intermediate 36: Step b

N-Methoxy-N-methyl-6-(trifluoromethyl)nicotinamide

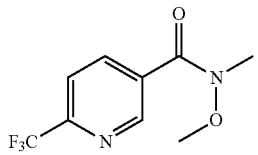 [SMILES: CON(C)C(=O)c1ccc(C(F)(F)F)nc1]

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235.2 mmol, Intermediate 36: step a), dichloromethane (493 mL), and N,O-dimethylhydroxylamine hydrochloride (25.63 g, 258.8 mmol). After the mixture was cooled to 7° C., diisopropylethylamine (90.263 mL, 517.6 mmol) was added such that the addition temperature did not exceed 16° C. After the addition, the reaction was allowed to warm to room temperature. The reaction was then transferred to a separatory funnel and the organic layer was washed with saturated aqueous NaHCO$_3$ (2×100 mL) followed by water (100 mL) and then dried over sodium sulfate, then filtered. Solvent removal afforded the title compound as a brownish oil.

Intermediate 36: Step c (1-Methyl-1H-imidazol-5-yl)(6-(trifluoromethyl)pyridin-3-yl)methanone

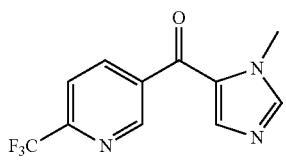 [SMILES: Cn1cncc1C(=O)c1ccc(C(F)(F)F)nc1]

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex [1.3 M in THF] (246.8 mL, 320.8 mmol) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.14 mmol, Intermediate 36: step b) in THF (268.3 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2N aqueous HCl to a pH=7, quenching temperature reached 12° C. The mixture was diluted with ethyl acetate (500 mL), phase split and the organic layer was washed with brine (2×200 mL) and dried over sodium sulfate, filtered, and the solvent was removed. Hot ether was added and then filtered to give the title compound as a solid.

Intermediate 37: Step a

6-Chloropyridine-3-carbonyl chloride

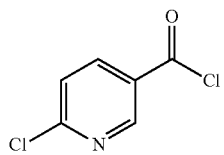

Into a 250-mL round-bottom flask was placed a solution of 6-chloropyridine-3-carboxylic acid (15.8 g, 100.28 mmol) in thionyl chloride (100 mL). The resulting solution was heated to reflux for 5 hours. The resulting mixture was concentrated under vacuum to give the title compound as yellow oil.

Intermediate 37: Step b

6-Chloro-N-methoxy-N-methylpyridine-3-carboxamide

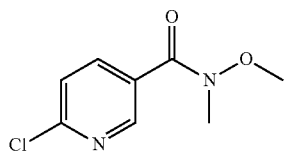

Into a 1000-mL round-bottom flask, was placed methoxy(methyl)amine hydrochloride (12 g, 123.02 mmol), triethylamine (40 g, 395.30 mmol). This was followed by the addition of a solution of 6-chloropyridine-3-carbonyl chloride (17.6 g, 100.00 mmol, Intermediate 37: step a) in dichloromethane (100 mL) dropwise with stirring. The resulting solution was stirred for 12 hours at room temperature. The solids were filtered out. The resulting mixture was concentrated under vacuum to give the title compound as yellow oil.

Intermediate 37: Step c

2-Chloro-5-[(1-methyl-1H-imidazol-5-yl)carbonyl]pyridine

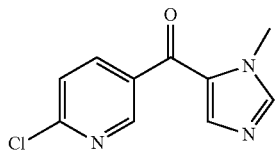

Into a 250-mL 3-necked round-bottom flask, was placed a solution of 1-methyl-1H-imidazole (5 g, 60.90 mmol) in tetrahydrofuran (40 mL). This was followed by the addition of n-BuLi (29.3 mL, 2.5 M in hexanes) at −78° C., then stirred for 45 minutes. To this was added Et$_3$SiCl (9.15 g, 61.00 mmol, 100%), the solution was stirred for 1 hour at −78° C. To the mixture was added n-BuLi (26 mL, 2.5M in hexanes), and stirred for another 45 minutes. To the mixture was added a solution of 6-chloro-N-methoxy-N-methylpyridine-3-carboxamide (8.13 g, 40.52 mmol, 37: step b) in tetrahydrofuran (20 mL) at −78° C. The resulting solution was stirred overnight at room temperature. The pH value of the solution was adjusted to 3-4 with aqueous hydrogen chloride (1 mol/L), then stirred for 2 hours at room temperature. Aqueous sodium hydroxide (1.5 mol/L) was employed to adjust the pH to 9-10. The resulting solution was diluted with 100 mL of H$_2$O. The resulting solution was extracted with 3×100 mL of dichloromethane and the organic layers combined and dried over anhydrous sodium sulfate, filtered, and concentrated under vacuum. The residue was applied onto a silica gel column with dichloromethane/methanol (100:0~15:1) to give the title compound as a yellow solid.

Intermediate 37: Step d (6-Methoxypyridin-3-yl)(1-methyl-1H-imidazol-5-yl)methanone

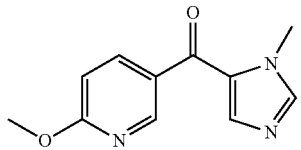 [SMILES: COc1ccc(C(=O)c2cncn2C)cn1]

Into a 50-mL round-bottom flask, was placed a solution of Na (260 mg, 11.30 mmol) in methanol (15 mL), the solution was stirred for 30 minutes at room temperature. Then 2-chloro-5-[(1-methyl-1H-imidazol-5-yl)carbonyl]pyridine (250 mg, 1.13 mmol, Intermediate 37: step c) was added. The resulting solution was stirred for 4 hours at 75° C. in an oil bath. The resulting mixture was concentrated under vacuum. The residue was applied onto a silica gel column with dichloromethane/methanol (100:0-20:1) to give the title compound as a light yellow solid.

Intermediate 38: Step a (2,4-Dichloro-3-(4-(methylsulfonyl)benzyl)quinolin-6-yl)(1-methyl-1H-imidazol-5-yl)methanone

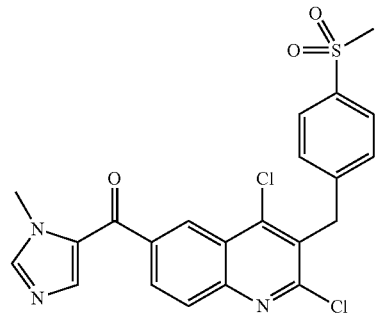 [SMILES: Cn1cncc1C(=O)c1ccc2nc(Cl)c(Cc3ccc(S(C)(=O)=O)cc3)c(Cl)c2c1]

A mixture of (4-aminophenyl)(1-methyl-1H-imidazol-5-yl)methanone (0.80 g, 3.976 mmol, Intermediate 20: step c) and 2-(4-Methylsulfonylbenzyl)malonic acid (1.08 g, 3.976 mmol, Intermediate 8: step b), in POCl$_3$ (10 mL) was heated at 105° C. for 4 hours, cooled to room temperature and concentrated to remove excess POCl$_3$. The residue was poured into ice H$_2$O and treated with aqueous NH$_4$OH to pH 8-9 (temperature of the aqueous mixture was kept cold during addition). The mixture was stirred for 2 hours and filtered to provide a crude brown solid. The crude solids were dried under reduced pressure overnight, rinsed with Et$_2$O and dried. The solids were diluted with DCM and filtered rinsing several times. The filtrate containing the product was evaporated to dryness to provide the title compound which was carried on without further purification.

Intermediate 38: Step b (4-Chloro-2-methoxy-3-(4-(methylsulfonyl)benzyl)quinolin-6-yl)(1-methyl-1H-imidazol-5-yl)methanone

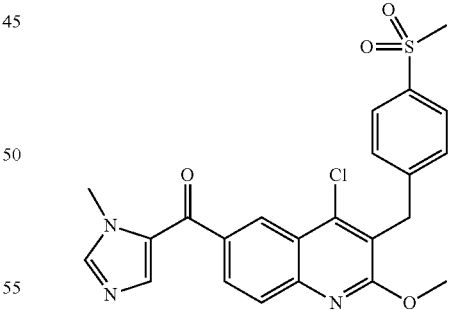

A mixture of (2,4-dichloro-3-(4-(methylsulfonyl)benzyl)quinolin-6-yl)(1-methyl-1H-imidazol-5-yl)methanone (1 g, 2.085 mmol, Intermediate 38: step a) and solid sodium methoxide (0.56 g, 10.42 mmol) in toluene (10 mL) was heated in a sealed tube at 105° C. for 12 hours, cooled to room temperature, diluted with DCM and the resulting suspension filtered through Celite® rinsing several times with CH$_2$Cl$_2$. The solvents were removed under reduced pressure and the residue chromatographed (Heptane/EtOAc) to provide the title compound as a white solid.

Intermediate 39: Step a

N-Methoxy-N,1-dimethyl-1H-imidazole-5-carboxamide

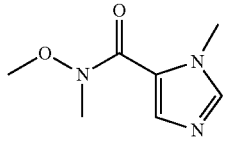

Triethylamine (5.51 mL, 39.646 mmol) was added slowly to a mixture of commercially available 1-methyl-1H-imidazole-5-carboxylic acid (2 g, 15.859 mmol), N,O-dimethylhydroxylamine hydrochloride (1.55 g, 15.859 mmol), and EDCI (3.65 g, 19.03 mmol) in $CH_2Cl_2$ (10 mL). The mixture was stirred at room temperature for 72 hours then quenched with saturated aqueous $NaHCO_3$. Water (50 mL) was added followed by additional $CH_2Cl_2$. The mixture was stirred for 10 minutes and layers were separated. The $CH_2Cl_2$ layer was dried over $Na_2SO_4$, then filtered. The solvent was removed under reduced pressure and the residual oil chromatographed ($CH_2Cl_2$/EtOAc) to provide the product as a solid.

Intermediate 39: Step b

Bis(1-methyl-1H-imidazol-5-yl)methanone

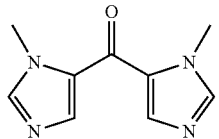

To a solution of 5-bromo-1-methyl-1H-imidazole (1.2 g, 7.448 mmol) in DCM (10 mL) was added ethyl magnesium bromide (2.5 mL, 7.448 mmol; 3.0 M in diethyl ether) dropwise over a 10 minute period. The resulting pale yellow solution was stirred at room temperature for 15 minutes, cooled in an ice bath to 0° C. and N-methoxy-N,1-dimethyl-1H-imidazole-5-carboxamide (1.0 g, 6.206 mmol, Intermediate 39: step a) dissolved in DCM (3 mL) was added dropwise. The cold bath was removed and the reaction mixture stirred at room temperature for 48 hours. To the resulting yellow suspension was added water followed by 6 M aqueous HCl to a neutral pH (pH=6-7). The aqueous mixture was extracted with DCM (2×). The combined DCM extracts were dried over $MgSO_4$, filtered and concentrated under reduced pressure. The product was precipitated with $Et_2O$, filtered and dried to provide the title compound as a tan solid.

Intermediate 40: Step a

N-Methoxy-N,3-dimethyl-4-nitrobenzamide

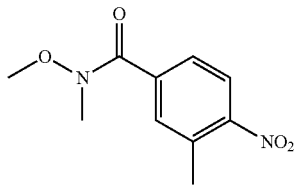 [SMILES: CON(C)C(=O)c1ccc([N+](=O)[O-])c(C)c1]

Triethylamine (7.6 mL, 54.651 mmol) was added slowly to a mixture of 3-methyl-4-nitrobenzoic acid (5 g, 27.326 mmol), N,O-dimethylhydroxylamine hydrochloride (2.99 g, 30.058 mmol), and EDCI (6.28 g, 32.791 mmol) in DCM (30 mL). The mixture was stirred at room temperature overnight, quenched with saturated aqueous $NaHCO_3$ and stirred at room temperature for 30 minutes. Water (50 mL) was added followed by additional DCM. The mixture was stirred for 10 minutes and layers were separated. The aqueous layer was again extracted with DCM. The combined organic layer was dried over $Na_2SO_4$, then filtered. The solvent was removed and the residual oil chromatographed (DCM/EtOAc) to provide the product as a white solid.

Intermediate 40: Step b (1-Methyl-1H-imidazol-5-yl)(3-methyl-4-nitrophenyl)methanone

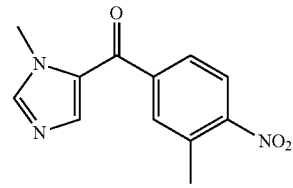 [SMILES: Cc1cc(C(=O)c2cncn2C)ccc1[N+](=O)[O-]]

A solution of EtMgBr (3.0 M in diethylether, 8.5 mL, 25.689 mmol) was added dropwise, over a 25 minutes period, to a solution of 5-bromo-1-methyl-1H-imidazole (4.1 g, 25.689 mmol) in dry DCM (25 mL). The mixture was stirred at room temperature for 15 minutes, cooled in an ice-brine bath and N-methoxy-N,3-dimethyl-4-nitrobenzamide (4.8 g, 21.408 mmol, Intermediate 40: step a) dissolved in 10 mL of DCM was added dropwise. A dark brown solid mass formed. The ice bath was removed and mixture stirred at room temperature for 48 hours. Water was added to the suspension followed by 6M aqueous HCl slowly to neutralize the mixture (pH=6-7). More DCM was added and layers separated. The organic layer was dried over $Na_2SO_4$, filtered and concentrated. $Et_2O$ was added, the slurry sonicated, and precipitates filtered to provide the title compound as a tan solid.

Intermediate 40: Step c (4-Amino-3-methylphenyl)(1-methyl-1H-imidazol-5-yl)methanone

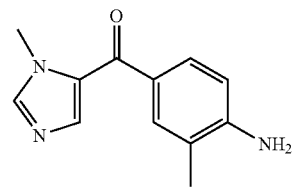

A mixture of (1-methyl-1H-imidazol-5-yl)(3-methyl-4-nitrophenyl)methanone (3.3 g, 13.456 mmol, Intermediate 40: step b) and tin(II)chloride dihydrate (15.6 g, 67.282 mmol) in EtOH (80 mL) was stirred at reflux for 1 hour, cooled to room temperature overnight and evaporated in vacuo to remove most of the EtOH. The residue was poured into a 3M aqueous NaOH/ice solution rinsing with EtOAc. The mixture was stirred at room temperature for 15 minutes and layers were separated. The aqueous layer was again extracted with EtOAc. The combined EtOAc extracts were washed with brine, dried ($Na_2SO_4$), filtered, and evaporated in vacuo to provide crude product. The tan solid title compound was precipitated from $Et_2O$, collected by filtration and dried.

Intermediate 40: Step d (2,4-Dichloro-8-methyl-3-(4-(methylsulfonyl)benzyl)quinolin-6-yl)(1-methyl-1H-imidazol-5-yl)methanone

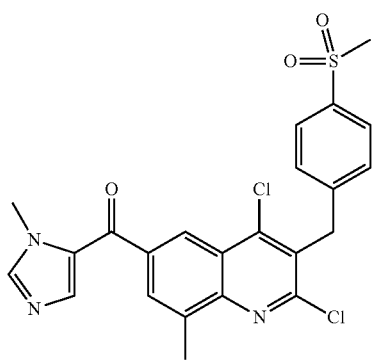 [SMILES: Cc1cc(C(=O)c2cncn2C)cc2c(Cl)c(Cc3ccc(S(C)(=O)=O)cc3)c(Cl)nc12]

A heterogeneous mixture of (4-amino-3-methylphenyl)(1-methyl-1H-imidazol-5-yl)methanone (0.8 g, 3.717 mmol, Intermediate 40: step c), 2-(4-methylsulfonylbenzyl)malonic acid (1.0 g, 3.717 mmol, Intermediate 8: step b) and POCl₃ (10 mL) was heated at 105° C. for 4 hours, cooled to room temperature, concentrated, ice water was added and mixture treated with aqueous NH₄OH (kept adding ice during addition) to a basic pH 8-9. The mixture was stirred for 2 hours and filtered to provide a crude tan solid. The crude solids were dried completely, rinsed with Et₂O and dried under reduced pressure. The solids were diluted with DCM and filtered rinsing several times. The filtrate was evaporated to dryness and the tan solid product precipitated with MeOH, filtered and dried.

Intermediate 40: Step e (4-Chloro-2-methoxy-8-methyl-3-(4-(methylsulfonyl)benzyl)quinolin-6-yl)(1-methyl-1H-imidazol-5-yl)methanone

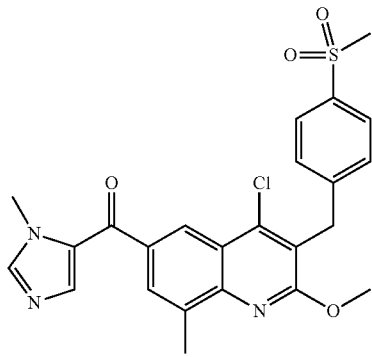 [SMILES: COc1nc2c(C)cc(C(=O)c3cncn3C)cc2c(Cl)c1Cc1ccc(S(C)(=O)=O)cc1]

A mixture of (2,4-dichloro-8-methyl-3-(4-(methylsulfonyl)benzyl)quinolin-6-yl)(1-methyl-1H-imidazol-5-yl)methanone (1.1 g, 2.15 mmol, Intermediate 40: step d) and dry sodium methoxide (0.58 g, 10.75 mmol) in toluene was heated in a sealed tube at 110° C. for 12 hours, cooled to room temperature, diluted with DCM, stirred for 30 minutes at room temperature and the resulting suspension filtered through Celite® rinsing several times with DCM. The solvents were removed under reduced pressure and the residue chromatographed (10% MeOH in DCM, gradient) to provide the title compound as a white solid after recrystallization from MeOH and drying under reduced pressure overnight.

Intermediate 41: Step a 3-(4-(1H-Pyrazol-1-yl)benzyl)-6-bromo-2,4-dichloro-8-fluoroquinoline

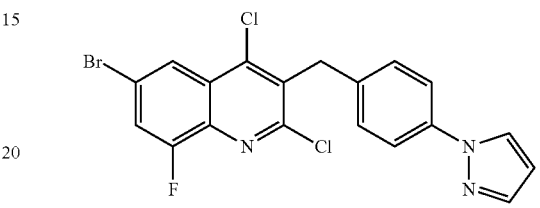

A mixture of 2-(4-(1H-pyrazol-1-yl)benzyl)malonic acid (4 g, 15.37 mmol, Intermediate 6: step b) and 4-bromo-2-fluoroaniline (2.7 g, 13.973 mmol) in POCl₃ (20 mL) was heated at 105° C. for 3 hours, cooled to room temperature and evaporated in vacuo to remove excess POCl₃. The residue was poured into ice H₂O and treated with aqueous NH₄OH to pH 8-9 (temperature of the aqueous mixture was kept cold during addition). The precipitates were collected, rinsed with H₂O and dried under reduced pressure. The solids were diluted with DCM and insoluble solids filtered off. The filtrate was evaporated to dryness to provide product as a tan solid.

Intermediate 41: Step b 3-(4-(1H-Pyrazol-1-yl)benzyl)-6-bromo-4-chloro-8-fluoro-2-methoxyquinoline and 3-(4-(1H-Pyrazol-1-yl)benzyl)-6-bromo-4-chloro-2,8-dimethoxyquinoline

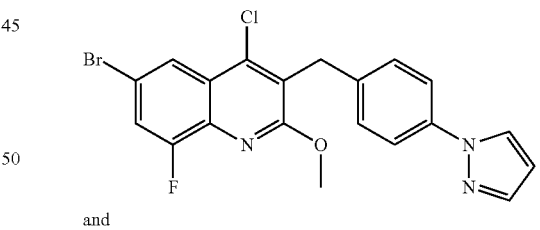

and

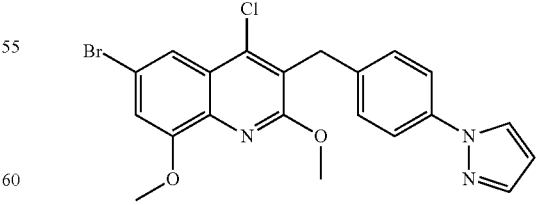

A mixture of 3-(4-(1H-pyrazol-1-yl)benzyl)-6-bromo-2,4-dichloro-8-fluoroquinoline (1.25 g, 2.771 mmol, Intermediate 41: step a) and dry sodium methoxide in toluene was heated in a sealed round bottom flask at 108-110° C. for 12 hours and the reaction was cooled to room temperature. DCM was added and the reaction mixture was filtered through Celite® rinsing several times with DCM. The filtrate was evaporated in vacuo, diluted with MeOH and filtered to provide a mixture of products (~1:9 ratio) as an off-white solid. Product mixture carried on without further purification.

Intermediate 42: Step a tert-Butyl 4-(hydroxy(1-methyl-1H-imidazol-5-yl) methyl)piperidine-1-carboxylate

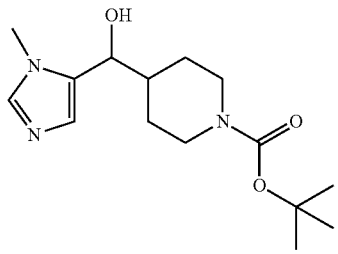 [SMILES: Cn1cncc1C(O)C1CCN(C(=O)OC(C)(C)C)CC1]

A solution of 5-bromo-1-methyl-1H-imidazole (25.0 g, 155 mmol; dried over 3 Å molecular sieves, then filtered) in DCM (310 mL) was stirred on an ice bath while iPrMgCl (72 mL, 2.01 M solution in THF, 145 mmol) was added rapidly dropwise under argon via pressure-equalizing addition funnel. Residual iPrMgCl was rinsed down with 50 mL THF, and the ice bath was removed and the reaction stirred for 25 minutes. A solution of tert-butyl 4-formylpiperidine-1-carboxylate (27.6 g, 130 mmol) (PharmaCore) in THF (65 mL) was added dropwise over ~5 minutes via pressure-equalizing addition funnel at room temperature. After stirring 1 hour at room temperature, the yellow mixture was quenched with 5 M aqueous NH$_4$Cl (250 mL) in one portion. The organic layer was dried (Na$_2$SO$_4$), filtered, and concentrated to provide the crude title compound as a clear light amber oil.

Intermediate 42: Step b tert-Butyl 4-(1-methyl-1H-imidazole-5-carbonyl) piperidine-1-carboxylate

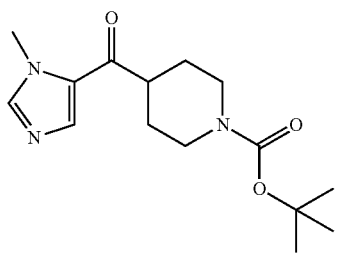 [SMILES: Cn1cncc1C(=O)C1CCN(C(=O)OC(C)(C)C)CC1]

A homogeneous solution of tert-butyl 4-(hydroxy(1-methyl-1H-imidazol-5-yl)methyl)piperidine-1-carboxylate (32.2 g, 109 mmol; Intermediate 42, step a) in dioxane (436 mL) was treated with MnO$_2$ (47.6 g, 547 mmol) and stirred at 100° C. under air overnight (17 hours). Since the reaction was only ~50% complete by NMR, the reaction was cooled to room temperature and additional MnO$_2$ was added (48.0 g, 552 mmol) and the reaction stirred under air at 100-° C. for 6.5 hours, then at room temperature for 18 days, then filtered through a pad of Celite® and the black filter cake washed with EtOAc. The crude filtrate was treated with a third portion of MnO$_2$ (28.5 g, 327 mmol) and stirred at room temperature overnight. The reaction was then filtered as above and concentrated to provide the crude title compound as a clear dark yellow oil. This was flash chromatographed with an EtOAc to 50% acetone/EtOAc gradient to provide the title compound as a clear dark yellow oil.

Intermediate 42: Step c 1-(4-(1-Methyl-1H-imidazole-5-carbonyl)piperidin-1-yl)ethanone

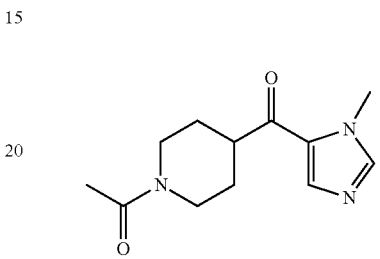

A homogeneous yellow solution of tert-butyl 4-(1-methyl-1H-imidazole-5-carbonyl)piperidine-1-carboxylate (10.1 g, 34.4 mmol; Intermediate 42, step b) in DCM (172 mL) was treated with TFA (26.4 mL, 344 mmol) and stirred at room temperature for 2.5 hours. The reaction was concentrated from toluene (2×100 mL), and the resulting clear light amber residue was taken up in DCM (344 mL) and TEA (23.9 mL, 172 mmol). Acetic anhydride (3.91 mL, 41.3 mmol) was added dropwise and the reaction stirred at room temperature for 1 hour. The reaction was concentrated under high vacuum and the residue flash chromatographed using 95:5 DCM/MeOH with 2% TEA as eluent. The combined fractions were concentrated, dissolved in DCM (200 mL), and washed with water (2×200 mL) to remove TEA. The organic layer was dried (Na$_2$SO$_4$), filtered, and concentrated, and the residue was triturated with MTBE (75 mL) at reflux for 15 minutes and then allowed to cool to room temperature. The mixture was filtered and the off-white filter cake was washed with MTBE (2×3 mL) to provide, after air drying at 100° C., the title compound as an off-white fine powder.

Intermediate 43

Bis(1-Methyl-1H-1,2,3-triazol-5-yl)methanone

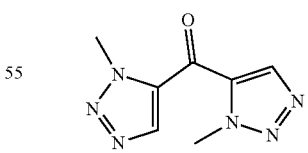

A solution of 1-methyl-1H-1,2,3-triazole (0.954 g, 11.4 mmol, prepared according to PCT Int. Appl., 2008098104) in THF (22 mL) was stirred at ~−70° C. under argon while n-BuLi (2.56 M in hexanes; 4.29 mL, 11.0 mmol) was added dropwise over 5 minutes. After stirring for another 5 minutes, a solution of ethyl methoxy(methyl)carbamate (0.665 g, 4.99 mmol) (Aldrich) in THF (3 mL) was added dropwise over 5 minutes. After stirring at ~−70° C. for an additional 5 minutes, the cold bath was removed and the light slurry was allowed to warm to room temperature with stirring for 1 hour 20 minutes. The reaction was then quenched at room temperature with 5 M aqueous NH₄Cl (3 mL) and the aqueous layer was extracted with THF (1×6 mL). The combined organic layers were dried (Na₂SO₄), filtered, and concentrated. A portion of the residue was crystallized from ~30 mL toluene to provide, after washing the filter cake with ether (1×3 mL) and heptane (1×3 mL), the title compound as blunt needles.

Intermediate 44: Step a

6-Bromo-4-hydroxyquinolin-2(1H)-one

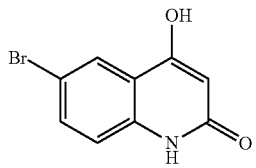

According to the general method described in Synthetic Communications 2010, 40, 732, a mixture of 4-bromoaniline (30.0 g, 174 mmol) and 2,2-dimethyl-1,3-dioxan-4,6-dione (25.1 g, 174 mmol) was heated to 80° C. for 1.5 hours and cooled to ambient temperature to receive 3-((4-bromophenyl)amino)-3-oxopropanoic acid. Acetone byproduct was removed under vacuum to provide the intermediate product as a dry solid. Eaton's reagent (100 mL) was added to the solid, then heated to 70° C. overnight and cooled to room temperature. The mixture was poured into water and the brown precipitate was filtered and rinsed with water. The brown precipitate was triturated with ethanol, then filtered to provide the title compound as a light brown solid.

Intermediate 44: Step b

6-Bromo-2,4-dichloroquinoline

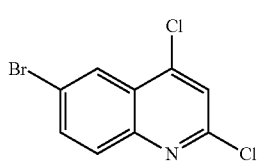 [SMILES: Clc1cc(Cl)c2cc(Br)ccc2n1]

A solution of 6-bromo-4-hydroxyquinolin-2(1H)-one (18.0 g, 75.1 mmol, Intermediate 44: step a) and POCl₃ (84 mL) was heated at 105° C. overnight. The solution was cooled to room temperature, then slowly poured portion-wise into a water bath, adding ice as needed to regulate the exotherm. Concentrated aqueous ammonium hydroxide was added to basify the mixture to pH 9-10. The solids that precipitated were filtered, rinsed with water and dried to provide the title compound as a brown solid.

Intermediate 44: Step c 4-((6-Bromo-2,4-dichloroquinolin-3-yl)methyl)benzonitrile

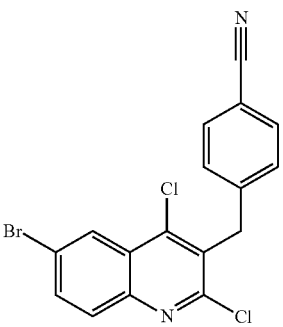 [SMILES: N#Cc1ccc(Cc2c(Cl)nc3ccc(Br)cc3c2Cl)cc1]

To a solution of diisopropylamine (1.40 mL, 9.96 mmol) in THF (12 mL) cooled to 0° C. was added n-butyllithium (2.5 M solution in hexanes, 3.80 mL, 9.50 mmol) dropwise via syringe. The reaction mixture was stirred at 0° C. for 10 minutes then cooled to −78° C. at which time a separate solution of 6-bromo-2,4-dichloroquinoline (1.80 g, 6.51 mmol, Intermediate 44: step b) in THF (29 mL) was added dropwise via syringe. The mixture was stirred at −78° C. for 30 minutes followed by the addition of 4-(bromomethyl)benzonitrile (1.52 g, 7.74 mmol) in THF (5 mL). After an additional 10 minutes of stirring at −78° C., the reaction was transferred to an ice bath and warmed to ambient temperature over 5 hours. The reaction was quenched with water and the aqueous phase was extracted with DCM. The organic phase was dried (Na₂SO₄), filtered, and concentrated. The crude product was purified by flash column chromatography (silica gel, 0-5% EtOAc-Hexanes) to provide the title compound as a white solid.

Intermediate 44: Step d 4-((6-Bromo-4-chloro-2-methoxyquinolin-3-yl)methyl)benzonitrile

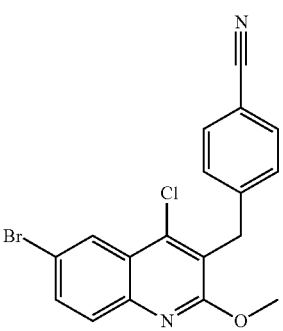 [SMILES: COc1nc2ccc(Br)cc2c(Cl)c1Cc1ccc(C#N)cc1]

A heterogeneous mixture of 4-((6-bromo-2,4-dichloroquinolin-3-yl)methyl)benzonitrile (650 mg, 1.16 mmol, Intermediate 44: step c) and sodium methoxide (314 mg, 5.81 mmol) in dry toluene (2.2 mL) was heated at 105° C. After 9 hours, the mixture was cooled to ambient temperature and filtered through Celite®, rinsing with DCM. The filtrate was concentrated and the crude was purified by flash column chromatography (silica gel, 0-5% EtOAc-Hexanes) to provide the title compound as a white solid.

Intermediate 45: Step a 4-(1H-1,2,4-Triazol-1-yl)benzaldehyde

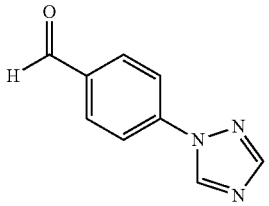 [SMILES: O=Cc1ccc(-n2cncn2)cc1]

4-Fluorobenzaldehyde (12.0 mL, 112 mmol) was added dropwise by syringe to a stirring, heterogeneous mixture of 1,2,4-triazole (11.6 g, 168 mmol) and potassium carbonate (24.7 g, 179 mmol) in dimethyl formamide (220 mL) at 23° C. The mixture was heated to 105° C. After 3.5 hours, the mixture was allowed to cool to 23° C. The cooled solution was transferred to a 2 L Erlenmeyer flask and diluted with water (500 mL) and ethyl acetate (1200 mL). The biphasic mixture was stirred until the layers cleanly separated. The layers were separated. The organic layer was washed with half-saturated aqueous sodium chloride solution (3×100 mL). The washed solution was dried with sodium sulfate, and the dried solution was filtered. The filtrate was concentrated to provide an off-white solid. The solid was suspended in a mixture of heptanes and isopropyl acetate (5:1, 600 mL). The mixture was filtered and the filter cake was washed with heptanes-isopropyl acetate (5:1). The solids were collected and dried under vacuum to afford the titled compound as a white solid.

Intermediate 45: Step b 5-(4-(1H-1,2,4-triazol-1-yl)benzyl)-2,2-dimethyl-1,3-dioxane-4,6-dione

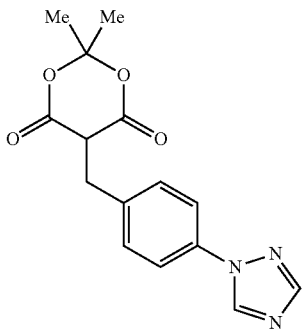 [SMILES: CC1(C)OC(=O)C(Cc2ccc(-n3cncn3)cc2)C(=O)O1]

L-Proline (1.81 g, 15.6 mmol) was added to a stirring, heterogeneous mixture of 4-(1H-1,2,4-triazol-1-yl)benzaldehyde (13.5 g, 78.0 mmol, Intermediate 45, step a) and 2,2-dimethyl-1,3-dioxane-4,6-dione (11.2 g, 78.0 mmol) in ethanol (520 mL) at 23° C. After 1.5 hours, diethyl 1,4-dihydro-2,6-dimethyl-3,5-pyridinedicarboxylate (19.7 g, 78.0 mmol) was added in one portion. After 16 hours, the ethanol was removed by rotary evaporation at 35° C. to afford a yellow solid. Isopropanol (300 mL) was added and the heterogeneous mixture was stirred for 10 minutes at 23° C. The mixture was filtered and the filter cake was washed with isopropanol (150 mL). The solids were collected and dried under vacuum to provide the titled compound as a white solid.

Intermediate 45: Step c 2-(4-(1H-1,2,4-triazol-1-yl)benzyl)malonic acid

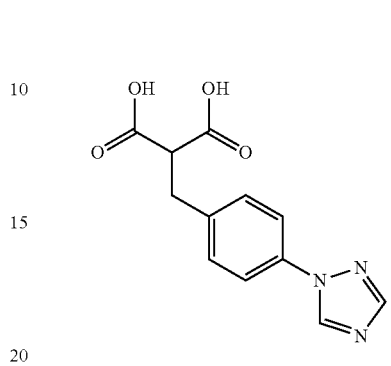

5-(4-(1H-1,2,4-triazol-1-yl)benzyl)-2,2-dimethyl-1,3-dioxane-4,6-dione (10.0 g, 33.2 mmol, Intermediate 45, step b) was dissolved in a mixture of water (30 mL) and trifluoroacetic acid (50 mL). The mixture was heated to 65° C. After 2.5 hours, the mixture was allowed to cool to 23° C. Water and trifluoroacetic acid were removed by rotary evaporation at 45° C. Toluene (100 mL) was added to the residue then the mixture was concentrated by rotary evaporation at 45° C. Tetrahydrofuran (100 mL) and 6 M aqueous hydrochloric acid solution (28 mL) was added to the residue in sequence. The resulting heterogeneous mixture was stirred at 23° C. After 10 minutes, the mixture was concentrated by rotary evaporation at 45° C. Tetrahydrofuran (100 mL) was added to the residue and the mixture concentrated by rotary evaporation at 45° C. Toluene (100 mL) was added to the residue and the mixture concentrated by rotary evaporation at 45° C. The resulting white solid was dried under vacuum at 40° C. The solid product was used directly in the next step without further purification.

Intermediate 45: Step d (3-(4-(1H-1,2,4-Triazol-1-yl)benzyl)-2,4-dichloroquinolin-6-yl)(4-chlorophenyl)methanone

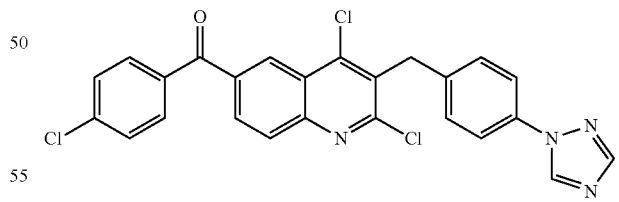

A mixture of 2-(4-(1H-1,2,4-triazol-1-yl)benzyl)malonic acid (1.50 g, 5.74 mmol, Intermediate 45, step c) and (4-aminophenyl)(4-chlorophenyl)methanone (1.0 g, 4.32 mmol, Intermediate 21: step b) in phosphorus oxychloride (16 mL) was heated at 95° C. After 16 hours, the mixture was cooled to 23° C. then diluted with dichloromethane (50 mL). The mixture was concentrated by rotary evaporation at 33° C. The resulting orange oil was dissolved in 100 mL dichloromethane then added slowly to ice water (100 mL) with vigorous stirring. The pH was adjusted to 8 by the slow addition of saturated aqueous ammonia solution. The layers were separated. The aqueous layer was extracted with dichloromethane (30 mL). The organic layers were combined and the combined solution was dried over sodium sulfate. The dried solution was filtered and the filtrate was absorbed onto 5 g of silica gel for dry-load flash-column chromatography eluting with 100% hexanes initially, grading to 80% ethyl acetate-hexanes over 30 minutes to provide the titled compound as a yellow solid.

Intermediate 45: Step e (3-(4-(1H-1,2,4-Triazol-1-yl)benzyl)-4-chloro-2-methoxyquinolin-6-yl)(4-chlorophenyl)methanone

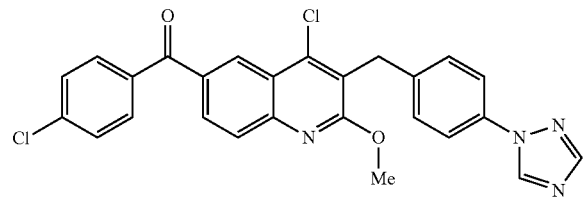 [SMILES: COc1nc2ccc(C(=O)c3ccc(Cl)cc3)cc2c(Cl)c1Cc1ccc(-n2cncn2)cc1]

A heterogeneous mixture of (3-(4-(1H-1,2,4-triazol-1-yl)benzyl)-2,4-dichloroquinolin-6-yl)(4-chlorophenyl)methanone (370 mg, 0.749 mmol, Intermediate 45, step d) and sodium methoxide (405 mg, 7.49 mmol) in toluene (3.7 mL) was heated at 110° C. After 30 minutes, the mixture was cooled to 23° C. and then filtered through Celite® rinsing with dichloromethane. The filtrate was absorbed onto 5 g of silica gel for dry-load flash-column chromatography on silica gel eluting with 30% ethyl acetate-hexanes initially, grading to 80% ethyl acetate-hexanes over 20 minutes to provide the titled compound as an off-white solid.

Intermediate 46

3-(4-(1H-Pyrazol-1-yl)benzyl)-6-bromo-4-chloro-N,N-diethylquinolin-2-amine

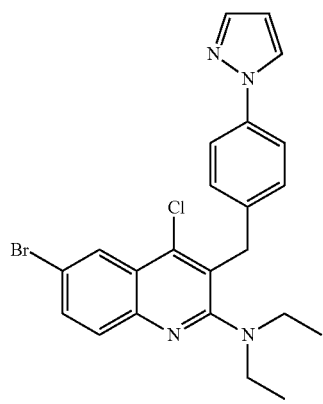 [SMILES: CCN(CC)c1nc2ccc(Br)cc2c(Cl)c1Cc1ccc(-n2cccn2)cc1]

A mixture of 3-(4-(1H-pyrazol-1-yl)benzyl)-6-bromo-2,4-dichloroquinoline (1.44 g, 3.33 mmol, Intermediate 6, step c) and diethylamine (6.91 mL, 66.5 mmol) in DMF (10 mL) in a sealed tube was heated in a 115° C. oil bath for 23 hours. The mixture was diluted with EtOAc and extracted with water (5×, saturated aqueous NaCl added as needed to achieve phase separation). The organic phase was dried ($Na_2SO_4$), filtered, and concentrated. The residue was purified by flash column chromatography (silica gel, dry loading, 2-10% EtOAc-Heptane first column, 0-4% EtOAc-Heptane second column) to afford the title compound as a white solid.

Intermediate 47: Step a 2,2-Dimethyl-5-(4-(trifluoromethyl)benzyl)-1,3-dioxane-4,6-dione

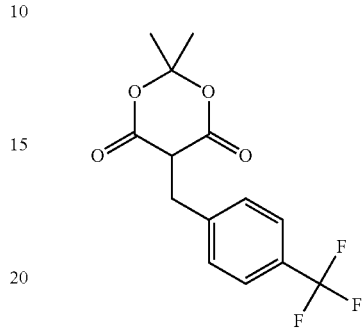

Similar procedures to those referenced in Tett. Lett. (2006), 651, D. Ramachary; Eur. J. Org. Chem. (2008), 975, D. Ramachary were employed. To a 5 L 3-necked flask fitted with an overhead mechanical stirrer was charged with 4-(trifluoromethyl)benzaldehyde (43.5 g, 250 mmol) followed by the addition of anhydrous EtOH (3,000 mL) and Meldrum's acid (37.5 g, 260 mmol), diethyl 2,6-dimethyl-1,4-dihydropyridine-3,5-dicarboxylate (67.5 g, 266 mmol) and lastly L-proline (6.0 g, 51 mmol) all at room temperature. The yellowish reaction mixture was stirred at room temperature under $N_2$. An aliquot was removed after 4 hours and rinsed with EtOH and then $Et_2O$, and air dried. The $^1H$ NMR of this aliquot showed the reaction to be complete. The full reaction was stopped and the white precipitate from the reaction was collected by filtration and rinsed with EtOH and then $Et_2O$ and dried under vacuum to give the title compound in the first crop as a fine white solid. The yellowish mother liquors were concentrated and allowed to crystallize overnight from EtOH and the solid material was collected as before to provide the title compound.

Intermediate 47: Step b 2-(4-(Trifluoromethyl)benzyl)malonic acid

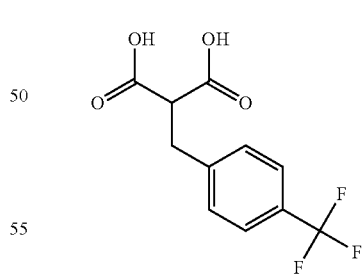

To a 2 L flask containing 2,2-dimethyl-5-(4-(trifluoromethyl)benzyl)-1,3-dioxane-4,6-dione (65 g, 215 mmol, Intermediate 47: step a) was added a TFA/water solution (v/v, 560 mL/280 mL) at room temperature and the white suspension was heated between 70° C. and 78° C. in a large oil bath. The suspension did not dissolve until a temperature of 72° C. was reached. After approximately 40 minutes, the suspension became a clear homogeneous solution. After 3 hours, HPLC indicated that the reaction was complete. The mixture was concentrated on the rotary evaporator and azeotroped with toluene (4×100 mL) to give white solid which was used without further purification.

Intermediate 47: Step c

6-Bromo-2,4-dichloro-3-(4-(trifluoromethyl)benzyl)quinoline

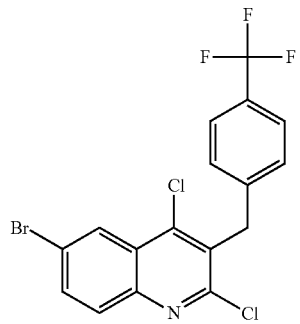 [SMILES: FC(F)(F)c1ccc(Cc2c(Cl)nc3ccc(Br)cc3c2Cl)cc1]

To a 500 mL 3-necked flask fitted with a reflux condenser and Drierite® drying tube, was charged with POCl₃ (190 mL) and then 2-(4-(trifluoromethyl)benzyl)malonic acid (28.5 g, 109 mmol, Intermediate 47: step b) was added followed by 4-bromoaniline (19 g, 110 mmol) at room temperature. The heterogeneous mixture was heated in an aluminum mantle to 100° C. which resulted in a light amber homogenous solution after approximately 10 minutes. The reaction was stirred at 110° C. for 6.5 hours, after which removal of an aliquot and TLC (20% Hexane-DCM) showed the reaction to be complete. The contents were transferred to a 1 L single-necked round bottom flask and the POCl₃ was removed by evaporation. The resulting dark brown material was then poured onto ice chips (~500 g) in a 2 L Erlenmeyer flask pre-cooled to 0° C. DCM was added (~500 mL) and the solution was stirred at 0° C. as a solution of 6 M aqueous KOH was added carefully (~500 mL). 5N aqueous NH₄OH (~100 mL) was also added to bring the pH to ~8-9. The neutralization process was kept at 0° C. throughout. More DCM was added and the organic phase was separated. The aqueous portion was washed with DCM (3×250 mL) and the combined organics were washed with brine, dried over Na₂SO₄, filtered and concentrated to provide a brown solid. The crude solid was triturated with CH₃CN which provided a white fluffy solid after filtration.

Intermediate 47: Step d

6-Bromo-4-chloro-2-methoxy-3-(4-(trifluoromethyl)benzyl)quinoline

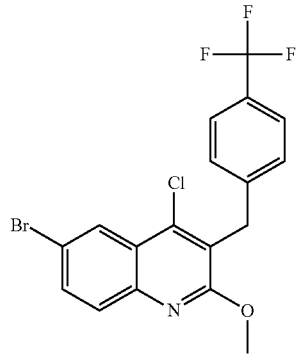 [SMILES: COc1nc2ccc(Br)cc2c(Cl)c1Cc1ccc(C(F)(F)F)cc1]

To a 1 L flask containing 6-bromo-2,4-dichloro-3-(4-(trifluoromethyl)benzyl)quinoline (32.5 g, 74.7 mmol, Intermediate 47: step c) was added toluene (550 mL) followed by solid sodium methoxide (40 g, 740 mmol, 97% purity) at room temperature. The suspension was stirred at reflux (~118° C.) in an aluminum mantle. TLC (50% Hexane-DCM) and HPLC after 5.5 hours showed the reaction to be complete. The reaction mixture was filtered through Celite® while still warm (~80° C.) and rinsed with warm toluene (~70° C., 500 mL). The colorless filtrate was concentrated which then solidified to give an off white solid.

Intermediate 47: Step e

(4-Chloro-2-methoxy-3-(4-(trifluoromethyl)benzyl)quinolin-6-yl)(2,6-dimethylpyridin-3-yl)methanol

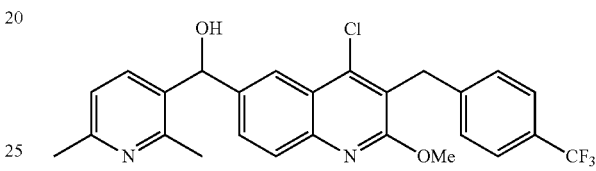

To a 100 mL flask containing 6-bromo-4-chloro-2-methoxy-3-(4-(trifluoromethyl)benzyl)quinoline (2.5 g, 5.8 mmol, Intermediate 47: step d) was added THF (55 mL) at room temperature which resulted in a colorless homogeneous mixture. The solution was cooled to −70° C. which remained homogeneous and then n-butyllithium (2.5 M in hexanes, 2.6 mL, 6.5 mmol) was added drop wise. The color of the solution became a reddish-brown color. After 1 minute, (2,6-dimethylpyridine-3-carboxaldehyde (1.01 g, 7.5 mmol in 2 mL THF) was introduced and the color of the mixture became a light greenish-yellow color. After 15 minutes, HPLC and TLC (50% acetone-hexane) indicated that the reaction was complete. The mixture was allowed to warm to −20° C. over 40 minutes at which time the reaction was quenched with aqueous NH₄Cl solution. The reaction was diluted further with water and extracted with EtOAc (3×50 mL). The combined organics were washed with brine, dried over Na₂SO₄, filtered and concentrated to provide an orange foam. The crude product was chromatographed on silica gel (10% acetone-hexane increasing to 30% acetone) to afford the title compound as a light yellow foam.

Intermediate 47: Step f

(4-Chloro-2-methoxy-3-(4-(trifluoromethyl)benzyl)quinolin-6-yl)(2,6-dimethylpyridin-3-yl)methanone

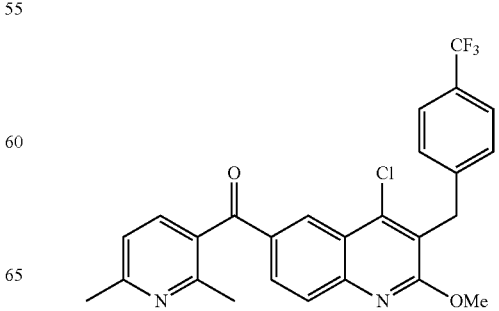

To a 100 mL flask containing (4-chloro-2-methoxy-3-(4-(trifluoromethyl)benzyl)quinolin-6-yl)(2,6-dimethylpyridin-3-yl)methanol (1.51 g, 3.1 mmol, Intermediate 47: step e) was added 1,4-dioxane (50 mL) followed by activated MnO$_2$ (1.3 g, 15 mmol) and the mixture was heated to reflux in an aluminum heating mantle under N$_2$. After 1 hour, TLC (25% acetone:hexane) indicated that the reaction was complete. The contents were filtered while still hot through Celite® and rinsed with THF. The resulting light yellow solution was concentrated and chromatographed by passing through a silica gel column (10% acetone-hexane increasing to 25% acetone) to give the title compound as a light yellowish amorphous solid.

Intermediate 48: Step a (2,4-Dimethylthiazol-5-yl)(1-methyl-1H-1,2,3-triazol-5-yl)methanol

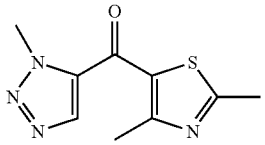

1-methyl-1H-1,2,3-triazole was prepared according to the literature reference WO2008/98104. To a 2 L flask containing 1-methyl-1H-1,2,3-triazole (9 g, 108.3 mmol) was added THF (1500 mL) and the solution was cooled to −40° C. To this colorless homogeneous solution was added n-butyllithium (2.5 M in hexanes, 45 mL, 112.5 mmol) dropwise which immediately afforded a dark brown viscous mixture. The mixture was kept between −10 to −20° C. for 60 minutes, then a THF solution of 2,4-dimethylthiazole-5-carbaldehyde (17.2 g, 121.8 mmol in 200 mL THF) was introduced via cannula. Once the aldehyde was added the reaction was allowed to warm to room temperature. After 3 hours, the reaction was quenched by pouring into a saturated solution of aqueous NH$_4$Cl. The aqueous portion was extracted with EtOAc in portions, 7×400 mL. The combined organics were washed with brine, dried over MgSO$_4$, filtered and concentrated to give a brown oil. Chromatography on silica gel (10% acetone-DCM increasing to 50% acetone and increasing to 10% MeOH-DCM) provided the title compound as an amber solid.

Intermediate 48: Step b (2,4-Dimethylthiazol-5-yl)(1-methyl-1H-1,2,3-triazol-5-yl)methanone

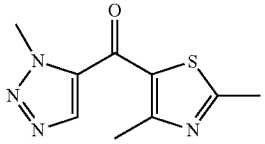

To a 500 ml flask containing (2,4-dimethylthiazol-5-yl)(1-methyl-1H-1,2,3-triazol-5-yl)methanol (10.5 g, 46.8 mmol, Intermediate 48: step a) was added 1,4-dioxane (400 mL) and the contents were warmed to form a homogeneous solution. Activated MnO$_2$ (18 g, 207 mmol) was added and the dark brownish mixture was heated to reflux in an aluminum heating mantle under an atmosphere of N$_2$. After 1.5 hours, the contents were filtered while still hot through Celite® and rinsed with warm THF. The resulting light orange solution was concentrated and passed through a silica gel column (25% acetone-DCM) to give the title compound as a light orange solid.

Intermediate 49: Step a (4-Chloro-2-methoxy-3-(4-(trifluoromethyl)benzyl)quinolin-6-yl)(1,2-dimethyl-1H-imidazol-5-yl)methanol

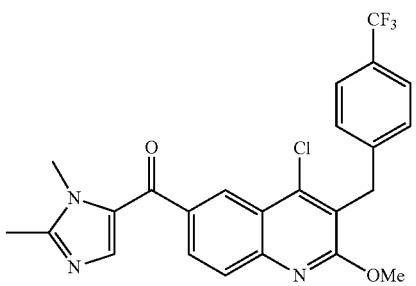 [SMILES: COc1nc2ccc(C(=O)c3cnc(C)n3C)cc2c(Cl)c1Cc1ccc(C(F)(F)F)cc1]

To a 50 mL flask containing 6-bromo-4-chloro-2-methoxy-3-(4-(trifluoromethyl)benzyl)quinoline (2 g, 4.64 mmol, Intermediate 47: step d) was added THF (25 mL) at room temperature which resulted in a colorless homogeneous mixture. The solution was cooled to −70° C. which remained homogeneous and then n-BuLi (2.5 M in hexanes, 1.8 mL, 4.5 mmol) was added drop wise. The color of the solution became a dark reddish-brown color. After 1 minute, 1,2-dimethyl-1H-imidazole-5-carbaldehyde (710 mg, 5.72 mmol in 4 mL THF) was introduced and the color of the mixture became greenish to light orange all within 1 minute. The mixture was allowed to warm to 0° C. over 45 minutes at which time the reaction was quenched with aqueous NH$_4$Cl solution. The reaction was diluted further with water and extracted with EtOAc (3×45 mL). The combined organics were washed with brine, dried over MgSO$_4$, filtered and concentrated to give a pale yellow solid. The solid was triturated with Et$_2$O and collected by filtration and rinsed with additional Et$_2$O and dried to afford the title compound as a white powder.

Intermediate 49: Step b (4-Chloro-2-methoxy-3-(4-(trifluoromethyl)benzyl)quinolin-6-yl)(1,2-dimethyl-1H-imidazol-5-yl)methanone

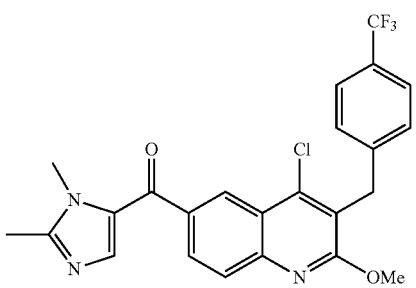 [SMILES: COc1nc2ccc(C(=O)c3cnc(C)n3C)cc2c(Cl)c1Cc1ccc(C(F)(F)F)cc1]

To a 100 mL flask containing (4-chloro-2-methoxy-3-(4-(trifluoromethyl)benzyl)quinolin-6-yl)(1,2-dimethyl-1H-imidazol-5-yl)methanol (1.68 g, 3.53 mmol, Intermediate 49: step a) was added 1,4-dioxane (85 mL) to give a suspension at room temperature. Heating to approximately 45° C. formed a clear homogeneous solution. Then activated $MnO_2$ (1.5 g, 17.2 mmol) was introduced and the mixture was heated to reflux in an aluminum heating mantle under an atmosphere of $N_2$. After 70 minutes, the contents were cooled to 60° C. and then filtered through a Celite® pad and rinsed with THF. The resulting solution was concentrated and passed through a silica gel column (5% MeOH-DCM) to give the title compound as a white powder.

Intermediate 50: Step a

1-Methyl-1H-1,2,3-triazole-5-carbaldehyde

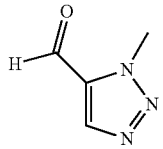

The title compound was prepared according to the patent application WO2008/135826. To a 50 mL 2-necked flask containing 1-methyl-1H-1,2,3-triazole (1.0 g, 12.0 mmol, prepared according to PCT Int. Appl., 2008098104) was added THF (45 mL) and the colorless solution was cooled to −40° C. Then, n-BuLi (2.5 M in hexanes, 4.8 mL) was added dropwise which afforded a dark reddish-brown viscous solution. The mixture was stirred between −30 to −20° C. for 45 minutes, then neat DMF (3 mL, 38.5 mmol) was introduced at −10° C. The mixture was allowed to warm up to room temperature and stirred for 60 minutes, followed by pouring into water. The aqueous portion was extracted with EtOAc (4×50 mL) and the combined organics were washed with brine, dried over $MgSO_4$, filtered and concentrated. The aqueous portion was back-extracted with DCM (3×50 mL) and dried as above. The combined organics were concentrated to give a light brown oil that was much more UV active than the starting material. TLC in either 25% $CH_3CN$-DCM or 25% EtOAc-DCM showed the product to have a slightly higher $R_f$ than the starting material. Chromatography on silica gel (100% DCM increasing to 25% $CH_3CN$-DCM) provided the titled material as a colorless oil.

Intermediate 50: Step b (4-Chloro-2-methoxy-3-(4-(trifluoromethyl)benzyl)quinolin-6-yl)(1-methyl-1H-1,2,3-triazol-5-yl)methanol

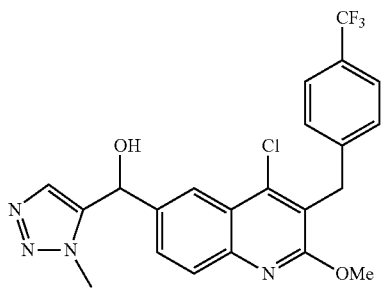 [SMILES: COc1nc2ccc(C(O)c3cnnn3C)cc2c(Cl)c1Cc1ccc(C(F)(F)F)cc1]

To a 50 mL flask containing 6-bromo-4-chloro-2-methoxy-3-(4-(trifluoromethyl)benzyl)quinoline (1.45 g, 3.37 mmol, Intermediate 47: step d) was added THF (25 mL) at room temp which resulted in a colorless homogeneous mixture. The solution was cooled to −70° C. which remained homogeneous and then n-BuLi (2.5 M in hexanes, 1.3 mL, 3.25 mmol) was added dropwise. The color of the solution became a dark reddish-brown color. After 2 minutes, 1-methyl-1H-1,2,3-triazole-5-carbaldehyde (580 mg, 5.22 mmol, in 3 mL THF, Intermediate 50: step a) was introduced and the color of the mixture went from dark brown to greenish to a yellow color within about 2 minutes. The mixture was allowed to warm to −20° C. over 45 minutes at which time the contents were quenched with aqueous $NH_4Cl$. The mixture was diluted further with water and extracted with EtOAc (5×40 mL). The combined organics were washed with brine, dried over $MgSO_4$, filtered and concentrated to give a yellowish oil. The crude material was chromatographed on silica gel (5% $CH_3CN$-DCM increasing to 30% $CH_3CN$+2% MeOH) to give the title compound as an off white foam.

Intermediate 50: Step c (4-Chloro-2-methoxy-3-(4-(trifluoromethyl)benzyl)quinolin-6-yl)(1-methyl-1H-1,2,3-triazol-5-yl)methanone

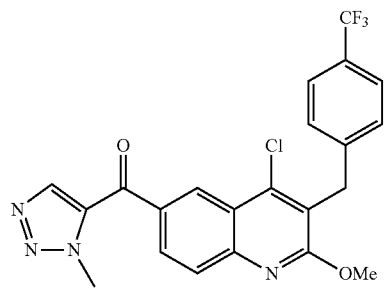 [SMILES: COc1nc2ccc(C(=O)c3cnnn3C)cc2c(Cl)c1Cc1ccc(C(F)(F)F)cc1]

To a 100 mL flask containing (4-chloro-2-methoxy-3-(4-(trifluoromethyl)benzyl)quinolin-6-yl)(1-methyl-1H-1,2,3-triazol-5-yl)methanol (745 mg, 1.61 mmol, Intermediate 50: step b) was added 1,4-dioxane (36 mL) and THF (11 mL) to give a suspension at room temperature. Heating to approximately 45° C. formed a homogeneous solution. Then, activated $MnO_2$ (719 mg, 8.3 mmol) was introduced and the mixture was heated to 80° C. in an aluminum heating mantle under an atmosphere of $N_2$. After 2 hours, the mixture was filtered through a Celite® pad, rinsed with THF and concentrated to give a white solid. Trituration from $Et_2O$ gave the title compound as a white solid.

Intermediate 51: Step a (4-Chloro-2-methoxy-3-(4-(trifluoromethyl)benzyl)quinolin-6-yl)(2,4-dimethyloxazol-5-yl)methanol

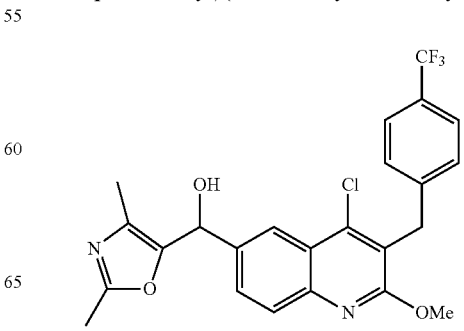

To a 50 mL flask containing 6-bromo-4-chloro-2-methoxy-3-(4-(trifluoromethyl)benzyl)quinoline (1.5 g, 3.48 mmol, Intermediate 47: step d) was added THF (65 mL) at room temperature which resulted in a colorless homogeneous mixture. The solution was cooled to −70° C. which remained homogeneous and then n-butyllithium (2.5 M in hexanes, 1.62 mL, 4.04 mmol) was added drop wise. The color of the solution became a dark opaque reddish-brown color. After 2 minutes, 2,4-dimethyloxazole-5-carbaldehyde (520 mg, 4.16 mmol, in 3 mL THF) was introduced and the color of the mixture went from an opaque dark brown to a light yellow homogeneous color within about 1 minute. After 25 minutes the mixture was quenched with aqueous NH$_4$Cl. The reaction was diluted further with water and extracted with EtOAc (5×40 mL). The combined organics were washed with brine, dried over MgSO$_4$, filtered and concentrated to give a light yellowish foam. The crude material was chromatographed on silica gel (10% CH$_3$CN-DCM grading to 30% CH$_3$CN containing 1% MeOH) to provide the title compound as a white amorphous solid.

Intermediate 51: Step b (4-Chloro-2-methoxy-3-(4-(trifluoromethyl)benzyl)quinolin-6-yl)(2,4-dimethyloxazol-5-yl)methanone

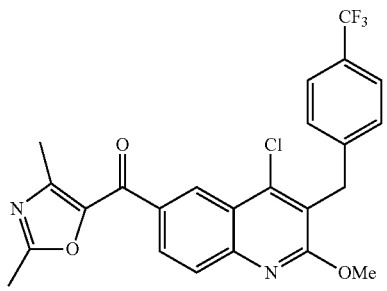 [SMILES: COc1nc2ccc(C(=O)c3oc(C)nc3C)cc2c(Cl)c1Cc1ccc(C(F)(F)F)cc1]

To a 100 mL flask containing (4-chloro-2-methoxy-3-(4-(trifluoromethyl)benzyl)quinolin-6-yl)(2,4-dimethyloxazol-5-yl)methanol (960 mg, 2.01 mmol, Intermediate 51: step a) was added 1,4-dioxane (50 mL) and activated MnO$_2$ (900 mg, 10.3 mmol) at room temperature. The mixture was heated to 85° C. in an aluminum heating mantle under a nitrogen atmosphere. After 60 minutes, the contents were filtered through Celite® while the solution is still warm and rinsed with THF, and concentrated to give an off white solid. The crude material was triturated with Et$_2$O to give a white solid.

Intermediate 52

1-(4-Benzoylpiperidin-1-yl)ethanone

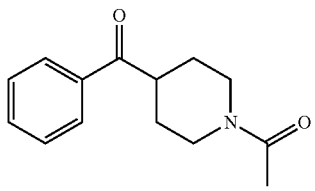 [SMILES: CC(=O)N1CCC(C(=O)c2ccccc2)CC1]

A mixture of phenyl(piperidin-4-yl)methanone hydrochloride (743 mg, 3.29 mmol) in dichloromethane (13.2 mL) and triethylamine (1.10 mL, 7.90 mmol) was treated with Ac$_2$O (0.373 mL, 3.95 mmol) dropwise over 1 minute in an ice bath under argon, and the resulting translucent mixture was immediately removed from the ice bath and stirred at room temperature overnight. The reaction was then extracted with 1 M aqueous HCl (1×8 mL) and 1 M aqueous NaOH (1×8 mL), and the organic layer was dried (Na$_2$SO$_4$), filtered, and concentrated to provide the title compound as a translucent beige oil that crystallized upon standing.

Intermediate 53: Step a (1-Methyl-1H-imidazol-5-yl)(2-(trifluoromethyl)pyridin-4-yl)methanol

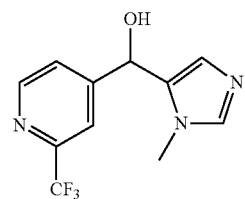

A solution of isopropylmagnesium chloride/lithium chloride complex (1.3 M in THF, 10.6 mL, 13.8 mmol) was added dropwise by syringe to a solution of 4-bromo-2-(trifluoromethyl)pyridine (3.12 g, 13.8 mmol) in dry THF (50 mL) at 0° C. After 30 min, a solution of 1-methyl-1H-imidazole-5-carbaldehyde in THF (1.38 g, 12.5 mmol) was added to the Grignard solution by syringe at 0° C. The reaction mixture was warmed to room temperature over 2 h after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried (MgSO$_4$), filtered, and concentrated. The crude product was purified by flash column chromatography (silica gel, 0-10% MeOH-DCM) to provide the title compound.

Intermediate 53: Step b (1-Methyl-1H-imidazol-5-yl)(2-(trifluoromethyl)pyridin-4-yl)methanone

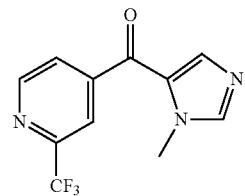

A heterogeneous mixture of (1-methyl-1H-imidazol-5-yl)(2-(trifluoromethyl)pyridin-4-yl)methanol (0.300 g, 1.16 mmol, Intermediate 53: step a) and manganese dioxide (0.506 g, 5.83 mmol) in 1,4-dioxane (12 mL) was stirred at 100° C. for 1 h. The reaction mixture was then cooled to room temperature, filtered through Celite®, washed with EtOAc, and concentrated. The organic phase was dried (MgSO$_4$), filtered, and concentrated. The crude product was purified by flash column chromatography (silica gel, 0-100% EtOAc-DCM) to provide the title compound as a white solid.

Intermediate 54: Step a (2,6-Dimethylpyridin-3-yl)(1-methyl-1H-1,2,3-triazol-5-yl)methanol

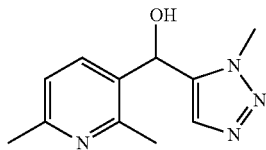 [SMILES: Cc1ccc(C(O)c2cnnn2C)c(C)n1]

A solution of n-butyllithium in hexanes (2.5 M, 22.5 mL, 56.3 mmol) was added dropwise by syringe to a stirring solution of 1-methyl-1H-1,2,3-triazole (5.00 g, 60.2 mmol, prepared according to PCT Int. Appl., 2008098104) in dry tetrahydrofuran (400 mL) at −55° C. The resulting off-white slurry was stirred at −45° C. for 20 min, whereupon a solution of 2,6-dimethyl-pyridine-3-carbaldehyde (8.33 g, 61.7 mmol) in dry tetrahydrofuran (10 mL) was added dropwise by syringe. After 5 min, the cooling bath was removed and the reaction mixture was allowed to slowly warm. After 45 min, saturated aqueous ammonium chloride solution (10 mL) and ethyl acetate (100 mL) were added. The whole was concentrated by rotary evaporation. The residue was dissolved in ethyl acetate (300 mL). The organic solution was washed with saturated aqueous sodium chloride solution (100 mL, containing excess solid sodium chloride). The aqueous layer was extracted with ethyl acetate (2×100 mL). The organic layers were combined and the combined solution was concentrated. Ether (100 mL) was added to the residue and the mixture was sonicated for 20 min during which time a white solid crashed out. The solids were collected by filtration. Ether (100 mL) was added to the collected solids and the mixture sonicated a second time. After 20 min, the mixture was filtered and the solids were collected to provide the title compound as a fine powder.

Intermediate 54: Step b (2,6-Dimethylpyridin-3-yl)(1-methyl-1H-1,2,3-triazol-5-yl)methanone

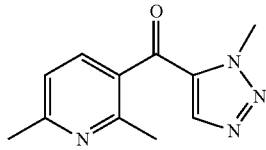

A mixture containing (2,6-dimethylpyridin-3-yl)(1-methyl-1H-1,2,3-triazol-5-yl)methanol (9.8 g, 44.9 mmol, Intermediate 54: step a) and manganese dioxide (18.8 g, 184 mmol) in dry dioxane (225 mL) was heated to 100° C. with stirring. After 1 h, the mixture was cooled to 40° C. The cooled mixture was filtered through a 2 cm pad of Celite rinsing with tetrahydrofuran (100 mL). The filtrate was concentrated to provide the title compound as an off-white solid.

Intermediate 55

(4-Chloro-2-methoxy-3-(4-(trifluoromethyl)benzyl)quinolin-6-yl)(2,6-dimethylpyridin-3-yl)(1-methyl-1H-1,2,3-triazol-5-yl)methyl acetate

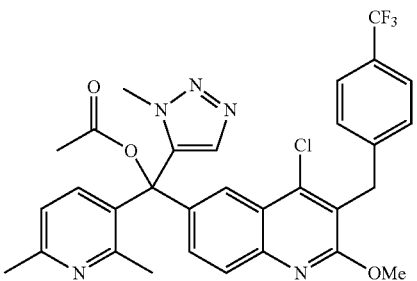 [SMILES: COc1nc2ccc(C(OC(C)=O)(c3ccc(C)nc3C)c3cnnn3C)cc2c(Cl)c1Cc1ccc(C(F)(F)F)cc1]

To a solution of (4-chloro-2-methoxy-3-(4-(trifluoromethyl)benzyl)quinolin-6-yl)(2,6-dimethylpyridin-3-yl)(1-methyl-1H-1,2,3-triazol-5-yl)methanol (544 mg, 0.960 mmol, Example 77B) in 20 mL of dry DMF at room temperature was added NaH (75 mg, 1.9 mmol, 60% in mineral oil). After stirring for 20 min, acetic anhydride (0.18 mL, 1.9 mmol) was added. The mixture was stirred for one hour and some suspension formed. After the mixture was quenched with a few drops of water, the suspension was filtered off and the filtrate was concentrated in vacuo. The residue was partitioned between dichloromethane and saturated NaHCO$_3$ (aq). The extracts were dried (Na$_2$SO$_4$), filtered, and concentrated to give the title compound as a semi-solid.

Intermediate 56

(2,4-Dichloro-3-(4-(trifluoromethyl)benzyl)quinolin-6-yl)(2,6-dimethylpyridin-3-yl)(1-methyl-1H-1,2,3-triazol-5-yl)methanol

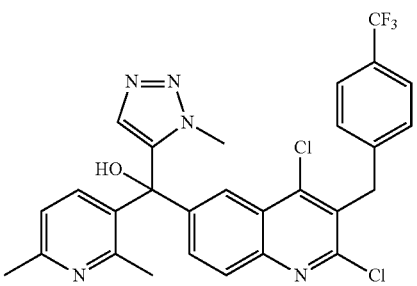 [SMILES: Cc1ccc(C(O)(c2ccc3nc(Cl)c(Cc4ccc(C(F)(F)F)cc4)c(Cl)c3c2)c2cnnn2C)c(C)n1]

A solution of 6-bromo-2,4-dichloro-3-(4-(trifluoromethyl)benzyl)quinoline (2.00 g, 4.60 mmol, Intermediate 47: step c) and 90 mL of THF in a 250 mL of 3-necked flask was purged with N$_2$ and cooled to −78° C. To the clear solution was added n-BuLi (3.05 mL, 4.88 mmol, 1.6 M in hexanes) dropwise and it became dark green almost black. After ~5 min, a suspension of (2,6-dimethylpyridin-3-yl)(1-methyl-1H-1,2,3-triazol-5-yl)methanone (0.950 g, 4.39 mmol, Intermediate 54: step b) in THF (~4 mL) was added and the color changed to green. The cooling bath was removed. After ~5 min stirring, the flask was immersed in an ice-water bath. During the ~40 min stirring at 4° C., the color gradually changed to light green. Saturated NH₄Cl (aq) was added and the yellow organic layer was separated. The aqueous layer was extracted with dichloromethane. The combined organic phases were dried (Na₂SO₄), filtered, and concentrated. The crude solidified over the weekend. 15 mL of CH₃CN and 5 mL of dichloromethane were added. The yellow solid was filtered, washed with Et₂O, and dried under vacuum overnight to give the title compound.

Intermediate 57: Step a

Ethyl 3-oxo-2-(4-(trifluoromethyl)benzyl)butanoate

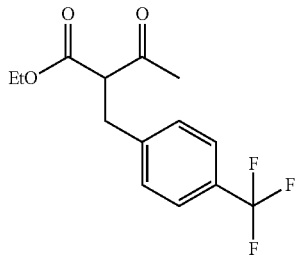 [SMILES: CCOC(=O)C(Cc1ccc(C(F)(F)F)cc1)C(C)=O]

Sodium hydride (60% dispersion in mineral oil, 1.5 g, 38.4 mmol) was added in portions over 2 min to an ice-cooled, stirring solution of ethyl 3-oxobutanoate (5 g, 38.4 mmol) in dry dimethoxyethane (65 mL). After 30 min, a solution of 4-(trifluoromethyl)benzyl bromide (9.2 g, 38.4 mmol) in dry dimethoxyethane (10 mL) was added dropwise over 2 min. The flask was removed from the cooling bath. After 2 h, water (10 mL) was added. The mixture was partitioned between half-saturated aqueous sodium chloride solution (50 mL) and ethyl acetate (150 mL). The layers were separated. The organic layer was dried with magnesium sulfate and the dried solution was filtered. The filtrate was concentrated and the residue was purified by flash-column chromatography on silica gel eluting with hexanes-ethyl acetate to provide the title compound as a colorless liquid.

Intermediate 57: Step b

6-Bromo-2-methyl-3-(4-(trifluoromethyl)benzyl)quinolin-4-ol

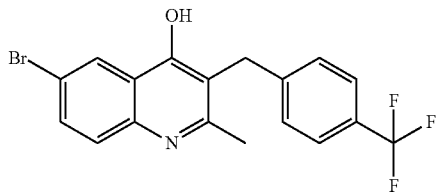

A round-bottomed flask equipped with a Dean-Stark apparatus was charged with ethyl 3-oxo-2-(4-(trifluoromethyl)benzyl)butanoate (7.00 g, 24.3 mmol, Intermediate 57: step a), 4-bromoaniline (4.20 g, 24.2 mmol), para-toluenesulfonic acid (0.418 g, 2.4 mmol), and toluene (121 mL). The mixture was heated to 125° C. After 16 h, the flask was cooled to room temperature. The toluene was removed by rotary evaporation to provide an orange colored solid. A mixture of the solid and diphenyl ether (48.4 mL) was heated to 220° C. After 60 min, the mixture was cooled to room temperature at which point a yellow solid crashed out of solution. Hexanes (150 mL) were added. The whole was filtered through paper, rinsing with hexanes. The yellow solids were collected, dried, and then used in the next step without further purification.

Intermediate 57: Step c

6-Bromo-4-chloro-2-methyl-3-(4-(trifluoromethyl)benzyl)quinoline

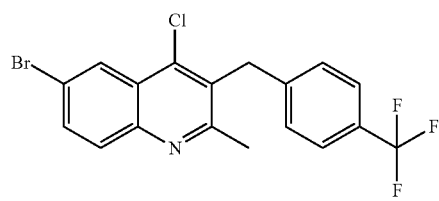 [SMILES: Cc1nc2ccc(Br)cc2c(O)c1Cc1ccc(C(F)(F)F)cc1]

A round-bottomed flask containing a mixture of 6-bromo-2-methyl-3-(4-(trifluoromethyl)benzyl)quinolin-4-ol (5.00 g, 12.6 mmol, Intermediate 57: step b), phosphorous oxychloride (5.90 mL, 63.1 mmol) and acetonitrile (42 mL) was warmed to 90° C. After 3 h, the reaction mixture was cooled to room temperature. The acetonitrile and excess phosphorous oxychloride was removed by rotary evaporation. The residue was dissolved in dichloromethane (100 mL) and the solution was cooled in an ice-water bath. Ice (100 mL) was added. Concentrated aqueous ammonia solution was added dropwise until the pH=~9 by litmus paper test. The biphasic mixture was separated and the aqueous layer was extracted with dichloromethane (50 mL). The combined organics were dried with magnesium sulfate and the dried solution was filtered. Celite (5 g) was added to the filtrate and the solvents were removed by rotary evaporation to provide a free-flowing powder. The powder was loaded onto a silica gel column. Elution with hexanes initially, grading to 20% ethyl acetate-hexanes provided the title compound as an off-white solid.

Intermediate 58: Step a

Ethyl 3-oxo-2-(4-(trifluoromethyl)benzyl)pentanoate

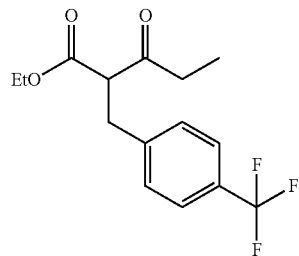 [SMILES: CCOC(=O)C(Cc1ccc(C(F)(F)F)cc1)C(=O)CC]

Sodium hydride (60% dispersion in mineral oil, 1.75 g, 43.7 mmol) was added in portions over 1 min to an ice-cooled, stirring solution of ethyl 3-oxopentanoate (6.30 g, 43.7 mmol) in dry dimethoxyethane (87 mL). After 5 min, the flask was removed from the cooling bath and stirring continued at room temperature. After 30 min, a solution of 4-(trifluoromethyl)benzyl bromide (10.4 g, 43.7 mmol) in dry dimethoxyethane (10 mL) was added dropwise over 2 min. After 2.5 h, ethyl acetate (300 mL) and water (100 mL) were added. The layers were separated. The organic layer was dried with sodium sulfate and the dried solution was filtered. The filtrate was concentrated and the residue was purified by flash-column chromatography on silica gel eluting with hexanes initially, grading to 50% dichloromethane-hexanes to provide the title compound as a colorless liquid.

Intermediate 58: Step b

6-Bromo-2-ethyl-3-(4-(trifluoromethyl)benzyl)quinolin-4-ol

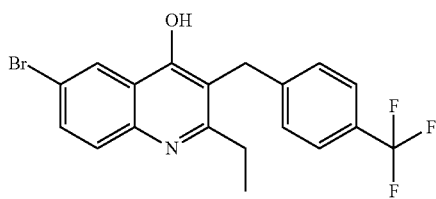 [SMILES: CCc1nc2ccc(Br)cc2c(O)c1Cc1ccc(C(F)(F)F)cc1]

A round-bottomed flask equipped with a Dean-Stark apparatus was charged with ethyl 3-oxo-2-(4-(trifluoromethyl)benzyl)pentanoate (8.84 g, 29.2 mmol, Intermediate 58: step a), 4-bromoaniline (5.00 g, 29.2 mmol), para-toluenesulfonic acid (0.503 g, 2.9 mmol), and toluene (146 mL). The mixture was heated to 125° C. After 18 h, the flask was cooled to room temperature. The toluene was removed by rotary evaporation to provide an amber colored solid. A mixture of the solid and diphenyl ether (29.1 mL) was heated to 220° C. After 70 min, the mixture was cooled to room temperature. Ether (100 mL) and hexanes (50 mL) were added. The mixture was allowed to stir for 30 min during which time a white solid crashed out of solution. The whole was filtered through paper, rinsing with ether. The gummy solids were collected. Acetonitrile (20 mL) was added and the mixture was sonicated for 5 min. The slurry was filtered through paper and the solids were rinsed with acetonitrile. The off-white solids were collected, dried, and then used in the next step without further purification.

Intermediate 58: Step c

6-Bromo-4-chloro-2-ethyl-3-(4-(trifluoromethyl)benzyl)quinoline

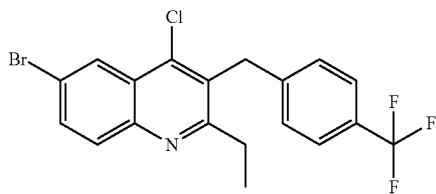 [SMILES: CCc1nc2ccc(Br)cc2c(Cl)c1Cc1ccc(C(F)(F)F)cc1]

A round-bottomed flask containing a mixture of 6-bromo-2-ethyl-3-(4-(trifluoromethyl)benzyl)quinolin-4-ol (4.00 g, 8.29 mmol, Intermediate 58: step b), phosphorous oxychloride (3.50 mL, 37.3 mmol) and acetonitrile (27 mL) was placed into a metal heating block at 90° C. After 65 min, the reaction mixture was cooled to room temperature. The acetonitrile and excess phosphorous oxychloride was removed by rotary evaporation. The residue was dissolved in dichloromethane (100 mL) and the solution was cooled in an ice-water bath. Ice (50 mL) was added. Concentrated aqueous ammonia solution was added dropwise until the pH=8-9 by litmus paper test. The biphasic mixture was separated and the aqueous layer was extracted with dichloromethane (50 mL). The combined organics were dried with sodium sulfate and the dried solution was filtered. Silica gel (8 g) was added to the filtrate and the solvents were removed by rotary evaporation to provide a free-flowing powder. The powder was loaded onto a silica gel column. Elution with hexanes initially, grading to 20% ethyl acetate-hexanes provided the title compound as an off-white solid.

Intermediate 59: Step a tert-Butyl 3-(hydroxy(1-methyl-1H-1,2,3-triazol-5-yl)methyl)azetidine-1-carboxylate

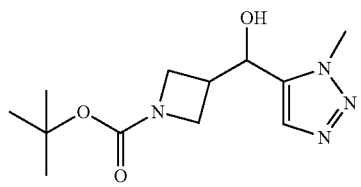 [SMILES: Cn1nncc1C(O)C1CN(C(=O)OC(C)(C)C)C1]

A 2.5 M solution of n-butyllithium in hexanes (9.60 mL, 24.0 mmol) was added dropwise to a stirring solution of 1-methyl-1H-1,2,3-triazole (2.00 g, 24.0 mmol, prepared according to PCT Int. Appl., 2008098104) in dry THF (100 mL) at −50° C. The reaction became heterogeneous and yellow during addition. After 15 min, a solution of tert-butyl 3-formylazetidine-1-carboxylate (4.45 g, 24.0 mmol) in dry THF (10 mL) was added dropwise by syringe. The reaction mixture became homogeneous and was allowed to slowly warm to 0° C. Water (10 mL) and ethyl acetate (100) mL were added. The biphasic mixture was warmed to 23° C. The mixture was partitioned between half-saturated aqueous sodium chloride solution (100 mL) and ethyl acetate (300 mL). The layers were separated. The organic layer was dried with sodium sulfate and the dried solution was filtered. Celite (14 g) was added to the filtrate and the solvents were removed by rotary evaporation to provide a free-flowing powder. The powder was loaded onto a silica gel column. Elution with ethyl acetate initially, grading to 5% methanol-ethyl acetate provided the title compound as a white foam.

Intermediate 59: Step b tert-Butyl 3-(1-methyl-1H-1,2,3-triazole-5-carbonyl)azetidine-1-carboxylate

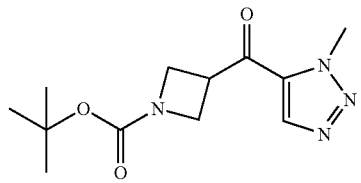 [SMILES: Cn1nncc1C(=O)C1CN(C(=O)OC(C)(C)C)C1]

Dess-Martin periodinane (10.9 g, 25.7 mmol) was added in one portion to a stirring solution of tert-butyl 3-(hydroxy(1-methyl-1H-1,2,3-triazol-5-yl)methyl)azetidine-1-carboxylate (4.60 g, 17.1 mmol, Intermediate 59: step a) in dry dichloromethane (86 mL). The resulting mixture was stirred at 23° C. After 18 h, a mixture containing equal parts water, saturated aqueous sodium thiosulfate solution, and saturated aqueous sodium bicarbonate solution was added (200 mL). Dichloromethane (100 mL) was added. The resulting biphasic mixture was stirred for 15 min. The layers were separated. The organic layer was dried with sodium sulfate and the dried solution was concentrated. The residue was purified by flash-column chromatography on silica gel eluting with dichloromethane initially, grading to 5% methanol-dichloromethane to provide the title compound as a clear, colorless oil.

Intermediate 60

(2,4-dichloro-3-(4-(trifluoromethyl)benzyl)quinolin-6-yl)(1-methyl-1H-imidazol-5-yl)(6-(trifluoromethyl)pyridin-3-yl)methanol

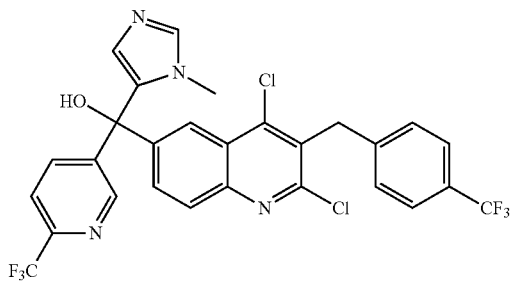 [SMILES: Cn1cncc1C(O)(c1ccc(C(F)(F)F)nc1)c1ccc2nc(Cl)c(Cc3ccc(C(F)(F)F)cc3)c(Cl)c2c1]

To a flask containing 6-bromo-2,4-dichloro-3-(4-(trifluoromethyl)benzyl)quinoline (2.99 g, 6.87 mmol, intermediate 47, step c), (1-methyl-1H-imidazol-5-yl)(6-(trifluoromethyl)pyridin-3-yl)methanone (1.95 g, 7.66 mmol, intermediate 36, step c) was added tetrahydrofuran (150 mL) and the solution was cooled to −45° C. n-BuLi (1.6M, 5.58 mL) was added drop wise over five minutes and the contents were allowed to stir at −45° C. for ten minutes. The reaction mixture was warmed to 0° C. and stirred at that temperature for one hour. The reaction was quenched with an aqueous ammonium chloride solution, warmed to room temperature, then transferred to a separatory funnel with ethyl acetate dilution. The organic phase was separated and the aqueous phase extracted two times with ethyl acetate. The combined organic layers were dried over magnesium sulfate, filtered and evaporated to dryness under reduced pressure. Chromatography on silica gel (dichloromethane increasing to 10% ((2M ammonia in methanol) in dichloromethane)) provided the title compound.

Intermediate 61

N-Methoxy-N,1-dimethyl-1H-1,2,3-triazole-5-carboxamide

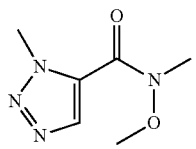

A solution of 1-methyl-1H-1,2,3-triazole (12.9 g, 155 mmol) in THF (260 mL) was cooled to −45° C. Maintaining a temperature of <−35° C., nBuLi (62.1 mL, 2.5 M in hexanes, 155 mmol) was added over 10 min. The reaction mixture was stirred for 30 min with cooling to −45° C. and then treated with a sub-surface stream of $CO_{2(g)}$ for a period of 2 h. After flushing the −35° C. slurry with $N_{2(g)}$ for 5 min, thionyl chloride (11.8 mL, 163 mmol) was added. The mixture was allowed to warm to room temperature with stirring over 1.25 h. Addition of N,O-dimethylhydroxylamine hydrochloride (18.14 g, 186 mmol) and N,N-diisopropylethylamine (68.3 mL, 396 mmol) was followed by stirring for 15 h. Aqueous sodium carbonate (500 mL, 10 wt %) was then added, and the layers were mixed and separated. The aqueous layer was washed with dichloromethane (250 mL and then 125 mL), and the combined organic layers were dried over $MgSO_4$, filtered, and concentrated. The concentrate was taken up in ethyl acetate (225 mL), treated with $MgSO_4$, and filtered through a pad of silica gel (115 g). The silica gel pad was washed with additional ethyl acetate (800 mL). The eluent was concentrated to provide the title compound as a yellow solid.

Intermediate 62: Step a

6-Iodo-3-(4-(trifluoromethyl)benzyl)quinoline-2,4-diol

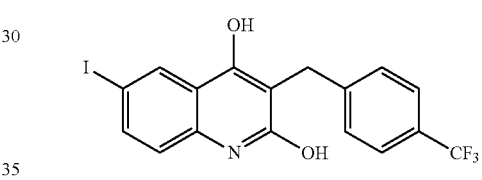

To a suspension of 6-iodoquinoline-2,4-diol (498.2 g, 1.736 mol) and diethyl 2,6-dimethyl-1,4-dihydropyridine-3,5-dicarboxylate (439.6 g, 1.736 mol) in pyridine (3.5 L) was added 4-(trifluoromethyl)benzaldehyde (332.4 g, 1.909 mol). The resulting mixture was warmed with stirring to 105° C. for a period of 6 h. After cooling to room temperature, the heterogeneous mixture was treated with ethanol (4.6 L). White solids were isolated through filtration, washed with 57:43 ethanol:pyridine (800 mL), and dried in a vacuum oven at 65° C. The title compound was obtained in a 1:0.92 ratio with pyridine and used directly in the subsequent step.

Intermediate 62: Step b 2,4-Dichloro-6-iodo-3-(4-(trifluoromethyl)benzyl)quinoline

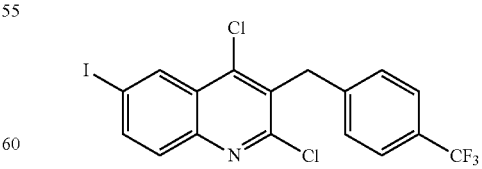

A thick slurry of 6-iodo-3-(4-(trifluoromethyl)benzyl)quinoline-2,4-diol (580.8 g, 1.122 mol, Intermediate 62: step a) in acetonitrile (5.8 L) was treated with phosphorous oxychloride (312.8 mL, 3.366 mol). The resulting solution was warmed to 80° C. for a period of 7 h and then cooled to room temperature over 1 h. The now heterogeneous mixture was stirred for 4 h and then diluted with water (5.8 L). After stirring for 1.5 h, the slurry was filtered, washed with 1:1 acetonitrile:water (4 L), and dried overnight in a vacuum oven at 65° C. to provide the title compound as a white solid.

Intermediate 62: Step c

4-Chloro-6-iodo-2-methoxy-3-(4-(trifluoromethyl)benzyl)quinoline

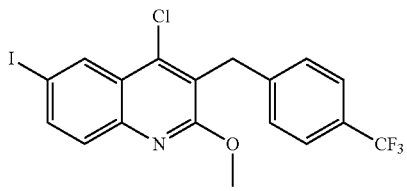 [SMILES: COc1nc2ccc(I)cc2c(Cl)c1Cc1ccc(C(F)(F)F)cc1]

A heterogeneous mixture of 2,4-dichloro-6-iodo-3-(4-(trifluoromethyl)benzyl)quinoline (515 g, 1.068 mol, Intermediate 62: step b) and sodium methoxide (577.1 g, 10.68 mol) in toluene (5.34 L) was heated to 92° C. for 18 h and then 100° C. for 13 h. After cooling to room temperature the slurry was poured over an aqueous solution of sodium bicarbonate (11.54 kg, 7 wt %, 9.615 mol). The biphasic system was mixed and then the layers were separated. The organic layer was dried over MgSO$_4$, filtered, and concentrated to afford the title compound as a white solid.

Intermediate 63

(4-Chloro-2-methoxy-3-(4-(trifluoromethyl)benzyl)quinolin-6-yl)(1-methyl-1H-1,2,3-triazol-5-yl)methanone

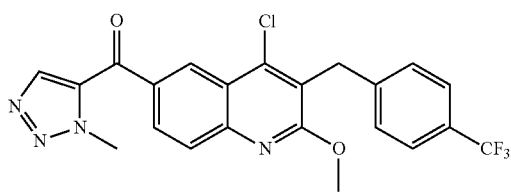 [SMILES: COc1nc2ccc(C(=O)c3cnnn3C)cc2c(Cl)c1Cc1ccc(C(F)(F)F)cc1]

A solution of 4-chloro-6-iodo-2-methoxy-3-(4-(trifluoromethyl)benzyl)quinoline (41.39 g, 86.6 mL, Intermediate 62: step c) in THF (800 mL) was cooled to 4° C., and isopropylmagnesium chloride (44.2 mL, 88.4 mmol, 2 M in THF) was added over 10 min. The mixture was stirred for 20 min and then N-methoxy-N,1-dimethyl-1H-1,2,3-triazole-5-carboxamide (14.74 g, 86.6 mmol, Intermediate 61) in THF (150 mL) was added. After warming to room temperature and stirring for 15 h, a solution of aqueous ammonium chloride (900 mL, 13 wt %) was added. The resulting biphasic mixture was stirred for 15 min. The layers were then separated, and the organic layer was washed with brine (450 mL). The organic layer was diluted with heptane (500 mL) and stirred for 1 h.

The resulting suspension was filtered, washed with heptane (100 mL), and dried in a 60° C. vacuum oven to afford the title compound as a white solid.

Intermediate 64

Methyl 4-chloro-2-methoxy-3-(4-(trifluoromethyl)benzyl)quinoline-6-carboxylate

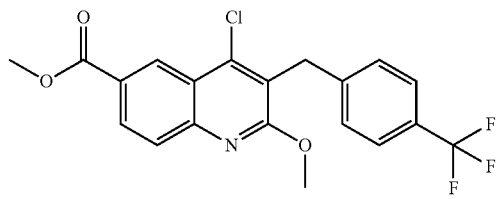 [SMILES: COC(=O)c1ccc2nc(OC)c(Cc3ccc(C(F)(F)F)cc3)c(Cl)c2c1]

n-BuLi (2.66 M in hexanes, 0.883 mL, 2.35 mmol) was added dropwise to a stirred solution of 6-bromo-4-chloro-2-methoxy-3-(4-(trifluoromethyl)benzyl)quinoline (1.01 g, 2.35 mmol, Intermediate 47, step d) in THF (11.5 mL) under argon at ~−70° C. After an additional 1 min, a pellet of dry ice (~4 g, ~90 mmol) was added to the dark solution, and the flask was quickly resealed, evacuated and flushed with argon. After another min, the resulting homogeneous yellow reaction was removed from the cold bath and stirred under ambient conditions for 5 min, and was then transferred to an ice bath and quenched with iodomethane (0.146 mL, 2.35 mmol) and DMSO (4.6 mL). The clear yellow reaction was stirred at 0° C. for 5 min, and was then rotovapped at rt to provide a thick light yellow slurry. This was treated with Li$_2$CO$_3$ (173 mg, 2.35 mmol) and iodomethane (0.438 mL, 7.03 mmol) and stirred at 40° C. for 30 min. The resulting opaque thin slurry was then diluted with DCM (15 mL), washed with water (2×25 mL), dried (Na$_2$SO$_4$), filtered, and concentrated to provide a white solid. This was recrystallized from hot heptane (10 mL), and the globular crystals were filtered and washed with heptane (2×6 mL) to provide the title compound as an off-white powder.

Intermediate 65: Step a 6-bromo-3-((6-(trifluoromethyl)pyridin-3-yl)methyl)quinoline-2,4-diol 6-Bromo-4-hydroxyquinolin-2(1H)-one (3.2 g, 18.3 mmol, Intermediate 44: step a), 6-(trifluoromethyl)nicotinaldehyde (4.0 g, 16.7 mmol), and diethyl 2,6-dimethyl-1,4-dihydropyridine-3,5-dicarboxylate (4.2 g, 16.7 mmol), in pyridine (34 mL) were heated to 105° C. for 3 hours. The solution was allowed to cool to ambient temperature, resulting in the formation of solid. Minimal isopropanol was added to the mixture and the slurry was stirred for 1 hour, sonicated, and filtered. The filtered solids were rinsed with isopropanol and dried under continuous air flow to provide the title compound as an off-white solid. Additional product was recrystallized from the filtrate, filtered, and rinsed with isopropanol.

Intermediate 65: Step b 6-bromo-2,4-dichloro-3-((6-(trifluoromethyl)pyridin-3-yl)methyl)quinoline

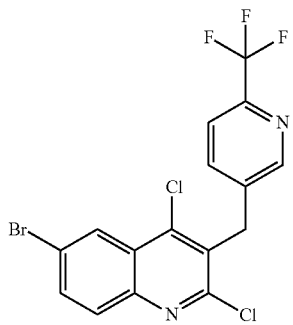 [SMILES: FC(F)(F)c1ccc(Cc2c(Cl)nc3ccc(Br)cc3c2Cl)cn1]

POCl$_3$ (1.5 mL) was added to a mixture of 6-bromo-3-((6-(trifluoromethyl)pyridin-3-yl)methyl)quinoline-2,4-diol (1.8 g, 4.6 mmol, Intermediate 65: step a) in acetonitrile (23 mL). The mixture was heated to 80° C. and refluxed overnight, forming an amber-colored solution. The solution was allowed to cool to ambient temperature and was quenched with water, resulting in the formation of precipitate. Concentrated ammonium hydroxide was added to the suspension to attain pH 9-10, and the slurry was stirred for 1 hour. The product solids were filtered then washed with 50:50 acetonitrile/water, followed by additional water, and dried in a high vacuum oven.

Intermediate 65: Step c 6-bromo-4-chloro-2-methoxy-3-((6-(trifluoromethyl)pyridin-3-yl)methyl)quinoline

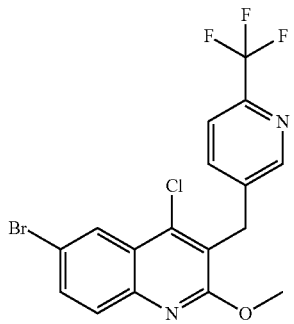 [SMILES: COc1nc2ccc(Br)cc2c(Cl)c1Cc1ccc(C(F)(F)F)nc1]

6-bromo-2,4-dichloro-3-(6-(trifluoromethyl)pyridin-3-yl)methyl)quinolone (1.0 g, 2.3 mmol, Intermediate 65: step b) and sodium methoxide (1.2 g, 22 mmol) in dry toluene (12 mL) were heated to 80° C. and refluxed under a positive pressure of nitrogen overnight. The mixture was allowed to cool to ambient temperature. Aqueous saturated sodium bicarbonate solution was added to the mixture and the layers were separated. The aqueous layer was extracted with ethyl acetate. The combined organic layers were dried over sodium sulfate, filtered, and concentrated to dryness. The crude material was purified by flash column chromatography (silica gel, 0-20% EtOAc-Hex) to provide the title compound as a white solid.

Intermediate 66: Step a tert-Butyl-3-((4-chloro-2-methoxy-3-(4-(trifluoromethyl)benzyl)quinolin-6-yl)(hydroxy)methyl)azetidine-1-carboxylate

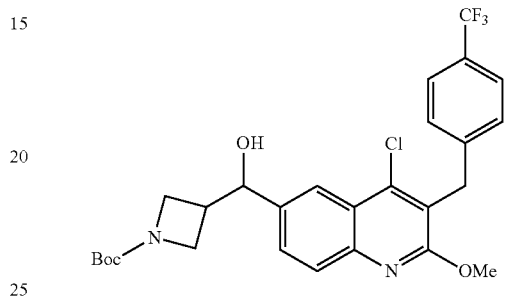

To a flask containing 6-bromo-4-chloro-2-methoxy-3-(4-(trifluoromethyl)benzyl)quinoline (1.0 g, 2.32 mmol, Intermediate 47: step d) was added THF (30 mL) resulting in a colorless homogeneous mixture. The solution was cooled to −70° C. and then n-BuLi (2.5M in hexanes, 1.08 mL, 2.69 mmol)) was added drop wise. The color of the solution became a dark opaque reddish-brown color. After 2 min, tert-butyl 3-formylazetidine-1-carboxylate (545 mg, 2.94 mmol, in 3 mL THF) was introduced. After 5 min, the reaction mixture was placed in an ice-water bath and allowed to stir for 30 min at which time the mixture was quenched with NH$_4$Cl solution. The contents were diluted further with water and extracted with EtOAc (5×40 mL). The combined organics were washed with brine, dried over MgSO$_4$, filtered and concentrated to provide a yellow foam. The crude material was chromatographed on silica gel (20% EtOAc-Hexanes increasing to 50% EtoAc) to give the title compound (950 mg) as a white solid. $^1$H NMR (500 MHz, CDCl$_3$) δ 8.06 (d, J=1.7 Hz, 1H), 7.84 (d, J=8.6 Hz, 1H), 7.63 (dd, J=8.6, 1.9 Hz, 1H), 7.50 (d, J=8.2 Hz, 2H), 7.38 (d, J=8.1 Hz, 2H), 4.99 (dd, J=8.0, 3.3 Hz, 1H), 4.35 (s, 2H), 4.05 (bs, 2H), 3.82 (t, J=8.7 Hz, 1H), 3.74-3.67 (m, 1H), 2.99-2.90 (m, 1H), 2.20-2.15 (m, 1H), 1.41 (s, 9H). MS (ESI): mass calcd. for C$_{27}$H$_{28}$ClF$_3$N$_2$O$_4$: 536.98, m/z found 537.2 [M+H]$^+$.

Intermediate 66: Step b tert-Butyl-3-(4-chloro-2-methoxy-3-(4-(trifluoromethyl)benzyl)quinoline-6-carbonyl)azetidine-1-carboxylate

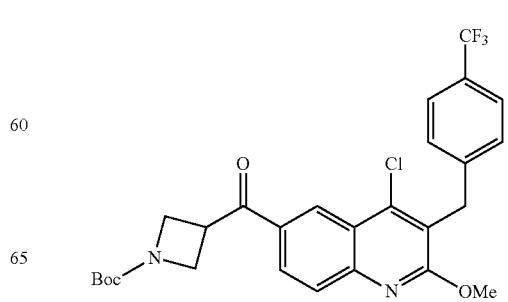

To a flask containing tert-butyl-3-(4-chloro-2-methoxy-3-(4-(trifluoromethyl)benzyl)quinolin-6-yl)(hydroxy)methyl)azetidine-1-carboxylate (525 mg, 0.98 mmol, Intermediate 66: step a) was added 1,4-dioxane (40 mL) to give a homogeneous solution at room temperature. Manganese dioxide (715 mg, 8.23 mmol) was then added and the mixture was heated to 85° C. in an aluminum heating mantle under nitrogen. After 60 min, the contents were filtered through a celite pad while the solution was still warm and rinsed with THF. The effluent was concentrated and purified by passing through a short column of silica gel (10% acetone-hexane increasing to 25% acetone) to give 505 mg of the title compound as a white amorphous solid. $^1$H NMR (500 MHz, CDCl$_3$) δ 8.57 (d, J=1.9 Hz, 1H), 8.14 (dd, J=8.7, 2.0 Hz, 1H), 7.90 (d, J=8.7 Hz, 1H), 7.52 (d, J=8.1 Hz, 2H), 7.39 (d, J=8.1 Hz, 2H), 4.36 (s, 2H), 4.29 (s, 4H), 4.11 (s, 3H), 1.58 (s, 2H), 1.45 (s, 9H). MS (ESI): mass calcd. for C$_{27}$H$_{26}$ClF$_3$N$_2$O$_4$: 534.97, m/z found 535.1 [M+H]$^+$.

Intermediate 66: Step c tert-Butyl-3-((4-chloro-2-methoxy-3-(4-(trifluoromethyl)benzyl)quinolin-6-yl)(hydroxy)(1-methyl-1H-1,2,3-triazol-5-yl)methyl)azetidine-1-carboxylate

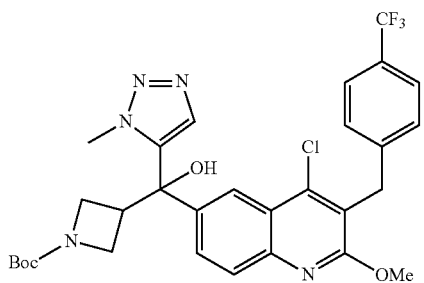 [SMILES: COc1nc2ccc(C(O)(c3cnnn3C)C3CN(C(=O)OC(C)(C)C)C3)cc2c(Cl)c1Cc1ccc(C(F)(F)F)cc1]

To a flask containing 1-methyl-1H-1,2,3-triazole (150 mg, 1.81 mmol) was added THF (15 mL) and the colorless homogeneous solution was cooled to −43° C. using a CH$_3$CN—CO$_2$ bath. n-BuLi (2.5M in hexanes, 0.7 mL, 1.75 mmol) was added drop wise via syringe which afforded an opaque mixture. The suspension was stirred at −40° C. for 30 min, then a THF solution of tert-butyl-3-(4-chloro-2-methoxy-3-(4-(trifluoromethyl)benzyl)quinoline-6-carbonyl)azetidine-1-carboxylate (430 mg, 0.8 mmol, in 2 mL THF, Intermediate 66: step b) was introduced at −40° C. The reaction mixture was allowed to warm gradually to room temperature over 45 min and then quenched with NH$_4$Cl solution. The aqueous portion was extracted with EtOAc (3×30 mL) and the combined organics were washed with brine, dried over MgSO$_4$, filtered and concentrated to provide an amber gum. Chromatography on silica gel (10% acetone-hexane increasing to 30% acetone) afforded the title compound (170 mg) as a white amorphous solid. $^1$H NMR (500 MHz, CDCl$_3$) δ 8.24 (d, J=2.1 Hz, 1H), 7.78 (d, J=8.8 Hz, 1H), 7.56-7.47 (m, 3H), 7.40 (d, J=8.1 Hz, 2H), 7.35 (dd, J=8.7, 2.1 Hz, 1H), 4.35 (s, 2H), 4.20 (t, J=8.8 Hz, 1H), 4.07 (s, 3H), 4.00 (dd, J=9.3, 5.6 Hz, 1H), 3.92 (dd, J=8.9, 5.7 Hz, 1H), 3.67 (s, 3H), 3.62 (t, J=8.8 Hz, 1H), 3.52-3.38 (m, 1H), 1.38 (s, 9H). MS (ESI): mass calcd. for C$_{30}$H$_{31}$ClF$_3$N$_5$O$_4$: 618.06, m/z found 619.9 [M+H]$^+$.

Intermediate 66: Step d

Azetidin-3-yl(4-chloro-2-methoxy-3-(4-(trifluoromethyl)benzyl)quinolin-6-yl)(1-methyl-1H-1,2,3-triazol-5-yl)methanol

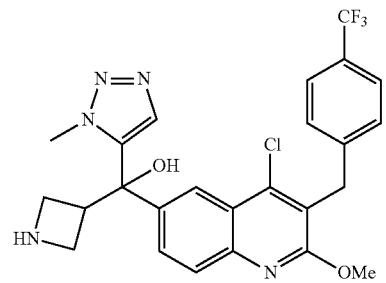 [SMILES: COc1nc2ccc(C(O)(c3cnnn3C)C3CNC3)cc2c(Cl)c1Cc1ccc(C(F)(F)F)cc1]

To a flask containing tert-butyl 3-(4-chloro-2-methoxy-3-(4-(trifluoromethyl)benzyl)quinolin-6-yl)(hydroxy)(1-methyl-1H-1,2,3-triazol-5-yl)methyl)azetidine-1-carboxylate (165 mg, 0.27 mmol, Intermediate 66: step c) was added formic acid (5 ml, 136 mmol) at room temperature followed by 6N HCl (210 μL, 1.24 mmol). The colorless mixture was stirred at room temperature for 40 min at which time LCMS and TLC (25% acetone-hexane) showed the reaction to be complete. MeOH (5 mL) was added and the mixture was stirred for 20 min before concentrating. The resulting oil was chromatographed directly on silica gel using (10% 2M NH$_3$-MeOH-dichloromethane increasing to 12% 2M NH$_3$-MeOH) to give initially 161 mg material. This material was dissolved in CHCl$_3$/MeOH and filtered through a celite plug to give 144 mg of the title compound as an off white powder. $^1$H NMR (500 MHz, CDCl$_3$) δ 8.30 (d, J=2.1 Hz, 1H), 8.20 (s, 1H), 7.92 (s, 1H), 7.76 (d, J=8.8 Hz, 1H), 7.47 (d, J=8.1 Hz, 2H), 7.42-7.32 (m, 3H), 4.52-4.34 (m, 2H), 4.33-4.16 (m, 3H), 4.05 (s, 3H), 3.96-3.80 (m, 1H), 3.71 (s, 4H). MS (ESI): mass calcd. for C$_{25}$H$_{23}$ClF$_3$N$_5$O$_2$: 517.94, m/z found 518.9 [M+H]$^+$.

Example 1

(3-Benzyl-2,4-dichloroquinolin-6-yl)(4-chlorophenyl)(1-methyl-1H-imidazol-5-yl)methanol

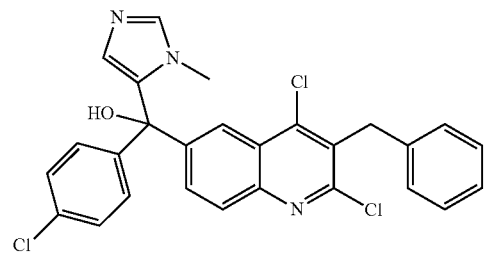 [SMILES: Cn1cncc1C(O)(c1ccc(Cl)cc1)c1ccc2nc(Cl)c(Cc3ccccc3)c(Cl)c2c1]

Into a 25-mL round-bottom flask purged and maintained with an inert atmosphere of nitrogen, was placed a solution of 3-benzyl-6-bromo-2,4-dichloroquinoline (500 mg, 1.36 mmol, Intermediate 2: step c) in tetrahydrofuran (10 mL). n-BuLi (0.6 mL, 2.5 M in hexanes) was then added at −78° C. The resulting solution was stirred for 1 hour at −78° C. (4-Chlorophenyl)(1-methyl-1H-imidazol-5-yl)methanone (301 mg, 1.36 mmol, Intermediate 1: step b) was added to this solution. The resulting solution was allowed to react, with stirring, for an additional 8 hours at room temperature. The reaction was then quenched by the addition of 10 mL of water/ice. The resulting solution was extracted with 3×20 mL of ethyl acetate. The combined organic layer was dried over anhydrous sodium sulfate, filtered, and concentrated under vacuum. The residue was purified by chromatography over a silica gel column with dichloromethane/methanol to give the title compound as a white solid. $^1$H NMR (400 MHz, DMSO-$d_6$) δ=8.20 (s, 1H), 8.01 (d, J=8.5 Hz, 1H), 7.69-7.79 (m, 2H), 7.44 (d, J=7.5 Hz, 2H), 7.25-7.37 (m, 4H), 7.14-7.25 (m, 4H), 6.20 (s, 1H), 4.47 (s, 2H), 3.31 (s, 3H); MS m/e 508 [M+H]$^+$.

Example 2

(3-Chlorophenyl)-(2,4-dichloro-3-(4-chlorobenzyl) quinolin-6-yl)-(pyridin-3-yl)methanol.TFA

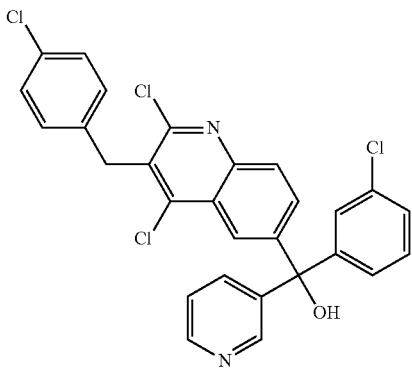 [SMILES: OC(c1cccnc1)(c1cccc(Cl)c1)c1ccc2nc(Cl)c(Cc3ccc(Cl)cc3)c(Cl)c2c1]

A mixture of 6-bromo-2,4-dichloro-3-(4-chlorobenzyl) quinoline (0.10 g, 0.249 mmol, Intermediate 3: step c) and (3-chlorophenyl)(3-pyridinyl)methanone (0.059 g, 0.274 mmol) in dry THF was cooled to −78° C. and n-BuLi (1.6 M in hexane, 0.202 mL) was added over a 30 minute period. Stirring was continued at 78° C. for an additional hour, the mixture warmed up to room temperature and saturated aqueous NH$_4$Cl added. The layers were separated and the aqueous mixture again extracted with EtOAc. The combined organic extracts were dried over Na$_2$SO$_4$, filtered, evaporated in vacuo, and chromatographed (2% MeOH in dichloromethane). Fractions containing the desired product were combined and further purified by Gilson HPLC (H$_2$O/acetonitrile/1% TFA) to provide the title compound as a white solid. $^1$H NMR (400 MHz, DMSO-$d_6$) δ ppm 4.46 (s, 2H) 7.12-7.28 (m, 3H) 7.35 (d, J=8.08 Hz, 2H) 7.43 (dd, J=6.32, 3.79 Hz, 4H) 7.65 (dd, J=8.08, 5.05 Hz, 1H) 7.78 (dd, J=8.59, 2.02 Hz, 1H) 7.91-8.07 (m, 2H) 8.16 (d, J=2.02 Hz, 1H) 8.62 (br. s., 1H) 8.67 (d, J=4.55 Hz, 1H); MS (ESI) 540.

Example 3

(3-Chlorophenyl)-(2,4-dichloro-3-(4-fluorobenzyl) quinolin-6-yl)-(pyridin-3-yl)methanol.TFA

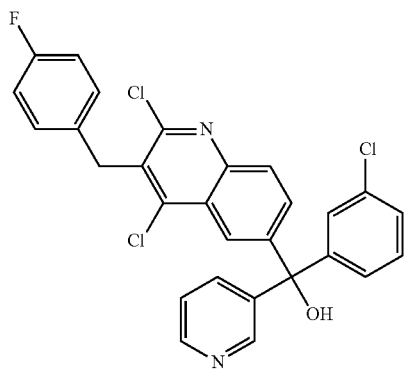 [SMILES: OC(c1cccnc1)(c1cccc(Cl)c1)c1ccc2nc(Cl)c(Cc3ccc(F)cc3)c(Cl)c2c1]

The title compound was prepared by substituting 6-bromo-2,4-dichloro-3-(4-chlorobenzyl)quinoline (Intermediate 3: step c) with 6-bromo-2,4-dichloro-3-(4-fluorobenzyl)quinoline (Intermediate 4: step c) then following the procedure described for the preparation of Example 2. $^1$H NMR (400 MHz, DMSO-$d_6$) δ ppm 4.45 (s, 2H) 7.03-7.17 (m, 2H) 7.17-7.30 (m, 3H) 7.35-7.49 (m, 4H) 7.61-7.74 (m, 1H) 7.79 (d, J=8.59 Hz, 1H) 7.94-8.09 (m, 2H) 8.16 (s, 1H) 8.55-8.81 (m, 2H); MS (ESI) 524.

Example 4

(3-Chlorophenyl)-(2,4-dichloro-3-(3-chlorobenzyl) quinolin-6-yl)-(pyridin-3-yl)methanol.TFA

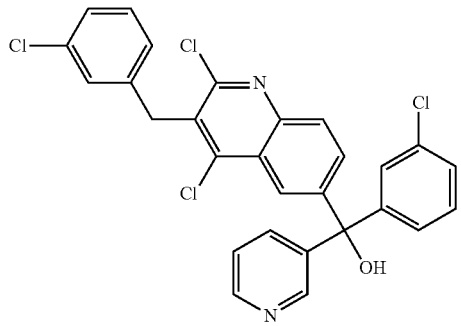 [SMILES: OC(c1cccnc1)(c1cccc(Cl)c1)c1ccc2nc(Cl)c(Cc3cccc(Cl)c3)c(Cl)c2c1]

The title compound was prepared by substituting 6-bromo-2,4-dichloro-3-(4-chlorobenzyl)quinoline (Intermediate 3: step c) with 6-bromo-2,4-dichloro-3-(3-chlorobenzyl)quinoline (Intermediate 5: step c) then following the procedure described for the preparation of Example 2. $^1$H NMR (400 MHz, DMSO-$d_6$) δ ppm 4.48 (s, 2H) 7.10 (d, J=6.06 Hz, 1H) 7.19-7.34 (m, 4H) 7.38-7.50 (m, 4H) 7.66 (br. s., 1H) 7.79

(dd, J=8.59, 2.02 Hz, 1H) 7.98 (d, J=8.08 Hz, 1H) 8.04 (d, J=8.59 Hz, 1H) 8.16 (d, J=2.02 Hz, 1H) 8.58-8.73 (m, 2H); MS (ESI) 541.

Example 5

(3-(4-(1H-Pyrazol-1-yl)benzyl)-2,4-dichloroquinolin-6-yl)(3-chlorophenyl)(pyridin-3-yl)methanol.TFA

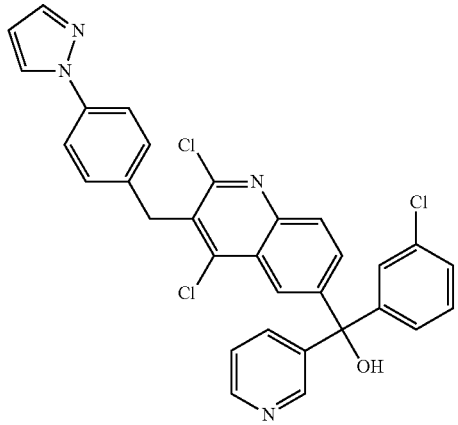 [SMILES: OC(c1cccnc1)(c1cccc(Cl)c1)c1ccc2nc(Cl)c(Cc3ccc(-n4cccn4)cc3)c(Cl)c2c1]

The title compound was prepared by substituting 6-bromo-2,4-dichloro-3-(4-chlorobenzyl)quinoline (Intermediate 3: step c) with 3-(4-(1H-pyrazol-1-yl)benzyl)-6-bromo-2,4-dichloroquinoline (Intermediate 6: step c) then following the procedure described for the preparation of Example 2. $^1$H NMR (400 MHz, DMSO-$d_6$) δ ppm 4.50 (s, 2H) 6.36-6.64 (m, 1H) 7.17-7.26 (m, 1H) 7.29 (d, J=8.59 Hz, 2H) 7.38-7.51 (m, 4H) 7.65 (dd, J=7.58, 5.05 Hz, 1H) 7.69-7.83 (m, 4H) 7.98 (d, J=8.08 Hz, 1H) 8.04 (d, J=9.09 Hz, 1H) 8.17 (d, J=2.02 Hz, 1H) 8.43 (d, J=2.53 Hz, 1H) 8.63 (d, J=2.02 Hz, 1H) 8.67 (d, J=3.54 Hz, 1H); MS (ESI) 571.

Example 6

(3-Chlorophenyl)-(2,4-dichloro-3-(4-methoxybenzyl)quinolin-6-yl)-(pyridin-3-yl)methanol.TFA

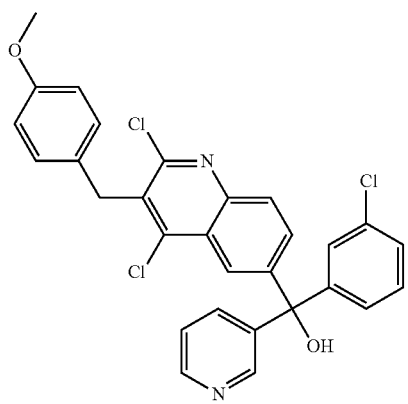 [SMILES: COc1ccc(Cc2c(Cl)nc3ccc(C(O)(c4cccnc4)c4cccc(Cl)c4)cc3c2Cl)cc1]

The title compound was prepared by substituting 6-bromo-2,4-dichloro-3-(4-chlorobenzyl)quinoline (Intermediate 3: step c) with 6-bromo-2,4-dichloro-3-(4-methoxybenzyl)quinoline (Intermediate 7: step c) then following the procedure described for the preparation of Example 2. $^1$H NMR (400 MHz, DMSO-$d_6$) δ ppm 3.69 (s, 3H) 4.39 (s, 2H) 6.85 (d, J=8.59 Hz, 2H) 7.10 (d, J=9.09 Hz, 2H) 7.23 (d, J=5.56 Hz, 1H) 7.38-7.49 (m, 4H) 7.66 (dd, J=8.08, 5.05 Hz, 1H) 7.77 (dd, J=8.59, 2.02 Hz, 1H) 7.96-8.06 (m, 2H) 8.15 (d, J=2.02 Hz, 1H) 8.63 (s, 1H) 8.68 (d, J=5.05 Hz, 1H); MS (ESI) 535.

Example 7

(4-Chloro-3-(4-fluorobenzyl)-2-methoxyquinolin-6-yl)(3-chlorophenyl)(pyridin-3-yl)methanol

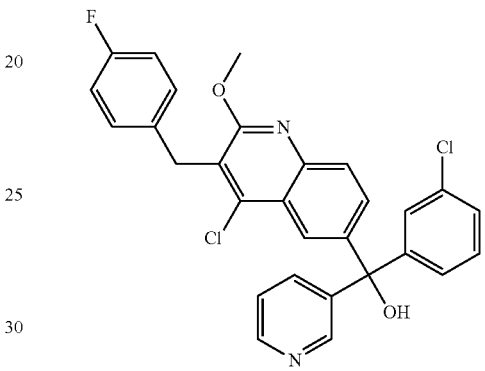

The title compound was prepared by substituting 6-bromo-2,4-dichloro-3-(4-chlorobenzyl)quinoline (Intermediate 3: step c) with 6-bromo-4-chloro-3-(4-fluorobenzyl)-2-methoxyquinoline (Intermediate 4: step d) then following the procedure described for the preparation of Example 2. $^1$H NMR (400 MHz, DMSO-$d_6$) δ ppm 4.02 (s, 3H) 4.22 (s, 2H) 7.08 (t, J=8.84 Hz, 2H) 7.16-7.33 (m, 4H) 7.36-7.47 (m, 3H) 7.54-7.70 (m, 2H) 7.84 (d, J=9.09 Hz, 1H) 7.95 (d, J=8.59 Hz, 1H) 8.00 (d, J=2.02 Hz, 1H) 8.61 (br. s., 1H) 8.65 (br. s., 1H); MS (ESI) 519.

Example 8

(3-Chlorophenyl)(2,4-dichloro-3-(4-(methylsulfonyl)benzyl)quinolin-6-yl)(pyridin-3-yl)methanol.TFA

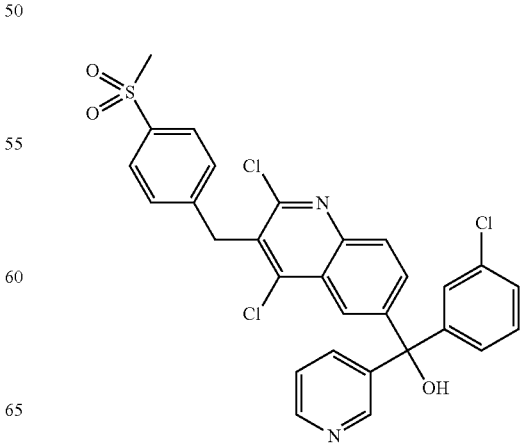

The title compound was prepared by substituting 6-bromo-2,4-dichloro-3-(4-chlorobenzyl)quinoline (Intermediate 3: step c) with 6-bromo-2,4-dichloro-3-(4-(methylsulfonyl)benzyl)quinoline (Intermediate 8: step c) then following the procedure described for the preparation of Example 2. $^1$H NMR (400 MHz, DMSO-$d_6$) δ ppm 3.19 (s, 3H) 4.59 (s, 2H) 7.18-7.29 (m, 1H) 7.36-7.48 (m, 6H) 7.65 (br. s., 1H) 7.76-7.82 (m, 1H) 7.85 (d, J=8.08 Hz, 2H) 7.95 (d, J=7.58 Hz, 1H) 8.05 (d, J=8.59 Hz, 1H) 8.17 (d, J=2.02 Hz, 1H) 8.56-8.71 (m, 2H); MS (ESI) 585.

Example 9

(2,4-Dichloro-3-(4-chlorobenzyl)quinolin-6-yl)(pyridin-3-yl)(thiazol-5-yl)methanol.TFA

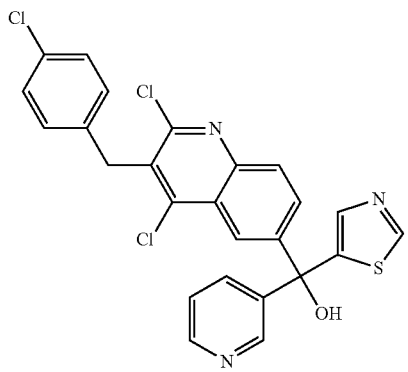 [SMILES: OC(c1cccnc1)(c1ccc2nc(Cl)c(Cc3ccc(Cl)cc3)c(Cl)c2c1)c1cncs1]

The title compound was prepared by using pyridin-3-yl(thiazol-5-yl)methanone (Intermediate 11: step b) in place of (3-chlorophenyl)(3-pyridinyl)methanone and following the procedure described for Example 2. $^1$H NMR (400 MHz, DMSO-$d_6$) δ ppm 4.47 (s, 2H) 7.20 (d, J=8.59 Hz, 2H) 7.35 (d, J=8.59 Hz, 2H) 7.60 (s, 1H) 7.65-7.74 (m, 1H) 7.79-7.94 (m, 2H) 7.98-8.14 (m, 2H) 8.29 (s, 1H) 8.63-8.82 (m, 2H) 9.17 (s, 1H); MS (ESI) 514.

Example 10

(2,4-Dichloro-3-(3-chlorobenzyl)quinolin-6-yl)(pyridin-3-yl)(thiazol-5-yl)methanol.TFA

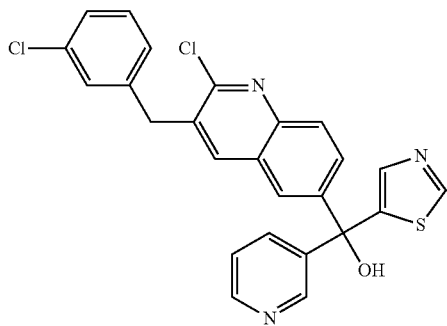 [SMILES: OC(c1cccnc1)(c1ccc2nc(Cl)c(Cc3cccc(Cl)c3)cc2c1)c1cncs1]

A mixture of 6-bromo-2-chloro-3-(3-chlorobenzyl)quinoline (0.095 g, 0.259 mmol, Intermediate 12: step b) and pyridin-3-yl(thiazol-5-yl)methanone (0.044 g, 0.207 mmol, Intermediate 11: step b) in dry THF (3 mL) were cooled to −78° C. and n-BuLi (0.21 mL, 0.336 mmol, 1.6 M in hexane) was added over a 30 minute period. Stirring was continued at −78° C. for 30 minutes, the mixture warmed up to 0° C., stirred for 1 hour and saturated aqueous NH$_4$Cl was added. The layers were separated and the aqueous mixture again extracted with EtOAc. The combined organic extract was dried over Na$_2$SO$_4$, filtered, evaporated in vacuo, and chromatographed (EtOAc/CH$_2$Cl$_2$) to provide the product. Further purification by Gilson HPLC(H$_2$O/acetonitrile/1% TFA) provided the title compound as a white solid. $^1$H NMR (400 MHz, DMSO-$d_6$) δ ppm 4.22 (s, 2H) 7.16-7.27 (m, 1H) 7.26-7.42 (m, 3H) 7.56 (s, 1H) 7.59-7.73 (m, 2H) 7.75-7.84 (m, 1H) 7.88-7.99 (m, 2H) 7.99-8.08 (m, 1H) 8.37-8.44 (m, 1H) 8.62-8.76 (m, 2H) 9.09-9.19 (m, 1H); MS (ESI) 478.

Example 11

(3-(4-(1H-Pyrazol-1-yl)benzyl)-2,4-dichloroquinolin-6-yl)(4-chlorophenyl)(1-methyl-1H-imidazol-5-yl)methanol.TFA

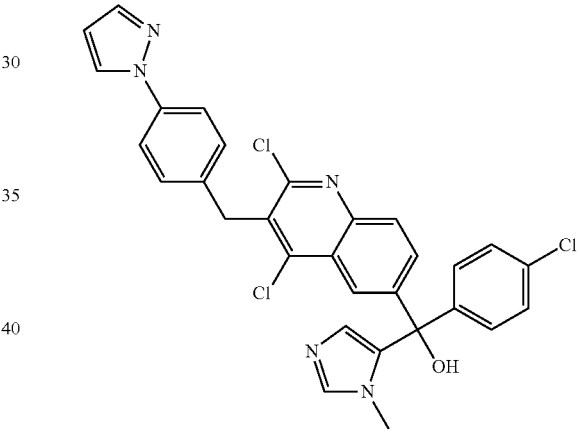

A mixture of 3-(4-(1H-pyrazol-1-yl)benzyl)-6-bromo-2,4-dichloroquinoline (0.2 g, 0.462 mmol, Intermediate 6: step c) and (4-chlorophenyl)(1-methyl-1H-imidazol-5-yl)methanone (0.113 g, 0.462 mmol, Intermediate 1: step b) in dry THF (5 mL) was cooled to −78° C. and n-BuLi (0.375 mL, 0.6 mmol, 1.6 M in hexane) was added dropwise over a 30 minute period. Stirring was continued at −78° C. for 30 minutes, the mixture warmed up to 0° C., stirred for 1 hour and saturated aqueous NH$_4$Cl was added. The layers were separated and the aqueous mixture again extracted with EtOAc. The combined organic extract was dried over Na$_2$SO$_4$, filtered, evaporated in vacuo, and chromatographed (EtOAc/CH$_2$Cl$_2$) to provide the product. Further purification by Gilson HPLC(H$_2$O/acetonitrile/1% TFA) provided the title compound as a white solid. $^1$H NMR (400 MHz, DMSO-$d_6$) δ ppm 3.55 (s, 3H) 4.51 (s, 2H) 6.53 (s, 1H) 7.04 (s, 1H) 7.31 (d, J=8.31 Hz, 2H) 7.41 (d, J=8.56 Hz, 2H) 7.47-7.58 (m, 2H) 7.66-7.84 (m, 5H) 8.08 (d, J=8.80 Hz, 1H) 8.25 (s, 1H) 8.44 (d, J=1.96 Hz, 1H) 9.15 (s, 1H); MS (ESI) 574; 576.

Example 12

(4-Chlorophenyl)(2,4-dichloro-3-(4-methoxybenzyl)quinolin-6-yl)(1-methyl-1H-imidazol-5-yl)methanol.TFA

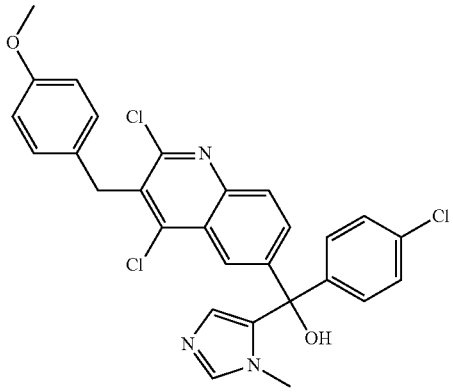 [SMILES: COc1ccc(Cc2c(Cl)nc3ccc(C(O)(c4ccc(Cl)cc4)c4cncn4C)cc3c2Cl)cc1]

The title compound was prepared by substituting 3-(4-(1H-pyrazol-1-yl)benzyl)-6-bromo-2,4-dichloroquinoline (Intermediate 6: step c) with 6-bromo-2,4-dichloro-3-(4-methoxybenzyl)quinoline (Intermediate 7: step c) then following the procedure used for the preparation of Example 11. $^1$H NMR (400 MHz, DMSO-d$_6$) δ ppm 3.54 (s, 3H) 3.70 (s, 3H) 4.40 (s, 2H) 6.85 (d, J=8.56 Hz, 2H) 7.03 (s, 1H) 7.11 (d, J=8.31 Hz, 2H) 7.41 (d, J=8.56 Hz, 2H) 7.46-7.55 (m, 2H) 7.70-7.79 (m, 2H) 8.06 (d, J=8.80 Hz, 1H) 8.23 (s, 1H) 9.15 (s, 1H); MS (ESI) 540.

Example 13

(4-Chloro-2-methoxy-3-(4-methoxybenzyl)quinolin-6-yl)(4-chlorophenyl)(1-methyl-1H-imidazol-5-yl)methanol.TFA

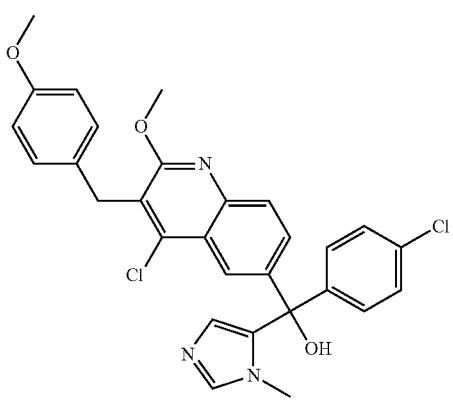 [SMILES: COc1ccc(Cc2c(OC)nc3ccc(C(O)(c4ccc(Cl)cc4)c4cncn4C)cc3c2Cl)cc1]

A mixture of (4-chlorophenyl)(2,4-dichloro-3-(4-methoxybenzyl)quinolin-6-yl)(1-methyl-1H-imidazol-5-yl)methanol.TFA (0.050 g, 0.093 mmol, Example 12) and a 0.5 M sodium methoxide in methanol solution (3.3 mL, 1.67 mmol) was heated in a sealed tube at 80° C. overnight. The mixture was cooled to room temperature and poured into ice water (20 mL). The aqueous mixture was stirred for 2 hours then filtered to provide a mixture of mono and disubstituted products as a tan solid. Further purification of the mixture by Gilson HPLC provided the title compound as a solid. $^1$H NMR (400 MHz, DMSO-d6) δ ppm 3.53 (s, 3H) 3.68 (s, 3H) 4.03 (s, 3H) 4.17 (s, 2H) 6.82 (d, J=8.31 Hz, 2H) 6.97 (s, 1H) 7.15 (d, J=8.31 Hz, 2H) 7.37 (d, J=8.31 Hz, 2H) 7.49 (d, J=8.31 Hz, 2H) 7.54-7.69 (m, 2H) 7.85 (d, J=8.80 Hz, 1H) 8.09 (s, 1H) 9.13 (s, 1H); MS (ESI) 534.

Example 14

(3-Benzyl-4-chloro-2-ethoxyquinolin-6-yl)(4-chlorophenyl)(1-methyl-1H-imidazol-5-yl)methanol.TFA

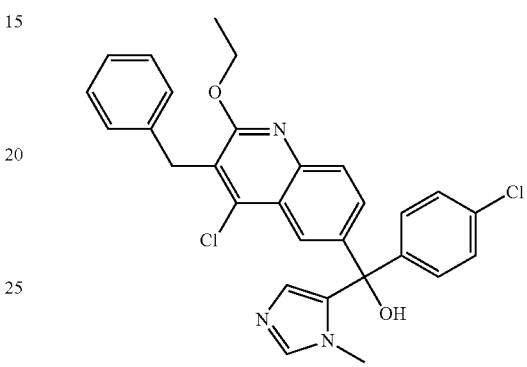

A mixture of (3-benzyl-2,4-dichloroquinolin-6-yl)(4-chlorophenyl)(1-methyl-1H-imidazol-5-yl)methanol (0.053 g, 0.104 mmol, Example 1) and a sodium ethoxide solution (0.1 mL, 21 wt % soln.) in EtOH (1 mL) was heated in a sealed tube at 80° C. overnight, cooled to room temperature and poured over ice water (20 mL). The mixture was stirred for 30 minutes then filtered to yield crude product as a solid. Further purification by Gilson HPLC provided the title compound as a white solid. $^1$H NMR (400 MHz, MeOH-d$_4$) δ ppm 1.38 (t, J=7.07 Hz, 3H) 3.69 (s, 3H) 4.29 (s, 2H) 4.52 (q, J=7.07 Hz, 2H) 6.87 (s, 1H) 7.11-7.18 (m, 1H) 7.19-7.29 (m, 4H) 7.35-7.42 (m, 2H) 7.42-7.49 (m, 2H) 7.63 (dd, J=8.84, 2.27 Hz, 1H) 7.84 (d, J=9.09 Hz, 1H) 8.13 (d, J=2.02 Hz, 1H) 8.95 (s, 1H); MS (ESI) 518.

Example 15

(3-(4-(1H-Pyrazol-1-yl)benzyl)-2,4-dichloroquinolin-6-yl)(1-methyl-1H-imidazol-5-yl)(thiazol-5-yl)methanol.TFA

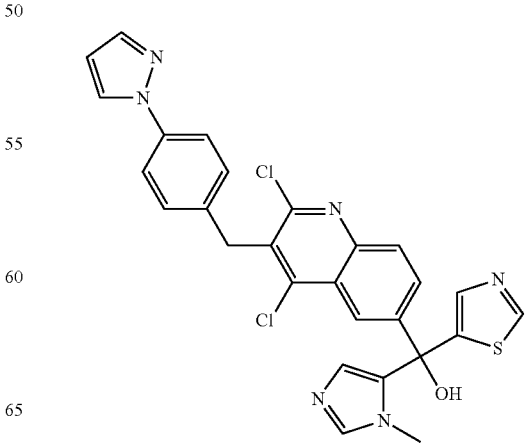

The title compound was prepared by substituting (4-chlorophenyl)(1-methyl-1H-imidazol-5-yl)methanone with (1-methyl-1H-imidazol-5-yl)(thiazol-5-yl)methanone (Intermediate 13) then following the procedure described for the preparation of Example 11. $^1$H NMR (400 MHz, MeOH-d$_4$) δ ppm 2.66 (s, 1H) 3.71 (s, 3H) 4.62 (s, 2H) 6.50 (s, 1H) 7.25 (s, 1H) 7.34 (d, J=8.31 Hz, 2H) 7.65 (d, J=8.31 Hz, 2H) 7.70 (d, J=6.85 Hz, 2H) 7.89 (d, J=8.80 Hz, 1H) 8.08 (d, J=8.80 Hz, 1H) 8.17 (d, J=1.96 Hz, 1H) 8.48 (s, 1H) 9.01 (s, 1H) 9.11 (s, 1H); MS (ESI) 546.

Example 16

(3-(4-(1H-Pyrazol-1-yl)benzyl)-4-chloro-2-ethoxyquinolin-6-yl)(1-methyl-1H-imidazol-5-yl)(thiazol-5-yl)methanol.TFA

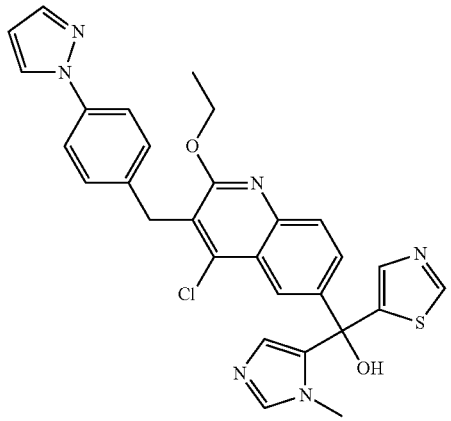 [SMILES: CCOc1nc2ccc(C(O)(c3cncs3)c3cncn3C)cc2c(Cl)c1Cc1ccc(-n2cccn2)cc1]

The title compound was prepared by using (3-(4-(1H-pyrazol-1-yl)benzyl)-2,4-dichloroquinolin-6-yl)(1-methyl-1H-imidazol-5-yl)(thiazol-5-yl)methanol.TFA (Example 15) in place of (3-benzyl-2,4-dichloroquinolin-6-yl)(4-chlorophenyl)(1-methyl-1H-imidazol-5-yl)methanol then following the procedure described for the preparation of Example 14. $^1$H NMR (400 MHz, MeOH-d$_4$) δ ppm 1.42 (t, J=7.07 Hz, 3H) 3.70 (s, 3H) 4.37 (s, 2H) 4.56 (q, J=7.07 Hz, 2H) 6.49 (t, J=2.27 Hz, 1H) 7.18 (d, J=2.02 Hz, 1H) 7.41 (d, J=8.59 Hz, 2H) 7.61 (d, J=8.59 Hz, 2H) 7.65-7.75 (m, 3H) 7.90 (d, J=9.09 Hz, 1H) 8.14 (d, J=2.53 Hz, 1H) 8.30 (d, J=2.02 Hz, 1H) 8.98 (s, 1H) 9.08 (s, 1H); MS (ESI) 557.

Example 17

(3-(4-(1H-Pyrazol-1-yl)benzyl)-4-chloro-2-(ethyl(methyl)amino)quinolin-6-yl)(4-chlorophenyl)(1-methyl-1H-imidazol-5-yl)methanol.TFA

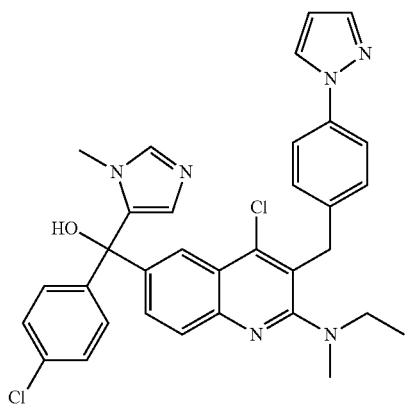 [SMILES: CCN(C)c1nc2ccc(C(O)(c3ccc(Cl)cc3)c3cncn3C)cc2c(Cl)c1Cc1ccc(-n2cccn2)cc1]

The title compound was prepared by substituting 3-(4-(1H-pyrazol-1-yl)benzyl)-6-bromo-2,4-dichloroquinoline (Intermediate 6: step c) with 3-(4-(1H-pyrazol-1-yl)benzyl)-6-bromo-4-chloro-N-ethyl-N-methylquinolin-2-amine (Intermediate 14) then following the procedure described for the preparation of Example 11. $^1$H NMR (400 MHz, DMSO-d$_6$) δ ppm 1.08 (t, J=6.82 Hz, 3H) 2.87 (s, 3H) 3.16 (q, J=6.91 Hz, 2H) 3.55 (s, 3H) 4.34 (s, 2H) 6.47-6.56 (m, 1H) 6.99 (s, 1H) 7.25 (d, J=8.08 Hz, 2H) 7.33-7.43 (m, 2H) 7.49 (d, J=8.59 Hz, 2H) 7.53-7.60 (m, 2H) 7.68-7.78 (m, 3H) 7.82 (d, J=8.59 Hz, 1H) 8.06 (s, 1H) 8.43 (d, J=2.53 Hz, 1H) 9.13 (s, 1H); MS (ESI) 597.

Example 18

(3-Benzyl-2,4-dichloroquinolin-6-yl)(6-methoxypyridin-3-yl)(thiazol-5-yl)methanol

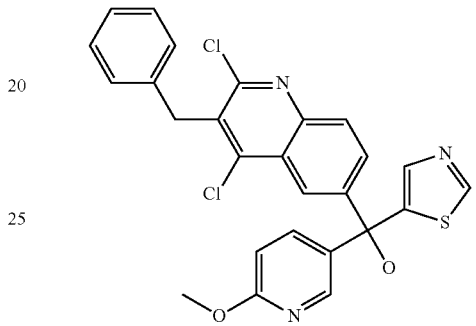

A mixture of 3-benzyl-6-bromo-2,4-dichloroquinoline (0.168 g, 0.458 mmol, Intermediate 2: step c) and (6-methoxypyridin-3-yl)(thiazol-5-yl)methanone (0.112 g, 0.458 mmol, Intermediate 15) in dry THF (5 mL) was cooled to −78° C. and n-BuLi (0.37 mL, 0.595 mmol, 1.6 M in hexane) was added dropwise. Stirring was continued at −78° C. for 5 minutes, the mixture warmed up to 0° C., stirred for 1 hour and saturated aqueous NH$_4$Cl was added. The layers were separated and the aqueous mixture again extracted with EtOAc. The combined organic extracts were dried over Na$_2$SO$_4$, filtered, evaporated in vacuo, and chromatographed (EtOAc/CH$_2$Cl$_2$) to provide the product. Further purification by Gilson HPLC(H$_2$O/acetonitrile/1% TFA) provided the TFA salt of the title compound as a white solid. $^1$H NMR (400 MHz, DMSO-d$_6$) δ ppm 3.17 (s, 1H) 3.84 (s, 3H) 4.48 (s, 1H) 6.83 (d, J=8.59 Hz, 1H) 7.17 (d, J=7.58 Hz, 2H) 7.21-7.24 (m, 1H) 7.28 (d, J=7.58 Hz, 2H) 7.55 (s, 2H) 7.67 (dd, J=8.84, 2.78 Hz, 1H) 7.83 (dd, J=9.09, 2.02 Hz, 1H) 7.95-8.11 (m, 2H) 8.28 (d, J=2.02 Hz, 1H) 9.12 (s, 1H); MS (ESI) 508.

Example 19

(3-Benzyl-4-chloro-2-ethoxyquinolin-6-yl)(6-methoxypyridin-3-yl)(thiazol-5-yl)methanol

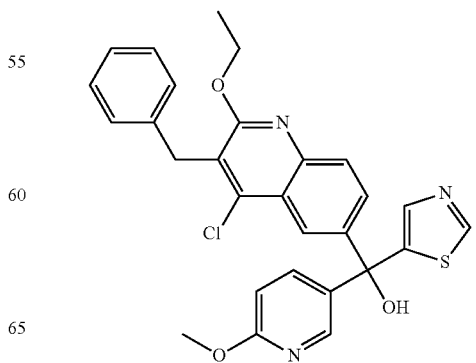

The title compound was prepared by substituting (3-benzyl-2,4-dichloroquinolin-6-yl)(4-chlorophenyl)(1-methyl-1H-imidazol-5-yl)methanol with (3-benzyl-2,4-dichloroquinolin-6-yl)(6-methoxypyridin-3-yl)(thiazol-5-yl)methanol (Example 18), then followed the procedure described for the preparation of Example 14. $^1$H NMR (400 MHz, DMSO-d$_6$) δ ppm 1.33 (t, J=6.82 Hz, 3H) 3.84 (s, 3H) 4.24 (s, 2H) 4.47 (q, J=7.07 Hz, 2H) 6.81 (d, J=8.59 Hz, 1H) 7.14-7.31 (m, 5H) 7.51 (s, 2H) 7.64 (dd, J=8.84, 2.27 Hz, 2H) 7.78 (d, J=8.59 Hz, 1H) 8.05 (d, J=2.02 Hz, 1H) 8.13 (d, J=2.02 Hz, 1H) 9.10 (s, 1H); MS (ESI) 518.

Example 20A (3-(4-(1H-Pyrazol-1-yl)benzyl)-4-chloro-2-methoxyquinolin-6-yl)(6-methoxypyridin-3-yl)(thiazol-5-yl)methanol

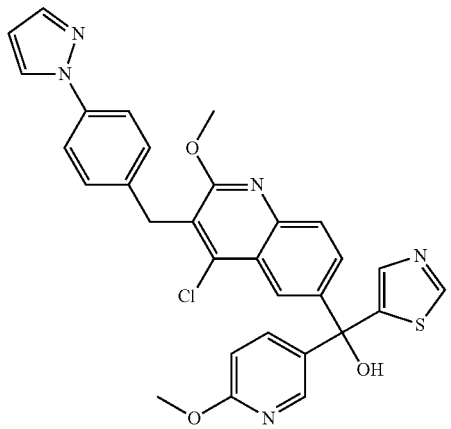 [SMILES: COc1ccc(C(O)(c2ccc3nc(OC)c(Cc4ccc(-n5cccn5)cc4)c(Cl)c3c2)c2cncs2)cn1]

n-Butyllithium (0.154 mL, 0.246 mmol; 1.6 M in hexane) was added dropwise to a solution of 3-(4-(1H-pyrazol-1-yl)benzyl)-6-bromo-4-chloro-2-methoxyquinoline (0.081 g, 0.189 mmol, Intermediate 16) in dry THF (4 mL) at −78° C. over a 5 minute period. After complete addition stirring was continued at −78° C. for 30 minutes then (6-methoxypyridin-3-yl)(thiazol-5-yl)methanone (0.046 g, 0.189 mmol, Intermediate 15) dissolved in THF (1.9 mL) was slowly added and the reaction warmed in an ice bath to 0° C. The mixture was stirred for 30 minutes, quenched with saturated aqueous NH$_4$Cl then warmed to room temperature. After stirring for 10 minutes layers were separated and the aqueous layer extracted with EtOAc. The combined organic extracts were dried over Na$_2$SO$_4$, filtered, evaporated in vacuo and chromatographed (0-100% EtOAc in DCM) to provide the title compound. $^1$H NMR (400 MHz, MeOH-d$_4$) δ ppm 3.94 (s, 3H) 4.08 (s, 3H) 4.35 (s, 2H) 6.43-6.52 (m, 1H) 6.88 (d, J=9.09 Hz, 1H) 7.37 (d, J=8.08 Hz, 2H) 7.54-7.63 (m, 3H) 7.66-7.72 (m, 2H) 7.77 (dd, J=8.59, 2.53 Hz, 1H) 7.85 (d, J=8.59 Hz, 1H) 8.12 (dd, J=13.14, 2.53 Hz, 2H) 8.20 (s, 1H) 9.08 (s, 1H); MS (ESI) 570.

(3-(4-(1H-pyrazol-1-yl)benzyl)-4-chloro-2-methoxyquinolin-6-yl)(6-methoxypyridin-3-yl)(thiazol-5-yl)methanol was purified by HPLC (Chiralpak AD column, 500 gram, 41 cm) ethanol eluent, 80 mL/minute, 230 nm wavelength) to give two enantiomers The first eluting enantiomer was Example 20B: $^1$H NMR (400 MHz, CDCl$_3$) δ ppm 3.15 (br. s., 1H) 3.94 (s, 3H) 4.08 (s, 3H) 4.32 (s, 2H) 6.43 (d, J=2.02 Hz, 1H) 6.74 (d, J=8.59 Hz, 1H) 7.35 (d, J=8.59 Hz, 2H) 7.51-7.65 (m, 5H) 7.69 (d, J=2.02 Hz, 1H) 7.82 (d, J=8.59 Hz, 1H) 7.86 (d, J=2.53 Hz, 1H) 8.12 (d, J=2.53 Hz, 1H) 8.18 (d, J=2.02 Hz, 1H) 8.84 (s, 1H) and the second eluting enantiomer was Example 20C: $^1$H NMR (400 MHz, CDCl$_3$) δ ppm 3.11 (br. s, 1H) 3.94 (s, 3H) 4.08 (s, 3H) 4.32 (s, 2H) 6.43 (s, 1H) 6.74 (d, J=9.09 Hz, 1H) 7.35 (d, J=8.59 Hz, 2H) 7.50-7.66 (m, 5H) 7.69 (s, 1H) 7.76-7.93 (m, 2H) 8.12 (d, J=2.53 Hz, 1H) 8.18 (d, J=2.02 Hz, 1H) 8.84 (s, 1H).

Example 21

(3-(4-(1H-Pyrazol-1-yl)benzyl)-2,4-dichloroquinolin-6-yl)(6-methoxypyridin-3-yl)(1-methyl-1H-imidazol-5-yl)methanol.TFA

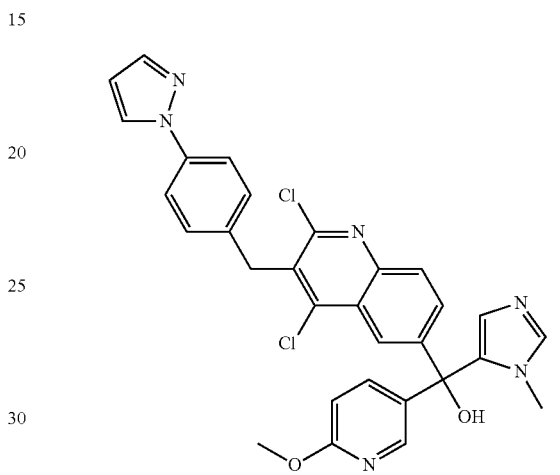

The title compound was prepared by substituting (4-chlorophenyl)(1-methyl-1H-imidazol-5-yl)methanone with (6-methoxypyridin-3-yl)(1-methyl-1H-imidazol-5-yl)methanone (Intermediate 37: step d) then following the procedure described for the preparation of Example 11. $^1$H NMR (400 MHz, DMSO-d$_6$) δ ppm 3.56 (s, 3H) 3.86 (s, 3H) 4.05 (s, 3H) 4.29 (s, 2H) 6.52 (d, J=2.02 Hz, 1H) 6.88 (d, J=8.59 Hz, 1H) 7.02 (s, 1H) 7.34 (d, J=8.59 Hz, 2H) 7.50-7.63 (m, 2H) 7.65-7.80 (m, 4H) 7.88 (d, J=8.59 Hz, 1H) 8.06 (br. s., 1H) 8.14 (s, 1H) 8.42 (s, 1H) 9.13 (br. s., 1H); MS (ESI) 567.

Example 22

(3-(4-(1H-Pyrazol-1-yl)benzyl)-4-chloro-2-methoxyquinolin-6-yl)(6-methoxypyridin-3-yl)(1-methyl-1H-imidazol-5-yl)methanol.TFA

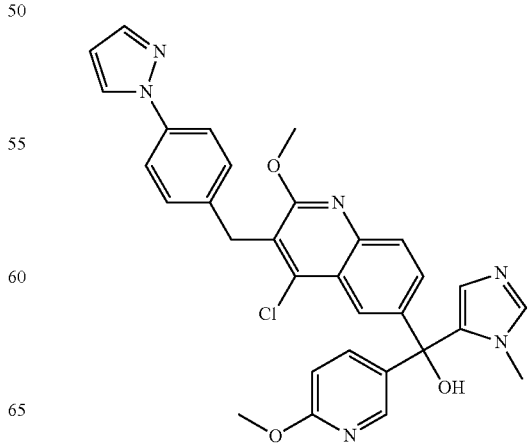

A mixture of the title compound prepared in Example 21 (0.030 g, 0.053 mmol) and a sodium methoxide solution (0.1 mL, 25% in methanol) in MeOH (3 mL) was heated in a sealed tube at 80° C. overnight. The mixture was cooled to room temperature, excess MeOH removed, diluted with ice H$_2$O and extracted with EtOAc. The organic extract was dried over Na$_2$SO$_4$, filtered, evaporated in vacuo and purified by Gilson HPLC to provide the title compound as a solid. $^1$H NMR (400 MHz, DMSO-d$_6$) δ ppm 3.56 (s, 3H) 3.86 (s, 3H) 4.05 (s, 3H) 4.29 (s, 2H) 6.52 (d, J=2.02 Hz, 1H) 6.88 (d, J=8.59 Hz, 1H) 7.02 (s, 1H) 7.34 (d, J=8.59 Hz, 2H) 7.50-7.63 (m, 2H) 7.65-7.80 (m, 4H) 7.88 (d, J=8.59 Hz, 1H) 8.06 (br. s., 1H) 8.14 (s, 1H) 8.42 (s, 1H) 9.13 (br. s., 1H); MS (ESI) 567.

Example 23

(3-(4-(1H-Pyrazol-1-yl)benzyl)-2,4-dichloroquinolin-6-yl)(1-methyl-1H-imidazol-5-yl)(6-(trifluoromethyl)pyridin-3-yl)methanol.TFA

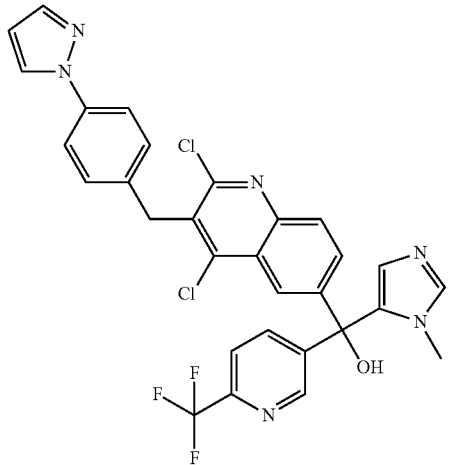 [SMILES: Cn1cncc1C(O)(c1ccc(C(F)(F)F)nc1)c1ccc2nc(Cl)c(Cc3ccc(-n4cccn4)cc3)c(Cl)c2c1]

The title compound was prepared by substituting (4-chlorophenyl)(1-methyl-1H-imidazol-5-yl)methanone with (1-methyl-1H-imidazol-5-yl)(6-(trifluoromethyl)pyridin-3-yl)methanone (Intermediate 36: step c) then following the procedure described for Example 11. $^1$H NMR (400 MHz, MeOH-d$_4$) δ ppm 3.71 (s, 3H) 4.61 (s, 2H) 6.50 (t, J=2.27 Hz, 1H) 7.12 (s, 1H) 7.33 (d, J=8.59 Hz, 2H) 7.60-7.72 (m, 3H) 7.79-7.92 (m, 2H) 8.08 (d, J=8.59 Hz, 2H) 8.16 (s, 1H) 8.40 (s, 1H) 8.84 (s, 1H) 9.03 (s, 1H); MS (ESI) 609.

Example 24

(2-Ethoxy-3-(4-methoxybenzyl)quinolin-6-yl)(1-methyl-1H-imidazol-5-yl)(thiazol-5-yl)methanol.TFA

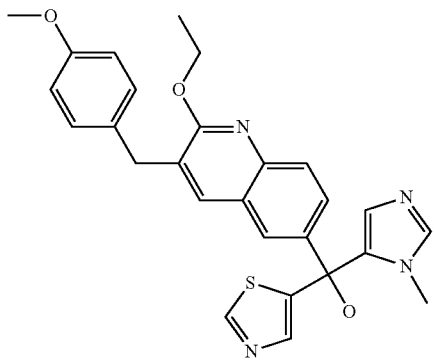 [SMILES: CCOc1nc2ccc(C(O)(c3cncs3)c3cncn3C)cc2cc1Cc1ccc(OC)cc1]

The title compound was prepared by using (2-chloro-3-(4-methoxybenzyl)quinolin-6-yl)(1-methyl-1H-imidazol-5-yl)(thiazol-5-yl)methanol.TFA (Example 52) in place of (3-benzyl-2,4-dichloroquinolin-6-yl)(4-chlorophenyl)(1-methyl-1H-imidazol-5-yl)methanol then following the procedure described for the preparation of Example 14. $^1$H NMR (400 MHz, MeOH-d$_4$) δ ppm 1.42 (t, J=7.07 Hz, 3H) 3.66 (s, 3H) 3.75 (s, 3H) 3.97 (s, 2H) 4.52 (q, J=7.07 Hz, 2H) 6.84 (d, J=8.59 Hz, 2H) 7.12-7.20 (m, 3H) 7.60-7.68 (m, 2H) 7.71 (d, J=2.53 Hz, 1H) 7.76 (s, 1H) 7.84 (d, J=8.59 Hz, 1H) 8.94 (s, 1H) 9.05 (s, 1H); MS (ESI) 487.

Example 25

(3-(4-(1H-Pyrazol-1-yl)benzyl)-2,4-dichloroquinolin-6-yl)(4-(dimethylamino)phenyl)(1-methyl-1H-imidazol-5-yl)methanol.TFA

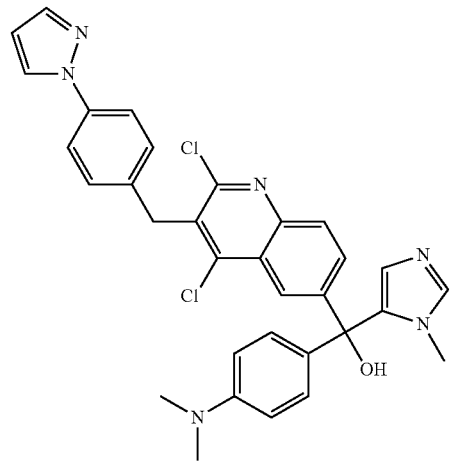 [SMILES: CN(C)c1ccc(C(O)(c2ccc3nc(Cl)c(Cc4ccc(-n5cccn5)cc4)c(Cl)c3c2)c2cncn2C)cc1]

The title compound was prepared by substituting (4-chlorophenyl)(1-methyl-1H-imidazol-5-yl)methanone with (4-(dimethylamino)phenyl)(1-methyl-1H-imidazol-5-yl)methanone (Intermediate 18) then following the procedure described for the preparation of Example 11. $^1$H NMR (400 MHz, MeOH-d$_4$) δ ppm 2.97 (s, 6H) 3.71 (s, 3H) 4.60 (s, 2H) 6.42-6.58 (m, 1H) 6.79-6.92 (m, 3H) 7.19 (d, J=9.09 Hz, 2H) 7.33 (d, J=8.59 Hz, 2H) 7.59-7.73 (m, 3H) 7.83 (dd, J=9.09, 2.02 Hz, 1H) 8.01 (d, J=9.09 Hz, 1H) 8.16 (d, J=2.02 Hz, 1H) 8.33 (d, J=2.02 Hz, 1H) 8.94 (s, 1H); MS (ESI) 583.

Example 26

(3-(4-(1H-Pyrazol-1-yl)benzyl)-4-chloro-2-methoxyquinolin-6-yl)(4-(dimethylamino)phenyl)(1-methyl-1H-imidazol-5-yl)methanol.TFA

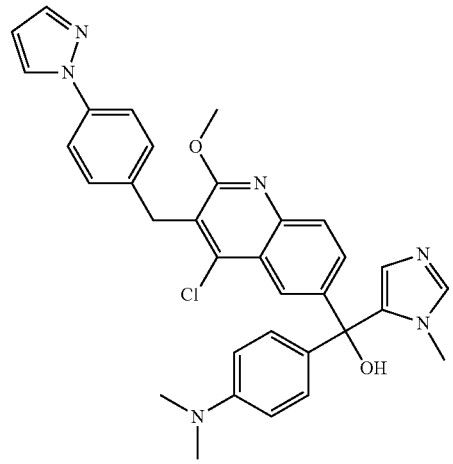 [SMILES: COc1nc2ccc(C(O)(c3ccc(N(C)C)cc3)c3cncn3C)cc2c(Cl)c1Cc1ccc(-n2cccn2)cc1]

The title compound was prepared by substituting (6-methoxypyridin-3-yl)(thiazol-5-yl)methanone (Intermediate 15) with (4-(dimethylamino)phenyl)(1-methyl-1H-imidazol-5-yl)methanone (Intermediate 18) then following the procedure described for the preparation of Example 20A. $^1$H NMR (400 MHz, MeOH-d$_4$) δ ppm 2.99 (s, 6H) 3.70 (s, 3H) 4.09 (s, 3H) 4.35 (s, 2H) 6.45-6.54 (m, 1H) 6.82 (s, 1H) 6.88 (d, J=8.59 Hz, 2H) 7.21 (d, J=8.59 Hz, 2H) 7.37 (d, J=8.59 Hz, 2H) 7.52-7.75 (m, 4H) 7.87 (d, J=9.09 Hz, 1H) 8.15 (dd, J=10.11, 2.02 Hz, 2H) 8.92 (s, 1H); MS (ESI) 579.

Example 27

(3-(4-(1H-Pyrazol-1-yl)benzyl)-2,4-dichloro-8-methylquinolin-6-yl)(4-chlorophenyl)(1-methyl-1H-imidazol-5-yl)methanol.TFA salt

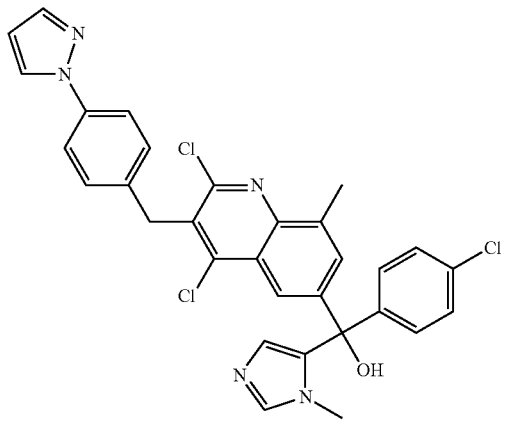 [SMILES: Cc1cc(C(O)(c2ccc(Cl)cc2)c2cncn2C)cc2c(Cl)c(Cc3ccc(-n4cccn4)cc3)c(Cl)nc12]

The title compound was prepared by substituting 3-(4-(1H-pyrazol-1-yl)benzyl)-6-bromo-2,4-dichloroquinoline (Intermediate 6: step c) with 3-(4-(1H-pyrazol-1-yl)benzyl)-6-bromo-2,4-dichloro-8-methylquinoline (Intermediate 19: step a) then following the procedure described for the preparation of Example 11. $^1$H NMR (400 MHz, DMSO-d$_6$) δ ppm 2.67 (s, 3H) 3.54 (s, 3H) 4.51 (s, 2H) 6.52 (s, 1H) 7.03 (s, 1H) 7.30 (d, J=8.59 Hz, 2H) 7.38-7.46 (m, 2H) 7.46-7.58 (m, 2H) 7.59-7.87 (m, 5H) 8.05 (s, 1H) 8.43 (d, J=2.53 Hz, 1H) 9.12 (s, 1H); MS (ESI) 589.

Example 28A (3-(4-(1H-Pyrazol-1-yl)benzyl)-4-chloro-2-methoxy-8-methylquinolin-6-yl)(4-chlorophenyl)(1-methyl-1H-imidazol-5-yl)methanol.TFA

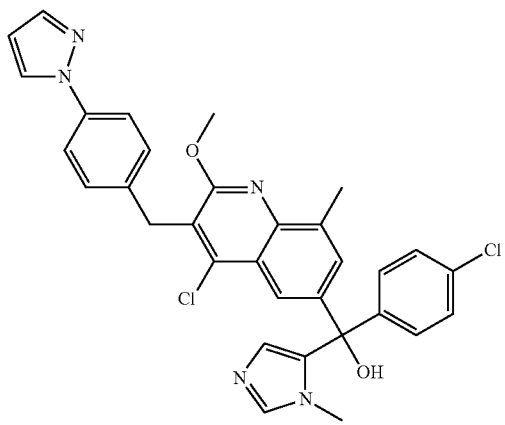 [SMILES: COc1nc2c(C)cc(C(O)(c3ccc(Cl)cc3)c3cncn3C)cc2c(Cl)c1Cc1ccc(-n2cccn2)cc1]

n-Butyllithium (1.6 M in hexane; 0.315 mL, 0.503 mmol) was added dropwise to a mixture of the 3-(4-(1H-pyrazol-1-yl)benzyl)-6-bromo-4-chloro-2-methoxy-8-methylquinoline (0.1 g, 0.226 mmol, Intermediate 19: step b) and (4-chlorophenyl)-(1-methyl-1H-imidazol-5-yl)methanone (0.055 g, 0.248 mmol, Intermediate 1: step b) in dry THF (3 mL) at −78° C. over a 2 minute period. After complete addition stirring was continued at −78° C. for 10 minutes then warmed in an ice bath to 0° C. The mixture was stirred for 1 hour then quenched with saturated aqueous NH$_4$Cl and warmed to room temperature. After stirring for 10 minutes layers were separated and the aqueous layer extracted with EtOAc. The combined organic extracts were dried over Na$_2$SO$_4$, filtered, evaporated in vacuo and chromatographed (0-100% EtOAc in DCM) to provide the product. Further purification by Gilson HPLC provided the title compound as a solid. $^1$H NMR (400 MHz, MeOH-d$_4$) δ ppm 2.69 (s, 3H) 3.69 (s, 3H) 4.11 (s, 3H) 4.35 (s, 2H) 6.49 (d, J=2.0 Hz, 1H) 6.87 (s, 1H) 7.30-7.41 (m, 4H) 7.41-7.47 (m, 2H) 7.55 (s, 1H) 7.60 (d, J=8.59 Hz, 2H) 7.68 (s, 1H) 7.95 (s, 1H) 8.14 (d, J=2.53 Hz, 1H) 8.95 (s, 1H); MS (ESI) 584.

(3-(4-(1H-pyrazol-1-yl)benzyl)-4-chloro-2-methoxy-8-methylquinolin-6-yl)(4-chlorophenyl)(1-methyl-1H-imidazol-5-yl)methanol was purified by HPLC (550 gram Chiralpak AD 20 µM column-diacel), 50:50 ethanol eluent, 80 mL/minute, 240 nm wavelength) to give 2 enantiomers. The first eluting enantiomer was Example 28B: $^1$H NMR (400 MHz, MeOH-d$_4$) δ ppm 2.67 (s, 3H) 3.54-3.68 (m, 4H) 4.10 (s, 3H) 4.34 (s, 2H) 6.49 (t, J=2.27 Hz, 1H) 6.66 (s, 1H) 7.29-7.47 (m, 6H) 7.51-7.65 (m, 3H) 7.68 (s, 1H) 7.94 (s, 1H) 8.13 (d, J=2.53 Hz, 1H) 8.50 (s, 1H) and the second eluting enantiomer was Example 28C: $^1$H NMR (400 MHz, MeOH-d$_4$) δ ppm 2.68 (s, 3H) 3.64 (s, 3H) 4.10 (s, 3H) 4.34 (s, 2H) 6.43-6.53 (m, 1H) 6.74 (s, 1H) 7.29-7.47 (m, 6H) 7.52-7.64 (m, 3H) 7.68 (s, 1H) 7.95 (s, 1H) 8.14 (d, J=2.02 Hz, 1H) 8.67 (s, 1H).

Example 29A (3-(4-(1H-Pyrazol-1-yl)benzyl)-4-chloro-2-methoxy-8-methylquinolin-6-yl)(1-methyl-1H-imidazol-5-yl)(6-(trifluoromethyl)pyridin-3-yl)methanol

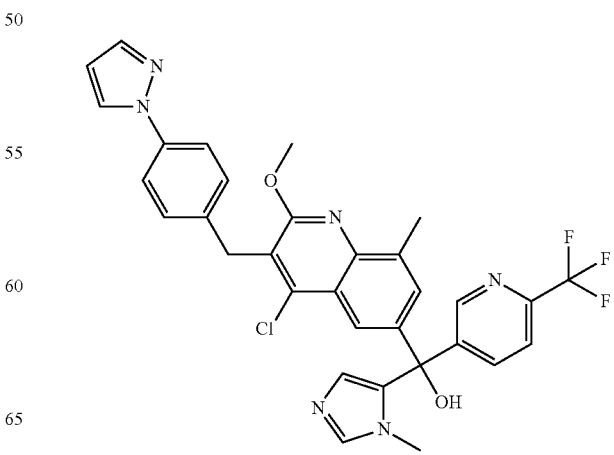

n-Butyllithium (1.6 M in hexane; 1.84 mL, 2.936 mmol) was added dropwise to a suspension of the 3-(4-(1H-pyrazol-1-yl)benzyl)-6-bromo-4-chloro-2-methoxy-8-methylquinoline (1 g, 2.26 mmol, Intermediate 19: step b) and (1-methyl-1H-imidazol-5-yl)(6-(trifluoromethyl)pyridin-3-yl) methanone (0.63 g, 2.49 mmol, Intermediate 36: step c) in dry THF (23 mL) at −78° C. over a 2 minute period. After complete addition stirring was continued at −78° C. for 10 minutes then warmed in an ice bath to 0° C. The mixture was stirred for 1 hour then quenched with saturated aqueous NH$_4$Cl and warmed to room temperature. After stirring for 10 minutes layers were separated and the aqueous layer extracted with EtOAc. The combined organic extracts were dried over Na$_2$SO$_4$, filtered, evaporated in vacuo and chromatographed (0-5% MeOH in acetonitrile) to provide the title compound as an amorphous solid. $^1$H NMR (400 MHz, DMSO-d$_6$) δ ppm 9.15 (s, 1H), 8.84 (d, J=2.0 Hz, 1H), 8.41 (d, J=2.5 Hz, 1H), 8.00-8.07 (m, 1H), 7.92-7.99 (m, 2H), 7.87 (s, 1H), 7.72 (d, J=8.6 Hz, 3H), 7.57 (s, 1H), 7.33 (d, J=9.1 Hz, 2H), 7.16 (s, 1H), 6.40-6.59 (m, 1H), 4.29 (s, 2H), 4.07 (s, 3H), 3.53 (s, 3H) 2.65 (s, 3H); MS (ESI) 619.

(3-(4-(1H-pyrazol-1-yl)benzyl)-4-chloro-2-methoxy-8-methylquinolin-6-yl)(1-methyl-1H-imidazol-5-yl)(6-(trifluoromethyl)pyridin-3-yl)methanol was purified by HPLC (Chiralpak AD column, 250 gram, 50:50% methanol:ethanol as eluent, 80 mL/minute, 265 nm wavelength) to give 2 enantiomers. The first eluting enantiomer was Example 29B: $^1$H NMR (400 MHz, CDCl$_3$) δ ppm 8.82 (br. s., 1H), 7.82-7.99 (m, 3H), 7.63-7.71 (m, 2H), 7.55 (d, J=7.1 Hz, 2H), 7.32-7.45 (m, 4H), 6.41 (d, J=13.1 Hz, 2H), 4.54 (br. s., 1H), 4.30 (s, 2H), 4.09 (s, 3H), 3.37 (s, 3H), 2.63 (s, 3H) mass calcd. C$_{32}$H$_{26}$ClF$_3$N$_6$O$_2$, 619.04; m/z found, 619.2 and the second eluting enantiomer was Example 29C: $^1$H NMR (400 MHz, CDCl$_3$) δ ppm 8.81 (d, J=2.0 Hz, 1H), 7.95 (s, 1H), 7.86-7.93 (m, 1H), 7.84 (d, J=2.0 Hz, 1H), 7.61-7.73 (m, 2H), 7.55 (d, J=8.6 Hz, 2H), 7.41 (s, 1H), 7.30-7.38 (m, 3H), 6.28-6.52 (m, 2H), 4.83 (br. s., 1H), 4.30 (s, 2H), 4.09 (s, 3H), 3.37 (s, 3H), 2.63 (s, 3H) mass calcd. C$_{32}$H$_{26}$ClF$_3$N$_6$O$_2$, 619.04; m/z found, 619.2.

Example 30

(3-(4-(1H-Pyrazol-1-yl)benzyl)-2,4-dichloroquinolin-6-yl)bis(1-methyl-1H-imidazol-5-yl)methanol.TFA

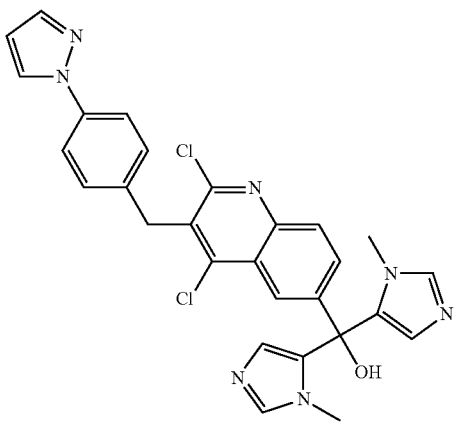 [SMILES: Cn1cncc1C(O)(c1ccc2nc(Cl)c(Cc3ccc(-n4cccn4)cc3)c(Cl)c2c1)c1cncn1C]

To a solution of 5-bromo-1-methyl-1H-imidazole (0.084 g, 0.519 mmol) in DCM (5 mL) was added ethyl magnesium bromide (0.173 mL, 0.519 mmol; 3M in diethyl ether) dropwise over a 10 minute period. The resulting cloudy mixture was stirred at room temperature for 20 minutes, cooled in an ice bath to 0° C. and (3-(4-(1H-pyrazol-1-yl)benzyl)-2,4-dichloroquinolin-6-yl)(1-methyl-1H-imidazol-5-yl)methanone (0.12 g, 0.26 mmol, Intermediate 20: step d) dissolved in THF (3 mL) was added. The cold bath was removed and the reaction mixture stirred at room temperature for 10 minutes then heated in a 60° C. oil bath for 8 hours. Water was added followed by 6M aqueous HCl to a neutral pH. The aqueous mixture was extracted with DCM (2×). The combined DCM extracts were dried over Na$_2$SO$_4$, filtered, concentrated under reduced pressure, chromatographed (0-10% MeOH in CH$_2$Cl$_2$) then further purified by Gilson HPLC (H$_2$O/acetonitrile/1% TFA) to afford the title compound as a white solid. $^1$H NMR (400 MHz, MeOH-d$_4$) δ ppm 3.81 (s, 6H) 4.63 (s, 2H) 6.51 (s, 1H) 7.13 (s, 2H) 7.35 (d, J=8.59 Hz, 2H) 7.58-7.81 (m, 4H) 8.11 (d, J=9.09 Hz, 1H) 8.17 (d, J=2.53 Hz, 1H) 8.49 (d, J=2.53 Hz, 1H) 8.85 (s, 2H); MS (ESI) 544.

Example 31

(4-Chloro-2-methoxy-3-(4-(methylsulfonyl)benzyl)quinolin-6-yl)(4-chlorophenyl)(1-methyl-1H-imidazol-5-yl)methanol.TFA

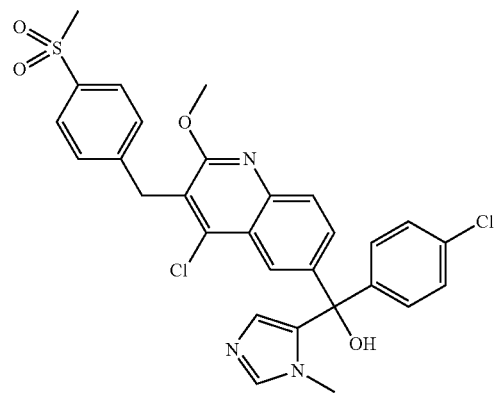 [SMILES: COc1nc2ccc(C(O)(c3ccc(Cl)cc3)c3cncn3C)cc2c(Cl)c1Cc1ccc(S(C)(=O)=O)cc1]

To a solution of 5-bromo-1-methyl-1H-imidazole (0.074 g, 0.46 mmol) in DCM (5 mL) was added ethyl magnesium bromide (0.153 mL, 0.46 mmol; 3M in diethyl ether) dropwise over a 10 minute period. The resulting cloudy mixture was stirred at room temperature for 20 minutes, cooled in an ice bath to 0° C. and (4-chloro-2-methoxy-3-(4-(methylsulfonyl)benzyl)quinolin-6-yl)(4-chlorophenyl)methanone (0.10 g, 0.20 mmol, Intermediate 22: step b) dissolved in THF (3 mL) was added. The cold bath was removed and the reaction mixture stirred at room temperature for 10 minutes then heated in an 80° C. oil bath for 16 hours. The mixture was cooled to room temperature, H$_2$O added followed by 6M aqueous HCl to a neutral pH. The aqueous mixture was extracted with DCM (2×). The combined DCM extracts were dried over Na$_2$SO$_4$, filtered, concentrated under reduced pressure, chromatographed (0-10% MeOH in CH$_2$Cl$_2$) then further purified by Gilson HPLC(H$_2$O/acetonitrile/1% TFA) to afford the title compound as a white solid. $^1$H NMR (400 MHz, DMSO-d$_6$) δ ppm 3.17 (s, 3H) 3.53 (s, 3H) 4.03 (s, 3H) 4.36 (br. s., 2H) 6.96 (s, 1H) 7.38 (d, J=8.59 Hz, 2H) 7.48 (t, J=8.84 Hz, 4H) 7.55-7.68 (m, 2H) 7.76-7.94 (m, 3H) 8.11 (s, 1H) 9.12 (br. s., 1H); MS (ESI) 582.

Example 32

(3-Chlorophenyl)(2,4-dichloro-3-(thiophen-2-ylmethyl)quinolin-6-yl)(pyridin-3-yl)methanol.TFA

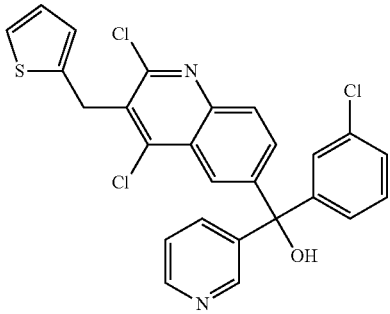 [SMILES: OC(c1cccnc1)(c1cccc(Cl)c1)c1ccc2nc(Cl)c(Cc3cccs3)c(Cl)c2c1]

The title compound was prepared by substituting 6-bromo-2,4-dichloro-3-(4-chlorobenzyl)quinoline (Intermediate 3: step c) with 6-bromo-2,4-dichloro-3-(thiophen-2-ylmethyl)quinoline (Intermediate 9: step c) then following the procedure described for the preparation of Example 2. $^1$H NMR (400 MHz, DMSO-$d_6$) δ ppm 4.61 (s, 2H) 6.90-6.99 (m, 2H) 7.19-7.27 (m, 1H) 7.33-7.39 (m, 1H) 7.43 (d, J=6.06 Hz, 4H) 7.62-7.69 (m, 1H) 7.77 (dd, J=8.84, 2.27 Hz, 1H) 7.93-8.06 (m, 2H) 8.15 (d, J=2.02 Hz, 1H) 8.63 (s, 1H) 8.68 (d, J=4.55 Hz, 1H); MS (ESI) 511.

Example 33A (3-(4-(1H-Pyrazol-1-yl)benzyl)-4-chloro-2-methoxyquinolin-6-yl)(4-chlorophenyl)(1-methyl-1H-imidazol-5-yl)methanol

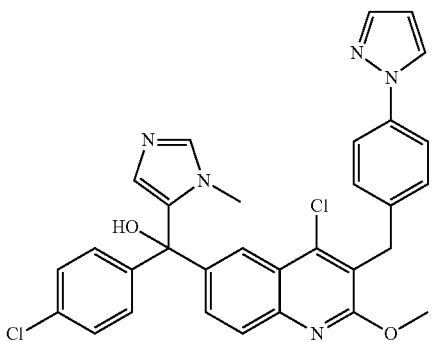 [SMILES: COc1nc2ccc(C(O)(c3ccc(Cl)cc3)c3cncn3C)cc2c(Cl)c1Cc1ccc(-n2cccn2)cc1]

A solution of n-BuLi (2.5 M in hexanes, 2.67 mL, 6.66 mmol) was added dropwise by syringe to a solution of 3-(4-(1H-pyrazol-1-yl)benzyl)-6-bromo-4-chloro-2-methoxyquinoline (3.00 g, 7.00 mmol, Intermediate 16) in dry THF (80 mL) at −78° C. After 3 minutes, a solution of (4-chlorophenyl)(1-methyl-1H-imidazol-5-yl)methanone (1.65 g, 7.48 mmol, Intermediate 1: step b) in dry THF (80 mL) was added dropwise over the course of 3 minutes. The reaction mixture was stirred for 10 minutes at −78° C., then the reaction flask was removed from the cooling bath. After 10 minutes, the reaction flask was placed into an ice-water bath. After 30 minutes, saturated aqueous ammonium chloride solution (10 mL) was added. The biphasic mixture was warmed to room temperature then partitioned between half-saturated aqueous ammonium chloride solution (300 mL) and ethyl acetate (300 mL). The layers were separated. The aqueous layer was extracted with ethyl acetate (150 mL). The organic layers were combined. The combined solution was dried with sodium sulfate. The dried solution was filtered and the filtrate was concentrated. The residue was purified by flash column chromatography (silica gel, 20% acetone-dichloromethane initially, grading to 100% acetone) to provide the title compound as an off-white solid. $^1$H NMR (500 MHz, CDCl$_3$) δ ppm 8.11 (d, J=2.1 Hz, 1H), 7.85 (d, J=2.5 Hz, 1H), 7.79 (d, J=8.7 Hz, 1H), 7.68 (d, J=1.7 Hz, 1H), 7.58-7.54 (m, 2H), 7.54-7.51 (m, 1H), 7.40-7.34 (m, 3H), 7.33-7.27 (m, 4H), 6.43 (t, J=2.1 Hz, 1H), 6.41-6.38 (m, 1H), 4.31 (s, 2H), 4.08 (s, 3H), 3.72 (s, 1H), 3.38 (s, 3H). MS (ESI): mass calcd. $C_{31}H_{25}Cl_2N_5O_2$, 569.1; m/z found, 570.1 [M+H]$^+$.

(3-(4-(1H-pyrazol-1-yl)benzyl)-4-chloro-2-methoxyquinolin-6-yl)(4-chlorophenyl)(1-methyl-1H-imidazol-5-yl)methanol was purified by HPLC (Chiralpak AD column, 500 gram, 41 cm×5 cm, ethanol eluent, 80 mL/minute, 230 nm wavelength) to give 2 enantiomers. The first eluting enantiomer was Example 33B: $^1$H NMR (400 MHz, CDCl$_3$) δ ppm 8.11 (d, J=2.1 Hz, 1H), 7.84 (d, J=2.4 Hz, 1H), 7.78 (d, J=8.8 Hz, 1H), 7.68 (d, J=1.7 Hz, 1H), 7.60-7.48 (m, 3H), 7.43-7.27 (m, 7H), 6.50-6.31 (m, 2H), 4.31 (s, 2H), 4.08 (s, 3H), 3.77 (s, 1H), 3.38 (s, 3H). MS (ESI): mass calcd. $C_{31}H_{25}Cl_2N_5O_2$, 569.1; m/z found, 570.1 [M+H]$^+$ and the second eluting enantiomer was Example 33C: $^1$H NMR (400 MHz, CDCl$_3$) δ ppm 8.10 (d, J=2.1 Hz, 1H), 7.85 (d, J=2.5 Hz, 1H), 7.79 (d, J=8.7 Hz, 1H), 7.68 (d, J=1.7 Hz, 1H), 7.60-7.49 (m, 3H), 7.43 (s, 1H), 7.40-7.27 (m, 6H), 6.50-6.34 (m, 2H), 4.31 (s, 2H), 4.08 (s, 3H), 3.55-3.24 (br s, 1H), 3.40 (s, 3H). MS (ESI): mass calcd. $C_{31}H_{25}Cl_2N_5O_2$, 569.1; m/z found, 570.1 [M+H]$^+$.

Example 34

(3-(4-(1H-Pyrazol-1-yl)benzyl)-2,4-dimethoxyquinolin-6-yl)(4-chlorophenyl)(1-methyl-1H-imidazol-5-yl)methanol.TFA

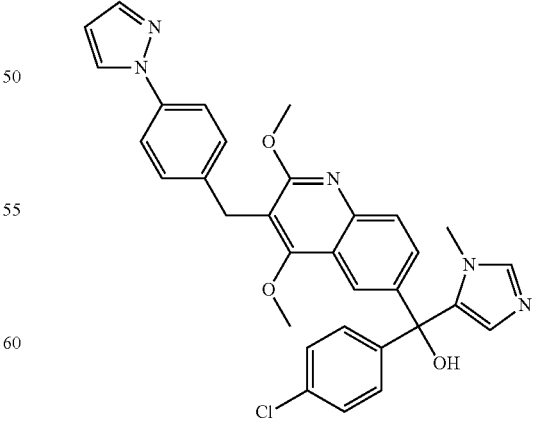

The title compound was prepared by combining (3-(4-(1H-pyrazol-1-yl)benzyl)-2,4-dichloroquinolin-6-yl)(4-chlorophenyl)(1-methyl-1H-imidazol-5-yl)methanol.TFA (0.058 g, 0.101 mmol, Example 11) and a 0.5 M sodium methoxide in MeOH solution (3.027 mL, 1.513 mmol) in a sealed tube and heating at 80° C. for 16 hours. Solid sodium methoxide (0.016 g, 0.303 mmol) was then added and heating was continued at 80° C. for an additional 16 hours, cooled to room temperature then poured into ice H₂O, Stirring was continued while warming to room temperature. The solid precipitates were collected, dried and purified by Gilson HPLC (H₂O/acetonitrile/1% TFA) to afford the title compound. ¹H NMR (400 MHz, DMSO-d₆) δ ppm 3.55 (s, 3H) 3.83 (s, 3H) 3.99 (s, 3H) 4.08 (s, 2H) 6.51 (s, 1H) 6.98 (s, 1H) 7.30 (d, J=8.07 Hz, 2H) 7.38 (d, J=8.31 Hz, 2H) 7.46-7.56 (m, 4H) 7.65-7.74 (m, 3H) 7.82 (d, J=8.56 Hz, 1H) 7.86 (s, 1H) 8.40 (s, 1H) 9.14 (s, 1H); MS (ESI) 566.

Example 35A (3-(4-(1H-Pyrazol-1-yl)benzyl)-4-chloro-2-methoxyquinolin-6-yl)(1-methyl-1H-imidazol-5-yl)(6-(trifluoromethyl)pyridin-3-yl)methanol.TFA

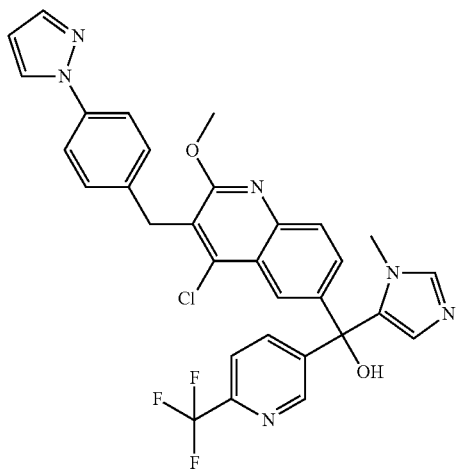 [SMILES: COc1nc2ccc(C(O)(c3ccc(C(F)(F)F)nc3)c3cncn3C)cc2c(Cl)c1Cc1ccc(-n2cccn2)cc1]

The title compound was prepared by substituting (4-chlorophenyl)(1-methyl-1H-imidazol-5-yl)methanone with (1-methyl-1H-imidazol-5-yl)(6-(trifluoromethyl)pyridin-3-yl)methanone (Intermediate 36: step C) and then following the procedure described for the preparation of Example 33A. ¹H NMR (400 MHz, CDCl₃) δ ppm 8.82 (d, J=2.1 Hz, 1H), 8.14 (d, J=2.1 Hz, 1H), 7.90 (dd, J=8.3, 2.2 Hz, 1H), 7.87-7.79 (m, 2H), 7.70-7.61 (m, 2H), 7.60-7.50 (m, 3H), 7.40 (s, 1H), 7.38-7.32 (m, 2H), 6.48-6.38 (m, 2H), 4.31 (s, 2H), 4.18 (s, 1H), 4.09 (s, 3H), 3.38 (s, 3H). MS (ESI): mass calcd. C₃₁H₂₄ClF₃N₆O₂, 604.2; m/z found, 605.2 [M+H]⁺.

(3-(4-(1H-pyrazol-1-yl)benzyl)-4-chloro-2-methoxyquinolin-6-yl)(1-methyl-1H-imidazol-5-yl)(6-(trifluoromethyl)pyridin-3-yl)methanol was purified by HPLC (Chiralpak AD column, 500 gram, 41 cm×5 cm, ethanol eluent, 80 mL/minute, 242 nm wavelength) to give 2 enantiomers. The first eluting enantiomer was Example 35B: ¹H NMR (500 MHz, CDCl₃) δ ppm 8.82 (d, J=2.1 Hz, 1H), 8.13 (d, J=2.2 Hz, 1H), 7.93-7.88 (m, 1H), 7.85 (dd, J=2.5, 0.7 Hz, 1H), 7.82 (d, J=8.6 Hz, 1H), 7.70-7.63 (m, 2H), 7.59-7.51 (m, 3H), 7.45 (s, 1H), 7.38-7.33 (m, 2H), 6.50-6.36 (m, 2H), 4.31 (s, 2H), 4.09 (s, 3H), 4.01 (s, 1H), 3.39 (s, 3H). MS (ESI): mass calcd. C₃₁H₂₄ClF₃N₆O₂, 604.2; m/z found, 605.2 [M+H]⁺ and the second eluting enantiomer was Example 35C: ¹H NMR (500 MHz, CDCl₃) δ ppm 8.82 (d, J=2.2 Hz, 1H), 8.13 (d, J=2.1 Hz, 1H), 7.94-7.88 (m, 1H), 7.86-7.84 (m, 1H), 7.83 (d, J=8.8 Hz, 1H), 7.70-7.64 (m, 2H), 7.58-7.51 (m, 3H), 7.47 (s, 1H), 7.39-7.33 (m, 2H), 6.47 (s, 1H), 6.44-6.42 (m, 1H), 4.31 (s, 2H), 4.09 (s, 3H), 3.84 (s, 1H), 3.40 (s, 3H). MS (ESI): mass calcd. C₃₁H₂₄ClF₃N₆O₂, 604.2; m/z found, 605.2 [M+H]⁺.

Example 36A (3-(Benzo[b]thiophen-2-ylmethyl)-4-chloro-2-methoxyquinolin-6-yl)(4-chlorophenyl)(1-methyl-1H-imidazol-5-yl)methanol

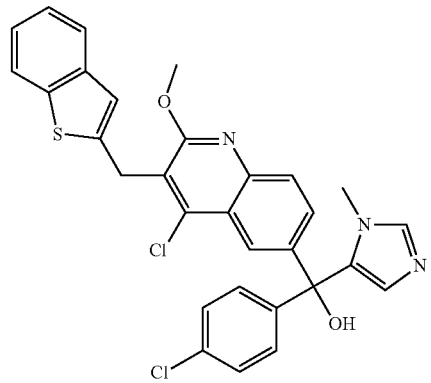 [SMILES: COc1nc2ccc(C(O)(c3ccc(Cl)cc3)c3cncn3C)cc2c(Cl)c1Cc1cc2ccccc2s1]

The title compound was prepared by substituting 3-(4-(1H-pyrazol-1-yl)benzyl)-6-bromo-4-chloro-2-methoxy-8-methylquinoline (Intermediate 19: step b) with 3-(benzo[b]thiophen-2-ylmethyl)-6-bromo-4-chloro-2-methoxyquinoline (Intermediate 23) then following the procedure described for the preparation of Example 28A. ¹H NMR (400 MHz, MeOH-d4) δ ppm 3.45 (s, 3H) 4.09 (s, 3H) 4.53 (s, 2H) 6.26 (s, 1H) 7.08 (s, 1H) 7.15-7.29 (m, 2H) 7.31-7.43 (m, 4H) 7.56-7.77 (m, 4H) 7.83 (d, J=9.09 Hz, 1H) 8.11 (s, 1H): MS (ESI) 560.

(3-(benzo[b]thiophen-2-ylmethyl)-4-chloro-2-methoxyquinolin-6-yl)(1-methyl-1H-imidazol-5-yl)methanol was purified by HPLC (250 gram Chiralpak AD 20 µM column-diacel), 50:50 ethanol:MeOH eluent, 80 mL/minute, 240 nm wavelength) to give 2 enantiomers. The first eluting enantiomer was Example 36B: ¹H NMR (400 MHz, CDCl₃) δ ppm 3.41 (s, 3H) 4.14 (s, 3H) 4.52 (s, 2H) 6.42 (s, 1H) 7.09 (s, 1H) 7.17-7.37 (m, 8H) 7.47-7.59 (m, 1H) 7.63 (d, J=7.58 Hz, 1H) 7.70 (d, J=8.08 Hz, 1H) 7.79 (d, J=8.59 Hz, 1H) 8.08 (s, 1H); MS (ESI) 560 and the second eluting enantiomer was Example 36C: ¹H NMR (400 MHz, CDCl₃) δ ppm 3.50 (s, 3H) 4.15 (s, 3H) 4.52 (s, 2H) 6.45 (s, 1H) 7.10 (s, 1H) 7.18-7.27 (m, 4H) 7.28-7.39 (m, 4H) 7.49-7.59 (m, 1H) 7.63 (d, J=7.07 Hz, 1H) 7.70 (d, J=8.08 Hz, 1H) 7.81 (d, J=8.59 Hz, 1H) 8.06 (d, J=2.02 Hz, 1H); MS (ESI) 560.

Example 37A (3-(Benzo[b]thiophen-2-ylmethyl)-4-chloro-2-methoxyquinolin-6-yl)(1-methyl-1H-imidazol-5-yl)(6-(trifluoromethyl)pyridin-3-yl)methanol.TFA

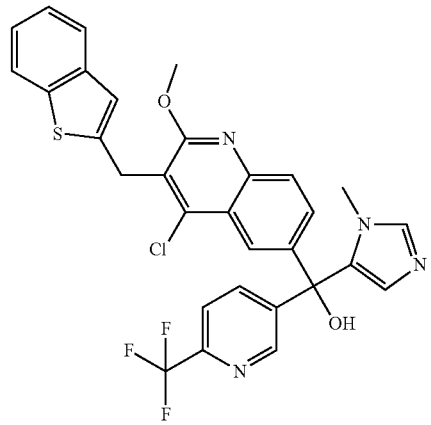 [SMILES: COc1nc2ccc(C(O)(c3ccc(C(F)(F)F)nc3)c3cncn3C)cc2c(Cl)c1Cc1cc2ccccc2s1]

The title compound was prepared by using (1-methyl-1H-imidazol-5-yl)(6-(trifluoromethyl)pyridin-3-yl)methanone (Intermediate 36: step C) in place of (4-chlorophenyl)(1-methyl-1H-imidazol-5-yl)methanone then following the procedure described for the preparation of Example 36A. $^1$H NMR (400 MHz, DMSO-d$_6$) δ ppm 3.53 (s, 3H) 4.10 (s, 3H) 4.52 (s, 2H) 7.12 (s, 1H) 7.22 (s, 1H) 7.23-7.36 (m, 2H) 7.59-7.67 (m, 1H) 7.72 (d, J=8.08 Hz, 1H) 7.84 (d, J=7.58 Hz, 1H) 7.88-7.99 (m, 3H) 8.00-8.07 (m, 1H) 8.19 (s, 1H) 8.83 (s, 1H) 9.12 (s, 1H); MS (ESI) 595.

(3-(benzo[b]thiophen-2-ylmethyl)-4-chloro-2-methoxyquinolin-6-yl)(1-methyl-1H-imidazol-5-yl)(6-(trifluoromethyl)pyridin-3-yl)methanol was purified by HPLC (Chiralpak AD column, 550 gram, 20 μM) ethanol eluent, 80 mL/minute, 240 nm wavelength) to give 2 enantiomers. The first eluting enantiomer was Example 37B: $^1$H NMR (400 MHz, MeOH-d$_4$) δ ppm 3.47 (s, 3H) 4.13 (s, 3H) 4.54 (s, 2H) 6.34 (br. s., 1H) 7.09 (s, 1H) 7.15-7.32 (m, 2H) 7.57-7.77 (m, 4H) 7.78-7.93 (m, 2H) 7.99 (d, J=6.57 Hz, 1H) 8.17 (d, J=2.02 Hz, 1H) 8.78 (s, 1H) and the second eluting enantiomer was Example 37C: $^1$H NMR (400 MHz, MeOH-d$_4$) δ ppm 3.47 (s, 3H) 4.13 (s, 3H) 4.54 (s, 2H) 6.27-6.42 (br. s, 1H) 7.09 (s, 1H) 7.16-7.30 (m, 2H) 7.56-7.78 (m, 4H) 7.79-7.91 (m, 2H) 8.00 (d, J=8.08 Hz, 1H) 8.17 (s, 1H) 8.78 (s, 1H).

Example 38

1-(4-((3-(4-(1H-Pyrazol-1-yl)benzyl)-4-chloro-2-methoxyquinolin-6-yl)(4-fluorophenyl)(hydroxy)methyl)piperidin-1-yl)ethanone

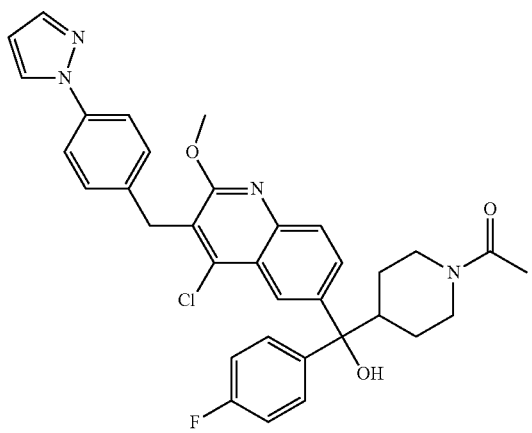 [SMILES: COc1nc2ccc(C(O)(c3ccc(F)cc3)C3CCN(C(C)=O)CC3)cc2c(Cl)c1Cc1ccc(-n2cccn2)cc1]

The title compound was prepared by substituting (6-methoxypyridin-3-yl)(thiazol-5-yl)methanone (Intermediate 15) with 1-(4-(4-fluorobenzoyl)piperidin-1-yl)ethanone (Intermediate 24) then following the procedure described for the preparation of Example 20A. $^1$H NMR (400 MHz, CDCl$_3$) δ ppm 1.28-1.44 (m, 2H) 1.58-1.71 (m, 2H) 2.05 (s, 3H) 2.51-2.65 (m, 1H) 2.72 (br. s., 1H) 3.00-3.19 (m, 1H) 3.73-3.92 (m, 1H) 4.09 (s, 3H) 4.32 (s, 2H) 4.60-4.79 (m, 1H) 6.44 (s, 1H) 7.01 (t, J=8.59 Hz, 2H) 7.36 (d, J=8.59 Hz, 2H) 7.49 (dd, J=8.34, 5.31 Hz, 2H) 7.56 (d, J=8.59 Hz, 2H) 7.65 (br. s., 1H) 7.69 (s, 1H) 7.79-7.89 (m, 2H) 8.26 (s, 1H); MS (ESI) 599.

Example 39

(3-(4-(1H-Pyrazol-1-yl)benzyl)-4-chloro-2-methoxyquinolin-6-yl)(4-fluorophenyl)(pyridin-3-yl)methanol

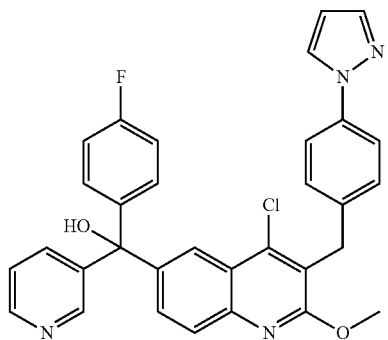 [SMILES: COc1nc2ccc(C(O)(c3ccc(F)cc3)c3cccnc3)cc2c(Cl)c1Cc1ccc(-n2cccn2)cc1]

A solution of n-BuLi (2.5 M in hexanes, 0.095 mL, 0.238 mmol) was added dropwise by syringe to a solution of 3-(4-(1H-pyrazol-1-yl)benzyl)-6-bromo-4-chloro-2-methoxyquinoline (105.5 mg, 0.246 mmol, Intermediate 16) in dry THF (2.5 mL) in a dry ice-acetone bath. After 1.5 minutes, a solution of commercially available (4-fluorophenyl)(pyridin-3-yl)methanone (58.7 mg, 0.292 mmol) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with methanol and water. The mixture was partitioned between water and ethyl acetate. The separated aqueous phase was further extracted with ethyl acetate. The organic phase was dried (Na$_2$SO$_4$), filtered, and concentrated. The crude product was purified by flash column chromatography (silica gel, 10-50% EtOAc-Hexanes followed by 0-10% MeOH-DCM) to provide the title compound as a white solid. $^1$H NMR (400 MHz, CDCl$_3$) δ ppm 8.50-8.48 (m, 1H), 8.43 (dd, J=4.8, 1.6 Hz, 1H), 8.02 (d, J=2.1 Hz, 1H), 7.83 (d, J=2.4 Hz, 1H), 7.77 (d, J=8.8 Hz, 1H), 7.67-7.64 (m, 2H), 7.55-7.52 (m, 2H), 7.50 (dd, J=8.8, 2.2 Hz, 1H), 7.33 (d, J=8.6 Hz, 2H), 7.26-7.20 (m, 3H), 7.03-6.96 (m, 2H), 6.42-6.40 (m, 1H), 4.28 (s, 2H), 4.07 (s, 3H); MS m/e 551.2 [M+H]$^+$.

Example 40

((3-(4-(1H-Pyrazol-1-yl)benzyl)-4-chloro-2-methoxyquinolin-6-yl)(pyridin-3-yl)(4-(trifluoromethyl)phenyl)methanol

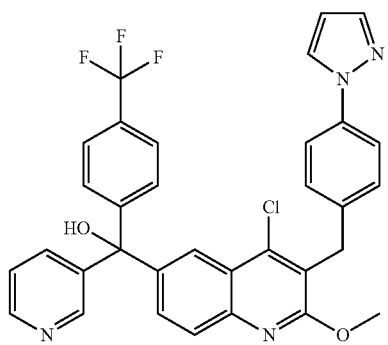 [SMILES: COc1nc2ccc(C(O)(c3ccc(C(F)(F)F)cc3)c3cccnc3)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (75.9 mg, 0.177 mmol, Intermediate 16) in dry THF (3 mL) in a dry ice-acetone bath. After 1.5 minutes, a solution of pyridin-3-yl(4-(trifluoromethyl)phenyl)methanone (48.0 mg, 0.191 mmol, Intermediate 26: step b) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with methanol and water. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 10-50% EtOAc-Hexanes) to provide the title compound as a white solid. $^1$H NMR (500 MHz, $CDCl_3$) δ ppm 8.51 (d, J=2.2 Hz, 1H), 8.48 (dd, J=4.8, 1.4 Hz, 1H), 8.02 (d, J=2.1 Hz, 1H), 7.83 (d, J=2.4 Hz, 1H), 7.79 (d, J=8.8 Hz, 1H), 7.66 (d, J=1.6 Hz, 1H), 7.66-7.63 (m, 1H), 7.59 (d, J=8.4 Hz, 2H), 7.54 (d, J=8.5 Hz, 2H), 7.49 (dd, J=8.8, 2.2 Hz, 1H), 7.46 (d, J=8.3 Hz, 2H), 7.34 (d, J=8.5 Hz, 2H), 7.26-7.23 (m, 1H), 6.42 (t, J=2.1 Hz, 1H), 4.29 (s, 2H), 4.08 (s, 3H); MS m/e 602.1 [M+H]$^+$.

Example 41

(3-(4-(1H-Pyrazol-1-yl)benzyl)-4-chloro-2-methoxyquinolin-6-yl)(3,4-dimethoxyphenyl)(pyridin-3-yl)methanol

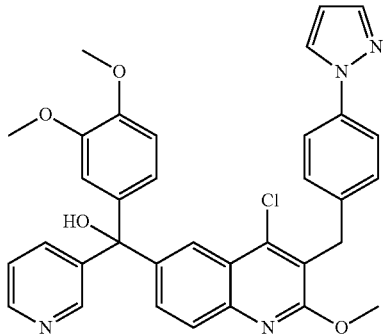 [SMILES: COc1ccc(C(O)(c2cccnc2)c2ccc3nc(OC)c(Cc4ccc(-n5cccn5)cc4)c(Cl)c3c2)cc1OC]

A solution of n-BuLi (2.5 M in hexanes, 0.05 mL, 0.125 mmol) was added dropwise by syringe to a solution of 3-(4-(1H-pyrazol-1-yl)benzyl)-6-bromo-4-chloro-2-methoxyquinoline (32.9 mg, 0.135 mmol, Intermediate 16) in dry THF (2 mL) in a dry ice-acetone bath. After 5 minutes, a solution of (3,4-dimethoxyphenyl)(pyridin-3-yl)methanone (32.9 mg, 0.135 mmol, Intermediate 27: step b) in dry THF (0.2 mL) was added dropwise. The reaction mixture was stirred for 5 minutes in a dry ice-acetone bath, then the reaction flask was placed into an ice-water bath. After 10 minutes, the mixture was warmed to room temperature and the reaction was quenched with saturated ammonium chloride. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 20-100% EtOAc-Hexanes) to provide the title compound as a white solid. $^1$H NMR (400 MHz, $CDCl_3$) δ ppm 8.61 (d, J=1.8 Hz, 1H), 8.53 (dd, J=4.8, 1.6 Hz, 1H), 8.10 (d, J=2.0 Hz, 1H), 7.85 (d, J=2.4 Hz, 1H), 7.79 (d, J=8.8 Hz, 1H), 7.69 (dt, J=8.0, 2.0 Hz, 2H), 7.57-7.52 (m, 3H), 7.35 (d, J=8.6 Hz, 2H), 7.29-7.25 (m, 1H), 6.91 (d, J=2.2 Hz, 1H), 6.79 (d, J=8.5 Hz, 1H), 6.66 (dd, J=8.4, 2.2 Hz, 1H), 6.44-6.42 (m, 1H), 4.31 (s, 2H), 4.08 (s, 3H), 3.88 (s, 3H), 3.76 (s, 3H); MS m/e 593.2 [M+H]$^+$.

Example 42

(3-(4-(1H-Pyrazol-1-yl)benzyl)-4-chloro-2-methoxyquinolin-6-yl)(4-(dimethylamino)phenyl)(pyridin-3-yl)methanol

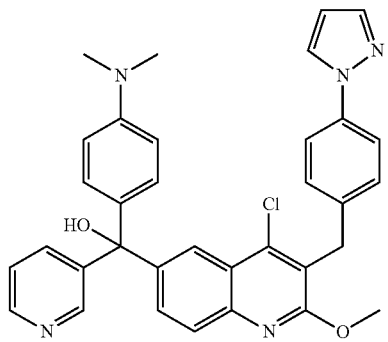 [SMILES: COc1nc2ccc(C(O)(c3ccc(N(C)C)cc3)c3cccnc3)cc2c(Cl)c1Cc1ccc(-n2cccn2)cc1]

The title compound was prepared analogously to the method in Example 41 using (4-(dimethylamino)phenyl)(pyridin-3-yl)methanone (Intermediate 28: step b) in place of (3,4-dimethoxyphenyl)(pyridin-3-yl)methanone (Intermediate 27: step b), except the crude product was purified using a solvent system of 0-5% MeOH-DCM to provide the title compound as a white solid. $^1$H NMR (400 MHz, $CDCl_3$) δ ppm 8.64 (d, J=2.3 Hz, 1H), 8.52 (dd, J=4.8, 1.6 Hz, 1H), 8.15 (d, J=2.1 Hz, 1H), 7.85 (d, J=2.4 Hz, 1H), 7.77 (d, J=8.8 Hz, 1H), 7.75-7.70 (m, 1H), 7.69 (d, J=1.6 Hz, 1H), 7.58-7.53 (m, 3H), 7.35 (d, J=8.5 Hz, 2H), 7.24 (d, J=4.7 Hz, 1H), 7.07 (d, J=8.9 Hz, 2H), 6.66 (d, J=8.9 Hz, 2H), 6.44-6.41 (m, 1H), 4.31 (s, 2H), 4.07 (s, 3H), 2.96 (s, 6H); MS m/e 576.3 [M+H]$^+$.

Example 43

(3-(4-(1H-Pyrazol-1-yl)benzyl)-4-chloro-2-methoxyquinolin-6-yl)(4-fluorophenyl)(1-methyl-1H-imidazol-5-yl)methanol

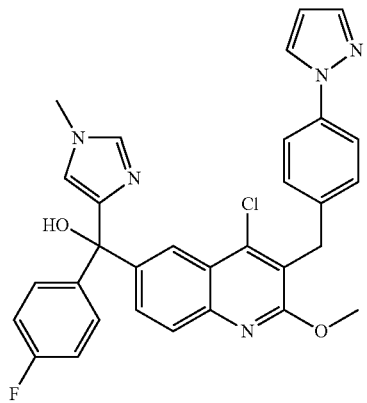 [SMILES: COc1nc2ccc(C(O)(c3ccc(F)cc3)c3cn(C)cn3)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (75.8 mg, 0.177 mmol, Intermediate 16) in dry THF (3 mL) in a dry ice-acetone bath. After 1 minute, a solution of (4-fluorophenyl)(1-methyl-1H-imidazol-5-yl)methanone (37.8 mg, 0.185 mmol, Intermediate 29: step b) in dry THF (0.6 mL) was added dropwise. The reaction mixture was stirred for 5 minutes in a dry ice-acetone bath, then warmed to room temperature and the reaction was quenched with methanol and water. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 0-50% EtOAc-Hexanes) to provide the title compound as a clear foam. $^1$H NMR (400 MHz, $CDCl_3$) δ ppm 8.12 (d, J=2.1 Hz, 1H), 7.84 (d, J=2.4 Hz, 1H), 7.77 (d, J=8.7 Hz, 1H), 7.66 (d, J=1.6 Hz, 1H), 7.57-7.50 (m, 3H), 7.35 (d, J=8.6 Hz, 2H), 7.34-7.29 (m, 2H), 7.25 (s, 1H), 7.04-6.96 (m, 2H), 6.45-6.40 (m, 1H), 6.30 (s, 1H), 4.30 (s, 2H), 4.08 (s, 3H), 3.34 (s, 3H); MS m/e 554.1 $[M+H]^+$.

Example 44

(3-(4-(1H-Pyrazol-1-yl)benzyl)-4-chloro-2-methoxyquinolin-6-yl)(3,4-dichlorophenyl)(pyridin-3-yl)methanol

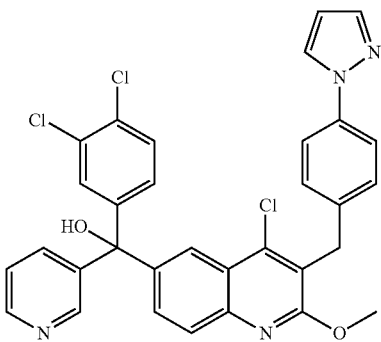 [SMILES: COc1nc2ccc(C(O)(c3cccnc3)c3ccc(Cl)c(Cl)c3)cc2c(Cl)c1Cc1ccc(-n2cccn2)cc1]

A solution of n-BuLi (2.5 M in hexanes, 0.07 mL, 0.175 mmol) was added dropwise by syringe to a solution of 3-(4-(1H-pyrazol-1-yl)benzyl)-6-bromo-4-chloro-2-methoxyquinoline (78.6 mg, 0.183 mmol, Intermediate 16) in dry THF (3 mL) in a dry ice-acetone bath. After 1 minute, a solution of (3,4-dichlorophenyl)(pyridin-3-yl)methanone (50.2 mg, 0.199 mmol, Intermediate 30: step b) in dry THF (0.2 mL) was added dropwise. The reaction mixture was stirred for 10 minutes in a dry ice-acetone bath, then the reaction flask was placed into an ice-water bath. After 20 minutes, the mixture was warmed to room temperature and the reaction was quenched with methanol. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 0-50% EtOAc-Hexanes) to provide the title compound as a clear oil. $^1$H NMR (400 MHz, $CDCl_3$) δ ppm 8.37 (d, J=2.0 Hz, 1H), 8.32 (dd, J=4.8, 1.4 Hz, 1H), 8.01 (d, J=2.1 Hz, 1H), 7.81 (dd, J=2.5, 0.4 Hz, 1H), 7.75 (d, J=8.8 Hz, 1H), 7.64-7.58 (m, 2H), 7.53-7.48 (m, 2H), 7.46 (d, J=2.2 Hz, 1H), 7.44 (dd, J=8.8, 2.2 Hz, 1H), 7.34-7.30 (m, 3H), 7.17 (dd, J=7.8, 4.7 Hz, 1H), 7.06 (dd, J=8.4, 2.2 Hz, 1H), 6.39 (dd, J=2.4, 1.9 Hz, 1H), 4.26 (s, 2H), 4.07 (s, 3H); MS m/e 601.1 $[M+H]^+$.

Example 45

(3-(4-(1H-Pyrazol-1-yl)benzyl)-2,4-dichloroquinolin-6-yl)(4-chlorophenyl)(pyridin-3-yl)methanol

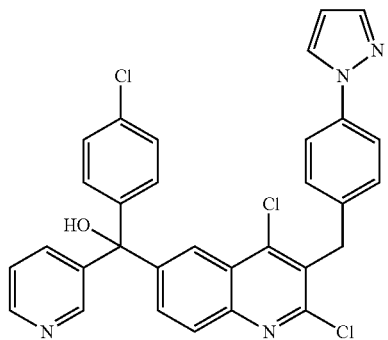 [SMILES: OC(c1ccc(Cl)cc1)(c1cccnc1)c1ccc2nc(Cl)c(Cc3ccc(-n4cccn4)cc3)c(Cl)c2c1]

A suspension of 3-(4-(1H-pyrazol-1-yl)benzyl)-6-bromo-2,4-dichloroquinoline (214.5 mg, 0.495 mmol, Intermediate 6: step c) in dry THF (5 mL) was heated with a heat gun to form a solution. The solution was cooled in a dry ice-acetone bath for 2 minutes, then a solution of n-BuLi (2.5 M in hexanes, 0.18 mL, 0.45 mmol) was added dropwise by syringe. After 1 minute, a solution of commercially available (4-chlorophenyl)(pyridin-3-yl)methanone (0.117 mg, 0.541 mmol) in dry THF (0.2 mL) was added dropwise. The reaction mixture was stirred for 5 minutes in a dry ice-acetone bath, then the reaction flask was placed into an ice-water bath that was allowed to warm to room temperature. The reaction was quenched with saturated ammonium chloride. The mixture was partitioned between water and ethyl acetate. The separated aqueous phase was further extracted with ethyl acetate. The organic phase was dried ($Na_2SO_4$), filtered, and concentrated. The crude product was purified by flash column chromatography (silica gel, 50-100% EtOAc-Hexanes) followed by reverse-phase chromatography (acetonitrile w/0.05% TFA in water). The free-base product was formed to provide the title compound as a clear oil. $^1$H NMR (400 MHz, $CDCl_3$) δ ppm 8.50 (s, 1H), 8.47 (d, J=4.0 Hz, 1H), 8.19 (d, J=2.0 Hz, 1H), 7.96 (d, J=8.8 Hz, 1H), 7.85 (d, J=2.4 Hz, 1H), 7.68-7.62 (m, 3H), 7.60-7.55 (m, 2H), 7.33-7.20 (m, 7H), 6.44-6.41 (m, 1H), 4.52 (s, 2H), 4.03 (s, 1H); MS m/e 571.1 $[M+H]^+$.

Example 46

(3-(4-(1H-Pyrazol-1-yl)benzyl)-2,4-dichloroquinolin-6-yl)(4-fluorophenyl)(pyridin-3-yl)methanol

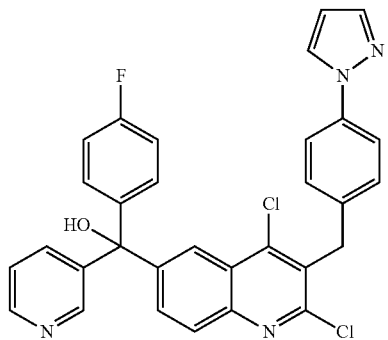 [SMILES: OC(c1ccc(F)cc1)(c1cccnc1)c1ccc2nc(Cl)c(Cc3ccc(-n4cccn4)cc3)c(Cl)c2c1]

The title compound was prepared analogously to the method in Example 45 using commercially available (4-fluorophenyl)(pyridin-3-yl)methanone in place of (4-chlorophenyl)(pyridin-3-yl)methanone. $^1$H NMR (400 MHz, CDCl$_3$) δ ppm 8.47 (s, 1H), 8.40 (s, 1H), 8.19 (d, J=1.9 Hz, 1H), 7.94 (d, J=8.9 Hz, 1H), 7.85 (dd, J=2.5, 0.5 Hz, 1H), 7.68-7.62 (m, 3H), 7.58-7.54 (m, 2H), 7.29 (d, J=8.7 Hz, 2H), 7.26-7.21 (m, 3H), 7.03-6.96 (m, 2H), 6.42 (dd, J=2.4, 1.9 Hz, 1H), 4.51 (s, 2H); MS m/e 555.1 [M+H]$^+$.

Example 47

(3-(4-(1H-Pyrazol-1-yl)benzyl)-2,4-dichloroquinolin-6-yl)(4-methoxyphenyl)(pyridin-3-yl)methanol

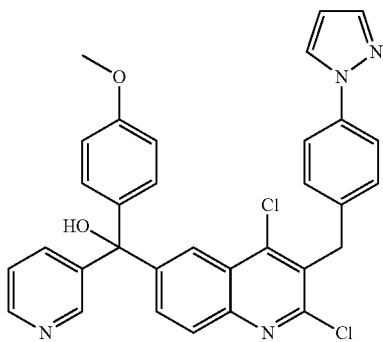 [SMILES: COc1ccc(C(O)(c2cccnc2)c2ccc3nc(Cl)c(Cc4ccc(-n5cccn5)cc4)c(Cl)c3c2)cc1]

The title compound was prepared analogously to the method in Example 45 using (4-methoxyphenyl)(pyridin-3-yl)methanone (Intermediate 31: step b) in place of (4-chlorophenyl)(pyridin-3-yl)methanone. $^1$H NMR (400 MHz, CDCl$_3$) δ ppm 8.48 (d, J=2.1 Hz, 1H), 8.36 (dd, J=4.8, 1.5 Hz, 1H), 8.24 (d, J=2.0 Hz, 1H), 7.92 (d, J=8.8 Hz, 1H), 7.84 (d, J=2.5 Hz, 1H), 7.70-7.62 (m, 3H), 7.56 (d, J=8.5 Hz, 2H), 7.28 (d, J=8.5 Hz, 2H), 7.22-7.17 (m, 1H), 7.17-7.11 (m, 2H), 6.84-6.78 (m, 2H), 6.42-6.39 (m, J=4.3, 2.1 Hz, 1H), 4.49 (s, 2H), 3.77 (s, 3H); MS m/e 567.1 [M+H]$^+$.

Example 48

(3-(4-(1H-Pyrazol-1-yl)benzyl)-2,4-dichloroquinolin-6-yl)(3-fluorophenyl)(pyridin-3-yl)methanol

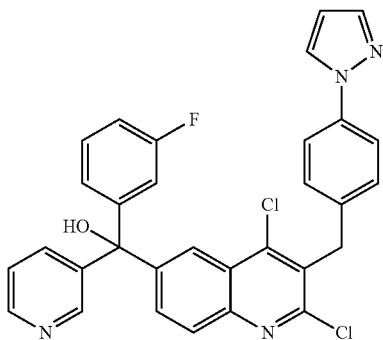 [SMILES: OC(c1cccnc1)(c1cccc(F)c1)c1ccc2nc(Cl)c(Cc3ccc(-n4cccn4)cc3)c(Cl)c2c1]

The title compound was prepared analogously to the method in Example 45 using (3-fluorophenyl)(pyridin-3-yl)methanone (Intermediate 32: step b) in place of (4-chlorophenyl)(pyridin-3-yl)methanone, except that 1.2 equivalents of Intermediate 32: step b and 1.1 equivalents of n-BuLi were used relative to 3-(4-(1H-pyrazol-1-yl)benzyl)-6-bromo-2,4-dichloroquinoline (Intermediate 6: step c). $^1$H NMR (400 MHz, MeOH-d$_4$) δ ppm 8.84 (s, 1H), 8.76 (d, J=5.3 Hz, 1H), 8.46-8.42 (m, 1H), 8.27 (d, J=2.0 Hz, 1H), 8.15 (d, J=2.5 Hz, 1H), 8.01 (d, J=8.9 Hz, 1H), 7.93 (dd, J=8.2, 5.6 Hz, 1H), 7.82 (dd, J=8.9, 2.1 Hz, 1H), 7.69 (d, J=1.7 Hz, 1H), 7.64 (d, J=8.6 Hz, 2H), 7.44 (td, J=8.1, 6.0 Hz, 1H), 7.31 (d, J=8.6 Hz, 2H), 7.22-7.17 (m, 1H), 7.17-7.11 (m, 2H), 6.51-6.49 (m, 1H), 4.59 (s, 2H); MS m/e 555.1 [M+H]$^+$.

Example 49

(3-Benzyl-2,4-dichloroquinolin-6-yl)(4-chlorophenyl)(1-methyl-1H-pyrazol-4-yl)methanol.TFA

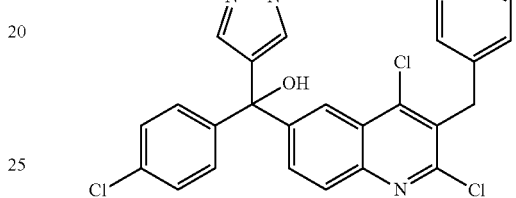

A solution of 4-iodo-1-methyl-1H-pyrazole (83.8 mg, 0.403 mmol) in THF (0.8 mL) was added dropwise under argon to a −72° C. solution of n-BuLi (0.156 mL, 0.403 mmol, 2.6 M in hexane) in THF (0.5 mL). The resulting mixture was stirred at −72° C. for 25 minutes, and was then treated dropwise with a solution of an inseparable mixture of (3-benzyl-2,4-dichloroquinolin-6-yl)(4-chlorophenyl)methanone (79 mg, 0.185 mmol, Intermediate 33: step d) and ethyl 3-benzyl-2,4-dichloroquinoline-6-carboxylate (66 mg, 0.183 mmol, Intermediate 33: step c) in THF (0.8 mL) and stirred at −72° C. for 30 minutes. The yellow reaction was then allowed to warm to 0° C. over 15 minutes and stirred for an additional 15 minutes at 0° C. The clear amber reaction was then quenched with 5 M aqueous NH$_4$Cl (3 mL). The aqueous layer was extracted with 4:1 ether/DCM (2×3 mL), and the combined organic layers were dried (Na$_2$SO$_4$), filtered, and concentrated. The residue was flash chromatographed with a heptane to 20% EtOAc/heptane gradient and further purified with C18 HPLC (20% to 100% CH$_3$CN, with 0.1% TFA throughout) to provide, after lyophilization, the title compound as a yellow powder. $^1$H NMR (400 MHz, CDCl$_3$) δ ppm 8.33 (d, J=1.96 Hz, 1H), 7.99 (d, J=8.80 Hz, 1H), 7.69 (dd, J=1.96, 8.80 Hz, 1H), 7.48 (s, 1H), 7.31-7.38 (m, 4H), 7.16-7.31 (m, 6H), 4.53 (s, 2H), 3.96 (s, 3H); MS m/e 507.7 [M+H]$^+$.

Example 50

(3-Benzyl-2,4-dimethylquinolin-6-yl)(4-chlorophenyl)(1-methyl-1H-imidazol-5-yl)methanol.TFA

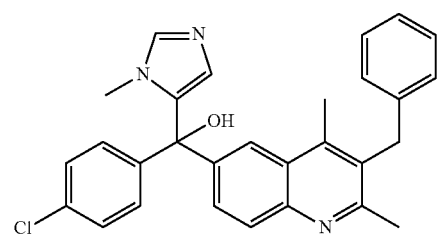 [SMILES: Cc1nc2ccc(C(O)(c3ccc(Cl)cc3)c3cncn3C)cc2c(C)c1Cc1ccccc1]

A solution of (3-benzyl-2,4-dimethylquinolin-6-yl)(1-methyl-1H-imidazol-5-yl)methanone (12.4 mg, 0.0349 mmol, Intermediate 34: step d) and 4-chloroiodobenzene (33.3 mg, 0.14 mmol) in THF (0.5 mL) was stirred at ~−70° C. while n-BuLi (53.9 µL, 2.59 M in hexane, 0.14 mmol) was added dropwise under argon. The resulting yellow solution was stirred while the dry ice/ether bath was allowed to warm to room temperature overnight. The clear yellow reaction was then quenched with 1 M aqueous NaHCO$_3$ (3 mL) and extracted with EtOAc (1×5 mL), and the organic layer was dried (Na$_2$SO$_4$), filtered, and concentrated. The residue was purified by C18 HPLC (20% to 100% CH$_3$CN, with 0.1% TFA throughout) to provide, after lyophilization, the title compound as a white powder. $^1$H NMR (400 MHz, MeOH-d$_4$) δ ppm 9.00 (s, 1H), 8.44 (s, 1H), 8.15 (d, J=8.59 Hz, 1H), 7.99-8.07 (m, 1H), 7.42-7.50 (m, 4H), 7.27-7.35 (m, 2H), 7.25 (d, J=7.07 Hz, 1H), 7.10 (d, J=8.08 Hz, 2H), 7.00 (s, 1H), 4.48 (s, 2H), 3.69 (s, 3H), 2.84 (s, 3H), 2.88 (s, 3H); MS m/e 468.0 [M+H]$^+$.

Example 51

3-Benzyl-6-((4-fluorophenyl)(hydroxy)(1-methyl-1H-imidazol-5-yl)methyl)-N-methyl-4-(trifluoromethyl)quinoline-2-carboxamide

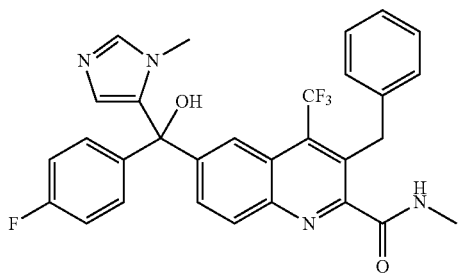 [SMILES: CNC(=O)c1nc2ccc(C(O)(c3ccc(F)cc3)c3cncn3C)cc2c(C(F)(F)F)c1Cc1ccccc1]

5-Bromo-1-methyl-1H-imidazole (1.36 mL, 0.5 M in DCM over 3 Å molecular sieves, 0.678 mmol) was treated with EtMgCl (0.325 mL, 2.09 M in THF, 0.678 mmol) dropwise under argon with stirring at room temperature over 1 minute, and the resulting translucent/semi-opaque reaction was stirred at room temperature for 20 minutes. This was treated dropwise over 2 minutes with a solution of 3-benzyl-6-(4-fluorobenzoyl)-N-methyl-4-(trifluoromethyl)quinoline-2-carboxamide (90.4 mg, 0.194 mmol, Intermediate 35: step f) in DCM (1.2 mL) with stirring at room temperature, and the resulting orange reaction was immediately stirred at 40° C. for 13 hours. The resulting orange opaque mixture was cooled to room temperature, partitioned with 5 M aqueous NH$_4$Cl (3 mL), and the aqueous layer was extracted with DCM (1×5 mL). The combined organic layers were dried (Na$_2$SO$_4$), filtered, and concentrated. The residue was dry load flash chromatographed using 2:3 toluene/acetone (isocratic elution) to yield the title compound as a pale yellow foam. $^1$H NMR (400 MHz, CDCl$_3$) δ ppm 8.32 (s, 1H), 7.88 (d, J=9.09 Hz, 1H), 7.69 (d, J=10.61 Hz, 1H), 7.30-7.38 (m, 3H), 7.10-7.24 (m, 4H), 6.97-7.09 (m, 4H), 6.29 (s, 1H), 4.91 (s, 2H), 3.39 (s, 3H), 2.89 (d, J=5.05 Hz, 3H); MS m/e 549.2 [M+H]$^+$.

Example 52

(2-Chloro-3-(4-methoxybenzyl)quinolin-6-yl)(1-methyl-1H-imidazol-5-yl)(thiazol-5-yl)methanol.TFA

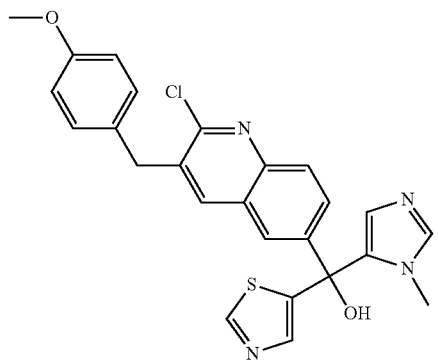 [SMILES: COc1ccc(Cc2cc3cc(C(O)(c4cncs4)c4cncn4C)ccc3nc2Cl)cc1]

6-Bromo-2-chloro-3-(4-methoxybenzyl)quinoline (0.200 g, 0.551 mmol, Intermediate 17: step a) and (1-methyl-1H-imidazol-5-yl)(thiazol-5-yl)methanone (0.135 g, 0.662 mmol, Intermediate 13) were combined in dry THF (5 mL), cooled to −78° C. then treated with n-BuLi (0.448 mL, 0.717 mmol; 1.6 M in hexanes) dropwise. The mixture was stirred for 30 minutes then warmed to 0° C. Stirring was continued for 1 hour then quenched with saturated aqueous NH$_4$Cl, and warmed to room temperature. After stirring for 10 minutes layers were separated and the aqueous layer extracted with EtOAc. The combined organic extracts was dried over Na$_2$SO$_4$, filtered, evaporated in vacuo and chromatographed (0-100% EtOAc in DCM) to yield the title compound after further purification using Gilson HPLC methods (H$_2$O/acetonitrile/1% TFA). $^1$H NMR (400 MHz, MeOH-d$_4$) δ ppm 2.03 (s, 1 H) 3.66 (s, 3 H) 3.77 (s, 3 H) 4.19 (s, 2 H) 6.88 (d, J=8.31 Hz, 2 H) 7.14-7.22 (m, 3 H) 7.65 (s, 1 H) 7.86 (d, J=8.80 Hz, 1 H) 7.91 (s, 1 H) 8.00 (d, J=8.80 Hz, 1 H) 8.07 (s, 1 H) 8.97 (s, 1 H) 9.07 (s, 1 H); MS (EI) 476.

Example 53

(4-Chloro-2-methoxy-3-(4-(methylsulfonyl)benzyl)quinolin-6-yl)(1-methyl-1H-imidazol-5-yl)(6-(trifluoromethyl)pyridin-3-yl)methanol

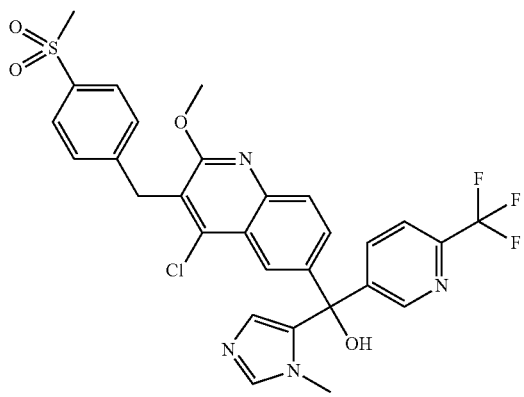 [SMILES: COc1nc2ccc(C(O)(c3ccc(C(F)(F)F)nc3)c3cncn3C)cc2c(Cl)c1Cc1ccc(S(C)(=O)=O)cc1]

Isopropyl magnesium chloride LiCl complex (1.3 M in THF, 0.7 mL, 0.904 mmol) was added dropwise to a solution of 5-bromo-2-(trifluoromethyl)pyridine (0.2 g, 0.904 mmol) in dry THF 5 mL) at 0° C. The mixture was stirred at 0° C. for five minutes then at room temperature for 30 minutes. A suspension of (4-chloro-2-methoxy-3-(4-(methylsulfonyl)benzyl)quinolin-6-yl)(1-methyl-1H-imidazol-5-yl)methanone (0.085 g, 0.181 mmol, Intermediate 38: step b) in THF (5 mL) was added rapidly at 0° C. and the reaction mixture was stirred and allowed to warm to room temperature. The homogeneous amber solution was stirred at room temperature for 4 hours, then heated at 45° C. for 12 hours. Once cooled the reaction mixture was quenched with saturated aqueous NH$_4$Cl, diluted with H$_2$O and extracted with EtOAc (2×). The EtOAc extracts were washed with brine, dried (Na$_2$SO$_4$), filtered, evaporated in vacuo and chromatographed (DCM/MeOH) to provide the title compound. $^1$H NMR (400 MHz, CDCl$_3$) δ ppm 8.80 (s, 1H), 8.15 (d, J=2.0 Hz, 1H), 7.87-8.00 (m, 1H), 7.78-7.87 (m, 3H), 7.65 (d, J=8.1 Hz, 1H), 7.57 (d, J=2.0 Hz, 1H), 7.46 (d, J=8.6 Hz, 2H), 7.32 (s, 1H), 6.33 (s, 1H), 5.30 (s, 1H), 4.37 (s, 2H), 4.08 (s, 3H), 3.36 (s, 3H), 3.01 (s, 3H); MS (ESI) 617.9.

Example 54A (4-Chloro-2-methoxy-3-(4-(methylsulfonyl)benzyl)quinolin-6-yl)(4-fluorophenyl)(1-methyl-1H-imidazol-5-yl)methanol.TFA

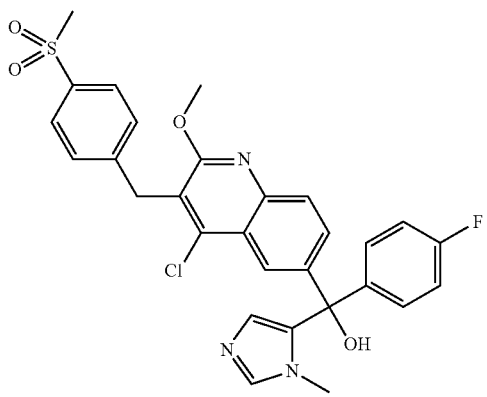 [SMILES: COc1nc2ccc(C(O)(c3ccc(F)cc3)c3cncn3C)cc2c(Cl)c1Cc1ccc(S(C)(=O)=O)cc1]

To a solution of (4-chloro-2-methoxy-3-(4-(methylsulfonyl)benzyl)quinolin-6-yl)(1-methyl-1H-imidazol-5-yl)methanone (0.12 g, 0.253 mmol, Intermediate 38: step b) in dry THF (5 mL) was slowly added 4-fluorophenyl magnesium bromide (1 M in THF, 1.15 mL). The mixture was stirred at room temperature overnight then at 50° C. for 2 hours. Once cooled, the mixture was quenched with saturated aqueous NH$_4$Cl, diluted with H$_2$O and extracted with EtOAc (2×). The EtOAc extracts were washed with brine, dried (Na$_2$SO$_4$), filtered, evaporated in vacuo and chromatographed (DCM/MeOH) to provide product that was further purified by HPLC to provide the title compound. $^1$H NMR (400 MHz, DMSO-d$_6$) δ ppm 9.12 (br. s., 1H), 8.09 (d, J=2.0 Hz, 1H), 7.88 (d, J=8.6 Hz, 2H), 7.83 (d, J=8.6 Hz, 2H), 7.62 (dd, J=8.6, 2.0 Hz, 1H), 7.47 (d, J=8.1 Hz, 2H), 7.39 (dd, J=8.8, 5.3 Hz, 2H), 7.21-7.30 (m, 2H), 6.93 (s, 1H), 4.36 (s, 2H), 4.03 (s, 3H), 3.53 (s, 3H), 3.17 (s, 3H); MS (ESI) 565.9.

(4-chloro-2-methoxy-3-(4-(methylsulfonyl)benzyl)quinolin-6-yl)(4-fluorophenyl)(1-methyl-1H-imidazol-5-yl)methanol was purified by HPLC (Chiralpak AD column, 250 gram, 50:50% methanol:ethanol as eluent, 80 mL/minute flow rate, 240 nm wavelength) to provide the two enantiomers. The first eluting enantiomer was Example 54B: $^1$H NMR (400 MHz, CDCl$_3$) δ ppm 8.03-8.14 (m, 1H), 7.82 (d, J=8.1 Hz, 3H), 7.52-7.62 (m, 2H), 7.43-7.50 (m, 2H), 7.30-7.39 (m, 2H), 6.96-7.10 (m, 2H), 6.35-6.49 (m, 1H), 4.37 (s, 2H), 4.08 (s, 3H), 3.44 (s, 3H), 3.01 (s, 3H), mass calcd. C$_{29}$H$_{25}$ClFN$_3$O$_4$S, 566.05; m/z found, 566.1 and the second eluting enantiomer was Example 54C: $^1$H NMR (400 MHz, CDCl$_3$) δ ppm 8.09 (d, J=2.0 Hz, 1H), 7.77-7.86 (m, 3H), 7.52-7.62 (m, 2H), 7.47 (d, J=8.6 Hz, 2H), 7.33 (dd, J=8.6, 5.1 Hz, 2H), 7.04 (t, J=8.6 Hz, 2H), 6.42 (s, 1H), 4.37 (s, 2H), 4.08 (s, 3H), 3.44 (s, 3H), 3.01 (s, 3H) mass calcd. C$_{29}$H$_{25}$ClFN$_3$O$_4$S, 566.05; m/z found, 566.1.

Example 55A 3-(4-(1H-Pyrazol-1-yl)benzyl)-4-chloro-6-((4-chlorophenyl)(hydroxy)(1-methyl-1H-imidazol-5-yl)methyl)quinolin-2-ol

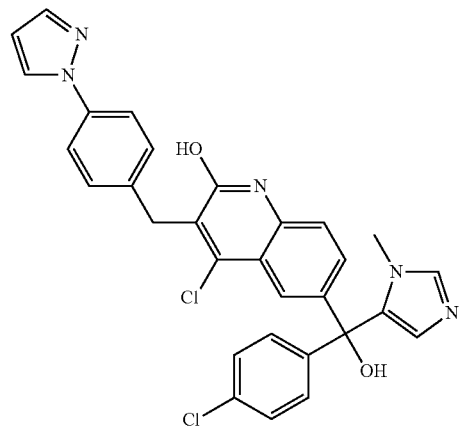 [SMILES: Cn1cncc1C(O)(c1ccc(Cl)cc1)c1ccc2nc(O)c(Cc3ccc(-n4cccn4)cc3)c(Cl)c2c1]

To a mixture of (3-(4-(1H-pyrazol-1-yl)benzyl)-4-chloro-2-methoxyquinolin-6-yl)(4-chlorophenyl)(1-methyl-1H-imidazol-5-yl)methanol (0.32 g, 0.561 mmol, Example 33A) in methanol (1.5 mL) was added 6.6 M aqueous HCl (5 mL). The resulting solution was stirred for 4 days, cooled in an ice bath and aqueous NaOH (3 M) added dropwise to a basic pH. The crude product was isolated by filtration then chromatographed (10% MeOH in DCM, gradient) to provide the product, $^1$H NMR (400 MHz, DMSO-d$_6$) δ ppm 12.23 (s, 1H), 8.41 (d, J=2.5 Hz, 1H), 7.85 (s, 1H), 7.58-7.77 (m, 4H), 7.32-7.48 (m, 6H), 7.28 (d, J=9.1 Hz, 2H), 6.97 (s, 1H), 6.51 (d, J=2.0 Hz, 1H), 6.12 (s, 1H), 4.11 (s, 2H), 3.32 (s, 3H); MS (ESI) 556.

3-(4-(1H-pyrazol-1-yl)benzyl)-4-chloro-6-((4-chlorophenyl)(hydroxy)(1-methyl-1H-imidazol-5-yl)methyl)quinolin-2-ol was purified by HPLC (Diacel OD column, 250 gram, 100% methanol eluent, 80 mL/minute, 240 nm wavelength) to give 2 enantiomers. The first eluting enantiomer was Example 55B: $^1$H NMR (400 MHz, DMSO-d$_6$) δ ppm 12.13-12.33 (m, 1H), 8.40 (s, 1H), 7.85 (s, 1H), 7.68-7.76 (m, 3H), 7.65 (s, 1H), 7.38-7.45 (m, 4H), 7.32-7.37 (m, 1H), 7.28 (d, J=8.6 Hz, 2H), 6.96 (s, 1H), 6.51 (s, 1H), 6.12 (s, 1H), 4.11 (s, 2H), 3.31 (s, 3H) mass calcd. C$_{30}$H$_{23}$C$_{12}$N$_5$O$_2$, 556.45; m/z found, 556.2 and the second eluting enantiomer was Example 55C: $^1$H NMR (400 MHz, DMSO-d$_6$) δ ppm 12.18 (br. s., 1H), 8.40 (d, J=2.5 Hz, 1H), 7.85 (s, 1H), 7.67-7.74 (m, 3H), 7.65 (s, 1H), 7.37-7.45 (m, 5H), 7.32-7.37 (m, 1H), 7.28 (d, J=8.6 Hz, 2H), 6.97 (s, 1H), 6.51 (s, 1H), 6.12 (s, 1H), 4.11 (s, 2H), 3.30 (s, 3H). mass calcd. C$_{30}$H$_{23}$C$_{12}$N$_5$O$_2$, 556.45; m/z found, 556.2

Example 56

(3-(4-(1H-Pyrazol-1-yl)benzyl)-4-chloro-2-methoxy-8-methylquinolin-6-yl)bis(1-methyl-1H-imidazol-5-yl)methanol

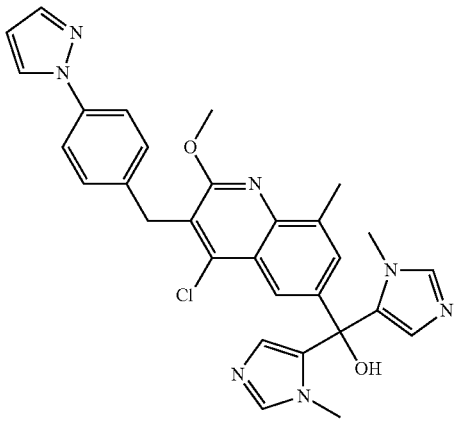 [SMILES: COc1nc2c(C)cc(C(O)(c3cncn3C)c3cncn3C)cc2c(Cl)c1Cc1ccc(-n2cccn2)cc1]

n-Butyllithium (1.6 M in hexane; 0.5 mL, 0.718 mmol) was added dropwise to a suspension of the 3-(4-(1H-pyrazol-1-yl)benzyl)-6-bromo-4-chloro-2-methoxy-8-methylquinoline (0.29 g, 0.653 mmol, Intermediate 19: step b) in dry THF (4 mL) over a 2 minute period at −78° C. A heterogeneous mixture of bis(1-methyl-1H-imidazol-5-yl)methanone (0.14 g, 0.653 mmol, Intermediate 39: step b) in THF (3 mL) was added as a slurry and stirring was continued at −78° C. for 5 minutes. The resulting homogeneous mixture was warmed up to 0° C. and stirred for 10 minutes. The mixture was warmed to room temperature and saturated aqueous NH$_4$Cl was added followed by EtOAc. H$_2$O was added and layers were separated. The aqueous layer was again extracted with EtOAc and the combined organic extracts washed with brine, dried over Na$_2$SO$_4$, filtered, evaporated to dryness. The crude product was purified by chromatography (10% MeOH in CH$_2$Cl$_2$; gradient) to provide the title compound. $^1$H NMR (400 MHz, CDCl$_3$) δ ppm 7.95-8.04 (m, 1H), 7.79-7.89 (m, 1H), 7.65-7.71 (m, 1H), 7.50-7.60 (m, 2H), 7.34-7.45 (m, 5H), 7.32 (s, 1H), 6.36-6.52 (m, 2H), 4.31 (s, 2H), 4.10 (s, 3H), 3.53 (s, 6H), 2.62 (s, 3H). mass calcd. C$_{30}$H$_{28}$ClN$_7$O$_2$, 554.05; m/z found, 554.2

Example 57

(4-Chloro-2-methoxy-8-methyl-3-(4-(methylsulfonyl)benzyl)quinolin-6-yl)bis(1-methyl-1H-imidazol-5-yl)methanol.Succinate

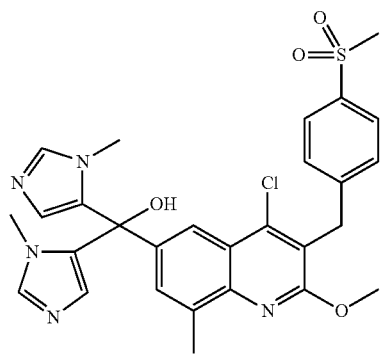

To a cold (ice bath) mixture of 5-bromo-1-methyl-1H-imidazole (0.13 g, 0.82 mmol) in dry THF (2 mL) was added isopropyl magnesium chloride (2M in THF, 0.37 mL, 0.773 mmol) dropwise. The resulting cloudy mixture was stirred in the cold bath for 10 minutes and a solution of (4-chloro-2-methoxy-8-methyl-3-(4-(methylsulfonyl)benzyl)quinolin-6-yl)(1-methyl-1H-imidazol-5-yl)methanone (0.27 g, 0.468 mmol, Intermediate 40: step e) and LaCl$_3$.2LiCl (0.86 mL, 0.515 mmol) in dry THF (2 mL) was added slowly. Stirring was continued at 0° C. for 40 minutes and saturated aqueous NH$_4$Cl was added. Water was added and the mixture extracted with EtOAc (2×). The combined organic extract was washed with brine, dried over Na$_2$SO$_4$, filtered, and evaporated in vacuo. The product was precipitated with acetonitrile and filtered, rinse with acetonitrile and dried to give the free base of the title compound as a white solid. The title compound was suspended in THF (1 mL) and succinic acid (1 equivalent) was added. The resulting clear homogeneous solution was stirred at room temperature for fifteen minutes and solvent removed under reduced pressure to provide the title compound. $^1$H NMR (400 MHz, CDCl$_3$) δ ppm 8.02 (s, 1H), 7.81 (d, J=8.6 Hz, 2H), 7.47 (d, J=8.1 Hz, 2H), 7.28-7.38 (m, 3H), 6.36 (s, 2H), 4.35 (s, 2H), 4.02-4.14 (m, 3H), 3.50 (s, 6H), 3.01 (s, 3H), 2.60 (s, 3H); mass calcd. C$_{28}$H$_{28}$ClN$_5$O$_4$S, 566.08; m/z found, 566.2.

Example 58A (3-(4-(1H-Pyrazol-1-yl)benzyl)-4-chloro-8-fluoro-2-methoxyquinolin-6-yl)(1-methyl-1H-imidazol-5-yl)(6-(trifluoromethyl)pyridin-3-yl)methanol

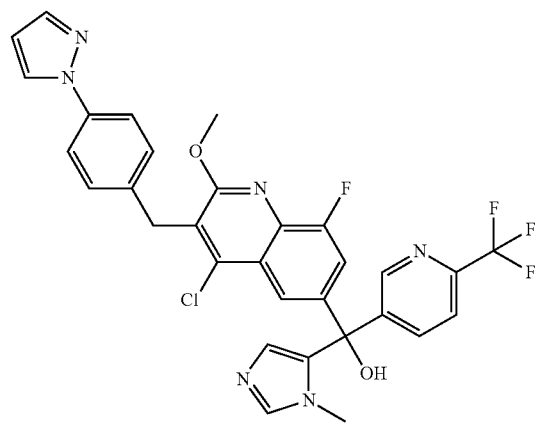 [SMILES: COc1nc2c(F)cc(C(O)(c3ccc(C(F)(F)F)nc3)c3cncn3C)cc2c(Cl)c1Cc1ccc(-n2cccn2)cc1]

n-BuLi (1.6 M in hexanes, 1.45 mL) was added to a mixture of 3-(4-(1H-pyrazol-1-yl)benzyl)-6-bromo-4-chloro-8-fluoro-2-methoxyquinoline and 3-(4-(1H-pyrazol-1-yl)benzyl)-6-bromo-4-chloro-2,8-dimethoxyquinoline (0.82 g, 1.781 mmol, Intermediate 41: step b) and (1-methyl-1H-imidazol-5-yl)(6-(trifluoromethyl)pyridin-3-yl)methanone (0.5 g, 1.96 mmol, Intermediate 36: step c) in dry THF 20 mL) at −78° C. over a 2 minute period resulting in an amber solution. Stirring was continued at −78° C. for 10 minutes and the reaction was warmed up to 0° C. resulting in a pale yellow solution. The mixture was stirred for 40 minutes, saturated aqueous NH$_4$Cl was added and the mixture was warmed to room temperature. Water was added and layers were separated. The aqueous layer was extracted with EtOAc. The combined organic extracts was dried over Na$_2$SO$_4$, filtered, evaporated in vacuo and the resulting crude mixture chromatographed (DCM/5% MeOH in EtOAc, gradient) to provide the title compounds as a mixture. Further purification by reverse phase HPLC yielded the above title compound (3-(4-(1H-pyrazol-1-yl)benzyl)-4-chloro-8-fluoro-2-methoxyquinolin-6-yl)(1-methyl-1H-imidazol-5-yl)(6-(trifluoromethyl)pyridin-3-yl)methanol. $^1$H NMR (400 MHz, CDCl$_3$) δ ppm 8.81 (s, 1H), 7.79-7.96 (m, 3H), 7.62-7.74 (m, 2H), 7.56 (d, J=8.6 Hz, 2H), 7.35 (d, J=8.6 Hz, 4H), 6.26-6.57 (m, 2H), 4.31 (s, 2H), 4.00-4.22 (m, 3H), 3.36 (s, 3H); MS (ESI), 623.2. (3-(4-(1H-pyrazol-1-yl)benzyl)-4-chloro-8-fluoro-2-methoxyquinolin-6-yl)(1-methyl-1H-imidazol-5-yl)(6-(trifluoromethyl)pyridin-3-yl)methanol was purified by HPLC (Diacel OD column, 0.2% isopropylamine in acetonitrile, 80 mL/minute, 254 nm wavelength) to give two enantiomers. The first eluting enantiomer was Example 58B: $^1$H NMR (400 MHz, CDCl$_3$) δ ppm 8.71-8.90 (m, 1H), 7.81-8.00 (m, 4H), 7.60-7.73 (m, 2H), 7.56 (d, J=8.6 Hz, 3H), 7.35 (d, J=8.1 Hz, 3H), 6.24-6.52 (m, 1H), 4.31 (s, 2H), 4.13 (s, 3H), 3.39 (s, 3H). 623.2 mass calcd. C$_{31}$H$_{23}$ClF$_4$N$_6$O$_2$, 623.0; m/z found, 623.1 and the second eluting enantiomer was Example 58C: $^1$H NMR (400 MHz, CDCl$_3$) δ ppm 8.83 (br. s., 1H), 7.86 (d, J=2.5 Hz, 4H), 7.69 (s, 2H), 7.48-7.63 (m, 3H), 7.35 (d, J=8.1 Hz, 3H), 6.43 (s, 1H), 4.32 (s, 2H), 4.13 (s, 3H), 3.42 (br. s., 3H) mass calcd. C$_{31}$H$_{23}$ClF$_4$N$_6$O$_2$, 623.0; m/z found, 623.2.

Example 59A (3-(4-(1H-Pyrazol-1-yl)benzyl)-4-chloro-2,8-dimethoxyquinolin-6-yl)(1-methyl-1H-imidazol-5-yl)(6-(trifluoromethyl)pyridin-3-yl)methanol

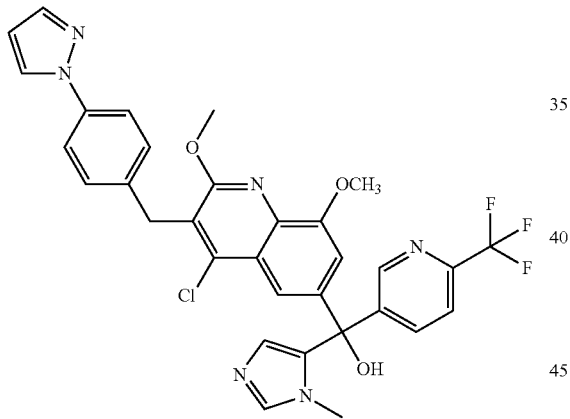

n-BuLi (1.6 M in hexanes, 1.45 mL) was added to a mixture of 3-(4-(1H-pyrazol-1-yl)benzyl)-6-bromo-4-chloro-8-fluoro-2-methoxyquinoline and 3-(4-(1H-pyrazol-1-yl)benzyl)-6-bromo-4-chloro-2,8-dimethoxyquinoline (0.82 g, 1.781 mmol, Intermediate 41: step b) and (1-methyl-1H-imidazol-5-yl)(6-(trifluoromethyl)pyridin-3-yl)methanone (0.5 g, 1.96 mmol, Intermediate 36: step c) in dry THF 20 mL) at −78° C. over a 2 minute period resulting in an amber solution. Stirring was continued at −78° C. for 10 minutes and the reaction was warmed up to 0° C. resulting in a pale yellow solution. The mixture was stirred for 40 minutes, saturated aqueous NH$_4$Cl was added and the mixture was warmed to room temperature. Water was added and layers were separated. The aqueous layer was extracted with EtOAc. The combined organic extracts was dried over Na$_2$SO$_4$, filtered, evaporated in vacuo and the resulting crude mixture chromatographed (DCM/5% MeOH in EtOAc, gradient) to provide the title compounds as a mixture. Further purification by reverse phase HPLC yielded the above title compound (3-(4-(1H-pyrazol-1-yl)benzyl)-4-chloro-2,8-dimethoxyquinolin-6-yl)(1-methyl-1H-imidazol-5-yl)(6-(trifluoromethyl)pyridin-3-yl)methanol. $^1$H NMR (400 MHz, CDCl$_3$) δ ppm 8.84 (d, J=2.0 Hz, 1H), 7.80-7.98 (m, 2H), 7.58-7.72 (m, 3H), 7.55 (d, J=8.6 Hz, 2H), 7.33 (d, J=8.6 Hz, 3H), 7.05 (s, 1H), 6.42 (s, 2H), 4.31 (s, 2H), 4.04-4.20 (m, 3H), 3.95 (s, 3H), 3.37 (s, 3H); MS (ESI) 635.2

(3-(4-(1H-pyrazol-1-yl)benzyl)-4-chloro-2,8-dimethoxyquinolin-6-yl)(1-methyl-1H-imidazol-5-yl)(6-(trifluoromethyl)pyridin-3-yl)methanol was purified by chiral HPLC (Diacel OD column, 0.2% isopropylamine in acetonitrile, 80 mL/minute, 254 nm wavelength) to give two enantiomers. Each enantiomer was converted to the succinate salt by addition of succinic acid (1 equivalent) to a suspension of the free base in dry THF. The resulting homogeneous mixture was stirred for 15 minutes and the solvent was removed under reduced pressure to provide the salt as an amorphous solid. The first eluting enantiomer was Example 59B: $^1$H NMR (400 MHz, DMSO-d$_6$) δ ppm 12.21 (br. s., 2H), 8.80 (s, 1H), 8.40 (d, J=2.5 Hz, 1H), 7.80-8.04 (m, 2H), 7.63-7.80 (m, 3H), 7.10-7.58 (m, 5H), 6.50 (s, 1H), 6.26 (s, 1H), 4.26 (s, 2H), 3.94-4.09 (m, 3H), 3.74-3.94 (m, 3H), 3.10-3.44 (m, 3H), 2.41 (m, 4H). mass calcd. C$_{32}$H$_{26}$ClF$_3$N$_6$O$_3$. C$_4$H$_6$O$_4$, 635.04/753.13; m/z found, 635.2 and the second eluting enantiomer was Example 59C: $^1$H NMR (400 MHz, DMSO-d$_6$) δ ppm 12.10-12.38 (broad s, 1H), 8.69-8.87 (m, 1H), 8.34-8.47 (m, 1H), 7.84-8.01 (m, 2H), 7.65-7.79 (m, 3H), 7.43-7.53 (m, 1H), 7.38 (s, 1H), 7.33 (s, 2H), 7.12-7.24 (m, 1H), 6.42-6.58 (m, 1H), 6.18-6.33 (m, 1H), 4.26 (s, 2H), 4.03 (s, 3H), 3.88 (s, 3H), 3.34 (d, J=9.6 Hz, 3H), 2.41 (m, 4H) mass calcd. C$_{32}$H$_{26}$ClF$_3$N$_6$O$_3$. C$_4$H$_6$O$_4$, 635.04/753.13; m/z found, 635.2.

Example 60A 1-(4-((3-(4-(1H-Pyrazol-1-yl)benzyl)-4-chloro-2-methoxyquinolin-6-yl)(hydroxy)(1-methyl-1H-imidazol-5-yl)methyl)piperidin-1-yl)ethanone

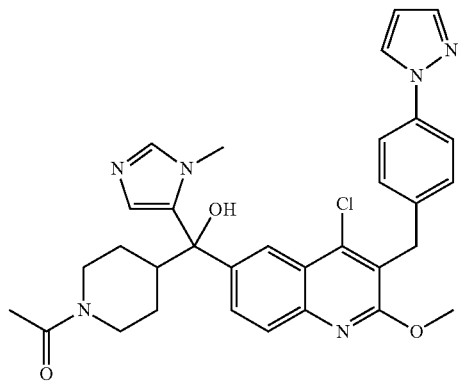 [SMILES: COc1nc2ccc(C(O)(c3cncn3C)C3CCN(C(C)=O)CC3)cc2c(Cl)c1Cc1ccc(-n2cccn2)cc1]

A solution of 3-(4-(1H-pyrazol-1-yl)benzyl)-6-bromo-4-chloro-2-methoxyquinoline (0.558 g, 1.30 mmol; Intermediate 16) in THF (13 mL) was stirred under argon at ~−70° C. while n-BuLi (2.56 M in hexanes, 0.484 mL, 1.24 mmol) was added dropwise over 1.5 minutes. After another 2.5 minutes, a solution of 1-(4-(1-methyl-1H-imidazole-5-carbonyl)piperidin-1-yl)ethanone (0.322 g, 1.37 mmol, Intermediate 42: step c) in THF (4.5 mL) was added dropwise over 2.5 minutes, and the dark mixture was stirred in the cold bath for another 5 minutes. The dry ice/acetone bath was then removed and the reaction stirred for 5 minutes under ambient conditions before transferring to an ice bath. After stirring for 2.5 hours at ~0° C., the reaction was quenched with 5 M aqueous NH₄Cl (2 mL) and the organic layer was dried (Na₂SO₄), filtered, and concentrated. The residue was flash chromatographed with a DCM to 10% MeOH/DCM gradient to provide the title compound as a light yellow foam. ¹H NMR (400 MHz, CDCl₃) (two conformers) δ ppm 8.17 (br. s, ~0.5H), 8.12 (br. s, ~0.5H), 7.85 (d, J=2.53 Hz, 1H), 7.76 (dd, J=2.78, 8.84 Hz, 1H), 7.67 (s, 1H), 7.57 (d, J=8.59 Hz, 2H), 7.44-7.36 (m, 3H), 7.21 (d, J=5.05 Hz, 1H), 7.10 (s, 1H), 6.43 (d, J=2.02 Hz, 1H), 4.71 (d, J=13.14 Hz, ~0.5H), 4.47-4.61 (m, ~0.5H), 4.32 (s, 2H), 4.08 (s, 3H), 3.89 (d, J=13.41 Hz, ~0.5H), 3.69 (d, J=13.14 Hz, ~0.5H), 3.25 (s, ~1.5H), 3.21 (s, ~1.5H), 3.10-3.18 (m, ~0.5H), 2.87-3.00 (m, ~0.5H), 2.60 (t, J=12.13 Hz, ~0.5H), 2.35-2.51 (m, ~1.5H), 2.29 (d, J=13.40 Hz, ~0.5H), 2.21 (d, J=13.14 Hz, ~0.5H), 2.00 (s, ~1.5H), 1.95 (s, ~1.5H), 1.10-1.46 (m, 3H). MS m/e 585.3 [M+H]⁺.

Example 60A was purified by chiral HPLC (Chiralpak OD, 100% EtOH) to give 2 enantiomers. To convert the enantiomers to their succinate salts, they were dissolved in CH₃CN, treated with 1.0 equivalent of 0.1 M succinic acid in 95:5 v/v CH₃CN/water to provide homogeneous solutions, frozen (with water added as necessary to ensure complete freezing), and lyophilized. The first eluting enantiomer was Example 60B.succinic acid: ¹H NMR (400 MHz, MeOH-d₄) (two conformers) δ ppm 8.22 (d, J=5.56 Hz, 1H), 8.13 (d, J=2.53 Hz, 1H), 7.79 (d, J=9.09 Hz, 1H), 7.68 (d, J=2.02 Hz, 1H), 7.56-7.63 (m, 3H), 7.51 (d, J=9.09 Hz, 1H), 7.32-7.40 (m, 3H), 6.49 (m, 1H), 4.62 (d, J=12.6 Hz, ~0.5H), 4.43 (d, J=12.6 Hz, ~0.5H), 4.35 (s, 2H), 4.07 (s, 3H), 4.01 (d, J=13.4 Hz, ~0.5H), 3.81 (d, J=13.4 Hz, ~0.5H), 3.33 (s, ~1.5H), 3.32 (s, ~1.5H), 3.25 (m, ~0.5H), 3.01 (td, J=13.14, 2.78 Hz, ~0.5H), 2.74 (m, ~0.5H), 2.45-2.64 (m, ~1.5H), 2.55 (s, 4H), 2.26 (m, 1H), 2.06 (s, ~1.5H), 2.00 (s, ~1.5H), 1.09-1.56 (m, 3H); MS m/e 584.8 [M+H]⁺ and the second eluting enantiomer was Example 60C.succinic acid: ¹H NMR (400 MHz, MeOH-d₄) (two conformers) δ ppm 8.22 (d, J=6.06 Hz, 1H), 8.12 (s, 1H), 7.78 (d, J=8.59 Hz, 1H), 7.67 (d, J=2.02 Hz, 1H), 7.64 (m, 1H), 7.56-7.61 (m, 2H), 7.50 (d, J=9.09 Hz, 1H), 7.33-7.39 (m, 3H), 6.48 (m, 1H), 4.62 (d, J=13.14 Hz, ~0.5H), 4.43 (d, J=13.0 Hz, ~0.5H), 4.32 (s, 2H), 4.06 (s, 3H), 4.00 (d, J=13.64 Hz, ~0.5H), 3.79 (d, J=13.64 Hz, ~0.5H), 3.34 (s, ~1.5H), 3.33 (s, ~1.5H), 3.25 (m, ~0.5H), 2.99 (td, J=2.53, 13.14 Hz, ~0.5H), 2.73 (m, ~0.5H), 2.44-2.64 (m, ~1.5H), 2.56 (s, 4H), 2.25 (m, 1H), 2.05 (s, ~1.5H), 1.99 (s, ~1.5H), 1.08-1.57 (m, 3H); MS m/e 585.3 [M+H]⁺.

Example 61

(3-(4-(1H-Pyrazol-1-yl)benzyl)-4-chloro-2-methoxyquinolin-6-yl)bis(1-methyl-1H-1,2,3-triazol-5-yl)methanol

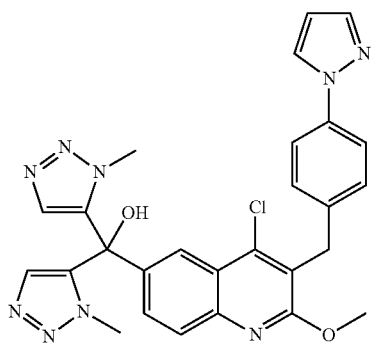 [SMILES: COc1nc2ccc(C(O)(c3cnnn3C)c3cnnn3C)cc2c(Cl)c1Cc1ccc(-n2cccn2)cc1]

A solution of 3-(4-(1H-pyrazol-1-yl)benzyl)-6-bromo-4-chloro-2-methoxyquinoline (0.271 g, 0.632 mmol; Intermediate 16) in THF (6 mL) was stirred under argon at ~-70° C. while n-BuLi (1.63 M in hexanes, 0.368 mL, 0.6 mmol) was added dropwise by syringe over 1 minute. After another 2 minutes, a solution of bis(1-methyl-1H-1,2,3-triazol-5-yl)methanone (0.128 g, 0.664 mmol; Intermediate 43) in THF (6 mL) was added dropwise over 2 minutes, and the reaction was allowed to warm to room temperature overnight as the dry ice/acetone bath slowly warmed (11 hours). The resulting yellow mixture was quenched in one portion at 0° C. with 5 M aqueous NH₄Cl (1 mL), and the organic layer was dried (Na₂SO₄), filtered, and concentrated. The residue was dry load flash chromatographed with a DCM to 100% EtOAc gradient to yield the impure title compound. This was then triturated from ~0.5 mL DMSO+~2 mL MeOH at 70° C., and the opaque milky mixture was allowed to cool to room temperature, filtered, and the white filter cake washed with MeOH (2×2 mL). The filter cake was air dried at 110° C. to provide the title compound as a white powder. ¹H NMR (400 MHz, DMSO-d₆) δ ppm 8.41 (d, J=2.53 Hz, 1H), 8.16 (d, J=2.02 Hz, 1H), 7.96 (s, 1H), 7.90 (d, J=8.59 Hz, 1H), 7.74 (s, 1H), 7.71 (d, J=4.55 Hz, 2H), 7.46 (dd, J=2.27, 8.84 Hz, 1H), 7.36 (d, J=8.59 Hz, 2H), 7.19 (s, 2H), 6.51 (s, 1H), 4.30 (s, 2H), 4.06 (s, 3H), 3.84 (s, 6H); MS m/e 542.3 [M+H]⁺.

Example 62A (4-Chloro-2-methoxy-3-(4-(trifluoromethyl)benzyl)quinolin-6-yl)(1-methyl-1H-imidazol-5-yl)(6-(trifluoromethyl)pyridin-3-yl)methanol

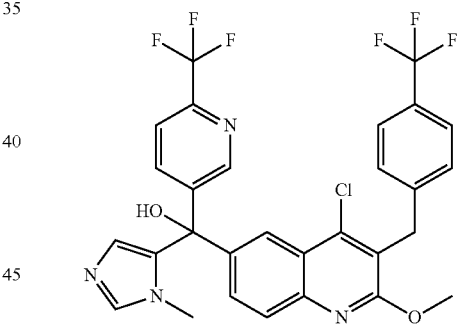

A solution of n-BuLi (2.5 M in hexanes, 1.85 mL, 4.62 mmol) was added dropwise by syringe to a solution of 6-bromo-4-chloro-2-methoxy-3-(4-(trifluoromethyl)benzyl)quinoline (2.00 g, 4.65 mmol, Intermediate 47: step d) in dry THF (30 mL) in a dry ice-acetone bath. After 1.5 minutes, a solution of (1-methyl-1H-imidazol-5-yl)(6-(trifluoromethyl)pyridin-3-yl)methanone (1.26 g, 4.92 mmol, Intermediate 36: step c) in dry THF (5 mL) was added dropwise. The reaction mixture was stirred for 2 minutes in a dry ice-acetone bath, then the reaction flask was placed into an ice-water bath. After 10 minutes, the mixture was warmed to room temperature and the reaction was quenched with saturated ammonium chloride. The mixture was partitioned between water and DCM. The separated aqueous phase was further extracted with DCM. The organic phase was dried (Na₂SO₄), filtered, and concentrated to provide the title compound as crude white solid. MS m/e 607.2 [M+H]⁺ Example 62A was purified by chiral HPLC (ChiralPak AD, 50:50 methanol/ethanol) to provide two enantiomers, Example 62B and Example 62C. The first eluting enantiomer was Example 62B: ¹H NMR (500 MHz, CDCl₃) δ ppm 8.80 (d, J=1.8 Hz, 1H), 8.19 (d, J=2.0 Hz, 1H), 7.94 (s, 1H), 7.85 (dd, J=8.2, 1.9 Hz, 1H), 7.79 (d, J=8.5 Hz, 1H), 7.61 (d, J=8.5 Hz, 1H), 7.52 (dd, J=8.8, 2.1 Hz, 1H), 7.47 (d, J=8.2 Hz, 2H), 7.36 (d, J=8.1 Hz, 2H), 7.05 (s, 1H), 6.15 (s, 1H), 4.30 (s, 2H), 4.07 (s, 3H), 3.29 (s, 3H); MS m/e 607.2 [M+H]⁺ and the second eluting enantiomer was Example 62C: ¹H NMR (500 MHz, CDCl₃) δ ppm 8.80 (d, J=1.7 Hz, 1H), 8.19 (d, J=2.0 Hz, 1H), 7.99 (s, 1H), 7.86 (dd, J=8.2, 1.8 Hz, 1H), 7.79 (d, J=8.8 Hz, 1H), 7.61 (d, J=8.3 Hz, 1H), 7.53 (dd, J=8.8, 2.1 Hz, 1H), 7.47 (d, J=8.2 Hz, 2H), 7.37 (d, J=8.1 Hz, 2H), 7.06 (s, 1H), 6.16 (s, 1H), 4.30 (s, 2H), 4.07 (s, 3H), 3.30 (s, 3H); MS m/e 607.2 [M+H]⁺.

Example 63A 4-((4-Chloro-6-((4-chlorophenyl)(hydroxy)(1-methyl-1H-imidazol-5-yl)methyl)-2-methoxyquinolin-3-yl)methyl)benzonitrile.TFA

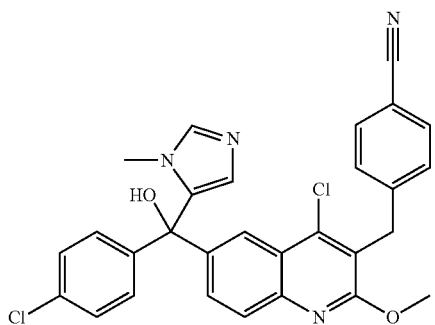 [SMILES: COc1nc2ccc(C(O)(c3ccc(Cl)cc3)c3cncn3C)cc2c(Cl)c1Cc1ccc(C#N)cc1]

A solution of n-BuLi (1.6 M solution in hexanes, 0.32 mL, 0.80 mmol) was added dropwise via syringe to a solution of 4-((6-bromo-4-chloro-2-methoxyquinolin-3-yl)methyl)benzonitrile (310. mg, 0.800 mmol, Intermediate 44: step d) and (4-chlorophenyl)(1-methyl-1H-imidazol-5-yl)methanone (196 mg, 0.800 mmol, Intermediate 1, step b) in dry THF (8 mL) at −78° C. The reaction mixture was stirred for 30 minutes at −78° C. and allowed to warm to room temperature overnight. The reaction was quenched using saturated aqueous NH₄Cl solution, followed by addition of DCM. The layers were separated, organics were dried (MgSO₄), filtered, and concentrated. Reverse phase HPLC was used for purification resulting in the isolation of the title compound as the TFA salt. ¹H NMR (500 MHz, CDCl₃) δ ppm 8.37 (s, 1H), 8.02 (d, J=2.1 Hz, 1H), 7.86 (d, J=8.7 Hz, 1H), 7.55-7.50 (m, 3H), 7.39-7.36 (m, 4H), 7.37 (dd, J=8.5, 3.4 Hz, 4H), 7.29-7.27 (m, 2H), 6.63 (s, 1H), 4.34 (s, 2H), 4.08 (s, 3H), 3.61 (s, 3H); MS m/e 529.2 [M+H]⁺. Example 63A was purified by chiral HPLC (ChiralPak AD, 50:50 methanol/ethanol) to provide two enantiomers. The first eluting enantiomer was Example 63B: ¹H NMR (400 MHz, CDCl₃) δ ppm 8.09 (s, 1H), 8.06-8.04 (m, 1H), 7.84 (d, J=8.8 Hz, 1H), 7.56-7.51 (m, 3H), 7.37 (d, J=9.2 Hz, 4H), 7.29 (d, J=8.8 Hz, 2H), 6.57 (s, 1H), 4.34 (s, 2H), 4.08 (s, 3H), 3.55 (s, 3H); MS m/e 529.2 [M+H]⁺ and the second eluting enantiomer was Example 63C: ¹H NMR (400 MHz, MeOH-d₄) δ ppm 8.11 (d, J=1.9 Hz, 1H), 7.90 (s, 1H), 7.84 (d, J=8.8 Hz, 1H), 7.66 (dd, J=8.8, 2.1 Hz, 1H), 7.61 (d, J=8.3 Hz, 2H), 7.43-7.35 (m, 6H), 6.37 (s, 1H), 4.38 (s, 2H), 4.05 (s, 3H), 3.50 (s, 3H); MS m/e 529.1 [M+H]⁺.

Example 64A (3-(4-(1H-1,2,4-Triazol-1-yl)benzyl)-4-chloro-2-methoxyquinolin-6-yl)(4-chlorophenyl)(1-methyl-1H-imidazol-5-yl)methanol

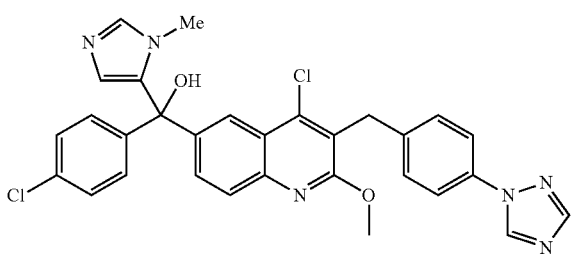 [SMILES: COc1nc2ccc(C(O)(c3ccc(Cl)cc3)c3cncn3C)cc2c(Cl)c1Cc1ccc(-n2cncn2)cc1]

Isopropylmagnesium chloride lithium chloride complex (1.3 M in tetrahydrofuran, 2.0 mL, 2.60 mmol) was added to an ice-water cooled solution of 5-bromo-1-methyl-1H-imidazole (444 mg, 2.76 mmol) in tetrahydrofuran (12 mL). The resulting white suspension was stirred for 5 minutes then the cooling bath was removed. After 10 minutes, the suspension was added dropwise by syringe to an ice-water cooled mixture of (3-(4-(1H-1,2,4-triazol-1-yl)benzyl)-4-chloro-2-methoxyquinolin-6-yl)(4-chlorophenyl)methanone (772 mg, 1.59 mmol, Intermediate 45, step e) and lanthanum(III) chloride bis(lithium chloride) complex solution (0.6 M in tetrahydrofuran, 5.25 mL, 3.16 mmol) in tetrahydrofuran (15 mL). After 20 minutes, saturated aqueous ammonium chloride solution was added (2 mL) then the cooling bath was removed. The mixture was diluted with water (25 mL) and ethyl acetate (50 mL). The layers were separated. The aqueous layer was extracted with ethyl acetate (25 mL). The organic layers were combined and the combined solution was dried with sodium sulfate. The dried solution was filtered and the filtrate was absorbed onto 6 g of silica gel for dry-load flash-column chromatography on silica gel eluting with 100% dichloromethane initially for 5 minutes, grading to 7% methanol-dichloromethane over 30 minutes to afford the titled compound as a white solid. ¹H NMR (400 MHz, CDCl₃) δ ppm 8.43 (s, 1H), 8.12 (d, J=2.1 Hz, 1H), 8.06 (s, 1H), 7.79 (d, J=8.8 Hz, 1H), 7.58-7.50 (m, 3H), 7.41 (d, J=8.5 Hz, 2H), 7.36 (d, J=1.1 Hz, 1H), 7.31 (s, 4H), 6.38 (d, J=1.1 Hz, 1H), 4.33 (s, 2H), 4.12 (s, 1H), 4.08 (s, 3H), 3.38 (s, 3H); MS m/e 571.1 [M+H]⁺. (3-(4-(1H-1,2,4-triazol-1-yl)benzyl)-4-chloro-2-methoxyquinolin-6-yl)(4-chlorophenyl)(1-methyl-1H-imidazol-5-yl)methanol was purified by HPLC (Chiralpak IA column, 50 mm×250 mm, ethanol with 0.2% triethylamine as eluent, 30 mL/minute, 254 nm wavelength) to give two enantiomers. The first eluting enantiomer was Example 64B: ¹H NMR (400 MHz, CDCl₃) δ ppm 8.43 (s, 1H), 8.12 (d, J=2.1 Hz, 1H), 8.06 (s, 1H), 7.78 (d, J=8.7 Hz, 1H), 7.56-7.50 (m, 3H), 7.41 (d, J=8.5 Hz, 2H), 7.36 (d, J=1.1 Hz, 1H), 7.31 (s, 4H), 6.38 (d, J=1.1 Hz, 1H), 4.33 (s, 2H), 4.08 (s, 3H), 3.38 (s, 3H); MS m/e 571.1 [M+H]+ and the second eluting enantiomer was Example 64C: ¹H NMR (400 MHz, CDCl₃) δ ppm 8.43 (s, 1H), 8.12 (d, J=2.1 Hz, 1H), 8.06 (s, 1H), 7.78 (d, J=8.7 Hz, 1H), 7.58-7.49 (m, 3H), 7.41 (d, J=8.6 Hz, 2H), 7.35 (s, 1H), 7.31 (s, 4H), 6.38 (s, 1H), 4.33 (s, 2H), 4.21 (s, 1H), 4.08 (s, 3H), 3.38 (s, 3H); MS m/e 571.1 [M+H]+.

Example 65A 3-(4-(1H-Pyrazol-1-yl)benzyl)-6-(hydroxy(1-methyl-1H-imidazol-5-yl)(6-(trifluoromethyl)pyridin-3-yl)methyl)-8-methylquinoline-2,4-dicarbonitrile

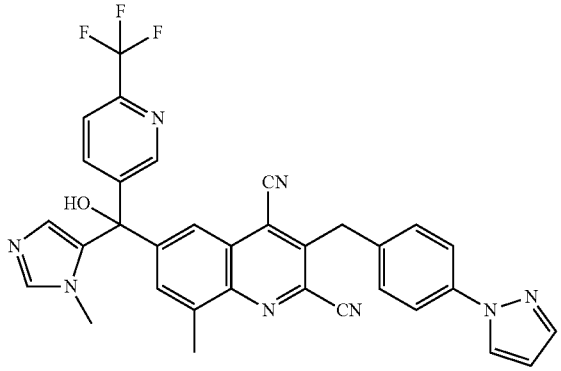 [SMILES: Cc1cc(C(O)(c2ccc(C(F)(F)F)nc2)c2cncn2C)cc2c(C#N)c(Cc3ccc(-n4cccn4)cc3)c(C#N)nc12]

A microwave vial was charged with (3-(4-(1H-pyrazol-1-yl)benzyl)-2,4-dichloro-8-methylquinolin-6-yl)(1-methyl-1H-imidazol-5-yl)(6-(trifluoromethyl)pyridin-3-yl)methanol (310 mg, 0.497 mmol, Example 84), $Zn(CN)_2$ (75.9 mg, 0.646 mmol), $Pd_2dba_3$ (46.6 mg, 0.0510 mmol), zinc dust (6.52 mg, 0.0990 mmol), and dicyclohexyl(2',4',6'-triisopropyl-[1,1'-biphenyl]-2-yl)phosphine (X-Phos, 24.5 mg, 0.0500 mmol). Dimethylacetamide (2.6 mL) was then added and the mixture was purged with nitrogen for 5 minutes and placed into a pre-heated aluminum block at 120° C. for 1.5 hours. The mixture was cooled to room temperature and was filtered through Celite®, and washed with EtOAc and the solvents were removed under reduced pressure. LCMS analysis indicated incomplete conversion, so additional portions of $Zn(CN)_2$, $Pd_2dba_3$, zinc dust, X-Phos, and DMA (amounts as above) were added, nitrogen was bubbled through the mixture for 5 minutes, and the mixture was heated at 120° C. for 4 hours. The mixture was cooled to room temperature and was filtered through Celite®, and washed with EtOAc. Attempted isolation by flash column chromatography (5% MeOH in dichloromethane) yielded an impure mixture. Further purification by RP-HPLC (1 to 99% acetonitrile/water/0.05% TFA), and then conversion to the free base (neutralized with saturated aqueous $NaHCO_3$ and extracted with ethyl acetate) and the organic fractions were concentrated to afford the title compound. MS (ESI) 605.3.

3-(4-(1H-pyrazol-1-yl)benzyl)-6-(hydroxy(1-methyl-1H-imidazol-5-yl)(6-(trifluoromethyl)pyridin-3-yl)methyl)-8-methylquinoline-2,4-dicarbonitrile was purified by chiral HPLC (Chiralcel OD, 100% ethanol) to give 2 enantiomers. The first eluting enantiomer was Example 65B: $^1$H NMR (600 MHz, $CDCl_3$) δ ppm 8.79 (s, 1H), 8.24 (s, 1H), 7.96 (d, J=8.7 Hz, 1H), 7.88 (d, J=2.4 Hz, 1H), 7.73-7.58 (m, 5H), 7.49 (d, J=8.4 Hz, 2H), 7.41 (s, 1H), 6.52-6.38 (m, 2H), 4.63 (s, 2H), 3.40 (s, 3H), 2.76 (s, 3H); MS m/e 605.2 [M+H]$^+$ and the second eluting enantiomer was Example 65C: $^1$H NMR (400 MHz, $CDCl_3$) δ ppm 8.80 (s, 1H), 8.24 (s, 1H), 7.96 (d, J=8.5 Hz, 1H), 7.88 (d, J=2.3 Hz, 1H), 7.75-7.58 (m, 5H), 7.49 (d, J=8.3 Hz, 3H), 6.50 (br s, 1H), 6.45 (br s, 1H), 4.64 (s, 2H), 3.41 (s, 3H), 2.76 (s, 3H); MS m/e 605.2 [M+H]$^+$.

Example 66A 3-(4-(1H-Pyrazol-1-yl)benzyl)-6-((4-cyanophenyl)(hydroxy)(1-methyl-1H-imidazol-5-yl)methyl)-8-methylquinoline-2,4-dicarbonitrile

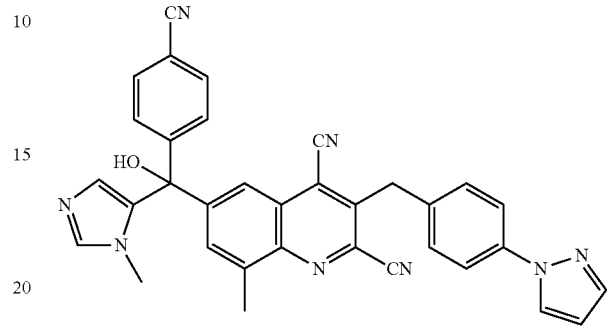

A microwave vial was charged with (3-(4-(1H-pyrazol-1-yl)benzyl)-2,4-dichloro-8-methylquinolin-6-yl)(4-chlorophenyl)(1-methyl-1H-imidazol-5-yl)methanol (240 mg, 0.408 mmol, Example 85), $Zn(CN)_2$ (62.2 mg, 0.530 mmol), $Pd_2dba_3$ (38.2 mg, 0.0420 mmol), zinc dust (5.34 mg, 0.0820 mmol), and dicyclohexyl(2',4',6'-triisopropyl-[1,1'-biphenyl]-2-yl)phosphine (X-Phos, 20.1 mg, 0.0410 mmol). Dimethylacetamide (2.1 mL) was then added and the mixture was purged with nitrogen for 10 minutes and placed in a pre-heated aluminum block at 120° C. for 1.5 hours. The mixture was cooled to room temperature and was filtered through Celite®, and washed with EtOAc. LCMS analysis indicated incomplete conversion, so additional portions of $Zn(CN)_2$, $Pd_2dba_3$, zinc dust, X-Phos, and DMA (amounts as above) were added, nitrogen was bubbled through the mixture for 5 minutes, and the mixture was again heated at 120° C. for 4 hours. The mixture was cooled to room temperature and was filtered through Celite®, and washed with EtOAc. Attempted isolation by flash column chromatography (5% MeOH in dichloromethane) yielded an impure mixture. Further purification by RP-HPLC (1 to 99% Acetonitrile/water/0.05% TFA) followed by conversion to the free base (neutralized with saturated aqueous $NaHCO_3$ and extracted with ethyl acetate) and the organic fractions were concentrated to afford the title compound. MS (ESI) 561.3.

3-(4-(1H-pyrazol-1-yl)benzyl)-6-((4-cyanophenyl)(hydroxy)(1-methyl-1H-imidazol-5-yl)methyl)-8-methylquinoline-2,4-dicarbonitrile was purified by chiral HPLC (Chiralcel OD, 50% ethanol/50% methanol) to give 2 enantiomers. The first eluting enantiomer was Example 66B: $^1$H NMR (500 MHz, $CDCl_3$) δ ppm 8.19 (d, J=1.5 Hz, 1H), 7.88 (d, J=2.5 Hz, 1H), 7.66 (dd, J=11.6, 8.6 Hz, 5H), 7.60 (s, 1H), 7.56 (d, J=8.5 Hz, 2H), 7.48 (d, J=8.6 Hz, 2H), 7.32 (s, 1H), 6.45 (t, J=2.1 Hz, 1H), 6.40 (s, 1H), 4.62 (s, 2H), 3.36 (s, 3H), 2.74 (s, 3H); MS m/e 561.3 [M+H]$^+$ and the second eluting enantiomer was Example 66C $^1$H NMR (600 MHz, $CDCl_3$) δ ppm 8.19 (d, J=1.6 Hz, 1H), 7.88 (d, J=2.2 Hz, 1H), 7.70-7.63 (m, 5H), 7.61 (s, 1H), 7.56 (d, J=8.6 Hz, 2H), 7.49 (d, J=8.7 Hz, 2H), 7.37 (s, 1H), 6.48-6.40 (m, 2H), 4.63 (s, 2H), 3.37 (s, 3H), 2.75 (s, 3H); MS m/e 561.3 [M+H]$^+$.

Example 67A (3-(4-(1H-Pyrazol-1-yl)benzyl)-4-chloro-2-(methoxy(methyl)amino)quinolin-6-yl)(1-methyl-1H-imidazol-5-yl)(6-(trifluoromethyl)pyridin-3-yl)methanol TFA?

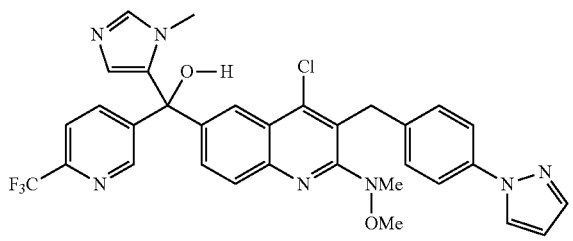 [SMILES: CON(C)c1nc2ccc(C(O)(c3ccc(C(F)(F)F)nc3)c3cncn3C)cc2c(Cl)c1Cc1ccc(-n2cccn2)cc1]

To a 5 mL sealed tube was added (3-(4-(1H-pyrazol-1-yl)benzyl)-2,4-dichloroquinolin-6-yl)(1-methyl-1H-imidazol-5-yl)(6-(trifluoromethyl)pyridin-3-yl)methanol (250 mg, 0.41 mmol, 1 equivalent, Example 23, free base), N,O-dimethylhydroxylamine hydrochloride (327 mg, 3.28 mmol, 10 equivalents) and dimethylformamide (2 mL). The reaction vessel was sealed and heated in a 100° C. oil bath. After overnight reaction, the vessel was cooled and contents transferred to a separatory funnel with ethyl acetate dilution. The organic phase was extracted with saturated, aqueous ammonium chloride solution and deionized water. The organic phase was separated, dried over magnesium sulfate, filtered and evaporated to dryness under reduced pressure. The crude material was purified via reverse phase chromatography using acetonitrile with 0.05% trifluoroacetic acid in water as eluent to provide racemic (3-(4-(1H-pyrazol-1-yl)benzyl)-4-chloro-2-(methoxy(methyl)amino)quinolin-6-yl)(1-methyl-1H-imidazol-5-yl)(6-(trifluoromethyl)pyridin-3-yl)methanol; MS (ESI): mass calcd. for $C_{32}H_{27}ClF_3N_7O_2$, 633.19; m/z found, 634.3 [M+H]$^+$. $^1$H NMR (600 MHz, MeOH-d$_4$) δ ppm 8.79 (d, J=2.1 Hz, 1H), 8.22 (d, J=2.0 Hz, 1H), 8.13-8.10 (m, 1H), 8.02 (dd, J=8.3, 2.1 Hz, 1H), 7.99 (d, J=8.8 Hz, 1H), 7.82 (d, J=8.3 Hz, 1H), 7.79 (s, 1H), 7.72 (dd, J=8.8, 2.1 Hz, 1H), 7.67 (d, J=1.7 Hz, 1H), 7.59-7.56 (m, 2H), 7.24 (d, J=8.7 Hz, 2H), 6.50-6.45 (m, 1H), 6.39 (s, 1H), 4.42 (s, 2H), 3.49 (s, 3H), 3.45 (s, 3H), 3.16 (s, 3H). Racemic (3-(4-(1H-pyrazol-1-yl)benzyl)-4-chloro-2-(methoxy(methyl)amino)quinolin-6-yl)(1-methyl-1H-imidazol-5-yl)(6-(trifluoromethyl)pyridin-3-yl)methanol was purified on a chiralcel OD column (20 um, Diacel) with ethanol/heptanes to provide two enantiomers. The first eluting enantiomer was Example 67B: MS (ESI): mass calcd. for $C_{32}H_{27}ClF_3N_7O_2$, 633.19; m/z found, 634.3 [M+H]$^+$. $^1$H NMR (600 MHz, MeOH-d$_4$) δ ppm 8.80 (d, J=2.0 Hz, 1H), 8.23 (d, J=1.9 Hz, 1H), 8.10 (dd, J=2.5, 0.4 Hz, 1H), 8.01 (dd, J=8.2, 2.0 Hz, 1H), 7.98 (d, J=8.9 Hz, 1H), 7.81 (d, J=8.2 Hz, 1H), 7.73 (s, 1H), 7.71 (dd, J=8.8, 2.1 Hz, 1H), 7.66 (d, J=1.4 Hz, 1H), 7.59-7.54 (m, 2H), 7.25-7.20 (m, 2H), 6.46 (dd, J=2.4, 1.9 Hz, 1H), 6.37 (s, 1H), 4.39 (s, 2H), 3.47 (s, 3H), 3.44 (s, 3H), 3.16 (s, 3H) and the second eluting enantiomer was Example 67C: MS (ESI): mass calcd. for $C_{32}H_{27}ClF_3N_7O_2$, 633.19; m/z found, 634.3 [M+H]$^+$. $^1$H NMR (600 MHz, MeOH-d$_4$) δ ppm 8.80 (d, J=2.0 Hz, 1H), 8.23 (d, J=2.0 Hz, 1H), 8.12-8.09 (m, 1H), 8.01 (dd, J=8.2, 2.1 Hz, 1H), 7.98 (d, J=8.8 Hz, 1H), 7.81 (d, J=8.2 Hz, 1H), 7.73 (s, 1H), 7.71 (dd, J=8.8, 2.1 Hz, 1H), 7.67 (d, J=1.5 Hz, 1H), 7.59-7.54 (m, 2H), 7.25-7.20 (m, 2H), 6.47 (dd, J=2.4, 1.9 Hz, 1H), 6.37 (s, 1H), 4.40 (s, 2H), 3.47 (s, 3H), 3.44 (s, 3H), 3.16 (s, 3H).

Example 68A (3-(4-(1H-Pyrazol-1-yl)benzyl)-2-(azetidin-1-yl)-4-chloroquinolin-6-yl)(1-methyl-1H-imidazol-5-yl)(6-(trifluoromethyl)pyridin-3-yl)methanol

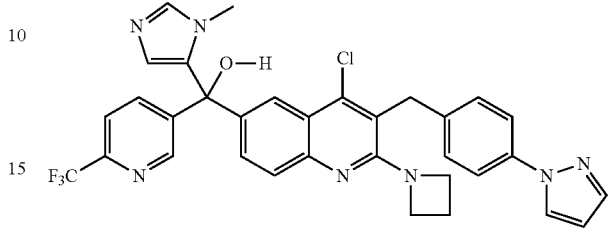

To a 5 mL sealed tube was added (3-(4-(1H-Pyrazol-1-yl)benzyl)-2,4-dichloroquinolin-6-yl)(1-methyl-1H-imidazol-5-yl)(6-(trifluoromethyl)pyridin-3-yl)methanol (200 mg, 0.33 mmol, 1 equivalent, Example 23, free base), azetidine (93.7 mg, 1.64 mmol, 5 equivalents) and dimethylformamide (2 mL). The reaction vessel was sealed and heated in a 100° C. oil bath. After two days, the vessel was cooled and contents transferred to a separatory funnel with ethyl acetate dilution. The organic phase was extracted with saturated aqueous ammonium chloride solution and deionized water. The organic phase was separated, dried over magnesium sulfate, filtered and evaporated to dryness under reduced pressure. The crude material was purified via reverse phase chromatography using acetonitrile with ammonium hydroxide in water as eluent to provide racemic (3-(4-(1H-pyrazol-1-yl)benzyl)-2-(azetidin-1-yl)-4-chloroquinolin-6-yl)(1-methyl-1H-imidazol-5-yl)(6-(trifluoromethyl)pyridin-3-yl)methanol. MS (ESI): mass calcd. for $C_{33}H_{27}ClF_3N_7O$, 629.19; m/z found, 630.2 [M+H]$^+$. $^1$H NMR (600 MHz, MeOH-d$_4$) δ ppm 8.78 (d, J=2.1 Hz, 1H), 8.15 (d, J=2.5 Hz, 1H), 8.06 (d, J=2.1 Hz, 1H), 8.02 (dd, J=8.2, 2.1 Hz, 1H), 7.97 (s, 1H), 7.84 (d, J=8.3 Hz, 1H), 7.76 (d, J=8.8 Hz, 1H), 7.69 (d, J=1.8 Hz, 1H), 7.65-7.62 (m, 2H), 7.57 (dd, J=8.9, 2.2 Hz, 1H), 7.24-7.18 (m, 2H), 6.51-6.49 (m, 1H), 6.47 (s, 1H), 4.38 (s, 2H), 4.25-4.20 (m, 4H), 3.53 (s, 3H), 2.30-2.21 (m, 2H). Racemic (3-(4-(1H-pyrazol-1-yl)benzyl)-2-(azetidin-1-yl)-4-chloroquinolin-6-yl)(1-methyl-1H-imidazol-5-yl)(6-(trifluoromethyl)pyridin-3-yl)methanol was purified on a chiralcel OD column (20 um, Diacel) with ethanol/heptanes to provide two enantiomers. The first eluting enantiomer was Example 68B: MS (ESI): mass calcd. for $C_{33}H_{27}ClF_3N_7O$, 629.19; m/z found, 630.2 [M+H]$^+$. $^1$H NMR (600 MHz, MeOH-d$_4$) δ ppm 8.78 (d, J=2.1 Hz, 1H), 8.12 (dd, J=2.5, 0.4 Hz, 1H), 8.05 (d, J=2.1 Hz, 1H), 8.00 (dd, J=8.2, 2.1 Hz, 1H), 7.84-7.78 (m, 1H), 7.76-7.70 (m, 2H), 7.69-7.66 (m, 1H), 7.64-7.58 (m, 2H), 7.56 (dd, J=8.8, 2.2 Hz, 1H), 7.18 (d, J=8.7 Hz, 2H), 6.48 (dd, J=2.4, 1.9 Hz, 1H), 6.35 (d, J=0.8 Hz, 1H), 4.32 (s, 2H), 4.20-4.14 (m, 4H), 3.48 (s, 3H), 2.25-2.15 (m, 2H), and the second eluting enantiomer was Example 68C: MS (ESI): mass calcd. for $C_{33}H_{27}ClF_3N_7O$, 629.19; m/z found, 630.2 [M+H]$^+$. $^1$H NMR (600 MHz, MeOH-d$_4$) δ ppm 8.78 (d, J=2.1 Hz, 1H), 8.15-8.11 (m, 1H), 8.05 (d, J=2.0 Hz, 1H), 8.00 (dd, J=8.2, 2.0 Hz, 1H), 7.81 (d, J=8.3 Hz, 1H), 7.76-7.70 (m, 2H), 7.68 (d, J=1.5 Hz, 1H), 7.64-7.59 (m, 2H), 7.56 (dd, J=8.9, 2.2 Hz, 1H), 7.18 (d, J=8.7 Hz, 2H), 6.48 (dd, J=2.4, 1.9 Hz, 1H), 6.35 (s, 1H), 4.32 (s, 2H), 4.17 (t, J=7.6 Hz, 4H), 3.48 (s, 3H), 2.24-2.17 (m, 2H).

Example 69

3-(4-(1H-Pyrazol-1-yl)benzyl)-6-((4-chlorophenyl)(hydroxy)(1-methyl-1H-imidazol-5-yl)methyl)-2-methoxyquinoline-4-carbonitrile

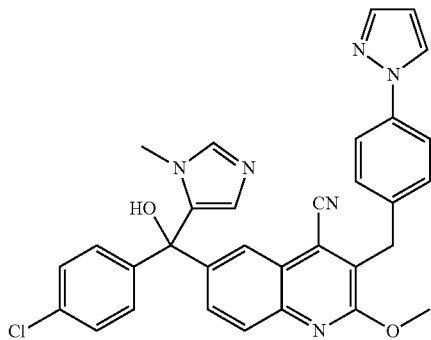 [SMILES: COc1nc2ccc(C(O)(c3ccc(Cl)cc3)c3cncn3C)cc2c(C#N)c1Cc1ccc(-n2cccn2)cc1]

A round bottom flask was charged with (3-(4-(1H-pyrazol-1-yl)benzyl)-4-chloro-2-methoxyquinolin-6-yl)(4-chlorophenyl)(1-methyl-1H-imidazol-5-yl)methanol (147 mg, 0.257 mmol, Example 33A), Zn(CN)$_2$ (36 mg, 0.31 mmol), Pd$_2$dba$_3$ (9.4 mg, 0.010 mmol), zinc nanopowder (4.0 mg, 0.062 mmol), and 1,1'-bis(diphenylphosphanyl) ferrocene (dppf, 11.4 mg, 0.021 mmol). The flask was evacuated and re-filled with argon (three cycles). Dimethylacetamide (0.5 mL) was then added and the mixture was heated at 120° C. for 2 days. LCMS analysis indicated incomplete conversion, so additional portions of Zn(CN)$_2$, Pd$_2$dba$_3$, zinc nanopowder, and 1,1'-bis(diphenylphosphanyl) ferrocene (amounts as above) were added, argon was bubbled through the mixture for 5 minutes, and it was again heated at 120° C. for 3 d. The mixture was cooled to room temperature, diluted with EtOAc, and washed sequentially with 2 M aqueous NH$_4$OH, water, and saturated aqueous NaCl. The organic phase was dried (Na$_2$SO$_4$), filtered, and concentrated. The residue was purified by reverse-phase HPLC (30-70% CH$_3$CN—H$_2$O, 0.1% TFA). The product was converted to the free base (neutralized with saturated aqueous NaHCO$_3$ and extracted with DCM) and the organic fractions were concentrated to afford the title compound. $^1$H NMR (400 MHz, CDCl$_3$) δ ppm 8.16 (d, J=1.71 Hz, 1H), 7.87 (d, J=1.96 Hz, 1H), 7.83 (d, J=8.80 Hz, 1H), 7.70 (d, J=1.22 Hz, 1H), 7.58-7.63 (m, 2H), 7.53-7.58 (m, 1H), 7.41-7.48 (m, 3H), 7.30-7.38 (m, 4H), 6.40-6.51 (m, 2H), 4.36 (s, 2H), 4.11 (s, 3H), 3.37-3.46 (m, 4H); MS m/e 561.0 [M+H]$^+$.

Example 70A 3-(4-(1H-Pyrazol-1-yl)benzyl)-6-(hydroxy(1-methyl-1H-imidazol-5-yl)(6-(trifluoromethyl)pyridin-3-yl)methyl)quinoline-2-carbonitrile

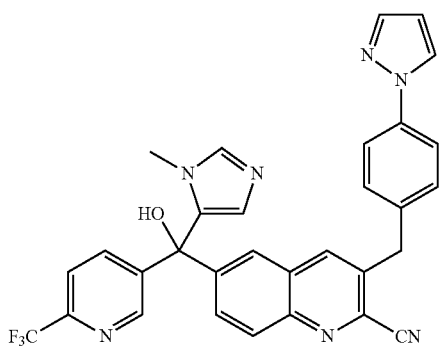 [SMILES: Cn1cncc1C(O)(c1ccc(C(F)(F)F)nc1)c1ccc2nc(C#N)c(Cc3ccc(-n4cccn4)cc3)cc2c1]

The title compound was prepared using (3-(4-(1H-pyrazol-1-yl)benzyl)-2,4-dichloroquinolin-6-yl)(1-methyl-1H-imidazol-5-yl)(6-(trifluoromethyl)pyridin-3-yl)methanol (Example 23 free base) in place of (3-(4-(1H-pyrazol-1-yl)benzyl)-4-chloro-2-methoxyquinolin-6-yl)(4-chlorophenyl)(1-methyl-1H-imidazol-5-yl)methanol using the procedure described for Example 69 (reaction time 18 h). $^1$H NMR (400 MHz, CDCl$_3$) δ ppm 8.78 (d, J=1.96 Hz, 1H), 8.13 (d, J=9.05 Hz, 1H), 7.90-7.96 (m, 2H), 7.88 (dd, J=2.08, 8.19 Hz, 1H), 7.79 (dd, J=2.08, 8.93 Hz, 1H), 7.61-7.74 (m, 5H), 7.30-7.41 (m, 3H), 6.47 (t, J=2.08 Hz, 1H), 6.37 (s, 1H), 4.74 (br. s., 1H), 4.40 (s, 2H), 3.34 (s, 3H); MS m/e 566.0 [M+H]$^+$.

Example 70A was purified by chiral HPLC (Chiralpak AD, 100% EtOH) to give 2 enantiomers. The enantiomers were then further purified on silica gel columns (0-1% MeOH-DCM) to give: Example 70B: (first enantiomer to elute off chiral column) $^1$H NMR (400 MHz, CDCl$_3$) δ ppm 8.78 (d, J=2.20 Hz, 1H), 8.14 (d, J=8.80 Hz, 1H), 7.86-7.99 (m, 3H), 7.80 (dd, J=2.20, 9.05 Hz, 1H), 7.63-7.76 (m, 5H), 7.33-7.45 (m, 3H), 6.44-6.54 (m, 1H), 6.40 (s, 1H), 4.34-4.47 (m, 3H), 3.36 (s, 3H); MS m/e 566.2 [M+H]$^+$ and Example 70C: (second enantiomer to elute off chiral column) $^1$H NMR (400 MHz, CDCl$_3$) δ ppm 8.78 (d, J=2.20 Hz, 1H), 8.14 (d, J=8.80 Hz, 1H), 7.86-7.96 (m, 3H), 7.80 (dd, J=2.20, 9.05 Hz, 1H), 7.63-7.75 (m, 5H), 7.33-7.42 (m, 3H), 6.45-6.53 (m, 1H), 6.40 (s, 1H), 4.35-4.46 (m, 3H), 3.36 (s, 3H); MS m/e 566.2 [M+H]$^+$.

Example 71A 3-(4-(1H-Pyrazol-1-yl)benzyl)-6-((4-chlorophenyl)(hydroxy)(1-methyl-1H-imidazol-5-yl)methyl)quinoline-2,4-dicarbonitrile

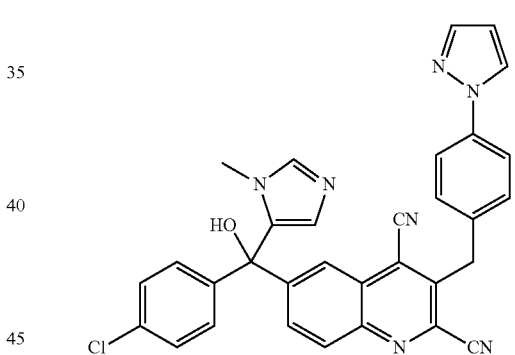

A round bottom flask was charged with (3-(4-(1H-pyrazol-1-yl)benzyl)-2,4-dichloroquinolin-6-yl)(4-chlorophenyl)(1-methyl-1H-imidazol-5-yl)methanol (425 mg, 0.740 mmol, Example 11 free base), Zn(CN)$_2$ (104 mg, 0.888 mmol), Pd$_2$dba$_3$ (27.1 mg, 0.0296 mmol), zinc nanopowder (11.6 mg, 0.178 mmol), and 1,1'-bis(diphenylphosphanyl) ferrocene (dppf, 32.8 mg, 0.0592 mmol). The flask was evacuated and re-filled with argon (three cycles). Dimethylacetamide (1.5 mL) was then added and the mixture was heated at 120° C. for 19 hours. The mixture was cooled to room temperature, diluted with EtOAc, and washed sequentially with 2 M aqueous NH$_4$OH and saturated aqueous NaCl. The organic phase was dried (Na$_2$SO$_4$), filtered, and concentrated. The residue was purified by reverse-phase HPLC (30-70% CH$_3$CN—H$_2$O, 0.1% TFA). The product was converted to the free base (neutralized with saturated aqueous NaHCO$_3$ and extracted with DCM) and the organic fractions were concentrated to afford the title compound. $^1$H NMR (400 MHz, CDCl$_3$) δ ppm 8.41 (d, J=1.96 Hz, 1H), 8.15 (d, J=9.05 Hz, 1H), 7.88 (d, J=2.45 Hz, 1H), 7.79 (dd, J=1.96, 8.80 Hz, 1H), 7.61-7.73 (m, 3H), 7.50 (d, J=8.56 Hz, 2H), 7.30-7.39 (m, 5H), 6.41-6.49 (m, 1H), 6.39 (d, J=0.98 Hz, 1H), 4.55-4.68 (m, 3H), 3.39 (s, 3H); MS m/e 556.0 [M+H]$^+$.

Example 71A was purified by chiral HPLC (Chiralpak AD, 80% heptanes, 20% EtOH) to give 2 enantiomers. The enantiomers were then further purified on silica gel columns (0-10% MeOH-DCM) to give Example 71B: (second enantiomer to elute off chiral column) $^1$H NMR (400 MHz, CDCl$_3$) δ ppm 8.42 (d, J=1.96 Hz, 1H), 8.16 (d, J=8.80 Hz, 1H), 7.89 (d, J=2.45 Hz, 1H), 7.81 (dd, J=1.96, 8.80 Hz, 1H), 7.63-7.73 (m, 3H), 7.51 (d, J=8.56 Hz, 2H), 7.40 (s, 1H), 7.30-7.39 (m, 4H), 6.45-6.49 (m, 1H), 6.44 (s, 1H), 4.65 (s, 2H), 4.22 (s, 1H), 3.41 (s, 3H); MS m/e 556.2 [M+H]$^+$ and Example 71C: (first enantiomer to elute off chiral column) $^1$H NMR (400 MHz, CDCl$_3$) δ ppm 8.42 (d, J=1.71 Hz, 1H), 8.16 (d, J=8.80 Hz, 1H), 7.89 (d, J=2.45 Hz, 1H), 7.81 (dd, J=1.96, 9.05 Hz, 1H), 7.61-7.75 (m, 3H), 7.51 (d, J=8.80 Hz, 2H), 7.41 (s, 1H), 7.30-7.38 (m, 4H), 6.39-6.52 (m, 2H), 4.65 (s, 2H), 4.18 (br. s., 1H), 3.41 (s, 3H); MS m/e 556.2 [M+H]$^+$.

Example 72A 3-(4-(1H-Pyrazol-1-yl)benzyl)-6-(hydroxy(1-methyl-1H-imidazol-5-yl)(6-(trifluoromethyl)pyridin-3-yl)methyl)quinoline-2,4-dicarbonitrile

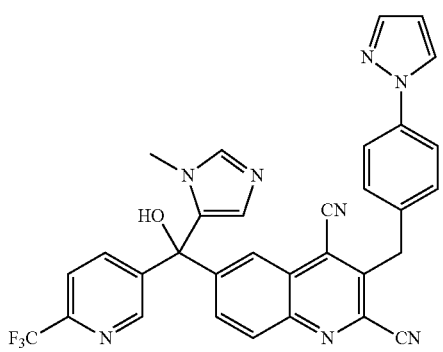 [SMILES: Cn1cncc1C(O)(c1ccc(C(F)(F)F)nc1)c1ccc2nc(C#N)c(Cc3ccc(-n4cccn4)cc3)c(C#N)c2c1]

A round bottom flask was charged with (3-(4-(1H-pyrazol-1-yl)benzyl)-2,4-dichloroquinolin-6-yl)(1-methyl-1H-imidazol-5-yl)(6-(trifluoromethyl)pyridin-3-yl)methanol (712 mg, 1.17 mmol, Example 23 free base), Zn(CN)$_2$ (247 mg, 2.10 mmol), Pd$_2$dba$_3$ (107 mg, 0.117 mmol), zinc nanopowder (15.3 mg, 0.234 mmol), and dicyclohexyl(2',4',6'-triisopropyl-[1,1'-biphenyl]-2-yl)phosphine (X-Phos, 115 mg, 0.234 mmol). The flask was evacuated and re-filled with argon (three cycles). Dimethylacetamide (6 mL, degassed by bubbling argon through for 30 minutes) was then added and the mixture was heated at 120° C. for 3 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. Attempted isolation by flash column chromatography yielded a mixture of the title compound and starting dichloroquinoline; this mixture was resubjected to the reaction conditions as above, except using 1.3 equivalents Zn(CN)$_2$. After work-up, the residue was purified by flash column chromatography (silica gel, 50-60% CH$_3$CN in [2% conc. aqueous NH$_4$OH in DCM, aqueous phase removed]) to afford the title compound. MS m/e 591.2 [M+H]$^+$.

Example 72A was purified by chiral HPLC (Chiralpak IC, 70% CO$_2$/30% iPrOH+0.2% isopropylamine) to give 2 enantiomers. The enantiomers were then further purified on plug silica gel columns (0-5% MeOH-DCM) to give Example 72B: (first enantiomer to elute off chiral column) $^1$H NMR (400 MHz, CDCl$_3$) δ ppm 8.78 (d, J=1.96 Hz, 1H), 8.45 (d, J=1.71 Hz, 1H), 8.20 (d, J=9.05 Hz, 1H), 7.95 (dd, J=1.96, 8.31 Hz, 1H), 7.89 (d, J=2.45 Hz, 1H), 7.77 (dd, J=1.96, 9.05 Hz, 1H), 7.62-7.74 (m, 4H), 7.50 (d, J=8.56 Hz, 2H), 7.34 (s, 1H), 6.42-6.50 (m, 1H), 6.38 (s, 1H), 5.79 (br. s., 1H), 4.65 (s, 2H), 3.39 (s, 3H); MS m/e 591.2 [M+H]$^+$ and Example 72C: (second enantiomer to elute off chiral column) $^1$H NMR (400 MHz, CDCl$_3$) δ ppm 8.79 (d, J=1.96 Hz, 1H), 8.45 (d, J=1.96 Hz, 1H), 8.20 (d, J=8.80 Hz, 1H), 7.96 (dd, J=1.96, 8.07 Hz, 1H), 7.89 (d, J=2.45 Hz, 1H), 7.78 (dd, J=1.96, 9.05 Hz, 1H), 7.62-7.74 (m, 4H), 7.50 (d, J=8.56 Hz, 2H), 7.36 (s, 1H), 6.42-6.48 (m, 1H), 6.40 (s, 1H), 5.53 (br. s., 1H), 4.65 (s, 2H), 3.39 (s, 3H); MS m/e 591.2 [M+H]$^+$.

Example 73A 3-(4-(1H-Pyrazol-1-yl)benzyl)-6-(hydroxy(1-methyl-1H-imidazol-5-yl)(6-(trifluoromethyl)pyridin-3-yl)methyl)-2-methoxyquinoline-4-carbonitrile

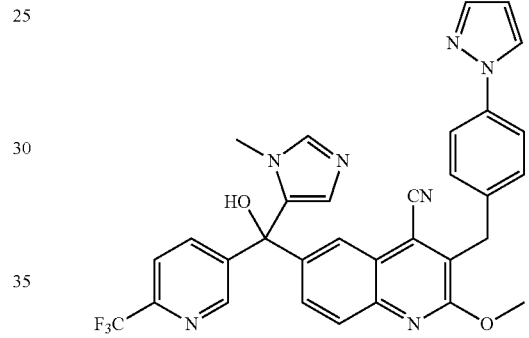

The title compound was prepared using (3-(4-(1H-pyrazol-1-yl)benzyl)-4-chloro-2-methoxyquinolin-6-yl)(1-methyl-1H-imidazol-5-yl)(6-(trifluoromethyl)pyridin-3-yl)methanol (Example 35A free base) in place of (3-(4-(1H-pyrazol-1-yl)benzyl)-4-chloro-2-methoxyquinolin-6-yl)(4-chlorophenyl)(1-methyl-1H-imidazol-5-yl)methanol using the procedure described for Example 69 (reaction time 20 h). $^1$H NMR (400 MHz, CDCl$_3$) δ ppm 8.80 (d, J=1.96 Hz, 1H), 8.19 (d, J=1.96 Hz, 1H), 7.94 (dd, J=1.83, 8.19 Hz, 1H), 7.80-7.89 (m, 2H), 7.64-7.72 (m, 2H), 7.60 (d, J=8.56 Hz, 2H), 7.47-7.53 (m, 1H), 7.43 (d, J=8.56 Hz, 2H), 7.36 (s, 1H), 6.39-6.46 (m, 2H), 4.91 (br. s., 1H), 4.36 (s, 2H), 4.11 (s, 3H), 3.39 (s, 3H); MS m/e 596.0 [M+H]$^+$.

Example 73A was purified by chiral HPLC (Chiralcel OD, 100% CH$_3$CN) to give 2 enantiomers. The enantiomers were then further purified on silica gel columns (0-10% MeOH-DCM). Example 73B: (first enantiomer to elute off chiral column) $^1$H NMR (400 MHz, CDCl$_3$) δ ppm 8.80 (d, J=1.71 Hz, 1H), 8.20 (d, J=1.96 Hz, 1H), 7.93-7.99 (m, 1H), 7.82-7.90 (m, 2H), 7.66-7.74 (m, 2H), 7.57-7.64 (m, 2H), 7.52 (dd, J=1.71, 8.56 Hz, 1H), 7.38-7.48 (m, 3H), 6.42-6.47 (m, 2H), 4.51 (br. s., 1H), 4.37 (s, 2H), 4.12 (s, 3H), 3.41 (s, 3H); MS m/e 596.3 [M+H]$^+$ and Example 73C: (second enantiomer to elute off chiral column) $^1$H NMR (400 MHz, CDCl$_3$) δ ppm 8.81 (d, J=1.47 Hz, 1H), 8.20 (d, J=1.96 Hz, 1H), 7.91-8.00 (m, 1H), 7.82-7.91 (m, 2H), 7.70 (dd, J=3.30, 5.01 Hz, 2H), 7.58-7.64 (m, 2H), 7.50-7.57 (m, 1H), 7.40-7.50 (m, 3H), 6.47-6.55 (m, 1H), 6.43-6.47 (m, 1H), 4.37 (s, 2H), 4.12 (s, 3H), 3.86 (s, 1H), 3.42 (s, 3H); MS m/e 596.3 [M+H]+.

Example 74A 3-(4-(1H-Pyrazol-1-yl)benzyl)-2-(diethylamino)-6-(hydroxy(1-methyl-1H-imidazol-5-yl)(6-(trifluoromethyl)pyridin-3-yl)methyl)quinoline-4-carbonitrile

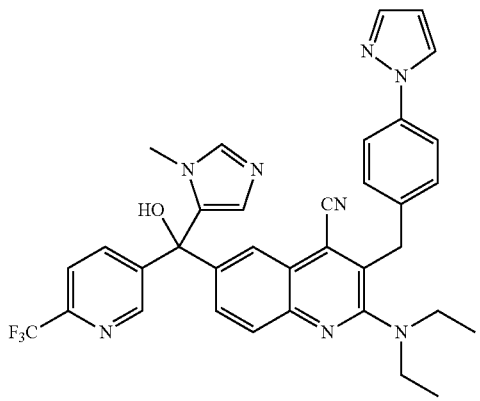 [SMILES: CCN(CC)c1nc2ccc(C(O)(c3ccc(C(F)(F)F)nc3)c3cncn3C)cc2c(C#N)c1Cc1ccc(-n2cccn2)cc1]

A round bottom flask was charged with (3-(4-(1H-pyrazol-1-yl)benzyl)-4-chloro-2-(diethylamino)quinolin-6-yl)(1-methyl-1H-imidazol-5-yl)(6-(trifluoromethyl)pyridin-3-yl)methanol (165 mg, 0.255 mmol, Example 86), Zn(CN)$_2$ (15.6 mg, 0.133 mmol), Pd$_2$dba$_3$ (23.4 mg, 0.0255 mmol), zinc nanopowder (3.3 mg, 0.051 mmol), and dicyclohexyl(2',4',6'-triisopropyl-[1,1'-biphenyl]-2-yl)phosphine (X-Phos, 14.2 mg, 0.0255 mmol). The flask was evacuated and re-filled with argon (three cycles). Dimethylacetamide (1.0 mL) was then added, argon was bubbled through the mixture for 5 minutes, and the mixture was heated at 120° C. for 4 hours. The mixture was cooled to room temperature, diluted with EtOAc, and filtered through Celite®. The filtrate was washed sequentially with 2 M aqueous NH$_4$OH and half-saturated aqueous NaCl. The organic phase was dried (Na$_2$SO$_4$), filtered, and concentrated. The residue was purified by reverse-phase HPLC (30-70% CH$_3$CN—H$_2$O, 0.1% TFA). The product was converted to the free base (neutralized with saturated aqueous NaHCO$_3$ and extracted with DCM) and the organic fractions were concentrated to afford the title compound as a yellow solid. $^1$H NMR (400 MHz, CDCl$_3$) δ ppm 8.79 (d, J=1.96 Hz, 1H), 8.11 (d, J=1.96 Hz, 1H), 7.94 (dd, J=1.96, 8.31 Hz, 1H), 7.87 (d, J=2.45 Hz, 1H), 7.83 (d, J=9.05 Hz, 1H), 7.63-7.70 (m, 2H), 7.56-7.63 (m, 2H), 7.47 (dd, J=1.96, 8.80 Hz, 1H), 7.35 (s, 1H), 7.29 (d, J=8.56 Hz, 2H), 6.45 (d, J=0.98 Hz, 1H), 6.42-6.44 (m, 1H), 4.87 (br. s., 1H), 4.42 (s, 2H), 3.39 (s, 3H), 3.33 (q, J=6.85 Hz, 4H), 1.11 (t, J=6.97 Hz, 6H); MS m/e 637.3 [M+H]+.

Example 74A was purified by chiral HPLC (Chiralcel OD, 80% heptanes, 20% EtOH) to give 2 enantiomers. The enantiomers were then further purified on silica gel columns (3-8% MeOH-DCM) to give Example 74B: (first enantiomer to elute off chiral column) $^1$H NMR (400 MHz, CDCl$_3$) δ ppm 8.79 (d, J=2.20 Hz, 1H), 8.12 (d, J=1.96 Hz, 1H), 7.95 (dd, J=2.08, 8.19 Hz, 1H), 7.79-7.90 (m, 2H), 7.63-7.73 (m, 2H), 7.56-7.63 (m, 2H), 7.48 (dd, J=2.20, 8.80 Hz, 1H), 7.37 (s, 1H), 7.30 (d, J=8.56 Hz, 2H), 6.46 (s, 1H), 6.43-6.45 (m, 1H), 4.79 (br. s., 1H), 4.43 (s, 2H), 3.40 (s, 3H), 3.34 (q, J=6.85 Hz, 4H), 1.12 (t, J=7.09 Hz, 6H); MS m/e 637.3 [M+H]+ and Example 74C: (second enantiomer to elute off chiral column) $^1$H NMR (400 MHz, CDCl$_3$) δ ppm 8.79 (d, J=1.96 Hz, 1H), 8.12 (d, J=1.96 Hz, 1H), 7.95 (dd, J=1.96, 8.31 Hz, 1H), 7.87 (d, J=2.45 Hz, 1H), 7.84 (d, J=8.80 Hz, 1H), 7.65-7.73 (m, 2H), 7.60 (d, J=8.56 Hz, 2H), 7.48 (dd, J=1.96, 8.80 Hz, 1H), 7.38 (s, 1H), 7.28-7.35 (m, 2H), 6.46 (s, 1H), 6.40-6.45 (m, 1H), 4.72 (br. s., 1H), 4.43 (s, 2H), 3.40 (s, 3H), 3.34 (q, J=7.01 Hz, 4H), 1.12 (t, J=6.97 Hz, 6H); MS m/e 637.3 [M+H]+.

Example 75A (3-(4-(1H-Pyrazol-1-yl)benzyl)-4-chloro-2-(diethylamino)quinolin-6-yl)(4-chlorophenyl)(1-methyl-1H-imidazol-5-yl)methanol

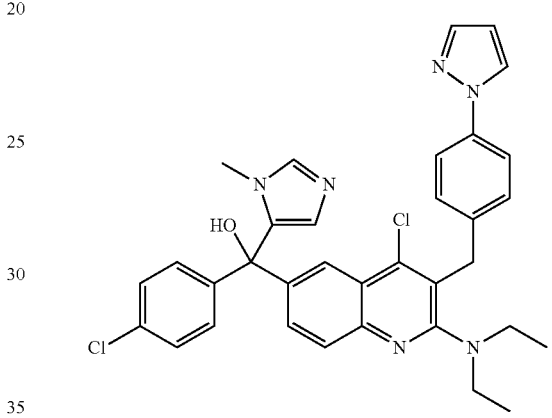

The title compound was prepared using (4-chlorophenyl)(1-methyl-1H-imidazol-5-yl)methanone (Intermediate 1: step b) in place of (1-methyl-1H-imidazol-5-yl)(6-(trifluoromethyl)pyridin-3-yl)methanone using the procedure described for Example 86. $^1$H NMR (400 MHz, CDCl$_3$) δ ppm 8.07 (d, J=2.20 Hz, 1H), 7.87 (d, J=1.96 Hz, 1H), 7.81 (d, J=8.80 Hz, 1H), 7.69 (d, J=1.71 Hz, 1H), 7.55-7.61 (m, 2H), 7.52 (dd, J=2.20, 8.80 Hz, 1H), 7.44 (s, 1H), 7.29-7.35 (m, 4H), 7.24 (d, J=8.80 Hz, 2H), 6.47 (d, J=0.98 Hz, 1H), 6.41-6.46 (m, 1H), 4.36 (s, 2H), 3.42 (s, 3H), 3.19-3.31 (m, 5H), 1.08 (t, J=6.97 Hz, 6H); MS m/e 611.2 [M+H]+.

Example 75A was purified by chiral HPLC (Chiralpak AD, 50% MeOH, 50% EtOH) to give 2 enantiomers. The first eluting enantiomer was Example 75B: $^1$H NMR (400 MHz, CDCl$_3$) δ ppm 8.08 (d, J=2.20 Hz, 1H), 7.88 (d, J=2.20 Hz, 1H), 7.82 (d, J=8.80 Hz, 1H), 7.70 (d, J=1.47 Hz, 1H), 7.58 (d, J=8.56 Hz, 2H), 7.53 (dd, J=2.20, 8.80 Hz, 1H), 7.46 (s, 1H), 7.30-7.37 (m, 4H), 7.25 (d, J=8.80 Hz, 2H), 6.49 (d, J=0.98 Hz, 1H), 6.41-6.47 (m, 1H), 4.37 (s, 2H), 3.43 (s, 3H), 3.27 (q, J=7.01 Hz, 4H), 3.11-3.20 (m, 1H), 1.09 (t, J=7.09 Hz, 6H); MS m/e 611.2 [M+H]+ and the second eluting enantiomer was Example 75C: $^1$H NMR (400 MHz, CDCl$_3$) δ ppm 8.07 (d, J=1.22 Hz, 1H), 7.87 (d, J=2.45 Hz, 1H), 7.82 (d, J=8.80 Hz, 1H), 7.69 (d, J=1.47 Hz, 1H), 7.58 (d, J=8.56 Hz, 2H), 7.49-7.55 (m, 1H), 7.29-7.36 (m, 4H), 7.21-7.26 (m, 3H), 6.49 (s, 1H), 6.39-6.46 (m, 1H), 4.36 (s, 2H), 3.44 (s, 3H), 3.26 (q, J=7.01 Hz, 4H), 1.09 (t, J=6.97 Hz, 6H); MS m/e 611.2 [M+H]+.

Example 76A 3-(4-(1H-Pyrazol-1-yl)benzyl)-6-((4-cyanophenyl)(hydroxy)(1-methyl-1H-imidazol-5-yl)methyl)-2-methoxyquinoline-4-carbonitrile

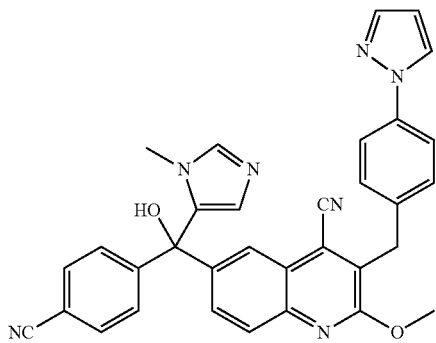 [SMILES: COc1nc2ccc(C(O)(c3ccc(C#N)cc3)c3cncn3C)cc2c(C#N)c1Cc1ccc(-n2cccn2)cc1]

A round bottom flask was charged with (3-(4-(1H-pyrazol-1-yl)benzyl)-4-chloro-2-methoxyquinolin-6-yl)(4-chlorophenyl)(1-methyl-1H-imidazol-5-yl)methanol (207 mg, 0.363 mmol, Example 33A), Zn(CN)$_2$ (76.7 mg, 0.653 mmol), Pd$_2$dba$_3$ (49.8 mg, 0.0544 mmol), zinc nanopowder (7.1 mg, 0.109 mmol), and dicyclohexyl(2',4',6'-triisopropyl-[1,1'-biphenyl]-2-yl)phosphine (X-Phos, 35.7 mg, 0.0726 mmol). The flask was evacuated and re-filled with argon (three cycles). Dimethylacetamide (1.9 mL, degassed by bubbling argon through for 30 minutes) was then added and the mixture was heated at 120° C. for 4 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. The residue was purified by flash column chromatography (silica gel, 45-60% CH$_3$CN in [2% conc. aqueous NH$_4$OH in DCM, aqueous phase removed]) to afford the title compound. $^1$H NMR (400 MHz, CDCl$_3$) δ ppm 8.14 (d, J=2.20 Hz, 1H), 7.86 (d, J=2.45 Hz, 1H), 7.82 (d, J=8.80 Hz, 1H), 7.69 (d, J=1.47 Hz, 1H), 7.63-7.68 (m, 2H), 7.58-7.62 (m, 2H), 7.56 (s, 1H), 7.49-7.55 (m, 2H), 7.43 (d, J=8.56 Hz, 2H), 7.38 (s, 1H), 6.42-6.46 (m, 1H), 6.41 (d, J=1.22 Hz, 1H), 4.31-4.41 (m, 3H), 4.10 (s, 3H), 3.37 (s, 3H); MS m/e 552.3 [M+H]$^+$.

Example 76A was purified by chiral HPLC (Chiralpak AD, 80% CO$_2$/20% iPrOH+0.2% isopropylamine) to give 2 enantiomers. To convert the enantiomers to their succinate salts, they were dissolved in EtOH, solutions of 1.05 equivalents succinic acid in EtOH were added, and the mixtures were concentrated to give Example 76B.succinic acid: (first enantiomer to elute off the chiral column) $^1$H NMR (400 MHz, DMSO-d$_6$) δ ppm 8.43 (d, J=2.69 Hz, 1H), 7.98 (d, J=1.96 Hz, 1H), 7.89 (d, J=8.80 Hz, 1H), 7.85 (d, J=8.56 Hz, 2H), 7.75 (d, J=8.56 Hz, 2H), 7.69-7.73 (m, 2H), 7.64 (dd, J=1.96, 8.80 Hz, 1H), 7.53 (d, J=8.31 Hz, 2H), 7.38 (d, J=8.56 Hz, 2H), 7.32 (s, 1H), 6.46-6.55 (m, 1H), 6.18 (d, J=0.98 Hz, 1H), 4.30 (s, 2H), 4.04 (s, 3H), 2.38 (s, 4H) (one methyl signal obscured by water peak); MS m/e 552.2 [M+H]$^+$ and Example 76C.succinic acid: (second enantiomer to elute off the chiral column) $^1$H NMR (400 MHz, DMSO-d$_6$) δ ppm 8.43 (d, J=2.45 Hz, 1H), 7.98 (d, J=1.71 Hz, 1H), 7.89 (d, J=8.80 Hz, 1H), 7.85 (d, J=8.56 Hz, 2H), 7.75 (d, J=8.56 Hz, 2H), 7.69-7.73 (m, 2H), 7.64 (dd, J=2.08, 8.93 Hz, 1H), 7.53 (d, J=8.56 Hz, 2H), 7.38 (d, J=8.56 Hz, 2H), 7.32 (s, 1H), 6.48-6.56 (m, 1H), 6.18 (s, 1H), 4.30 (s, 2H), 4.04 (s, 3H), 2.39 (s, 4H) (one methyl signal obscured by water peak); MS m/e 552.3 [M+H]$^+$.

Example 77A (4-Chloro-2-methoxy-3-(4-(trifluoromethyl)benzyl)quinolin-6-yl)(2,6-dimethylpyridin-3-yl)(1-methyl-1H-1,2,3-triazol-5-yl)methanol

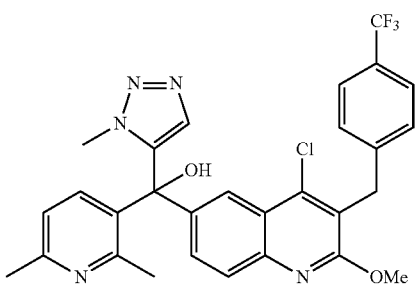

To a flask containing 1-methyl-1H-1,2,3-triazole (275 mg, 3.31 mmol, prepared according to PCT Int. Appl., 2008098104) was added THF (35 mL) and the colorless solution was cooled to −50° C. Then, n-butyllithium (2.5 M in hexanes, 1.2 mL, 3.0 mmol) was added dropwise which afforded a dark reddish-brown viscous solution. The mixture was stirred between −20 to −10° C. for 30 minutes, then a homogeneous THF solution of (4-chloro-2-methoxy-3-(4-(trifluoromethyl)benzyl)quinolin-6-yl)(2,6-dimethylpyridin-3-yl)methanone (700 mg, 1.44 mmol in 4 mL THF, Intermediate 47: step f) was introduced at 0° C. The reaction mixture became a dark brown color and was allowed to warm gradually to room temperature. The mixture was stirred for 60 minutes at room temperature then quenched with aqueous NH$_4$Cl solution. The aqueous portion was extracted with EtOAc, 3×50 mL. The combined organics were washed with brine, dried over MgSO$_4$, filtered and concentrated to provide a brown oil. Chromatography on silica gel (1% MeOH-DCM increasing to 5% MeOH-DCM) provided the product as a light brown solid. MS m/e 586.1 [M+H]$^+$. $^1$H NMR (500 MHz, CDCl$_3$) δ ppm 8.13 (d, J=1.8 Hz, 1H), 7.76 (d, J=8.8 Hz, 1H), 7.49 (d, J=8.1 Hz, 2H), 7.37 (d, J=7.9 Hz, 3H), 6.93 (q, J=8.1 Hz, 2H), 6.80 (s, 1H), 5.51 (s, 1H), 4.36-4.22 (m, 2H), 4.07 (s, 3H), 3.90 (s, 3H), 2.49 (s, 3H), 2.32 (s, 3H). Racemic (4-chloro-2-methoxy-3-(4-(trifluoromethyl)benzyl)quinolin-6-yl)(2,6-dimethylpyridin-3-yl)(1-methyl-1H-1,2,3-triazol-5-yl)methanol was separated into its individual enantiomers using the following conditions: Chiralcel OD, 20 uM (Diacel) using ethanol with 242 nM detection to give the first eluting enantiomer Example 77B: $^1$H NMR (500 MHz, CD$_2$Cl$_2$) δ ppm 8.09 (d, J=2.2 Hz, 1H), 7.79 (d, J=8.7 Hz, 1H), 7.51 (d, J=8.1 Hz, 2H), 7.44-7.36 (m, 3H), 6.95 (q, J=8.1 Hz, 2H), 6.85 (s, 1H), 4.34 (s, 2H), 4.07 (s, 3H), 3.90 (s, 3H), 2.49 (s, 3H), 2.31 (s, 3H); and the second eluting enantiomer Example 77C: $^1$H NMR (500 MHz, CD$_2$Cl$_2$) δ ppm 8.09 (d, J=2.2 Hz, 1H), 7.79 (d, J=8.7 Hz, 1H), 7.51 (d, J=8.1 Hz, 2H), 7.44-7.36 (m, 3H), 6.95 (q, J=8.1 Hz, 2H), 6.85 (s, 1H), 4.34 (s, 2H), 4.07 (s, 3H), 3.90 (s, 3H), 2.49 (s, 3H), 2.31 (s, 3H).

Example 78A 6-((2,6-Dimethylpyridin-3-yl)(hydroxy)(1-methyl-1H-1,2,3-triazol-5-yl)methyl)-2-methoxy-3-(4-(trifluoromethyl)benzyl)quinoline-4-carbonitrile

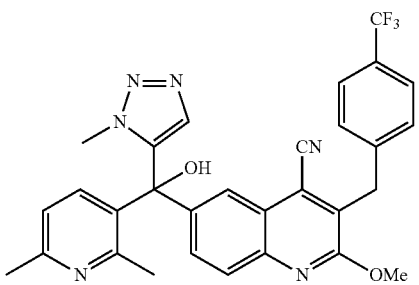 [SMILES: COc1nc2ccc(C(O)(c3ccc(C)nc3C)c3cnnn3C)cc2c(Cl)c1Cc1ccc(C(F)(F)F)cc1]

(4-Chloro-2-methoxy-3-(4-(trifluoromethyl)benzyl)quinolin-6-yl)(2,6-dimethylpyridin-3-yl)(1-methyl-1H-1,2,3-triazol-5-yl)methanol (250 mg, 0.44 mmol, Example 77A), zinc cyanide (90 mg, 0.77 mmol), 2-dicyclohexylphosphino-2',4',6'-triisopropylbiphenyl (X-phos, 40 mg, 0.084 mmol), zinc powder (8 mg, 0.12 mmol), tris(dibenzylideneacetone) dipalladium(0), ($Pd_2(dba)_3$; 60 mg, 0.066 mmol) were added to a large microwave vial, then dimethylacetamide (7 mL, degassed with argon) was added and the vial was sealed and evacuated. The mixture was heated to 125° C. in an aluminum heating mantle. The mixture was cooled to 80° C. and then filtered through a Celite® pad and rinsed with EtOAc-MeOH (10:1, v/v) and the light brown filtrate was concentrated under vacuum to afford a brown oil. The crude material was chromatographed directly on silica gel (100% DCM increasing to 10% MeOH-DCM) which provided the product contaminated with dimethylacetamide. This material was further purified by RP-HPLC to the title compound as a white foam. MS m/e 559.2 [M+H]$^+$. $^1$H NMR (500 MHz, CDCl$_3$) δ ppm 8.05 (s, 1H), 7.92 (d, J=8.8 Hz, 1H), 7.59 (d, J=8.3 Hz, 1H), 7.53 (d, J=8.2 Hz, 2H), 7.45 (d, J=8.2 Hz, 2H), 7.42-7.34 (m, 2H), 7.06 (s, 1H), 4.37 (s, 2H), 4.13 (s, 3H), 3.94 (s, 3H), 2.77 (s, 3H), 2.62 (s, 3H). The racemic material was separated into its individual enantiomers using the following conditions: Chiralpack OD, 80% heptanes:20% ethanol; wavelength at 220 nM to provide the two enantiomers. The first eluting enantiomer was Example 78B and the second eluting enantiomer was Example 78C.

Example 79A (4-Chloro-2-methoxy-3-(4-(trifluoromethyl)benzyl)quinolin-6-yl)(2,4-dimethylthiazol-5-yl)(1-methyl-1H-1,2,3-triazol-5-yl)methanol

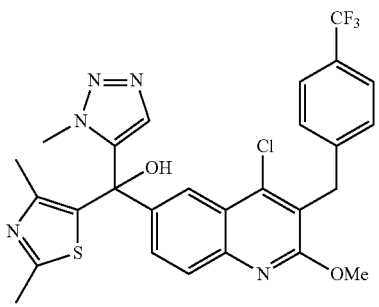 [SMILES: COc1nc2ccc(C(O)(c3sc(C)nc3C)c3cnnn3C)cc2c(Cl)c1Cc1ccc(C(F)(F)F)cc1]

To a flask containing 6-bromo-4-chloro-2-methoxy-3-(4-(trifluoromethyl)benzyl)quinoline (500 mg, 116 mmol, Intermediate 47: step d) was added THF (15 mL) at room temperature which resulted in a colorless homogeneous mixture. The solution was cooled to −70° C. which remained homogeneous and then n-butyllithium (2.5 M in hexanes, 0.45 mL, 1.13 mmol) was added drop wise. The color of the solution became a dark brown. After 1 minute, (2,4-dimethylthiazol-5-yl)(1-methyl-1H-1,2,3-triazol-5-yl)methanone (275 mg, 1.24 mmol in 2 mL THF, Intermediate 48: step b) was introduced and the color of the mixture went from dark brown to greenish to light orange color all within 1 minute. The mixture was allowed to warm to 0° C. over 45 minutes at which time the reaction was quenched with aqueous NH$_4$Cl solution. The mixture was diluted further with water and extracted with EtOAc, 3×45 mL. The combined organics were washed with brine, dried over MgSO$_4$, filtered and concentrated to give a light orange foam. The crude was chromatographed on silica gel (initially using 10% CH$_3$CN-toluene then changing to 80% CH$_3$CN-DCM) to afford the title compound as an off white solid. MS m/e 574.1 [M+H]$^+$. $^1$H NMR (500 MHz, CDCl$_3$) δ ppm 8.14 (d, J=2.1 Hz, 1H), 7.85 (d, J=8.8 Hz, 1H), 7.56-7.48 (m, 3H), 7.39 (d, J=8.1 Hz, 2H), 7.21-7.13 (m, 1H), 4.44-4.64 (m, 1H), 4.34 (s, 2H), 4.09 (s, 3H), 3.91 (s, 3H), 2.57 (s, 3H), 2.36 (s, 3H), 2.13 (s, 3H). Example 79A was separated into its individual enantiomers using the following conditions: Chiralpack OD, 80% heptanes: 20% ethanol; wavelength=242 nM to provide the two enantiomers. The first eluting enantiomer was Example 79B and the second eluting enantiomer was Example 79C.

Example 80A (4-Chloro-2-methoxy-3-(4-(trifluoromethyl)benzyl)quinolin-6-yl)(1,2-dimethyl-1H-imidazol-5-yl)(1-methyl-1H-1,2,3-triazol-5-yl)methanol

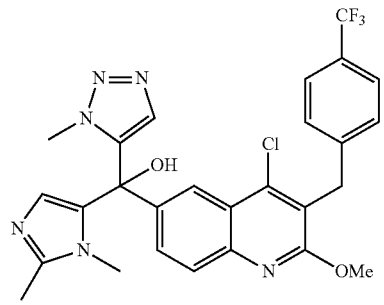 [SMILES: COc1nc2ccc(C(O)(c3cnnn3C)c3cnc(C)n3C)cc2c(Cl)c1Cc1ccc(C(F)(F)F)cc1]

Procedure A

To a flask containing 1-methyl-1H-1,2,3-triazole (400 mg, 4.81 mmol, prepared according to PCT Int. Appl., 2008098104) was added THF (25 mL) and the colorless solution was cooled to −50° C. Then, n-BuLi (2.5 M in hexanes, 1.88 mL) was added drop wise which afforded a dark reddish-brown solution. The mixture was allowed to warm gradually to −10° C. over 30 minutes, then a solution of (4-chloro-2-methoxy-3-(4-(trifluoromethyl)benzyl)quinolin-6-yl)(1,2-dimethyl-1H-imidazol-5-yl)methanone (750 mg, 1.58 mmol, Intermediate 49: step b) in THF (5 mL) was introduced at −10° C. The reaction mixture became a dark brown color and was allowed to warm gradually to room temperature. The mixture was stirred for 60 minutes at room temperature, then quenched with aqueous NH$_4$Cl solution. The aqueous portion was extracted with EtOAc-THF (~10:2, v/v) 5×50 mL. The combined organics were washed with brine, dried over MgSO$_4$, filtered and concentrated to provide a brown foam. Chromatography on silica gel (5% MeOH-DCM increasing to 10% MeOH) provided the title compound as a yellow solid. MS m/e 557.2 [M+H]$^+$. $^1$H NMR (500

MHz, CDCl$_3$) δ 8.23 (d, J=1.8 Hz, 1H), 7.72 (d, J=8.7 Hz, 1H), 7.49 (d, J=11.5 Hz, 2H), 7.38 (d, J=8.0 Hz, 3H), 7.30 (s, 1H), 7.06 (d, J=5.9 Hz, 1H), 5.99 (s, 1H), 4.33-4.19 (m, 2H), 4.06 (s, 3H), 3.88 (s, 3H), 3.33 (s, 3H), 2.14 (s, 3H). The racemic material was separated into its individual enantiomers using the following conditions: Chiralpack OD column; 80% heptanes: 20% ethanol; wavelength=242 nM to provide the two enantiomers. The first eluting enantiomer was Example 80B and the second eluting enantiomer was Example 80C.

Procedure B

A solution of 5-bromo-1,2-dimethyl-1H-imidazole (10.6 g, 60.8 mmol) in THF (400 mL) was cooled to −77° C. Maintaining a temperature of <−70° C., nBuLi (27.7 mL, 72.0 mmol, 2.5 M in hexanes) was added over 10 min. After 10 min, a solution of (4-chloro-2-methoxy-3-(4-(trifluoromethyl)benzyl)quinolin-6-yl)(1-methyl-1H-1,2,3-triazol-5-yl)methanone (20.0 g, 43.4 mmol, Intermediate 63) in THF (290 mL) was added over 10 min maintaining a temperature of <−60° C. The reaction mixture was allowed to warm to 0° C. over 1 h and then quenched with aqueous ammonium chloride (500 mL, 13 wt %). The resulting layers were separated and the organic layer was washed with brine (400 mL). The organic layer was dried over MgSO$_4$, filtered, and concentrated. The residue was taken up in acetone (200 mL) and allowed to stir for 2 h. The resulting suspension was filtered and washed with acetone (20 mL). After drying in a vacuum oven at 60° C. the title compound was obtained as a white solid. $^1$H NMR (400 MHz, CDCl$_3$) δ ppm 8.24 (d, J=2.2 Hz, 1H), 7.72 (d, J=8.7 Hz, 1H), 7.54-7.47 (m, 3H), 7.42-7.33 (m, 3H), 7.06 (s, 1H), 5.97 (s, 1H), 4.32-4.22 (m, 2H), 4.06 (s, 3H), 3.88 (s, 3H), 3.32 (s, 3H), 2.13 (s, 3H); MS m/e 557.1 (M+H). (4-chloro-2-methoxy-3-(4-(trifluoromethyl)benzyl)quinolin-6-yl)(1,2-dimethyl-1H-imidazol-5-yl)(1-methyl-1H-1,2,3-triazol-5-yl)methanol was resolved into its constituent enantiomers by chiral HPLC [Chiralcel OD, mobile phase: 85% heptane, 15% ethanol]. After resolution, the individual enantiomers were crystallized from acetone (7.5 mL/g) and isolated by filtration after the addition of heptane (15 mL/g). The first eluting enantiomer was Example 80B: $^1$H NMR (400 MHz, CDCl$_3$) δ ppm 8.23 (d, J=2.2 Hz, 1H), 7.72 (d, J=8.8 Hz, 1H), 7.51 (d, J=8.2 Hz, 2H), 7.43-7.33 (m, 3H), 7.05 (s, 1H), 6.99 (bs, 1H), 6.01 (s, 1H), 4.30 (s, 2H), 4.06 (s, 3H), 3.88 (s, 3H), 3.34 (s, 3H), 2.17 (s, 3H); MS m/e 557.1 (M+H). The second eluting enantiomer was Example 80C: $^1$H NMR (500 MHz, CDCl$_3$) δ ppm 8.19 (d, J=2.2 Hz, 1H), 7.74 (d, J=8.7 Hz, 1H), 7.52 (d, J=8.2 Hz, 2H), 7.43-7.35 (m, 3H), 7.14 (s, 1H), 6.08 (s, 1H), 5.32 (bs, 1H), 4.33 (s, 2H), 4.07 (s, 3H), 3.91 (s, 3H), 3.38 (s, 3H), 2.28 (s, 3H); MS m/e 557.1 (M+H).

Example 81A 6-((1,2-Dimethyl-1H-imidazol-5-yl)(hydroxy)(1-methyl-1H-1,2,3-triazol-5-yl)methyl)-2-methoxy-3-(4-(trifluoromethyl)benzyl)quinoline-4-carbonitrile

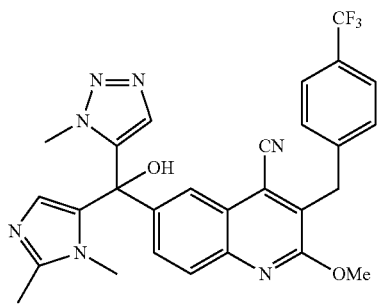 [SMILES: COc1nc2ccc(C(O)(c3cnnn3C)c3cnc(C)n3C)cc2c(C#N)c1Cc1ccc(C(F)(F)F)cc1]

(4-Chloro-2-methoxy-3-(4-(trifluoromethyl)benzyl)quinolin-6-yl)(1,2-dimethyl-1H-imidazol-5-yl)(1-methyl-1H-1,2,3-triazol-5-yl)methanol (370 mg, 0.66 mmol, Example 80A), zinc cyanide (147 mg, 1.26 mmol), X-phos (64.5 mg, 0.14 mmol), zinc powder (12 mg, 0.19 mmol) tris(dibenzylideneacetone)dipalladium (0), (Pd$_2$(dba)$_3$, 98 mg, 0.11 mmol) were added to a large microwave vial, then DMA (8 mL, degassed with argon) was added and the vial was sealed and evacuated. The mixture was heated to 125° C. in an aluminum heating mantle (for how long?). The mixture was filtered through a Celite® pad while still warm, rinsed with EtOAc-MeOH (10:1) and concentrated under vacuum providing a brown oil. The crude material was purified by RP-HPLC to give the title compound as an off white solid. MS m/e 548.2 [M+H]$^+$. $^1$H NMR (500 MHz, CDCl$_3$) δ ppm 8.19 (s, 1H), 7.87 (d, J=8.7 Hz, 1H), 7.50 (d, J=8.3 Hz, 2H), 7.42 (apparent d, 8.1 Hz, 3H), 7.3-7.4 (m, 1H) 6.41 (s, 1H), 4.41-4.26 (m, 2H), 4.10 (s, 3H), 3.90 (s, 3H), 3.64 (s, 3H), 2.58 (s, 3H). The racemic material was separated into its individual enantiomers using the following conditions: Chiralpak IA SFC column (5 u), 85% hexane: 15% EtOH (containing 0.2% Et$_3$N) to provide the two enantiomers. The first eluting enantiomer was Example 81B and the second eluting enantiomer was Example 81C.

Example 82

(4-chloro-2-methoxy-3-(4-(trifluoromethyl)benzyl)quinolin-6-yl)(2,4-dimethyloxazol-5-yl)(1-methyl-1H-1,2,3-triazol-5-yl)methanol

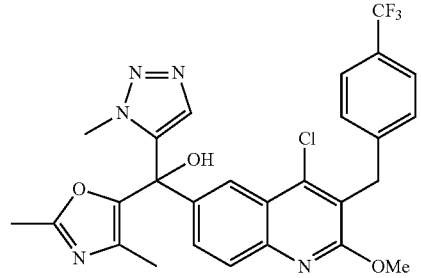 [SMILES: COc1nc2ccc(C(O)(c3oc(C)nc3C)c3cnnn3C)cc2c(Cl)c1Cc1ccc(C(F)(F)F)cc1]

To a flask containing 1-methyl-1H-1,2,3-triazole (200 mg, 2.41 mmol, prepared according to PCT Int. Appl., 2008098104) was added THF (20 mL) and the colorless solution was cooled to −40° C. Then, n-BuLi (2.5 M in hexanes, 1.0 mL, 2.5 mmol) was added drop wise which afforded a dark reddish-brown viscous solution. The mixture was stirred at −30° C. for 35 minutes, then a homogeneous THF solution of (4-chloro-2-methoxy-3-(4-(trifluoromethyl)benzyl)quinolin-6-yl)(2,4-dimethyloxazol-5-yl)methanone (500 mg, 1.05 mmol, in 4 mL THF, Intermediate 51: step b) was introduced at −20° C. The reaction mixture became a dark brown color and was then placed in an ice-water bath and allowed to warm gradually to room temperature. After 45 minutes, the mixture was quenched with aqueous NH$_4$Cl solution and extracted with EtOAc:THF (10:2), 4×50 mL. The combined organics were washed with brine, dried over Na$_2$SO$_4$, filtered and concentrated to provide a brown oil. Chromatography on silica gel (3% MeOH-DCM increasing to 5% MeOH-DCM) to provide the title compound as a faint amber solid. MS m/e 558.2 [M+H]$^+$. $^1$H NMR (400 MHz, CDCl$_3$) δ ppm 8.15 (d, J=2.0 Hz, 1H), 7.86 (d, J=8.8 Hz, 1H), 7.54-7.47 (m, 3H), 7.40 (d, J=8.1 Hz, 2H), 7.14 (s, 1H), 4.35 (s, 2H), 4.10 (s, 3H), 4.03 (s, 1H), 3.92 (s, 3H), 2.40 (s, 3H), 1.54 (s, 3H).

Example 83A 1-(4-((3-(4-(1H-Pyrazol-1-yl)benzyl)-4-chloro-2-methoxyquinolin-6-yl)(hydroxy)(phenyl)methyl)piperidin-1-yl)ethanone

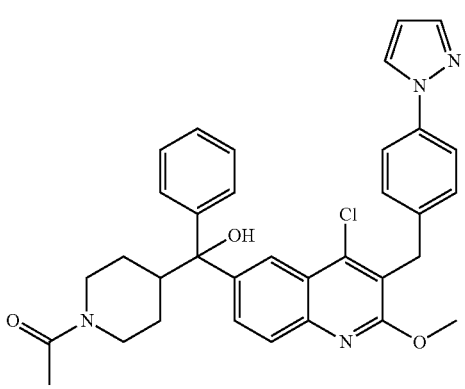 [SMILES: COc1nc2ccc(C(O)(c3ccccc3)C3CCN(C(C)=O)CC3)cc2c(Cl)c1Cc1ccc(-n2cccn2)cc1]

A solution of n-BuLi (2.5 M in hexanes, 0.208 mL, 0.333 mmol) was added dropwise by syringe to a solution of 3-(4-(1H-pyrazol-1-yl)benzyl)-6-bromo-4-chloro-2-methoxyquinoline (150 mg, 0.350 mmol, Intermediate 16) in dry THF (3.5 mL) at −78° C. After 3 minutes, a solution of 1-(4-benzoylpiperidin-1-yl)ethanone (80.9 mg, 0.350 mmol, Intermediate 52) in dry THF (3.5 mL) was added dropwise. An additional 0.5 mL of dry THF was used to quantitate the transfer. The reaction mixture was stirred for 5 minutes at −78° C., and the flask was placed into an ice-water bath. After 30 minutes, water (5 mL) was added. The biphasic mixture was warmed to room temperature then partitioned between water (25 mL) and ethyl acetate (40 mL). The layers were separated. The organic layer was dried with sodium sulfate. The dried solution was filtered and the filtrate was concentrated. The residue was purified by flash column chromatography (silica gel, 50% ethyl acetate-hexanes initially, grading to 100% ethyl acetate) and then by reverse phase HPLC [5% acetonitrile-water (containing 0.05% TFA v/v) initially, grading to 5% water (containing 0.05% TFA v/v)-acetonitrile] to provide the title compound as a white solid. $^1$H NMR (500 MHz, CDCl$_3$) δ ppm 8.31-8.25 (m, 1H), 7.85 (d, J=2.4 Hz, 1H), 7.80-7.72 (m, 1H), 7.71-7.61 (m, 2H), 7.59-7.47 (m, 4H), 7.39-7.29 (m, 4H), 7.27-7.19 (m, 1H), 6.46-6.40 (m, 1H), 4.76-4.62 (m, 1H), 4.31 (s, 2H), 4.05 (s, 3H), 3.83 (t, J=16.3 Hz, 1H), 3.17-3.00 (m, 1H), 2.83-2.71 (m, 1H), 2.66-2.53 (m, 1H), 2.06 (s, 3H), 1.75-1.29 (m, 4H). MS (ESI): mass calcd. C$_{34}$H$_{33}$ClN$_4$O$_3$, 580.2; m/z found, 581.2 [M+H]$^+$. This racemate was separated by chiral HPLC (Chiralpak AD column, 250 gram, 50 mm×21 cm, ethanol eluent, 80 mL/minute, 240 nm wavelength) to give two enantiomers. The first eluting enantiomer was Example 83B: $^1$H NMR (500 MHz, CDCl$_3$) δ ppm 8.29 (dd, J=8.1, 2.1 Hz, 1H), 7.87-7.82 (m, 1H), 7.79-7.72 (m, 1H), 7.71-7.61 (m, 2H), 7.59-7.48 (m, 4H), 7.38-7.29 (m, 4H), 7.26-7.18 (m, 1H), 6.46-6.39 (m, 1H), 4.75-4.61 (m, 1H), 4.31 (s, 2H), 4.05 (s, 3H), 3.81 (t, J=16.2 Hz, 1H), 3.14-3.00 (m, 1H), 2.82-2.69 (m, 1H), 2.64-2.51 (m, 1H), 2.03 (s, 3H), 1.76-1.20 (m, 4H); MS (ESI): mass calcd. C$_{34}$H$_{33}$ClN$_4$O$_3$, 580.2; m/z found, 581.2 [M+H]$^+$ and the second eluting enantiomer was Example 83C: $^1$H NMR (500 MHz, CDCl$_3$) δ ppm 8.29 (dd, J=8.1, 2.1 Hz, 1H), 7.85 (d, J=2.3 Hz, 1H), 7.79-7.72 (m, 1H), 7.71-7.61 (m, 2H), 7.59-7.48 (m, 4H), 7.38-7.29 (m, 4H), 7.26-7.18 (m, 1H), 6.45-6.40 (m, 1H), 4.75-4.60 (m, 1H), 4.31 (s, 2H), 4.05 (s, 3H), 3.89-3.75 (m, 1H), 3.15-2.98 (m, 1H), 2.82-2.70 (m, 1H), 2.64-2.49 (m, 1H), 2.04 (s, 3H), 1.75-1.28 (m, 4H); MS (ESI): mass calcd. C$_{34}$H$_{33}$ClN$_4$O$_3$, 580.2; m/z found, 581.2 [M+H]$^+$.

Example 84

(3-(4-(1H-Pyrazol-1-yl)benzyl)-2,4-dichloro-8-methylquinolin-6-yl)(1-methyl-1H-imidazol-5-yl)(6-(trifluoromethyl)pyridin-3-yl)methanol

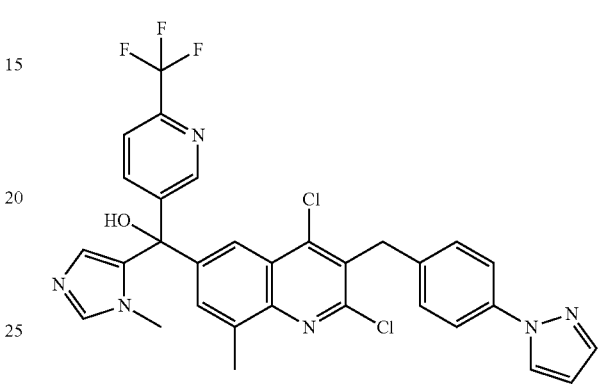

A mixture of 3-(4-(1H-pyrazol-1-yl)benzyl)-6-bromo-2,4-dichloro-8-methylquinoline (393 mg, 0.880 mmol, Intermediate 19: step a) and (1-methyl-1H-imidazol-5-yl)(6-(trifluoromethyl)pyridin-3-yl)methanone (224 mg, 0.880 mmol, Intermediate 36: step c) in dry degassed THF (16 mL, THF was degassed with nitrogen for 1 h) was cooled to −78° C. and n-BuLi (1.6 M in hexane, 0.5 mL, 0.8 mmol) was added over 1.5 minutes. Stirring was continued at −78° C. for 10 minutes and the dry ice bath was replaced with an ice water bath. Stirring was continued for 1 hour after which the reaction mixture was quenched with saturated aqueous NH$_4$Cl solution. EtOAc was added and the layers were separated and the aqueous mixture again extracted with EtOAc. The combined organic extracts were dried over MgSO$_4$, filtered, and the solvents were removed under reduced pressure. Purification using flash column chromatography (5% MeOH in dichloromethane) yielded the substantially pure title compound. MS (ESI) 623.2.

Example 85

(3-(4-(1H-Pyrazol-1-yl)benzyl)-2,4-dichloro-8-methylquinolin-6-yl)(4-chlorophenyl)(1-methyl-1H-imidazol-5-yl)methanol

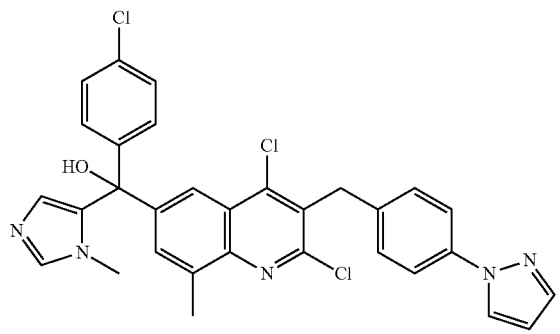 [SMILES: Cc1cc(C(O)(c2ccc(Cl)cc2)c2cncn2C)cc2c(Cl)c(Cc3ccc(-n4cccn4)cc3)c(Cl)nc12]

A mixture of 3-(4-(1H-pyrazol-1-yl)benzyl)-6-bromo-2,4-dichloro-8-methylquinoline (393 mg, 0.880 mmol, Intermediate 19: step a) and (4-chlorophenyl)(1-methyl-1H-imidazol-5-yl)methanone (194 mg, 0.880 mmol, Intermediate 1: step b) in dry degassed THF (16 mL) was cooled to −78° C. and n-BuLi (1.6 M in hexane, 0.5 mL, 0.8 mmol) was added over 1.5 minutes. Stirring was continued at −78° C. for 10 minutes and the dry ice acetone bath was replaced with an ice water bath. Stirring was continued for 1 hour and the reaction mixture was quenched with saturated aqueous NH₄Cl solution. EtOAc was added and the layers were separated and the aqueous mixture again extracted with EtOAc. The combined organic extracts were dried over MgSO₄, filtered, and the solvents were removed under reduced pressure. Purification using flash column chromatography (5% MeOH in dichloromethane) yielded the substantially pure title compound. MS (ESI) 588.2.

Example 86

(3-(4-(1H-Pyrazol-1-yl)benzyl)-4-chloro-2-(diethylamino)quinolin-6-yl)(1-methyl-1H-imidazol-5-yl)(6-(trifluoromethyl)pyridin-3-yl)methanol

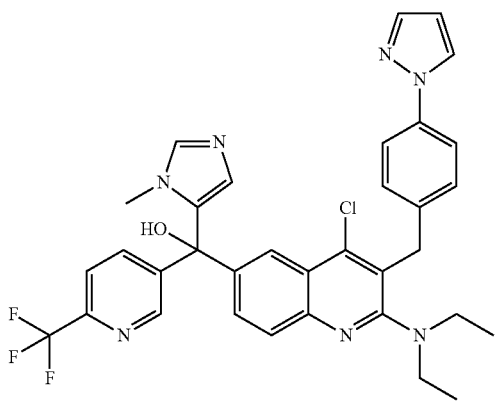 [SMILES: CCN(CC)c1nc2ccc(C(O)(c3ccc(C(F)(F)F)nc3)c3cncn3C)cc2c(Cl)c1Cc1ccc(-n2cccn2)cc1]

A round bottom flask was charged with 3-(4-(1H-pyrazol-1-yl)benzyl)-6-bromo-4-chloro-N,N-diethylquinolin-2-amine (380 mg, 0.809 mmol, Intermediate 46) and (1-methyl-1H-imidazol-5-yl)(6-(trifluoromethyl)pyridin-3-yl)methanone (206 mg, 0.809 mmol, Intermediate 36, step c) and was evacuated and re-filled with argon. THF (13.5 mL) was added, and the solution was cooled in a dry ice acetone bath for 10 minutes. n-BuLi (1.6 M in hexane, 0.506 mL, 0.809 mmol), was added dropwise by syringe. The mixture was stirred at −78° C. for 30 minutes, then in an ice water bath for 30 minutes. The reaction was quenched by addition of saturated aqueous NH₄Cl, diluted with water and extracted with EtOAc (3×). The organic phase was dried (Na₂SO₄), filtered, and concentrated. The residue was purified by flash column chromatography (silica gel, 50-100% EtOAc-heptanes) to provide the title compound as a white foam.

Example 87A (4-Chloro-2-methoxy-3-(4-(trifluoromethyl)benzyl)quinolin-6-yl)(2,6-dimethylpyridin-3-yl)(1-methyl-1H-1,2,3-triazol-5-yl)methanamine

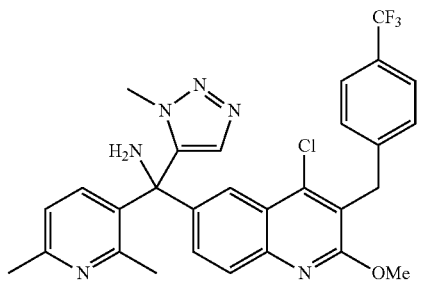 [SMILES: COc1nc2ccc(C(N)(c3ccc(C)nc3C)c3cnnn3C)cc2c(Cl)c1Cc1ccc(C(F)(F)F)cc1]

A mixture of (S)-(4-chloro-2-methoxy-3-(4-(trifluoromethyl)benzyl)quinolin-6-yl)(2,6-dimethylpyridin-3-yl)(1-methyl-1H-1,2,3-triazol-5-yl)methyl acetate (646 mg, 1.06 mmol, Intermediate 55) and ammonia in MeOH (3.3 mL, 23 mmol, 7.0 M) in a sealed pressure tube was heated at 65° C. for 18 h, and concentrated in vacuo. The residue was purified by flash column chromatography (40 g silica gel column, 50-100% EtOAc in heptanes, and 5-10% MeOH in CH₂Cl₂) to give the title compound as an oil. ¹H NMR (400 MHz, CDCl₃) δ 8.02 (d, J=2.02 Hz, 1H), 7.82 (d, J=9.09 Hz, 1H), 7.51 (d, J=8.08 Hz, 2H), 7.37-7.44 (m, 3H), 7.08 (d, J=8.08 Hz, 1H), 7.02 (s, 1H), 6.98 (d, J=8.08 Hz, 1H), 4.34 (s, 2H), 4.09 (s, 3H), 3.94 (s, 3H), 2.56 (s, 3H), 2.30 (s, 3H).

Purification by chiral HPLC (Chiralcel OD, 100% MeOH) provided two pure enantiomers. Example 87B: ¹H NMR (400 MHz, CDCl₃) δ 8.02 (d, J=2.02 Hz, 1H), 7.82 (d, J=9.09 Hz, 1H), 7.51 (d, J=8.08 Hz, 2H), 7.37-7.44 (m, 3H), 7.07 (d, J=8.08 Hz, 1H), 7.02 (s, 1H), 6.98 (d, J=8.08 Hz, 1H), 4.34 (s, 2H), 4.09 (s, 3H), 3.94 (s, 3H), 2.56 (s, 3H), 2.52 (s, 2H), 2.29 (s, 3H); MS m/e 567.2 (M+H) and Example 87C: ¹H NMR (400 MHz, CDCl₃) δ 8.02 (d, J=2.02 Hz, 1H), 7.82 (d, J=8.59 Hz, 1H), 7.51 (d, J=8.08 Hz, 2H), 7.37-7.44 (m, 3H), 7.07 (d, J=8.08 Hz, 1H), 7.02 (s, 1H), 6.98 (d, J=8.08 Hz, 1H), 4.34 (s, 2H), 4.09 (s, 3H), 3.94 (s, 3H), 2.56 (s, 3H), 2.53 (s, 2H), 2.29 (s, 3H); MS m/e 567.2 (M+H).

Example 88A 6-((2,6-Dimethylpyridin-3-yl)(hydroxy)(1-methyl-1H-1,2,3-triazol-5-yl)methyl)-3-(4-(trifluoromethyl)benzyl)quinoline-2,4-dicarbonitrile

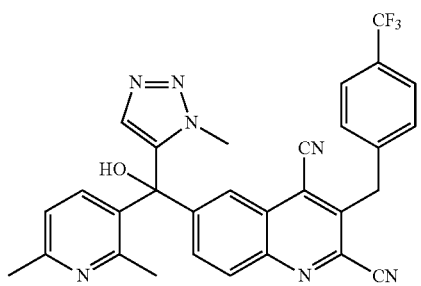 [SMILES: Cc1ccc(C(O)(c2ccc3nc(C#N)c(Cc4ccc(C(F)(F)F)cc4)c(C#N)c3c2)c2cnnn2C)c(C)n1]

A pressure tube containing (2,4-dichloro-3-(4-(trifluoromethyl)benzyl)quinolin-6-yl)(2,6-dimethylpyridin-3-yl)(1-methyl-1H-1,2,3-triazol-5-yl)methanol (900 mg, 1.57 mmol, Intermediate 56), Pd$_2$dba$_3$ (145 mg, 0.160 mmol), dicyclohexyl(2',4',6'-triisopropyl-[1,1'-biphenyl]-2-yl)phosphine (X-Phos, 75 mg, 0.16 mmol), zinc cyanide (98 mg, 0.83 mmol), and zinc nanopowder (18 mg, 0.28 mmol) in N,N-dimethylacetamide (11 mL) was purged with nitrogen for 8 min, and then heated at 94° C. for 4 h. The mixture was allowed to cool to room temperature and filtered. The filtrate was concentrated in vacuo, EtOAc and saturated NH$_4$Cl(aq) were added. The organic layer was separated, and the aqueous layer was extracted with EtOAc. The combined organic layers were dried (Na$_2$SO$_4$), filtered, and concentrated. The residue was purified by reverse phase HPLC (water/acetonitrile/0.1% TFA) to give the title compound as a TFA salt. $^1$H NMR (400 MHz, MeOD-d$_4$) δ 8.37-8.40 (m, 1H), 8.31 (d, J=9.09 Hz, 1H), 7.80-7.88 (m, 2H), 7.70 (d, J=8.08 Hz, 1H), 7.66 (d, J=8.08 Hz, 2H), 7.53-7.57 (m, 2H), 7.21 (s, 1H), 4.75 (s, 2H), 4.00 (s, 3H), 2.77 (s, 3H), 2.65 (s, 3H); MS m/e 554.2 (M+H).

The above TFA salt was dissolved in dichloromethane and washed with saturated NaHCO$_3$(aq). The aqueous layer was extracted with dichloromethane. The combined organic layers were dried (Na$_2$SO$_4$), filtered, concentrated, and purified by chiral HPLC (Chiralpak OD-H column, 80% heptanes/20% EtOH) to give two pure enantiomers.

Example 88B: $^1$H NMR (400 MHz, CDCl$_3$) δ 8.40 (s, 1H), 8.20 (d, J=9.09 Hz, 1H), 7.58-7.68 (m, 3H), 7.52-7.58 (m, 2H), 6.97 (d, J=8.08 Hz, 1H), 6.88 (d, J=7.58 Hz, 1H), 6.80 (s, 1H), 5.17 (br. s., 1H), 4.67 (s, 2H), 3.96 (s, 3H), 2.53 (s, 3H), 2.36 (s, 3H); MS m/e 554.1 (M+H) and Example 88C: $^1$H NMR (400 MHz, CDCl$_3$) δ 8.40 (d, J=2.02 Hz, 1H), 8.20 (d, J=8.59 Hz, 1H), 7.58-7.66 (m, 3H), 7.52-7.57 (m, 2H), 6.97 (d, J=8.08 Hz, 1H), 6.88 (d, J=8.08 Hz, 1H), 6.81 (s, 1H), 4.96 (br. s., 1H), 4.67 (s, 2H), 3.96 (s, 3H), 2.53 (s, 3H), 2.36 (s, 3H); MS m/e 554.1 (M+H).

Example 89 tert-Butyl 3-((4-chloro-2-ethyl-3-(4-(trifluoromethyl)benzyl)quinolin-6-yl)(hydroxy)(1-methyl-1H-1,2,3-triazol-5-yl)methyl)azetidine-1-carboxylate

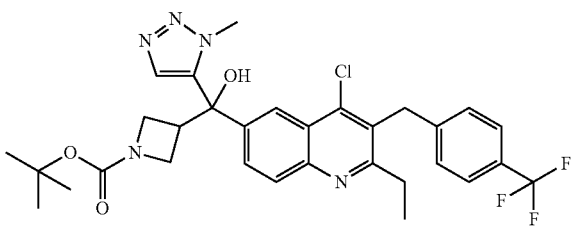 [SMILES: CCc1nc2ccc(C(O)(c3cnnn3C)C3CN(C(=O)OC(C)(C)C)C3)cc2c(Cl)c1Cc1ccc(C(F)(F)F)cc1]

A solution of n-BuLi (2.5 M in hexanes, 0.746 mL, 1.87 mmol) was added dropwise by syringe to a stirring solution of 6-bromo-4-chloro-2-ethyl-3-(4-(trifluoromethyl)benzyl)quinoline (0.800 g, 1.87 mmol, Intermediate 58: step c) in dry THF (18 mL) at −78° C. After 5 min, a solution of tert-butyl 3-(1-methyl-1H-1,2,3-triazole-5-carbonyl)azetidine-1-carboxylate (0.604 g, 2.27 mmol, Intermediate 59: step b) in dry THF (5 mL) was added dropwise by syringe. After 5 min, the flask was removed from the cooling bath and allowed to warm. After 5 min, the flask was placed into an ice-water bath. After 20 min, water (20 mL) and ethyl acetate (100 mL) were added. The layers were separated. The organic layer was dried with sodium sulfate and the dried solution was filtered. Celite (5 g) was added to the filtrate and the solvents were removed by rotary evaporation to provide a free-flowing powder. The powder was loaded onto a silica gel column. Elution with 30% ethyl acetate-hexanes initially, grading to 80% ethyl acetate-hexanes provided the title compound as a yellow solid. $^1$H NMR (500 MHz, CDCl$_3$) δ ppm 8.37 (d, J=2.0 Hz, 1H), 8.00 (d, J=8.8 Hz, 1H), 7.55 (s, 1H), 7.53 (d, J=8.1 Hz, 2H), 7.45-7.40 (m, 1H), 7.21 (d, J=8.0 Hz, 2H), 4.50 (s, 2H), 4.26-4.20 (m, 1H), 4.05-3.99 (m, 1H), 3.97-3.90 (m, 1H), 3.71 (s, 3H), 3.67-3.60 (m, 1H), 3.54-3.46 (m, 1H), 2.97-2.89 (m, 2H), 1.39 (s, 9H), 1.33-1.28 (m, 3H), 1.71-1.63 (m, 1H); MS (ESI): mass calcd. for C$_{31}$H$_{33}$ClF$_3$N$_5$O$_3$, 615.2; m/z found, 616.0 [M+H]$^+$.

Example 90A 1-(3-((4-Chloro-2-ethyl-3-(4-(trifluoromethyl)benzyl)quinolin-6-yl)(hydroxy)(1-methyl-1H-1,2,3-triazol-5-yl)methyl)azetidin-1-yl)ethanone

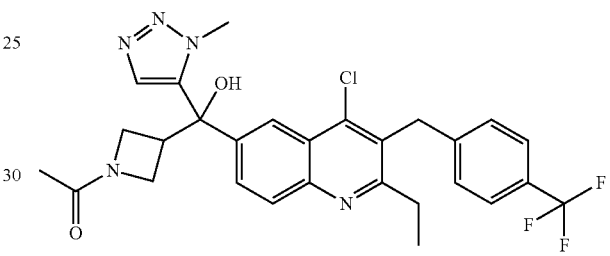

Trifluoroacetic acid (0.442 mL, 5.78 mmol) was added dropwise by syringe to an ice-cooled, stirring solution of tert-butyl 3-((4-chloro-2-ethyl-3-(4-(trifluoromethyl)benzyl)quinolin-6-yl)(hydroxy)(1-methyl-1H-1,2,3-triazol-5-yl)methyl)azetidine-1-carboxylate (0.356 g, 0.578 mmol, Example 89) in dichloromethane (2.9 mL). After 20 min, the flask was removed from the cooling bath and allowed to warm to room temperature. After 18 h, dichloromethane (15 mL) and saturated aqueous sodium bicarbonate solution (10 mL) were added in sequence. The biphasic mixture was stirred for 10 min. The mixture was partitioned between water (10 mL) and dichloromethane (10 mL). The layers were separated. The organic layer was dried with sodium sulfate. The dried solution was filtered and the filtrate was concentrated to afford an oily residue. The residue was dissolved in dichloromethane (5.8 mL). Triethylamine (0.401 mL, 2.89 mmol) and acetic anhydride (0.218 mL, 2.31 mmol) were added in sequence and the solution was heated to 46° C. After 2 h, the reaction was cooled to room temperature. Dichloromethane (50 mL) and saturated aqueous sodium bicarbonate solution were added in sequence. The biphasic mixture was stirred for 10 min. The layers were separated. The organic layer was dried over sodium sulfate and the dried solution was filtered. Celite (4 g) was added to the filtrate and the solvents were removed by rotary evaporation to provide a free-flowing powder. The powder was loaded onto a silica gel column. Elution with dichloromethane initially, grading to 10% methanol-dichloromethane provided the title compound as a white solid. $^1$H NMR (500 MHz, CDCl$_3$, 3:1 mixture of amide rotamers, * denotes minor rotamer isomer) δ ppm 8.44 (d, J=2.0 Hz, 1H), 8.39* (d, J=2.1 Hz, 1H), 8.03-7.97 (m, 1H), 7.57-7.50 (m, 3H), 7.48-7.42 (m, 1H), 7.24-7.18 (m, 2H), 6.42 (s, 1H), 5.48* (s, 1H), 4.56-4.46 (m, 2H), 4.43-4.36* (m, 1H), 4.36-4.31* (m, 1H), 4.26-4.19 (m, 1H), 4.19-4.13 (m, 1H), 4.07-3.99 (m, 1H), 3.81-3.62 (m, 4H), 3.61-3.46 (m, 1H), 2.97-2.90 (m, 2H), 1.81* (s, 3H), 1.58 (s, 3H), 1.35-1.26 (m, 3H); MS (ESI): mass calcd. for $C_{28}H_{27}ClF_3N_5O_2$, 557.2; m/z found, 558.0 [M+H]$^+$.

1-(3-(4-chloro-2-ethyl-3-(4-(trifluoromethyl)benzyl) quinolin-6-yl)(hydroxy)(1-methyl-1H-1,2,3-triazol-5-yl) methyl)azetidin-1-yl)ethanone was purified by chiral SFC [Chiracel OD-H column, 5 μm, 250 mm×20 mm, mobile phase: 60% carbon dioxide, 40% ethanol (containing 0.3% diisopropylamine)] to give two enantiomers. The first eluting enantiomer was Example 90B: $^1$H NMR (500 MHz, CDCl$_3$, 1.5:1 mixture of amide rotamers, * denotes minor rotamer) δ ppm 8.41 (d, J=2.0 Hz, 1H), 8.37* (d, J=2.0 Hz, 1H), 8.01 (d, J=8.8 Hz, 1H), 7.59 (s, 1H), 7.53 (d, J=8.1 Hz, 2H), 7.51* (d, J=8.0 Hz, 2H), 7.47-7.42 (m, 1H), 7.21 (d, J=7.9 Hz, 2H), 7.18* (d, J=7.9 Hz, 2H), 5.66 (s, 1H), 5.22* (s, 1H), 4.50 (s, 2H), 4.48* (s, 2H), 4.42-4.35* (m, 1H), 4.34-4.28* (m, 1H), 4.23-4.08 (m, 3H), 4.04-3.98* (m, 1H), 3.81-3.67 (m, 4H), 3.63-3.48 (m, 1H), 2.98-2.88 (m, 2H), 1.83 (s, 3H), 1.76* (s, 3H), 1.34-1.26 (m, 3H); MS (ESI): mass calcd. for $C_{28}H_{27}ClF_3N_5O_2$, 557.2; m/z found, 558.2 [M+H]$^+$ and the second eluting enantiomer was Example 90C: $^1$H NMR (500 MHz, CDCl$_3$, 1.5:1 mixture of amide rotamers, * denotes minor rotamer) δ ppm 8.42 (d, J=2.0 Hz, 1H), 8.38* (d, J=2.1 Hz, 1H), 8.03-7.98 (m, 1H), 7.58 (s, 1H), 7.53 (d, J=8.1 Hz, 2H), 7.51* (d, J=7.9 Hz, 2H), 7.48-7.43 (m, 1H), 7.21 (d, J=8.0 Hz, 2H), 7.18* (d, J=8.0 Hz, 2H), 5.95 (s, 1H), 5.51* (s, 1H), 4.50 (s, 2H), 4.48* (s, 2H), 4.41-4.36* (m, 1H), 4.35-4.31* (m, 1H), 4.22-4.10 (m, 3H), 4.04-3.99* (m, 1H), 3.80-3.67 (m, 4H), 3.62-3.56* (m, 1H), 3.56-3.49 (m, 1H), 2.93 (app p, J=7.5 Hz, 2H), 1.83 (s, 3H), 1.75* (s, 3H), 1.33-1.27 (m, 3H); MS (ESI): mass calcd. for $C_{28}H_{27}ClF_3N_5O_2$, 557.2; m/z found, 558.2 [M+H]$^+$.

Example 91A (4-Chloro-2-ethyl-3-(4-(trifluoromethyl)benzyl) quinolin-6-yl)(1-methyl-1H-1,2,3-triazol-5-yl)(1-(methylsulfonyl)azetidin-3-yl)methanol

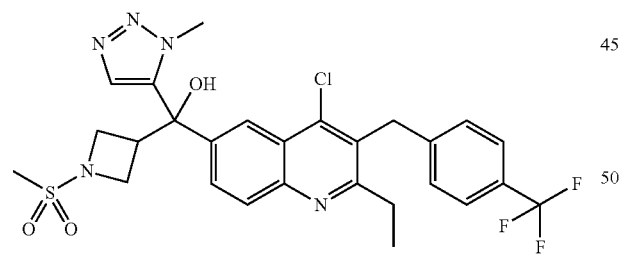

Trifluoroacetic acid (0.511 mL, 6.67 mmol) was added dropwise by syringe to an ice-cooled, stirring solution of tert-butyl 3-((4-chloro-2-ethyl-3-(4-(trifluoromethyl)benzyl) quinolin-6-yl)(hydroxy)(1-methyl-1H-1,2,3-triazol-5-yl) methyl)azetidine-1-carboxylate (0.411 g, 0.667 mmol, Example 89) in dichloromethane (3.3 mL). After 20 min, the flask was removed from the cooling bath and allowed to warm to room temperature. After 18 h, dichloromethane (15 mL) and saturated aqueous sodium bicarbonate solution (10 mL) were added in sequence. The biphasic mixture was stirred for 10 min. The mixture was partitioned between water (10 mL) and dichloromethane (10 mL). The layers were separated. The organic layer was dried with sodium sulfate. The dried solution was filtered and the filtrate was concentrated to afford an off-white solid. The solid was dissolved in dry dichloromethane (6.1 mL). The resulting solution was cooled in an ice-water bath. Triethylamine (0.257 mL, 1.85 mmol) and methanesulfonyl chloride (0.072 mL, 0.924 mmol) were added in sequence. After 25 min, dichloromethane (50 mL) and water (25 mL) were added. The layers were separated. The aqueous layer was extracted with dichloromethane (15 mL). The organic layers were combined and the combined solution was dried with sodium sulfate. The dried solution was filtered. Celite (5 g) was added to the filtrate and the solvents were removed by rotary evaporation to provide a free-flowing powder. The powder was loaded onto a silica gel column. Elution with dichloromethane initially, grading to 7% methanol-dichloromethane provided the title compound as a white solid, which was not pure. Additional purification by rp-HPLC(H$_2$O/acetonitrile/TFA) followed by partitioning between dichloromethane and saturated aqueous sodium bicarbonate solution to neutralize any ammonium salts provided the title compound as a white solid. $^1$H NMR (400 MHz, CDCl$_3$) δ ppm 8.38 (d, J=2.0 Hz, 1H), 8.02 (d, J=8.8 Hz, 1H), 7.54 (d, J=8.1 Hz, 2H), 7.49 (s, 1H), 7.44-7.40 (m, 1H), 7.21 (d, J=8.0 Hz, 2H), 5.25 (s, 1H), 4.51 (s, 2H), 4.27-4.08 (m, 3H), 3.72 (s, 3H), 3.63-3.51 (m, 2H), 2.99-2.87 (m, 5H), 1.35-1.27 (m, 3H); MS (ESI): mass calcd. for $C_{27}H_{27}ClF_3N_5O_3S$, 593.1; m/z found, 594.0 [M+H]$^+$.

(4-Chloro-2-ethyl-3-(4-(trifluoromethyl)benzyl)quinolin-6-yl)(1-methyl-1H-1,2,3-triazol-5-yl)(1-(methylsulfonyl) azetidin-3-yl)methanol was purified by chiral SFC (Chiralpak AD-H column, 5 μm, 250 mm×20 mm, mobile phase: 75% carbon dioxide, 25% isopropanol) to give two enantiomers. The first eluting enantiomers was Example 91B: $^1$H NMR (400 MHz, CDCl$_3$) δ ppm 8.36 (d, J=2.0 Hz, 1H), 8.03 (d, J=8.8 Hz, 1H), 7.57 (s, 1H), 7.54 (d, J=8.0 Hz, 2H), 7.41 (dd, J=8.8, 2.1 Hz, 1H), 7.21 (d, J=7.9 Hz, 2H), 4.51 (s, 2H), 4.28-4.22 (m, 1H), 4.17-4.09 (m, 2H), 3.90 (s, 1H), 3.73 (s, 3H), 3.67-3.54 (m, 2H), 2.98-2.90 (m, 2H), 2.89 (s, 3H), 1.34-1.28 (m, 3H); MS (ESI): mass calcd. for $C_{27}H_{27}ClF_3N_5O_3S$, 593.1; m/z found, 594.0 [M+H]$^+$ and the second eluting enantiomer was Example 91C: $^1$H NMR (400 MHz, CDCl$_3$) δ ppm 8.36 (d, J=2.0 Hz, 1H), 8.03 (d, J=8.8 Hz, 1H), 7.59 (s, 1H), 7.54 (d, J=8.0 Hz, 2H), 7.43-7.39 (m, 1H), 7.21 (d, J=8.0 Hz, 2H), 4.51 (s, 2H), 4.30-4.23 (m, 1H), 4.15-4.07 (m, 2H), 3.73 (s, 3H), 3.69-3.55 (m, 3H), 2.99-2.90 (m, 2H), 2.89 (s, 3H), 1.33-1.28 (m, 3H); MS (ESI): mass calcd. for $C_{27}H_{27}ClF_3N_5O_3S$, 593.1; m/z found, 594.0 [M+H]$^+$.

Example 92A (2-(Azetidin-1-yl)-4-chloro-3-(4-(trifluoromethyl) benzyl)quinolin-6-yl)(1-methyl-1H-imidazol-5-yl) (6-(trifluoromethyl)pyridin-3-yl)methanol

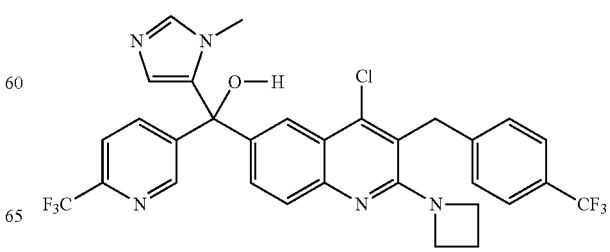

To a 75 mL sealed tube was added (2,4-dichloro-3-(4-(trifluoromethyl)benzyl)quinolin-6-yl)(1-methyl-1H-imidazol-5-yl)(6-(trifluoromethyl)pyridin-3-yl)methanol (2.50 g, 4.09 mmol, intermediate 60), azetidine (0.83 mL, 12.3 mmol) and dimethylformamide (30 mL). The reaction vessel was sealed and heated in a 100° C. oil bath. After overnight heating, the vessel was cooled and contents transferred to a separatory funnel with ethyl acetate dilution. The organic phase was extracted with a saturated, aqueous ammonium chloride solution and deionized water. The organic phase was separated, dried over magnesium sulfate, filtered and evaporated to dryness under reduced pressure. Chromatography on silica gel (dichloromethane increasing to 10% ((2M ammonia in methanol)) in dichloromethane)) provided the title compound. MS (ESI): mass calcd. for $C_{31}H_{24}ClF_6N_5O$, 631.16; m/z found, 632.5 [M+H]$^+$. $^1$H NMR (600 MHz, Chloroform-d) δ 8.81 (d, J=2.2 Hz, 1H), 8.05 (d, J=2.1 Hz, 1H), 7.87 (dd, J=8.3, 2.2 Hz, 1H), 7.70 (d, J=8.8 Hz, 1H), 7.60 (d, J=8.3 Hz, 1H), 7.52 (d, J=8.0 Hz, 2H), 7.46 (dd, J=8.8, 2.2 Hz, 1H), 7.21 (d, J=8.0 Hz, 2H), 7.09 (d, J=1.1 Hz, 1H), 6.19 (d, J=1.1 Hz, 1H), 4.32 (s, 2H), 4.13 (t, J=7.7 Hz, 4H), 3.31 (s, 3H), 2.29-2.20 (m, 2H).

Racemic (2-(azetidin-1-yl)-4-chloro-3-(4-(trifluoromethyl)benzyl)quinolin-6-yl)(1-methyl-1H-imidazol-5-yl)(6-(trifluoromethyl)pyridin-3-yl)methanol was purified via chiral SFC (Stationary phase: CHIRALPAK AD-H 5 μm 250×20 mm, Mobile phase: 60% $CO_2$, 40% mixture of MeOH/iPrOH 50/50 v/v) to provide two enantiomers: Example 92B: MS (ESI): mass calcd. for $C_{31}H_{24}ClF_6N_5O$, 631.16; m/z found, 632.5 [M+H]$^+$. $^1$H NMR (400 MHz, Chloroform-d) δ 8.79 (d, J=2.1 Hz, 1H), 8.05 (d, J=2.1 Hz, 1H), 7.86 (dd, J=8.2, 2.2 Hz, 1H), 7.69 (d, J=8.8 Hz, 1H), 7.61 (d, J=8.2 Hz, 1H), 7.52 (d, J=8.1 Hz, 2H), 7.46 (dd, J=8.8, 2.1 Hz, 1H), 7.20 (d, J=8.0 Hz, 2H), 7.08 (s, 1H), 6.18 (s, 1H), 4.31 (s, 2H), 4.13 (t, J=7.6 Hz, 4H), 3.31 (s, 3H), 2.24 (p, J=7.5 Hz, 2H), and Example 92C: MS (ESI): mass calcd. for $C_{31}H_{24}ClF_6N_5O$, 631.16; m/z found, 632.5 [M+H]$^+$. $^1$H NMR (400 MHz, Chloroform-d) δ 8.79 (d, J=2.4 Hz, 1H), 8.05 (d, J=2.1 Hz, 1H), 7.86 (dd, J=8.2, 2.2 Hz, 1H), 7.69 (d, J=8.8 Hz, 1H), 7.61 (dd, J=8.2, 0.8 Hz, 1H), 7.52 (d, J=8.1 Hz, 2H), 7.46 (dd, J=8.8, 2.2 Hz, 1H), 7.20 (d, J=7.9 Hz, 2H), 7.08 (s, 1H), 6.18 (d, J=1.2 Hz, 1H), 4.31 (s, 2H), 4.13 (t, J=7.6 Hz, 4H), 3.30 (s, 3H), 2.24 (p, J=7.5 Hz, 2H).

Example 93

(4-Chloro-2-methoxy-3-(4-(trifluoromethyl)benzyl)quinolin-6-yl)bis(1,2-dimethyl-1H-imidazol-5-yl)methanol

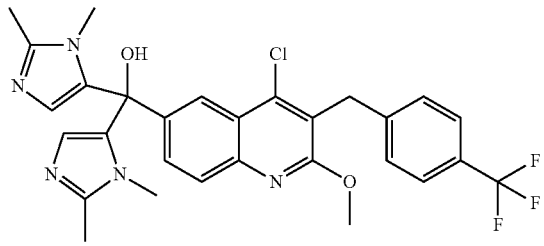 [SMILES: COc1nc2ccc(C(O)(c3cnc(C)n3C)c3cnc(C)n3C)cc2c(Cl)c1Cc1ccc(C(F)(F)F)cc1]

n-BuLi (2.66 M in hexanes, 0.963 mL, 2.56 mmol) was added dropwise to a stirred slurry of 5-bromo-1,2-dimethyl-1H-imidazole (470 mg, 2.68 mmol) in THF (7 mL) at ~−70° C. under argon. After stirring for another 7 min, the slurry was treated dropwise over 5 min with a solution of methyl 4-chloro-2-methoxy-3-(4-(trifluoromethyl)benzyl)quinoline-6-carboxylate (500 mg, 1.22 mmol, Intermediate 64) in THF (6 mL). The reaction was stirred in the dry ice/acetone bath for another 10 min, then removed from the cold bath and stirred for 6 min, then stirred in an ice bath for 2 min, then quenched with 5 M NH$_4$Cl (0.77 mL, 3.85 mmol) to give an orange solution. The reaction was dried (Na$_2$SO$_4$), filtered, and concentrated, and the residue was purified by silica flash column chromatography (0-10% MeOH/DCM) to provide the title compound. $^1$H NMR (400 MHz, CDCl$_3$) δ 8.21 (d, J=1.97 Hz 1H), 7.68 (d, J=8.59 Hz, 1H), 7.52 (d, J=8.08 Hz, 2H), 7.37-7.44 (m, 3H), 6.19 (s, 2H), 4.90 (br s, 1H), 4.33 (s, 2H), 4.06 (s, 3H), 3.41 (s, 6H), 2.30 (s, 6H); MS m/e 570.2 (M+H).

Example 94A (4-Chloro-2-methoxy-3-((6-(trifluoromethyl)pyridin-3-yl)methyl)quinolin-6-yl)(1-methyl-1H-imidazol-5-yl)(6-(trifluoromethyl)pyridin-3-yl)methanol

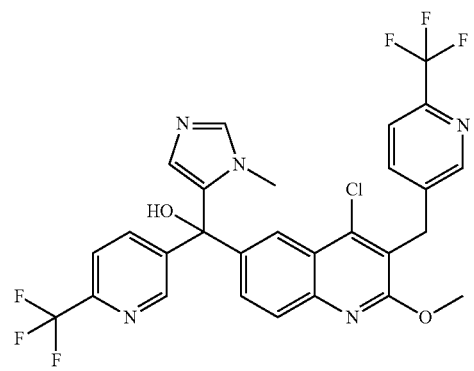 [SMILES: COc1nc2ccc(C(O)(c3ccc(C(F)(F)F)nc3)c3cncn3C)cc2c(Cl)c1Cc1ccc(C(F)(F)F)nc1]

A solution of n-BuLi (2.5 M in hexanes, 2.75 mL, 6.88 mmol) was added drop-wise by syringe to a solution of 6-bromo-4-chloro-2-methoxy-3-((6-(trifluoromethyl)pyridin-3-yl)methyl)quinolone (3.00 g, 6.95 mmol, Intermediate 65: step c) in dry THF (35 mL) in a dry ice-acetone bath. After 1.5 min, a solution of 1-methyl-1H-imidazol-5-yl)(6-(trifluoromethyl)pyridin-3-yl)methanone (1.69 g, 6.61 mmol, Intermediate 36: step c) in dry THF (25 mL) was added drop-wise via syringe. An additional 10 mL of THF was used to complete the quantitative addition. The reaction mixture was stirred for 7 minutes in the dry ice-acetone bath, then placed into an ice-water bath. After 10 min, the ice-water bath was removed and the mixture was allowed to warm to ambient temperature. The reaction was quenched with saturated aqueous ammonium chloride and the mixture was partitioned between water and DCM. The layers were separated and the aqueous phase was further extracted with DCM. The organic phase was dried (Na$_2$SO$_4$), filtered, and concentrated to dryness. The crude product was purified by flash column chromatography (silica gel, 0-5% MeOH-DCM) to provide the title compound. $^1$H NMR (400 MHz, CDCl$_3$) δ 8.81 (d, J=2.1 Hz, 1H), 8.71 (d, J=2.1 Hz, 1H), 8.17 (d, J=2.1 Hz, 1H), 7.88 (ddd, J=8.3, 2.4, 0.9 Hz, 1H), 7.81 (d, J=8.8 Hz, 1H), 7.76 (ddd, J=8.2, 2.2, 1.0 Hz, 1H), 7.62 (dd, J=8.2, 0.9 Hz, 1H), 7.58-7.54 (m, 2H), 7.17-7.15 (m, 1H), 6.71 (s, 1H), 6.22 (d, J=1.2 Hz, 1H), 4.34 (s, 2H), 4.08 (s, 3H), 3.32 (s, 3H). MS m/e 608.0 (M+H).

Example 94

Example 94A was purified by chiral SFC (ChiralPak AD, 75:25 CO$_2$/ethanol) to provide two pure enantiomers. The first eluting enantiomer Example 94B: $^1$H NMR (400 MHz, CDCl$_3$) δ 8.80 (d, J=2.2 Hz, 1H), 8.72-8.70 (m, 1H), 8.17-8.15 (m, 1H), 7.91-7.88 (m, 1H), 7.81 (dd, J=8.7, 0.6 Hz, 1H), 7.78-7.73 (m, 1H), 7.65 (dd, J=8.3, 0.8 Hz, 1H), 7.58-7.54 (m, 2H), 7.25 (s, 1H), 6.29 (d, J=1.2 Hz, 1H), 5.71 (s, 1H), 4.34 (s, 2H), 4.08 (s, 3H), 3.34 (s, 3H). MS m/e 608.1 (M+H) and the second eluting enantiomer Example 94C: $^1$H NMR (500 MHz, CDCl$_3$) δ 8.80 (d, J=2.3 Hz, 1H), 8.72 (d, J=2.0 Hz, 1H), 8.15 (d, J=2.1 Hz, 1H), 7.91-7.88 (m, 1H), 7.82 (d, J=8.6 Hz, 1H), 7.77-7.74 (m, 1H), 7.65 (d, J=8.3 Hz, 1H), 7.58-7.54 (m, 2H), 7.29 (s, 1H), 6.33 (s, 1H), 5.22 (s, 1H), 4.34 (s, 2H), 4.08 (s, 3H), 3.35 (s, 3H). MS m/e 608.1 (M+H).

Example 95

(4-Chloro-2-methoxy-3-(4-(trifluoromethyl)benzyl)quinolin-6-yl)(4-chlorophenyl)(1-methyl-1H-imidazol-5-yl)methanol

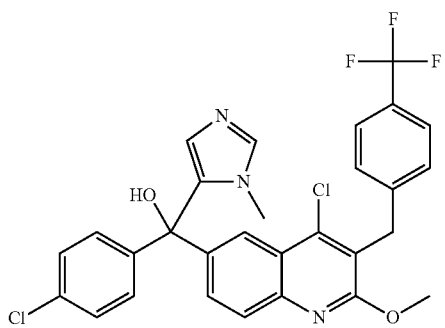 [SMILES: COc1nc2ccc(C(O)(c3ccc(Cl)cc3)c3cncn3C)cc2c(Cl)c1Cc1ccc(C(F)(F)F)cc1]

A solution of n-BuLi (2.5 M in hexanes, 4.6 mL, 11.5 mmol) was added drop-wise by syringe to a solution of 6-bromo-4-chloro-2-methoxy-3-(4-(trifluoromethyl)benzyl)quinoline (5.0 g, 11.6 mmol, Intermediate 47: step d) in dry THF (58 mL) in a dry ice-acetone bath. After 1 min, a solution of (4-chlorophenyl)(1-methyl-1H-imidazol-5-yl)methanone (2.6 g, 11.6 mmol, Intermediate 1: step b) in dry THF (58 mL) was added drop-wise via syringe. An additional 10 mL of THF was used to complete the quantitative addition. The reaction mixture was stirred for 5 minutes in the dry ice-acetone bath then placed into an ice-water bath. After 10 minutes, the ice-water bath was removed and the mixture was allowed to warm to ambient temperature. The reaction was quenched with saturated aqueous ammonium chloride and the mixture was partitioned between water and DCM. The layers were separated and the aqueous phase was further extracted with DCM. The organic phase was dried (Na$_2$SO$_4$), filtered, and concentrated. Crude product was purified by flash column chromatography (silica gel, 0-3% MeOH-DCM) to provide the title compound. $^1$H NMR (400 MHz, CDCl$_3$) δ 8.12 (d, J=2.1 Hz, 1H), 7.77 (d, J=8.7 Hz, 1H), 7.53 (dd, J=8.8, 2.1 Hz, 1H), 7.51-7.47 (m, 2H), 7.40-7.36 (m, 2H), 7.28-7.32 (m, 4H), 7.23-7.21 (m, 1H), 6.29 (d, J=1.2 Hz, 1H), 5.06 (s, 1H), 4.32 (s, 2H), 4.07 (s, 2H), 3.33 (s, 3H). MS m/e 572.0 (M+H).

Example 96

6-((4-cyanophenyl)(hydroxy)(1-methyl-1H-imidazol-5-yl)methyl)-2-methoxy-3-(4-(trifluoromethyl)benzyl)quinoline-4-carbonitrile

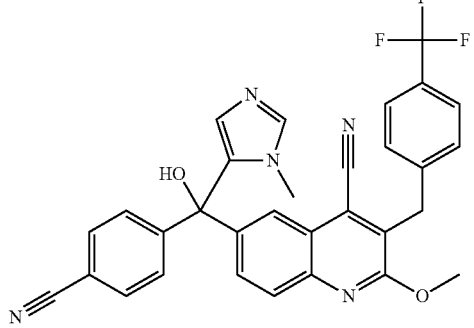

(4-chloro-2-methoxy-3-(4-(trifluoromethyl)benzyl)quinolin-6-yl)(4-chlorophenyl)(1-methyl-1H-imidazol-5-yl)methanol (2.8 g, 4.9 mmol, Example 95), zinc cyanide (1.7 g, 9.9 mmol), zinc dust (82.6 mg, 1.3 mmol), X-Phos (457.8 mg, 1.0 mmol), and Pd$_2$(dba)$_3$ (457 mg, 0.5 mmol) were charged to a round-bottom flask. The flask was evacuated and back-filled with nitrogen. Dimethylacetamide (34 mL) was sparged with argon and added to the mixture. Argon was bubbled through the reaction mixture for 1 minute then the flask was sealed and put under a positive pressure of nitrogen. The reaction mixture was stirred and heated at 120° C. overnight. The mixture was allowed to cool to ambient temperature, filtered through Celite®, and rinsed with excess DCM. The filtrate was washed with saturated aqueous sodium bicarbonate, the layers were separated and the aqueous layer was extracted with DCM. The combined organic layers were dried (Na$_2$SO$_4$), filtered, and concentrated to dryness. The crude product was purified by flash column chromatography (silica gel, 0-5% MeOH-DCM) to provide the title compound. $^1$H NMR (400 MHz, CDCl$_3$) δ 8.18-8.15 (m, 1H), 7.82-7.78 (m, 1H), 7.66-7.61 (m, 2H), 7.57-7.51 (m, 4H), 7.51-7.44 (m, 3H), 7.18-7.16 (m, 1H), 6.31 (s, 1H), 6.27 (d, J=1.1 Hz, 1H), 4.37 (s, 2H), 4.10 (s, 3H), 3.33 (s, 3H). MS m/e 554.2 (M+H).

Example 96A was purified by chiral SFC (ChiralPak IC, 60:40 CO$_2$/isopropanol (0.3% isopropylamine)) to provide two pure enantiomers. The first eluting enantiomer Example 96B: $^1$H NMR (500 MHz, CDCl$_3$) δ 8.16-8.14 (m, 1H), 7.80 (d, J=8.8 Hz, 1H), 7.67-7.64 (m, 2H), 7.56-7.52 (m, 4H), 7.50 (dd, J=8.8, 2.1 Hz, 1H), 7.48-7.44 (m, 2H), 6.34 (d, J=1.1 Hz, 1H), 5.35 (s, 1H), 4.37 (s, 2H), 4.10 (s, 3H), 3.35 (s, 3H). MS m/e 554.2 (M+H) and the second eluting enantiomer Example 96C: $^1$H NMR (500 MHz, CDCl$_3$) δ 8.15 (d, J=2.1 Hz, 1H), 7.80 (d, J=8.8 Hz, 1H), 7.67-7.63 (m, 2H), 7.57-7.52 (m, 4H), 7.49 (dd, J=8.8, 2.1 Hz, 1H), 7.48-7.44 (m, 2H), 7.24 (d, J=1.3 Hz, 1H), 6.32 (d, J=1.1 Hz, 1H), 5.54 (s, 1H), 4.37 (s, 2H), 4.10 (s, 3H), 3.35 (s, 3H). MS m/e 554.2 (M+H).

Example 97A 1-(3-((4-Chloro-2-methoxy-3-(4-(trifluoromethyl)benzyl)quinolin-6-yl)(hydroxy)(1-methyl-1H-1,2,3-triazol-5-yl)methyl)azetidin-1-yl)ethanone

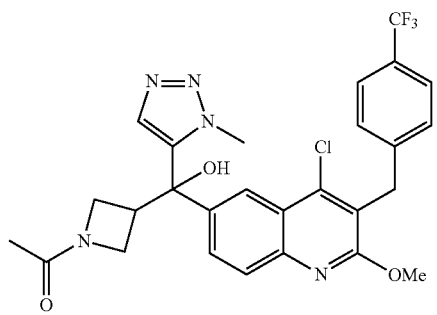 [SMILES: COc1nc2ccc(C(O)(c3cnnn3C)C3CN(C(C)=O)C3)cc2c(Cl)c1Cc1ccc(C(F)(F)F)cc1]

To a flask containing azetidin-3-yl(4-chloro-2-methoxy-3-(4-(trifluoromethyl)benzyl)quinolin-6-yl)(1-methyl-1H-1,2,3-triazol-5-yl)methanol (140 mg, 0.27 mmol, Intermediate 66: step d) was added dichloromethane (8 mL) which gave a suspension at room temperature. $Et_3N$ (0.13 mL, 0.9 mmol) was added, followed by acetic anhydride (0.3 mL, 0.32 mmol). After stirring at room temperature for 4 h, more $Et_3N$ (200 µL) was added along with more acetyl chloride (25 µL) and the suspension was heated to 35° C. for 18 h. The reaction was quenched with the addition of 1N NaOH (2 mL) and water (5 mL). The aqueous portion was extracted with dichloromethane (3×25 mL). The combined organics were dried over $MgSO_4$, filtered and concentrated. The crude material was chromatographed on silica gel (5% MeOH-dichloromethane) to give the title compound (88 mg) as an off white solid. $^1H$ NMR (500 MHz, $CD_3CN$, racemate) δ 8.25 (dd, J=14.0, 1.9 Hz, 1H), 7.74 (dd, J=8.7, 2.6 Hz, 1H), 7.66 (d, J=4.4 Hz, 1H), 7.58-7.49 (m, 2H), 7.48-7.33 (m, 3H), 5.17 (s, 0.5H), 5.06 (s, 0.5H), 4.43-4.28 (m, 3H), 4.22-4.10 (m, 1H), 4.07-3.98 (m, 4H), 3.93 (dd, J=9.9, 6.0 Hz, 1H), 3.82 (dd, J=9.1, 5.6 Hz, 1H), 3.72 (t, J=8.6 Hz, 1H), 3.65-3.48 (m, 5H). MS (ESI) 560.1 $[M+H]^+$.

The racemic material was resolved using SFC (Stationary phase: CHIRALCEL OJ-H 5 µm 250×20 mm), Mobile phase: 70% $CO_2$, 30% MeOH (0.3% $iPrNH_2$), yielding Example 97B: the first enantiomer eluted and Example 97C: the second enantiomer eluted.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS 1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 µL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 µM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the renilla luciferase gene under control of the SV40 promoter. *Renilla* luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 ng of pBIND-RORγt LBD or pBIND-RORγt LBD-AF2 and 5 µg pGL4.31 (Promega Cat no. C935A) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 µL 1× Glo Lysis Buffer (Promega). Dual Glo Luciferase Reagent (50 µL/well) was then added and firefly luciferase luminescence was read on an Envision after a ten minute incubation. Finally, Stop and Glo reagent (50 µL/well) was added and renilla luciferase luminescence was read on an Envision after a ten minute incubation. To calculate the effect of compounds on RORγt activity, the ratio of firefly to renilla luciferase was determined and plotted against compound concentration. Agonist compounds increase RORγt-driven luciferase expression, and antagonist or inverse agonist compounds decrease luciferase expression.

Human Th17 Assay

The human Th17 assay tests the effect of RORγt modulatory compounds on IL-17 production by CD4 T cells under conditions which favor Th17 differentiation.

Total CD4+ T cells were isolated from the peripheral blood mononuclear cells (PBMC) of healthy donors using a CD4+ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5\times10^5$ per 100 µL per well. 50 µL of compound at titrated concentrations in DMSO were added into each well at final DMSO concentration at 0.2%. Cells were incubated for 1 hour, then 50 µL of Th17 cell differentiation medium was added to each well. The final concentrations of antibodies and cytokines (R&D Systems) in differentiation medium were: $3\times10^6$/mL anti-CD3/CD28 beads (prepared using human T cell activation/expansion kit, Miltenyi Biotec), 10 µg/mL anti-IL4, 10 µg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor ® Assay, Kd µM | RORγt reporter Assay, $IC_{50}$ µM | RORγt reporter Assay, % inhibition @ 6 µM | Human Th17 Assay, $IC_{50}$ µM |
|---|---|---|---|---|
| 1 | 0.018 | 0.35 | 72 | 0.59 |
| 2 | 0.017 | 0.05 | 70 | ND |
| 3 | 0.032 | >6 | 30 | ND |
| 4 | 0.0077 | ~6 | 46 | ND |
| 5 | 0.011 | 0.057 | 117 | 0.066 |
| 6 | 0.015 | ~2 | 96 | ND |
| 7 | 0.04 | >6 | 32 | ND |
| 8 | 0.043 | 0.068 | 103 | 0.079 |
| 9 | 0.00083 | 0.0065 | 85 | 0.085 |
| 10 | 0.099 | 2.3 | 77 | ND |
| 11 | 0.075 | 0.16 | 104 | 0.3 |
| 12 | 0.016 | ~7 | 77 | ND |
| 13 | 0.031 | ~1 | 70 | ND |
| 14 | 0.091 | 0.56 | 74 | ND |
| 15 | 0.0043 | 0.013 | 104 | 0.024 |
| 16 | 0.0066 | 0.038 | 104 | 0.054 |
| 17 | 0.31 | 0.38 | 96 | 1.2 |
| 18 | 0.0045 | >6 | 41 | ND |
| 19 | 0.0027 | 6.6 | 57 | ND |
| 20A | 0.0038 | 0.026 | 101 | 0.015 |
| 20B | 0.0014 | 0.047 | 100 | 0.039 |
| 20C | 0.0053 | 0.06 | 102 | 0.069 |
| 21 | 0.0061 | 0.036 | 103 | ND |
| 22 | 0.0028 | 0.091 | 96 | 0.016 |
| 23 | 0.004 | 0.014 | 95 | 0.15 |
| 24 | 0.75 | >6 | 35 | ND |
| 25 | 0.44 | 0.33 | 87 | 0.38 |
| 26 | 0.22 | 0.48 | 85 | ND |
| 27 | 0.085 | 0.29 | 97 | 0.3 |
| 28A | 0.053 | 0.18 | 100 | 0.2 |
| 28B | 1.6 | 1.1 | 90 | ND |
| 28C | 0.0058 | 0.087 | 97 | 0.066 |
| 29A | 0.0048 | 0.091 | 96 | ND |
| 29B | 0.093 | 0.13 | 102 | 0.19 |
| 29C | 0.0049 | 0.081 | 97 | 0.09 |
| 30 | 0.0022 | 0.025 | 98 | 0.063 |
| 31 | 0.064 | 0.19 | 103 | 0.28 |
| 32 | 0.033 | 0.11 | 103 | 1.8 |
| 33A | 0.043 | 0.19 | 101 | 0.14 |
| 33B | 0.81 | 0.67, ~4 | 87 | ND |
| 33C | 0.02 | 0.073 | 99 | 0.067 |
| 34 | 0.25 | 0.46 | 101 | 1.8 |
| 35A | 0.008 | 0.16 | 97 | 0.3 |
| 35B | 0.07 | 0.17 | 99 | 0.074 |
| 35C | 0.005 | 0.089 | 97 | 0.051 |
| 36A | 0.04 | 0.18 | 98 | 0.1 |
| 36B | 0.4 | 0.74 | 62 | ND |
| 36C | 0.011 | 0.1 | 101 | 0.066 |
| 37A | 0.0078 | 0.028 | 100 | 0.12 |
| 37B | 0.044 | 0.16 | 99 | 0.11 |
| 37C | 0.0035 | 0.11 | 102 | 0.15 |
| 38 | 0.0039 | ~0.007 | 93 | ND |
| 39 | 0.021 | 0.057 | 97 | ND |
| 40 | 0.02 | 0.31 | 90 | 0.25 |
| 41 | 0.029 | 0.12 | 107 | 0.2 |
| 42 | 0.36 | 0.18 | 96 | ND |
| 43 | 0.049 | 0.059 | 112 | 0.089 |
| 44 | 0.015 | 0.057 | 96 | 0.082 |
| 45 | 0.068 | 0.13 | 103 | 0.1 |
| 46 | 0.022 | 0.052 | 89 | ND |
| 47 | 0.14 | 0.17 | 102 | 0.18 |
| 48 | 0.01 | 0.058 | 100 | 0.04 |
| 49 | 0.33 | 1.8 | 77 | ND |
| 50 | 0.32 | >6 | 71 | ND |
| 51 | 1.1 | 1.9 | 98 | ND |
| 52 | 1.9 | >6 | 34 | ND |
| 53 | 0.037 | 0.046 | 101 | ND |
| 54A | ND | ND | ND | ND |
| 54B | 0.84 | 2 | 86 | ND |
| 54C | 0.023 | 0.098 | 93 | 0.057 |
| 55A | 7.6 | 1.7 | 94 | ND |
| 55B | >81 | 2.4 | 85 | ND |
| 55C | 3.5 | 3.2 | 92 | ND |
| 56 | 0.00029 | 0.012 | 102 | ND |

TABLE 1-continued

| Example Number | ThermoFluor ® Assay, Kd μM | RORγt reporter Assay, IC$_{50}$ μM | RORγt reporter Assay, % inhibition @ 6 μM | Human Th17 Assay, IC$_{50}$ μM |
|---|---|---|---|---|
| 57 | 0.0084 | 0.057 | 100 | ND |
| 58A | ND | ND | ND | ND |
| 58B | 0.014 | 0.055 | 103 | 0.1 |
| 58C | 0.27 | 0.66 | 109 | ND |
| 59A | ND | ND | ND | ND |
| 59B | 0.0044 | 0.14 | 106 | 0.098 |
| 59C | 0.22 | 0.57 | 108 | ND |
| 60A | 0.018 | 0.069 | 102 | ND |
| 60B | 0.033 | 0.059 | 107 | 0.17 |
| 60C | 0.02 | 0.046 | 100 | 0.16 |
| 61 | 0.005 | 0.0066, <0.002 | 91 | 0.0042 |
| 62A | 0.0095 | 0.098 | 97 | ND |
| 62B | 0.033 | 0.13 | 99 | 0.1 |
| 62C | 0.0015 | 0.12 | 102 | 0.064 |
| 63A | 0.037 | 0.11 | 90 | ND |
| 63B | 0.35 | 0.77 | 88 | ND |
| 63C | 0.0062 | 0.14 | 94 | 0.038 |
| 64A | 0.063 | 0.033 | 99 | ND |
| 64B | 0.45 | 0.56 | 101 | ND |
| 64C | 0.016 | 0.096, ~0.5 | 94 | 0.086 |
| 65A | ND | ND | ND | ND |
| 65B | 0.14 | 0.13 | 101 | 0.22 |
| 65C | 0.0042 | 0.046 | 100 | 0.045 |
| 66A | ND | ND | ND | ND |
| 66B | 0.27 | 0.42 | 95 | 1.1 |
| 66C | 0.0079 | 0.029 | 101 | 0.04 |
| 67A | 0.018 | 0.044 | 115 | ND |
| 67B | 0.0063 | 0.035 | 101 | 0.01 |
| 67C | 0.057 | 0.12 | 101 | 0.1 |
| 68A | 0.0083 | 0.21 | 99 | ND |
| 68B | 0.0021 | ~0.05 | 96 | 0.01 |
| 68C | 0.03 | 0.21 | 100 | 0.2 |
| 69 | 0.05 | 0.17 | 103 | ND |
| 70A | ND | ND | ND | ND |
| 70B | 1.1 | 1 | 101 | ND |
| 70C | 16 | 1.6 | 85 | ND |
| 71A | ND | 0.11 | 97 | ND |
| 71B | 0.0016 | 0.011 | 105 | 0.011 |
| 71C | 0.13 | 0.26 | 103 | 0.3 |
| 72A | ND | ND | ND | ND |
| 72B | 0.00071 | 0.031 | 99 | 0.025 |
| 72C | 0.0071 | 0.047 | 100 | 0.055 |
| 73A | ND | ND | ND | ND |
| 73B | 0.0045 | 0.046 | 97 | 0.02 |
| 73C | 0.034 | 0.31 | 99 | 0.13 |
| 74A | ND | ND | ND | ND |
| 74B | 1.3 | 0.17 | 95 | 0.091 |
| 74C | 21 | 0.93 | 90 | ND |
| 75A | ND | ND | ND | ND |
| 75B | 8.6 | >6 | 39 | ND |
| 75C | 0.15 | 0.18 | 90 | 0.14 |
| 76A | ND | ND | ND | ND |
| 76B | 0.076 | 0.12 | 102 | ND |
| 76C | 0.015 | 0.045 | 101 | 0.033 |
| 77A | 0.0011 | 0.032, ~0.008 | 103 | ND |
| 77B | 0.32 | 0.25 | 98 | 0.36 |
| 77C | 0.00014 | 0.0075, ~0.003 | 100 | 0.0021 |
| 78A | 0.00052 | 0.011 | 97 | ND |
| 78B | 0.12 | 0.15 | 94 | ND |
| 78C | 0.00028 | 0.0017 | 99 | 0.004 |
| 79A | ND | ND | ND | ND |
| 79B | 0.057 | 0.038 | 99 | 0.052 |
| 79C | 0.000024 | 0.0025 | 94 | 0.0015 |
| 80A | 0.00014 | 0.011 | 103 | ND |
| 80B | 0.00011 | 0.0030, ~0.004 | 92 | 0.05 |
| 80C | 0.000026 | 0.0048, ~0.08 | 93 | 0.002 |
| 81A | 0.00012 | 0.0021 | 104 | ND |
| 81B | 0.00005 | 0.0020, ~0.0002 | 104 | 0.0022 |
| 81C | 0.00012 | 0.0050, ~0.0001 | 103 | 0.002 |
| 82 | 0.00063 | 0.0066 | 94 | ND |
| 83A | 0.012 | 0.039 | 104 | ND |
| 83B | 0.0047 | 0.024, ~0.07 | 100 | 0.016 |
| 83C | 0.077 | 0.14 | 103 | 0.12 |
| 84 | ND | ND | ND | ND |
| 85 | 0.085 | 0.29 | 97 | 0.3 |
| 86 | ND | ND | ND | ND |
| 87A | ND | ND | ND | ND |
| 87B | 2.3 | 0.85 | 95 | ND |
| 87C | 0.0013 | 0.012 | 99 | 0.0045 |
| 88A | ND | ND | ND | ND |
| 88B | 0.029 | 0.14 | 96 | ND |
| 88C | 0.00004 | 0.0088 | 95 | 0.0028 |
| 89 | 0.00077 | 0.021 | 102 | ND |
| 90A | 0.00044 | 0.011 | 98 | ND |
| 90B | 0.00056 | ~0.004 | 98 | 0.012 |
| 90C | 0.00032 | 0.0054 | 98 | 0.0061 |
| 91A | 0.00025 | 0.0022 | 100 | ND |
| 91B | 0.0061 | 0.029 | 97 | 0.022 |
| 91C | 0.00023 | ~0.006 | 102 | 0.0025 |
| 92A | 0.0025 | 0.029 | 100 | ND |
| 92B | 0.012 | 0.1 | 96 | 0.034 |
| 92C | 0.0014 | 0.017 | 97 | 0.0086 |
| 93 | 0.000017 | 0.16 | 87 | 0.01 |
| 94A | 0.012 | 0.069 | 98 | ND |
| 94B | 0.098 | 0.21 | 96 | 1.9 |
| 94C | 0.0065 | 0.16 | 95 | 0.048 |
| 95 | 0.018 | 0.16 | 99 | ND |
| 96A | 0.0019 | 0.0078 | 99 | ND |
| 96B | 0.048 | 0.16 | 97 | 0.05 |
| 96C | 0.0022 | 0.018 | 97 | 0.0045 |
| 97A | 0.0014 | 0.0042 | 100 | 0.0014 |
| 97B | 0.0014 | 0.0059 | 98 | 0.0034 |
| 97C | 0.00064 | ~0.004 | 99 | 0.015 |

All data shown in Table 1 is either the value of one data point or the average of more than one data point. In cases where more than one value is shown in a table cell, values with qualifiers such as ~, > or < shown on the right side of the table cell could not be included in the averaging calculation for the value shown on the left side of the table cell.
ND—no data While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I wherein:

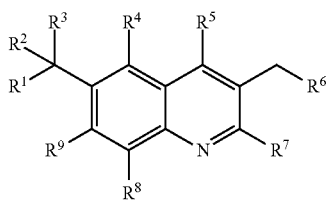

Formula I

R[1] is pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl;

wherein said pyridyl, pyridyl N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, -$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$, $SC_{(1-4)}$alkyl, $CF_3$, F, Cl, and $C_{(1-4)}$alkyl;

R[2] is triazolyl, pyridyl, pyridyl-N-oxide, pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N-$C_{(1-3)}$alkyl-piperidinyl, thiazolyl, pyridazyl, pyrazinyl, 1-(3-methoxypropyl)-imidazolyl, thiadiazolyl, oxadiazolyl, or imidazolyl;

wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, or $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyrazolyl is optionally substituted with up to three $CH_3$ groups;

R[3] is H, OH, $OCH_3$, or $NH_2$;

R[4] is H, or F;

R[5] is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, or 4-hydroxy-piperidinyl;

R[6] is phenyl, pyridyl, benzothiophenyl, thiophenyl, pyrimidinyl, pyridazyl, or pyrazinyl;

wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl or said pyridyl is optionally substituted up to two times with $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, or $OCH_2CF_3$; wherein the selection of each optional substituent is independent; and wherein said pyrazolyl, triazolyl, imidazolyl, tetrazolyl, oxazolyl, and thiazolyl are optionally substituted with $CH_3$;

R[7] is H, Cl, —CN, $C_{(1-4)}$alkyl, $OC_{(1-4)}$alkyl$CF_3$, $OCF_3$, $OCHF_2$, $OCH_2CH_2OC_{(1-4)}$alkyl, $CF_3$, $SCH_3$, $C_{(1-4)}$alkylN$A^1A^2$, $CH_2OC_{(2-3)}$alkylN$A^1A^2$, $NA^1A^2$, $C(O)NA^1A^2$, $CH_2NHC_{(2-3)}$alkylN$A^1A^2$, $CH_2N(CH_3)C_{(2-3)}$alkylN$A^1A^2$, $NHC_{(2-3)}$alkylN$A^1A^2$, $N(CH_3)C_{(2-4)}$alkylN$A^1A^2$, $OC_{(2-4)}$alkylN$A^1A^2$, $OC_{(1-4)}$alkyl, $OCH_2$-(1-methyl)-imidazol-2-yl, phenyl, thiophenyl, furyl, pyrazolyl, imidazolyl, pyridyl, pyridazyl, pyrazinyl, or pyrimidinyl; wherein said phenyl, thiophenyl, furyl, pyrazolyl, imidazolyl, pyridyl, pyridazyl, pyrazinyl, and pyrimidinyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

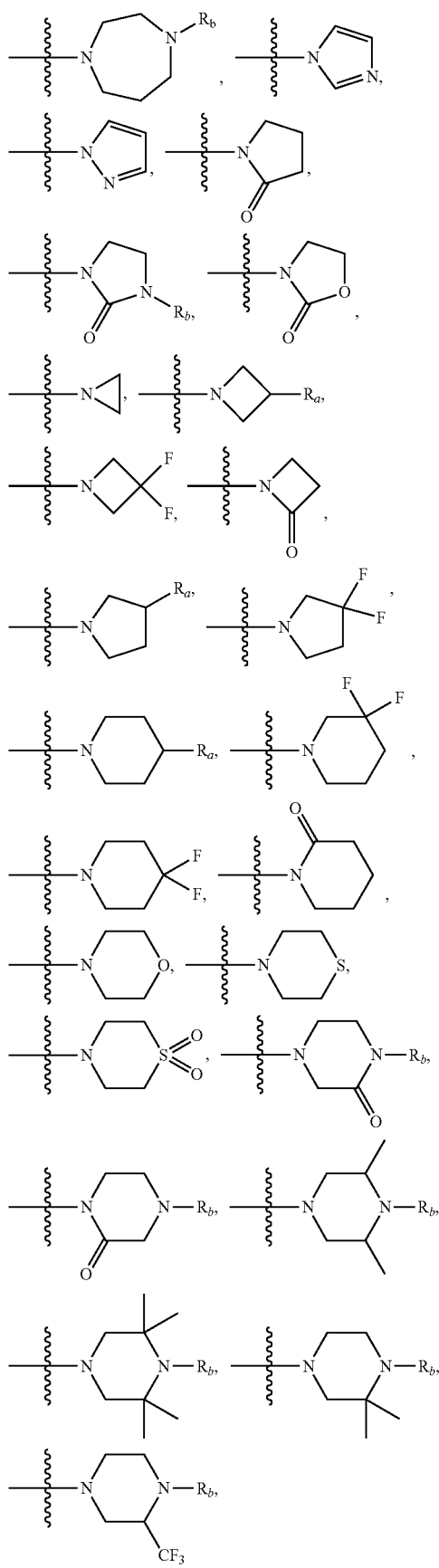

-continued

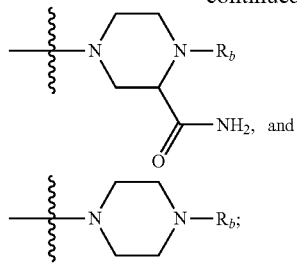

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl, $OC_{(1-3)}$alkyl, $CF_3$, $NH_2$, $NHCH_3$, —CN, or F;

$R^9$ is H, or F;

and pharmaceutically acceptable salts thereof;

provided that (4-chloro-2-methoxy-3-(4-(trifluoromethyl) benzyl)quinolin-6-yl)bis(1,2,5-trimethyl-1H-imidazol-4-yl)methanol, N-(2-((3-(4-(1H-pyrazol-1-yl)benzyl)-6-((4-chlorophenyl)(hydroxy)(l-methyl-1H-imidazol-5 -yl)methyl)-4-hydroxyquinolin-2-yl) oxy)ethyl)acetamide and (3-(4-(1H-pyrazol-1-yl)benzyl)-4-chloro-2-(4-methylpiperazin-1-yl)quinolin-6-yl)(1 -methyl- 1H-imidazol-5 -yl)(6-(trifluoromethyl) pyridin-3 -yl)methanol are excluded from the claim.

2. A compound of claim 1 wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, imidazolyl, phenyl, thiophenyl, benzoxazolyl, pyrazolyl, pyridyl, pyridyl N-oxide, pyrazinyl, pyrimidinyl, pyridazyl, or quinolinyl are optionally substituted with $C(O)C_{(1-4)}$ alkyl, $C(O)NH_2$, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3$ $OCH_3$, $SC_{(1-4)}$ alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$ alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$ alkyl, $(CH_2)_{(2-3)}OCH_3$, $SCH_3$, $CF_3$, F, Cl, and $C_{(1-2)}$ alkyl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$ alkyl, $(CH_2)_{(2-3)}OCH_3$, $SC_{(1-4)}$alkyl, $CF_3$, F, Cl, and $C_{(1-4)}$alkyl;

$R^2$ is 1-methyl triazolyl, pyridyl, pyridyl-N-oxide, 1-methyl pyrazolyl, pyrimidinyl, oxazolyl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N-$C_{(1-3)}$alkyl-piperidinyl, thiazolyl, pyridazyl, pyrazinyl, 1-(3-methoxypropyl)-imidazolyl, or 1-$C_{(1-2)}$alkyl imidazolyl; wherein said 1-$C_{(1-2)}$alkyl imidazolyl is optionally substituted with up to two additional substituents independently selected from the group consisting of $C_{(1-2)}$alkyl, $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, C(O)$NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiazolyl, oxazolyl and isoxazolyl are optionally substituted with up to two substituents independently selected from the group consisting of $SO_2CH_3$, $SO_2NH_2$, C(O)$NH_2$, —CN, $OC_{(1-2)}$alkyl, $(CH_2)_{(2-3)}OCH_3$, $SCH_3$, $CF_3$, F, Cl, and $C_{(1-2)}$alkyl; and said 1-methyl pyrazolyl is optionally substituted with up to two additional $CH_3$ groups;

$R^6$ is phenyl, pyridyl, benzothiophenyl, thiophenyl, pyrimidinyl, pyridazyl, or pyrazinyl;

wherein said phenyl or said pyridyl is optionally substituted with $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, CONHCH$_3$, $CON(CH_3)_2$, Cl, F, —CN, $CO_2H$, OH, $CH_2OH$, $NHCOC_{(1-2)}$alkyl, $COC_{(1-2)}$alkyl, or $SCH_3$;

$R^7$ is H, Cl, —CN, $C_{(1-4)}$alkyl, $OC_{(1-4)}$alkylCF$_3$, $OCH_2CH_2OC_{(1-4)}$alkyl, $CF_3$, $SCH_3$, $CH_2NA^1A^2$, $CH_2OC_{(2-3)}$alkylNA$^1$A$^2$, NA$^1$A$^2$, C(O)NA$^1$A$^2$, $N(CH_3)C_{(2-4)}$alkylNA$^1$A$^2$, $OC_{(2-4)}$alkylNA$^1$A$^2$, $OC_{(1-4)}$alkyl, $OCH_2$-(1-methyl)-imidazol-2-yl, furyl, pyrazolyl, imidazolyl, pyridyl, pyridazyl, pyrazinyl, or pyrimidinyl; wherein said imidazolyl or pyrazolyl is optionally substituted with one $CH_3$ group;

$A^1$ is, H or $C_{(1-4)}$alkyl;

$A^2$ is H, $C_{(1-4)}$alkyl, $C_{(1-4)}$alkylOC$_{(1-4)}$alkyl, $C_{(1-4)}$alkylOH, C(O)C$_{(1-4)}$alkyl, or $OC_{(1-4)}$alkyl; or $A^1$ and $A^2$ may be taken together with their attached nitrogen to form a ring selected from the group consisting of:

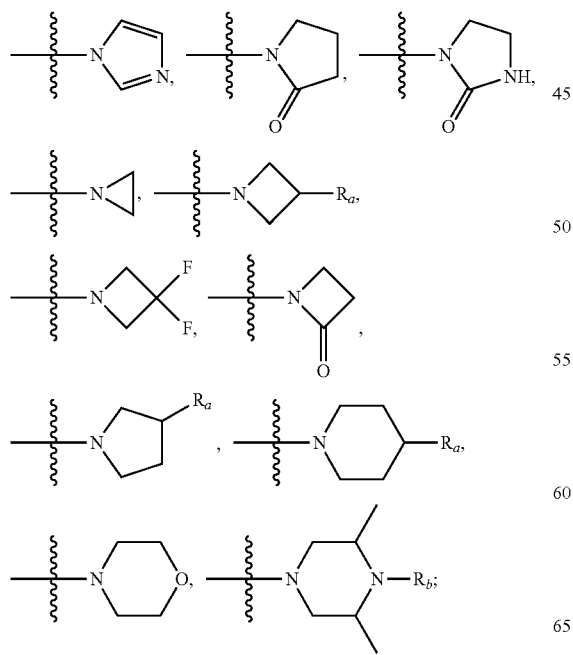

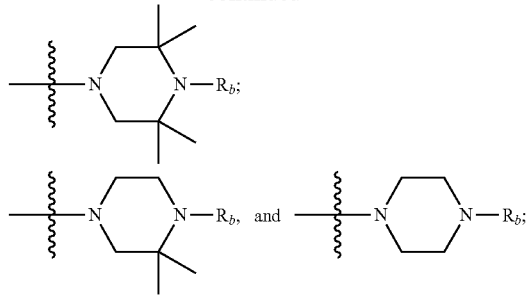

$R_a$ is H, $OC_{(1-4)}$alkyl, $CH_2OH$, $NH(CH_3)$, $N(CH_3)_2$, $NH_2$, $CH_3$, F, or OH;

$R_b$ is H, $CO_2C(CH_3)_3$, $C_{(1-4)}$alkyl, C(O)C$_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $CH_3$, $OCH_3$, or F;

and pharmaceutically acceptable salts thereof.

3. A compound of claim 2 wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with C(O)$C_{(1-4)}$alkyl, C(O)$NH_2$, $C_{(1-4)}$alkyl, $CF_3$, $CH_2CF_3$, Cl, F, —CN, $OC_{(1-4)}$alkyl, $N(C_{(1-4)}alkyl)_2$, -$(CH_2)_3$ $OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is 1-methyl triazolyl, pyridyl, pyridyl-N-oxide, 1-methyl pyrazolyl, pyrimidinyl, pyrazinyl, oxazolyl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N-C$_{(1-2)}$alkyl-piperidinyl, thiazolyl, pyridazyl, 1-(3-methoxypropyl)-imidazolyl, or 1 -C$_{(1-2)}$alkyl imidazolyl; wherein said 1-C$_{(1-2)}$alkyl imidazolyl is optionally substituted with up to two additional $CH_3$ groups, or one substituent selected from the group consisting of $SCH_3$, and Cl; and said pyridyl, and pyridyl-N-oxide are optionally substituted with up to two subsitutents independently selected from the group consisting of $SO_2CH_3$, $SO_2NH_2$, C(O)$NH_2$, —CN, $OCH_3$, $CF_3$, Cl, and $CH_3$; and said thiazolyl, oxazolyl and isoxazolyl are optionally substituted with up to two $CH_3$ groups; and said 1-methyl pyrazolyl is optionally substituted with up to two additional $CH_3$ groups;

$R^6$ is phenyl, pyridyl, benzothiophenyl, thiophenyl, pyrimidinyl, pyridazyl, or pyrazinyl; wherein said phenyl or said pyridyl is optionally substituted with $OCF_3$, $SO_2CH_3$, $CF_3$, $CHF_2$, pyrazolyl, triazolyl, imidazolyl, tetrazolyl, oxazolyl, thiazolyl, $CH_3$, $OCH_3$, $N(CH_3)_2$, $SO_2NH_2$, $CONH_2$, Cl, F, —CN, $CO_2H$, OH, $CH_2OH$, $NHCOCH_3$, or $COCH_3$;

$R^7$ is H, Cl, —CN, $C_{(1-4)}$alkyl, $OC_{(1-4)}$alkylCF$_3$, $OCH_2CH_2OC_{(1-4)}$alkyl, $CF_3$, $SCH_3$, NA$^1$A$^2$, C(O)NA$^1$A$^2$, $N(CH_3)C_{(2-4)}$alkylNA$^1$A$^2$, $OC_{(2-4)}$alkylNA$^1$A$^2$, $OC_{(1-4)}$alkyl, $OCH_2$-(1-methyl)-imidazol-2-yl, imidazolyl, furyl, pyrazolyl, pyridyl, or pyrimidinyl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl;

or $A^1$ and $A^2$ may be taken together with their attached nitrogen to form a ring selected from the group consisting of:

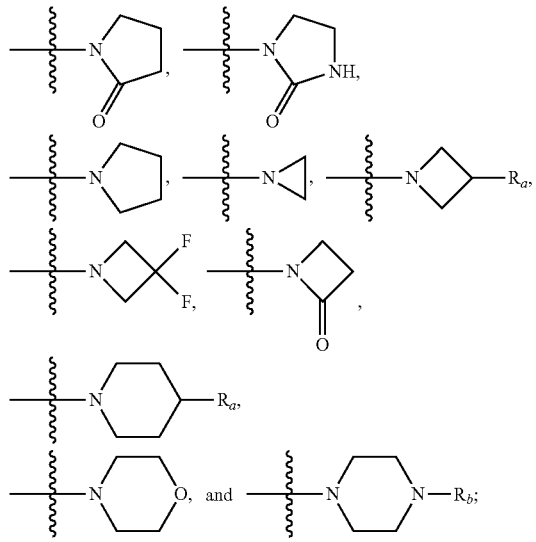

$R_a$ is H, F, $OC_{(1-4)}$alkyl, or OH;
$R_b$ is $C_{(1-4)}$alkyl, $C(O)CH_3$, or phenyl;
and pharmaceutically acceptable salts thereof.

4. A compound of claim 3 wherein:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3$ $OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$;

and wherein said triazolyl, oxazolyl, isoxazolyl, and thiazolyl are optionally substituted with one or two $CH_3$ groups;

$R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N-$C_{(1-2)}$alkyl-piperidinyl, thiazol-5-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl;

and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, and said isoxazolyl are optionally substituted with up to two $CH_3$ groups; and said 1-methyl pyrazol-4-yl is optionally substituted with up to two additional $CH_3$ groups;

$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl$)_2$, or 4-hydroxy-piperidinyl;

$R^6$ is pyridyl, phenyl, benzothiophenyl, or thiophenyl; wherein said pyridyl or phenyl is optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;

$R^7$ is H, Cl, —CN, $C_{(1-4)}$alkyl, $OCH_2CF_3$, $OCH_2CH_2OCH_3$, $CF_3$, $SCH_3$, $NA^1 A^2$, $C(O)NHCH_3$, $N(CH_3)CH_2CH_2NA^1 A^2$, $OCH_2CH_2NA^1 A^2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

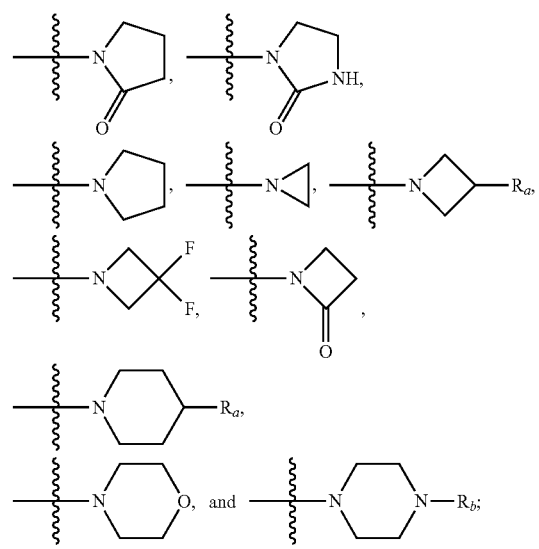

$R_a$ is H, F, $OCH_3$, or OH;
$R_b$ is $CH_3$, or phenyl;
and pharmaceutically acceptable salts thereof.

5. A compound of claim 4 wherein:

$R^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with $SO_2CH_3$, $C(O)CH_3$, $CH_3$, $CF_3$, Cl, F, —CN, $OCH_3$, —$CF_3$, or $N(CH_3)_2$; and optionally substituted with up to one additional group independently selected from Cl, $OCH_3$, and $CH_3$; and wherein said triazolyl, oxazolyl, and thiazolyl are optionally substituted with one or two $CH_3$ groups;

$R^2$ is 1-methyl-1,2-3triazol-5-yl, pyrid-3-yl, 1-methyl pyrazol-4-yl, thiazol-5-yl, N-acetyl-piperidin-4-yl, N-acetyl-azetidin-3-yl, N-methylsulfonyl-azetidin-3-yl, N-Boc-azetidin-3-yl, 1,2-dimethyl imidazol-5-yl or 1-methyl imidazol-5-yl;

$R^3$ is OH, or $NH_2$;

$R^4$ is H;

R⁵ is H, Cl, —CN, CF₃, CH₃, OH, N(CH₃)OCH₃, or OCH₃;

R⁶ is pyridyl, phenyl, benzothiophenyl, or thiophenyl; wherein said pyridyl or phenyl is optionally substituted with pyrazol-1-yl, 1,2,4-triazol-1-yl, CF₃, OCH₃, SO₂CH₃, Cl, F, or —CN;

R⁷ is Cl, —CN, CF₃, C₍₁₋₄₎alkyl, NA¹ A², C(O)NHCH₃, OCH₂CH₂OCH₃, 1-methyl imidazol-2-yl, 1-methyl pyrazol-4-yl, or OC₍₁₋₂₎alkyl;

A¹ is C₍₁₋₂₎alkyl;

A² is C₍₁₋₂₎alkyl, CH₂CH₂OCH₃, or OCH₃; or A¹ and A² may be taken together with their attached nitrogen to form a ring selected from the group consisting of:

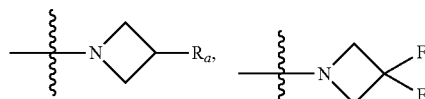
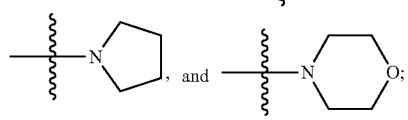

Rₐ is OH, OCH₃, F, or H;

R⁹ is H;

and pharmaceutically acceptable salts thereof.

6. A compound of claim 5 wherein:

R¹ is imidazolyl, triazolyl, thiazolyl, pyridyl, piperidinyl, phenyl, or oxazolyl; wherein said piperidinyl, pyridyl, imidazolyl, and phenyl are optionally substituted with C(O)CH₃, CH₃, CF₃, Cl, F, —CN, OCH₃, or N(CH₃)₂; and optionally substituted with up to one additional group independently selected from Cl, OCH₃, and CH₃; and wherein said triazolyl, oxazolyl, and thiazolyl are optionally substituted with one or two CH₃ groups;

R² is 1-methyl-1,2-3triazol-5-yl, pyrid-3-yl, 1-methyl pyrazol-4-yl, thiazol-5-yl, N-acetyl-piperidin-4-yl, 1,2-dimethyl imidazol-5-yl or 1-methyl imidazol-5-yl;

R₃ is OH;

R⁵ is H, Cl, —CN, CF₃, CH₃, or OCH₃;

R⁶ is phenyl, thiophen-2-yl, benzothiophen-2-yl; wherein said phenyl is optionally substituted with pyrazol-1-yl, 1,2,4-triazol-1-yl, OCH₃, SO₂CH₃, Cl, F, CF₃, or —CN;

R⁷ is Cl, —CN, CH₃, NA¹ A², C(O)NHCH₃, or OC₍₁₋₂₎alkyl;

A¹ is C₍₁₋₂₎alkyl;

A² is C₍₁₋₂₎alkyl, or OCH₃; or A¹ and A² may be taken together with their attached nitrogen to form a ring which is:

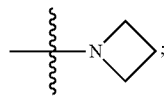

and pharmaceutically acceptable salts thereof.

7. A compound of claim 1 selected from the group consisting of:

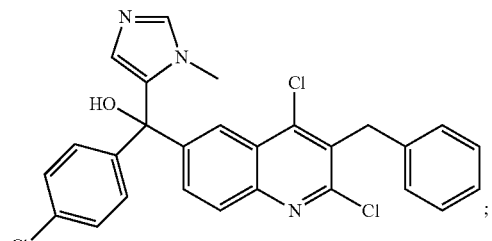

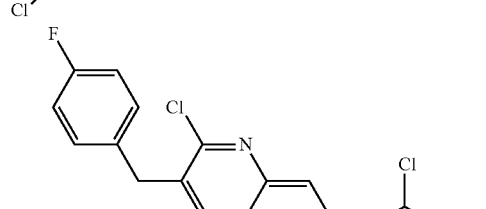

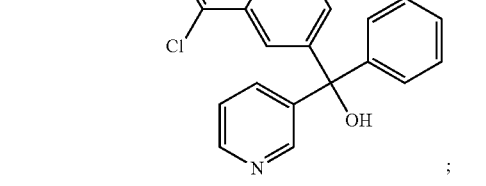

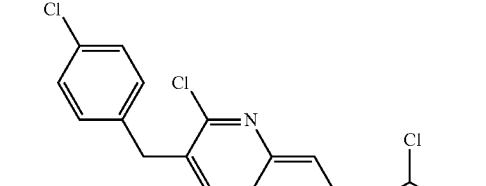

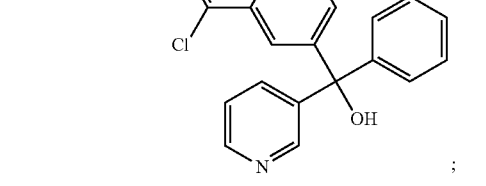

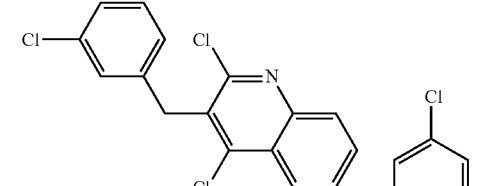

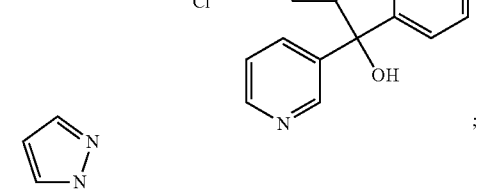

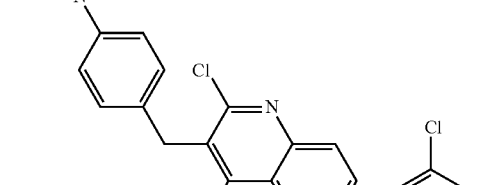

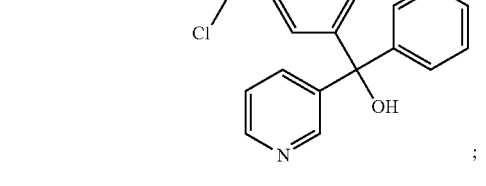

255
-continued
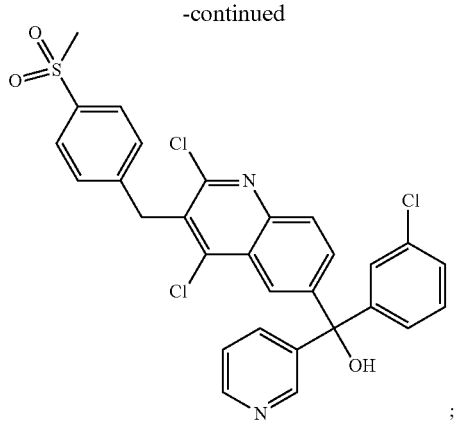
;
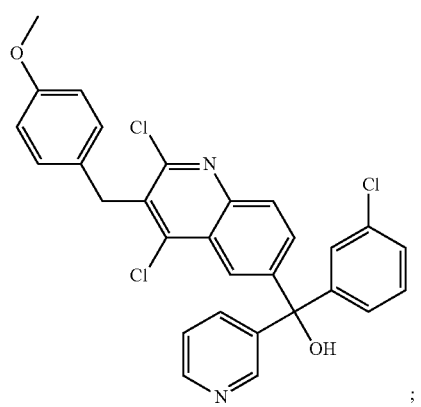
;
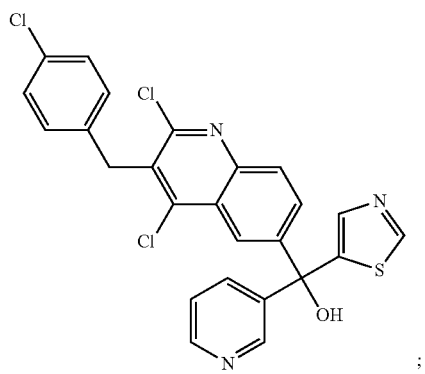
;
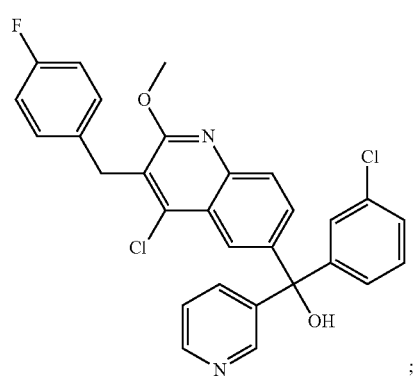
;
256
-continued
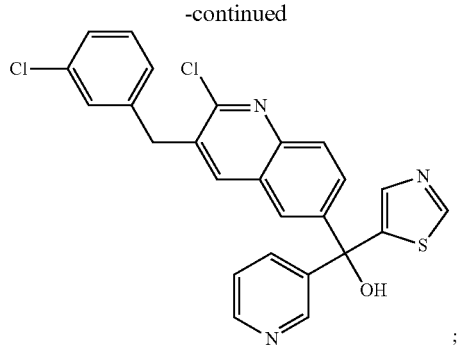
;
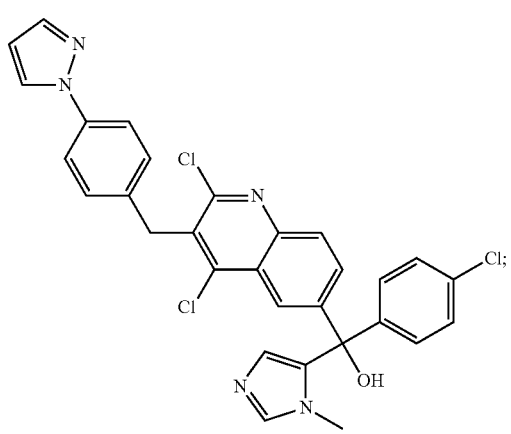
;
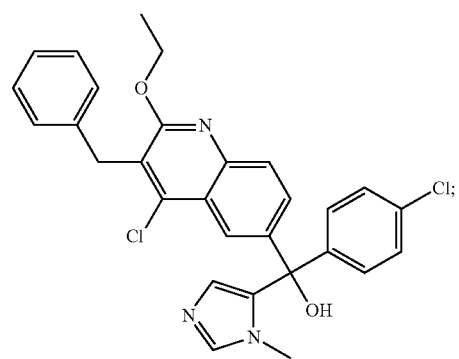
;
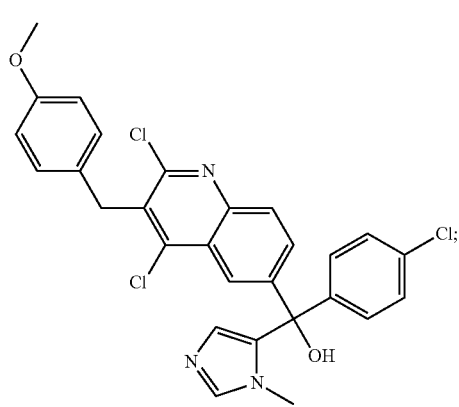

257
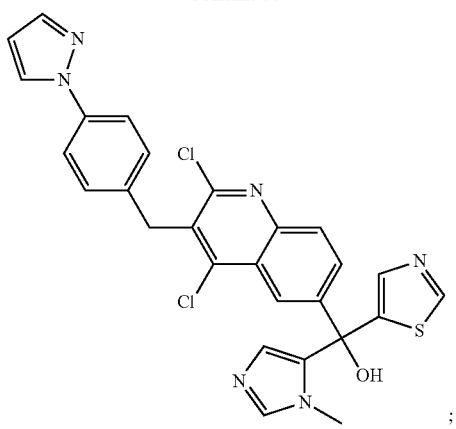
;
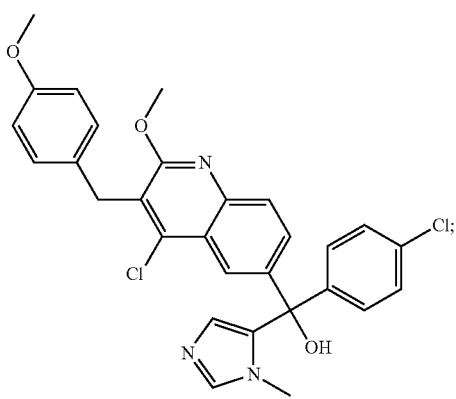
;
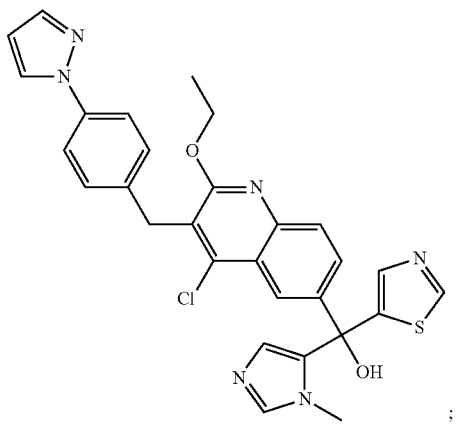
;
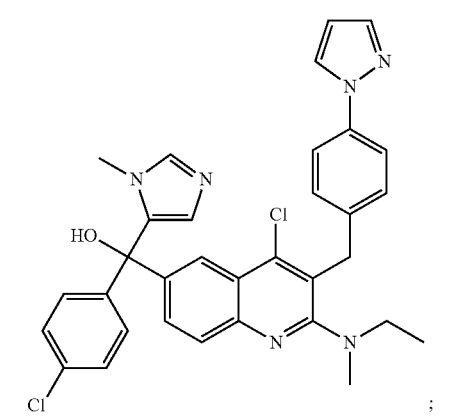
;
258
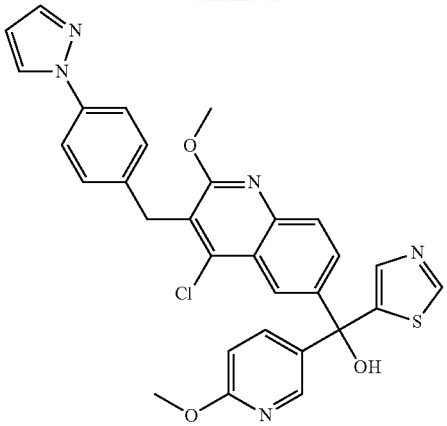
;
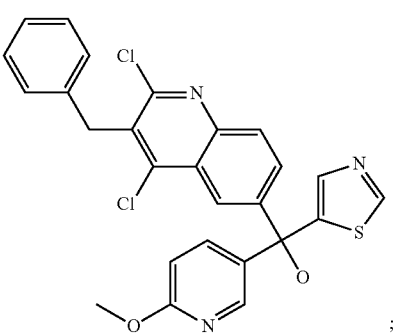
;
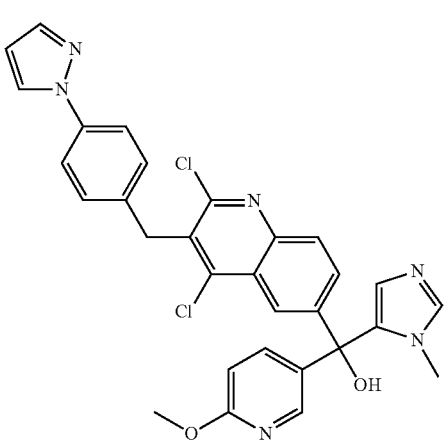
;
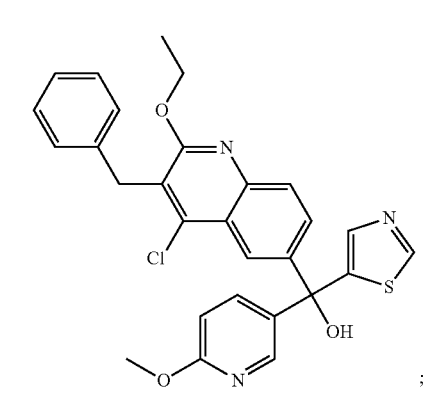
;

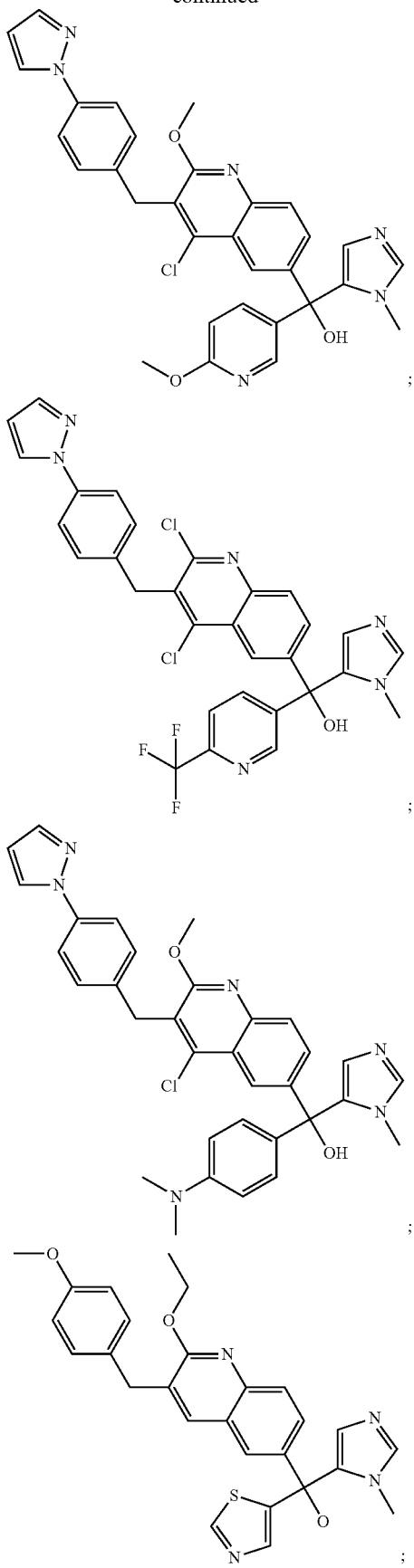
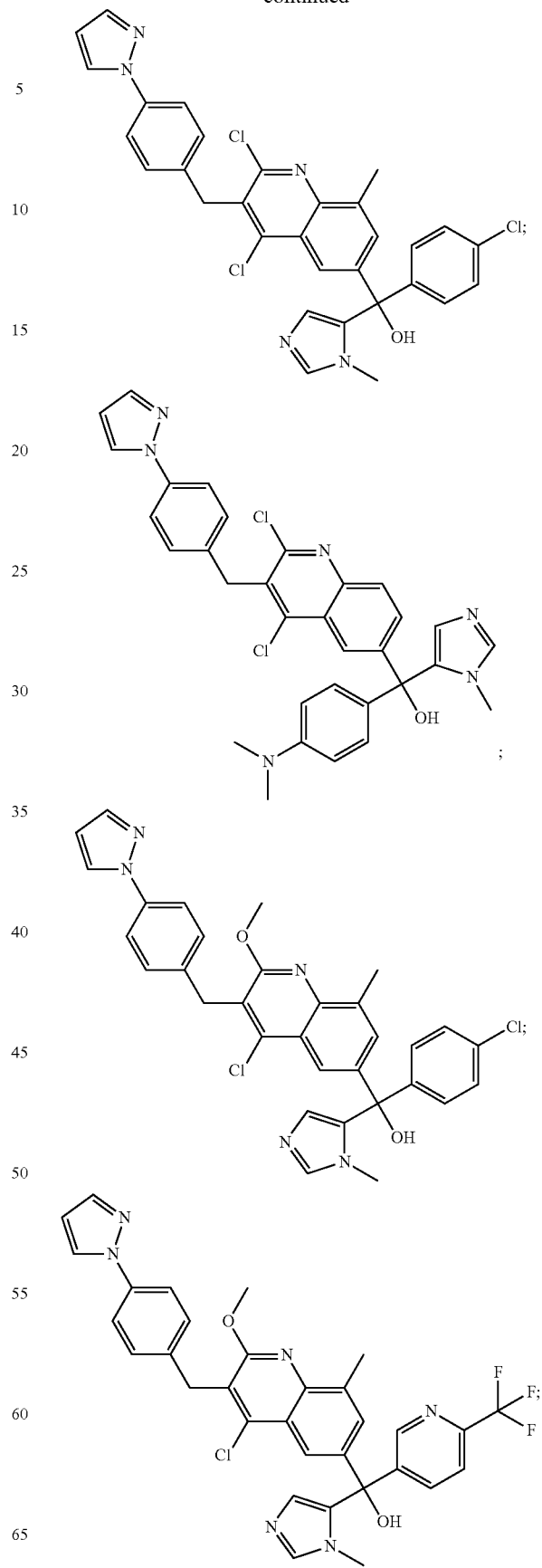

261
-continued
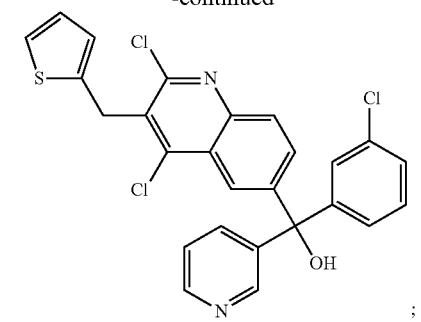
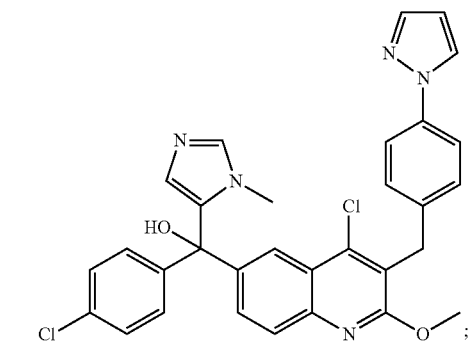
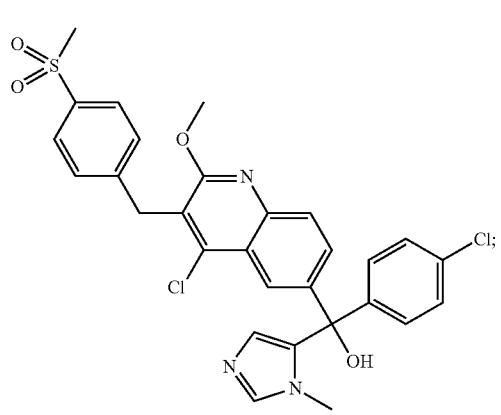
262
-continued
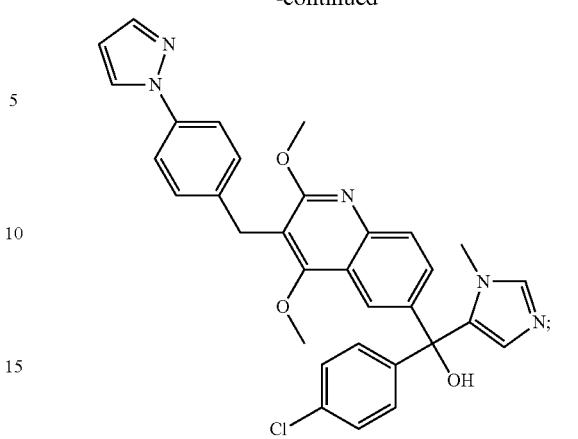
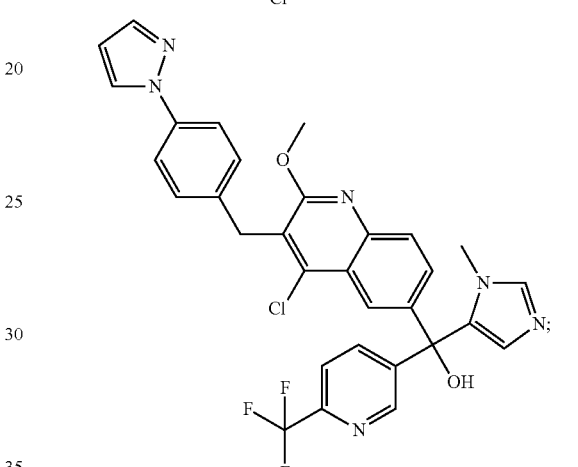
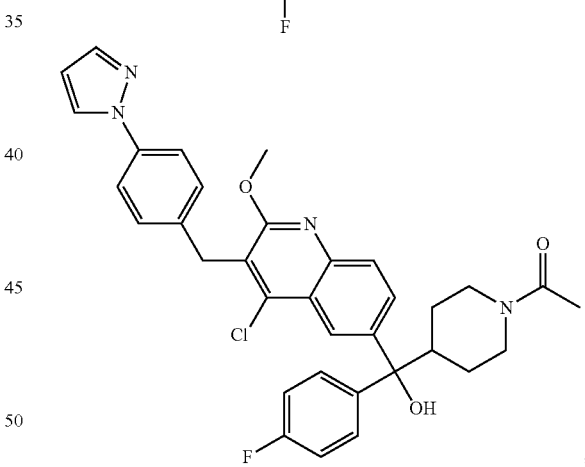
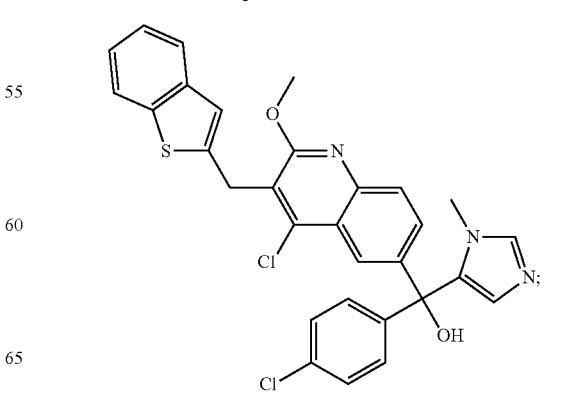

263
-continued
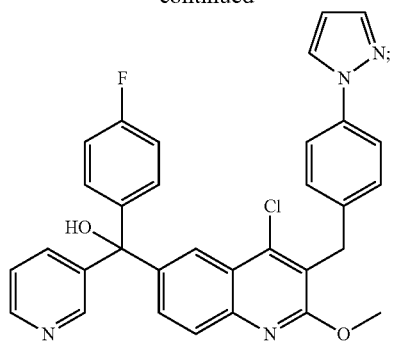
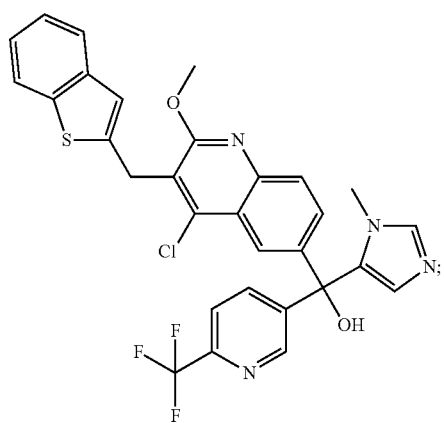
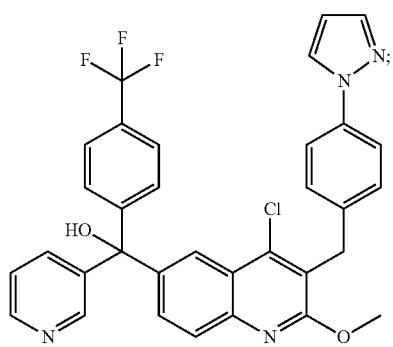
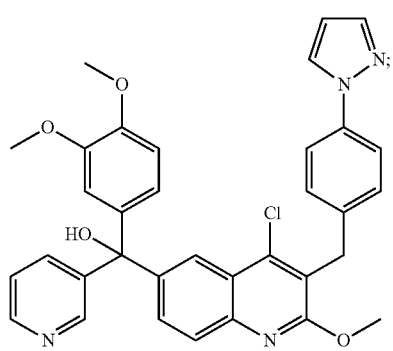
264
-continued
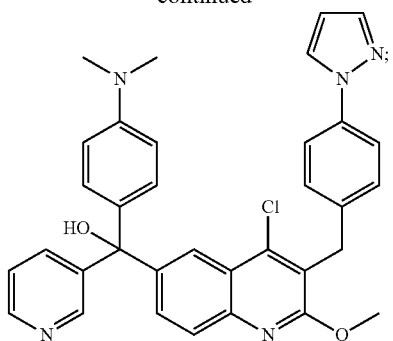
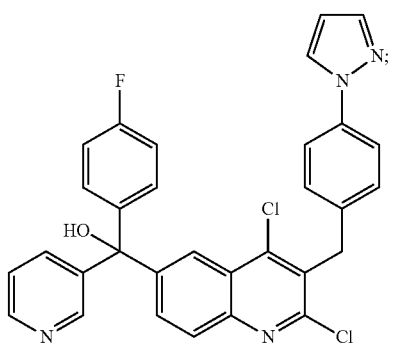
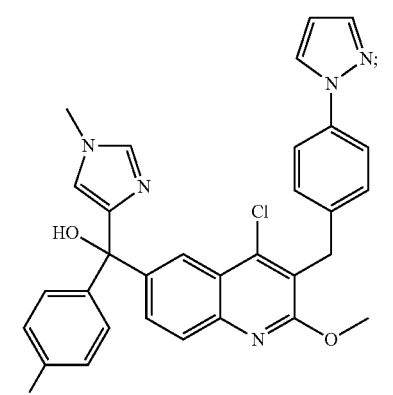
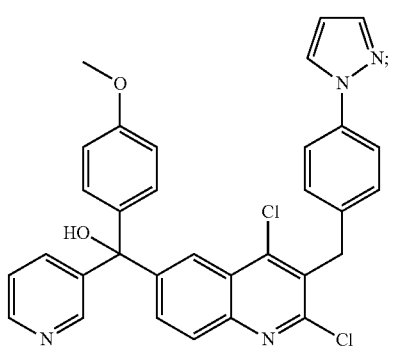

265
-continued
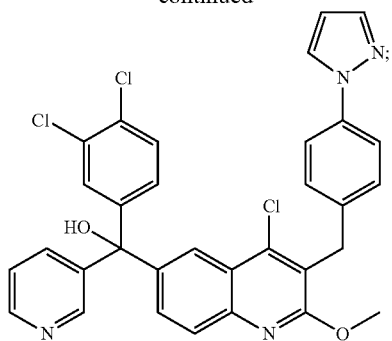
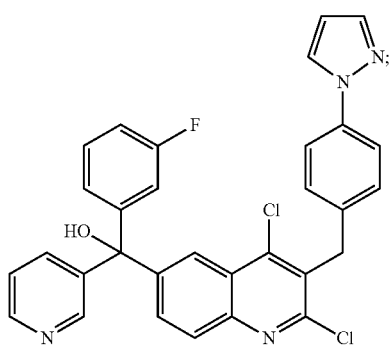
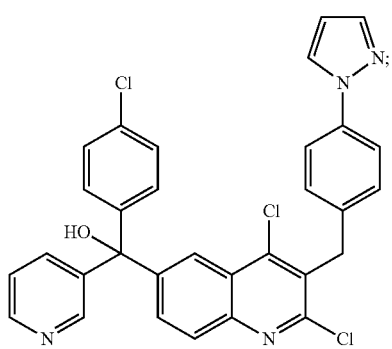
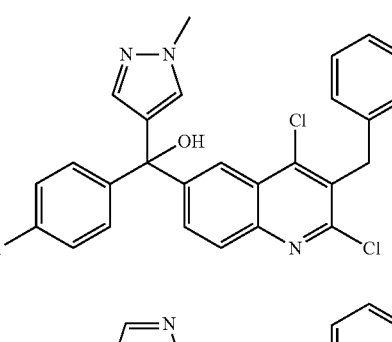
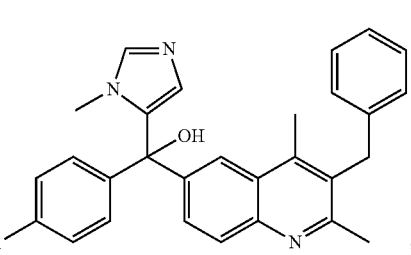
266
-continued
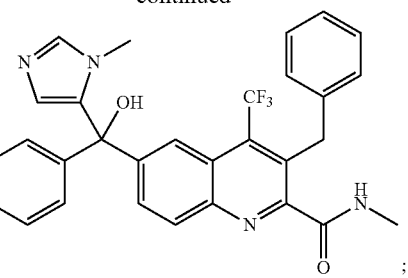
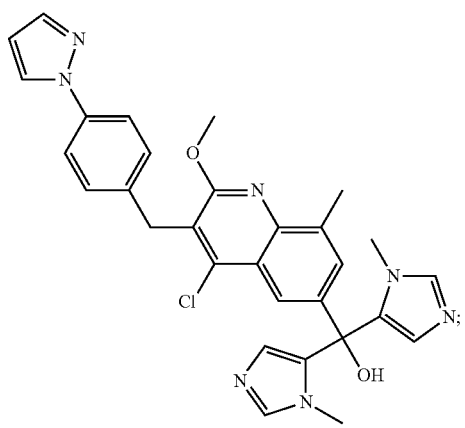
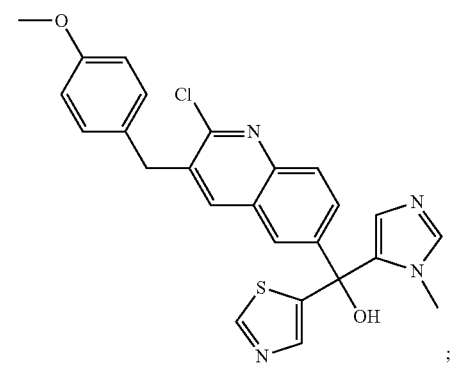
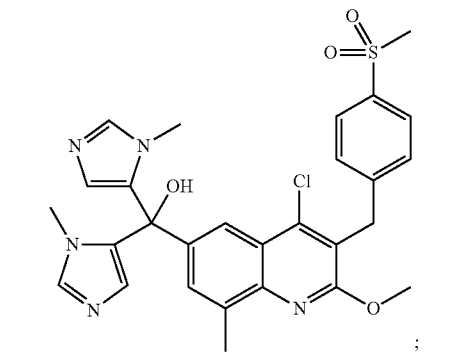

267
-continued
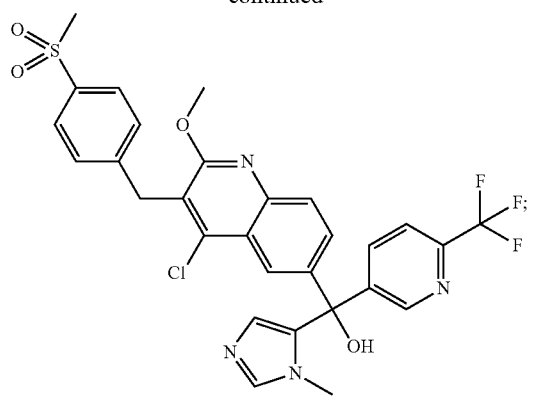
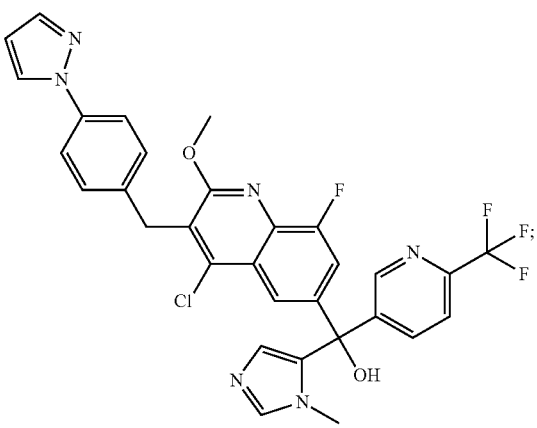
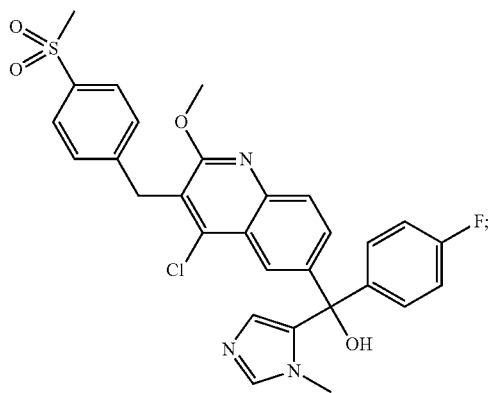
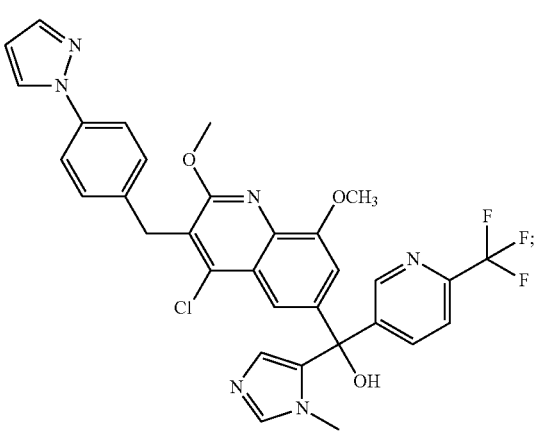
268
-continued
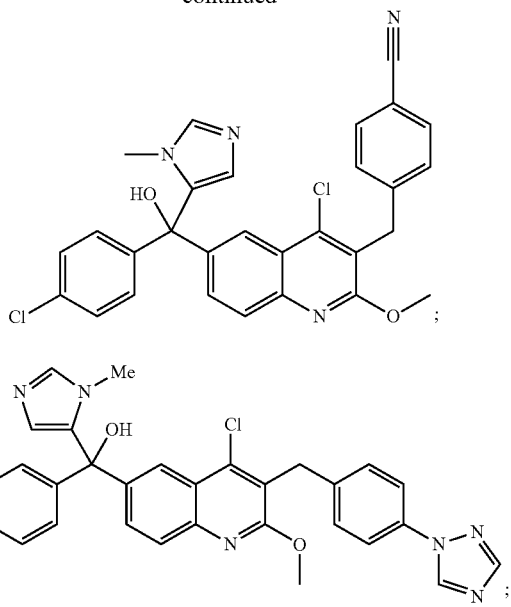
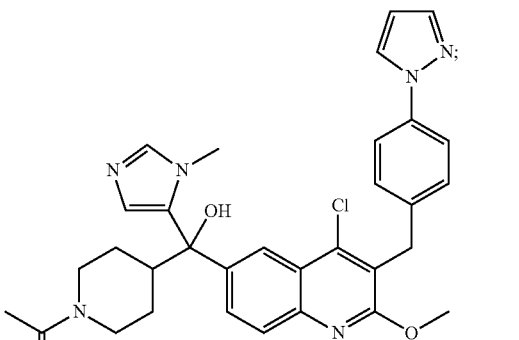
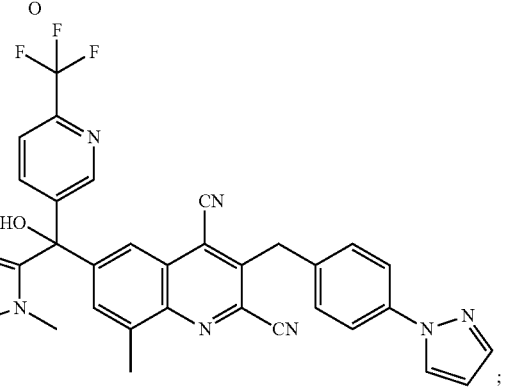
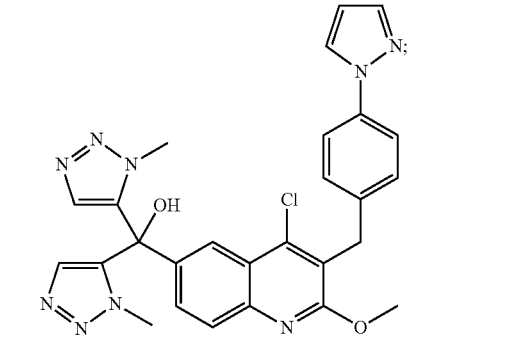

269
-continued
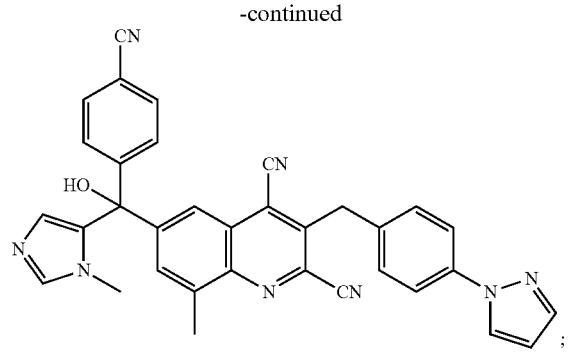
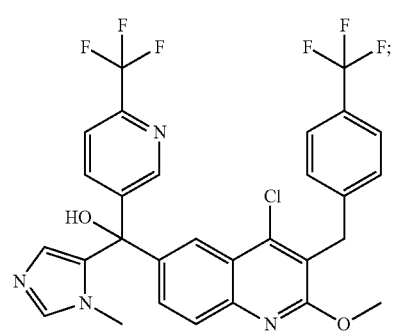
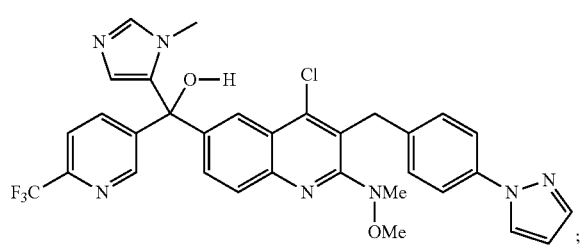
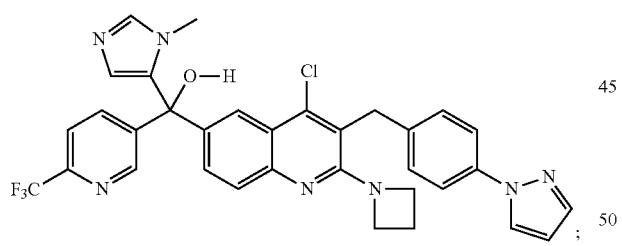
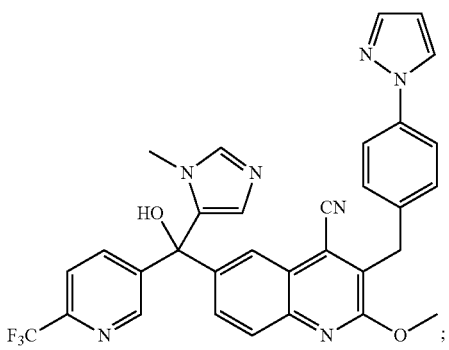
270
-continued
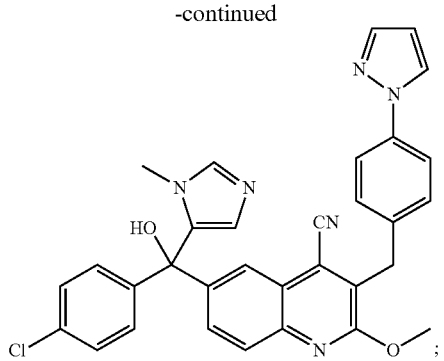
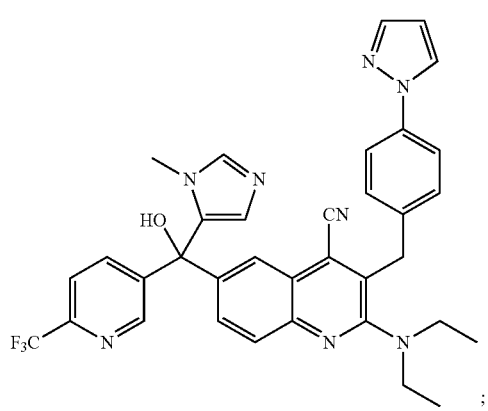
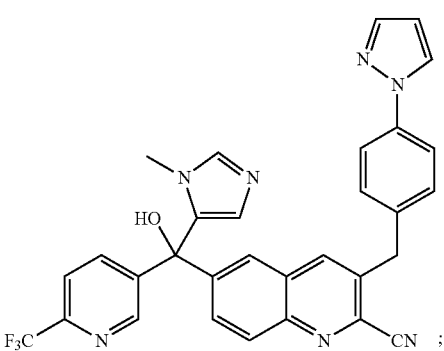
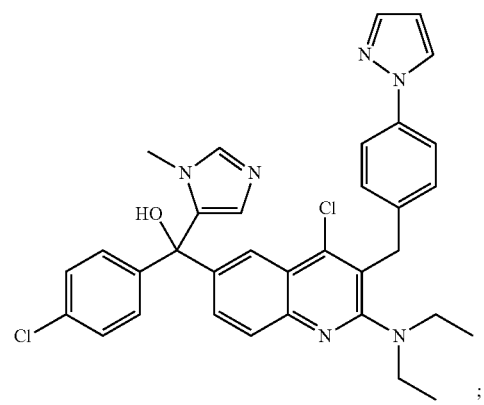

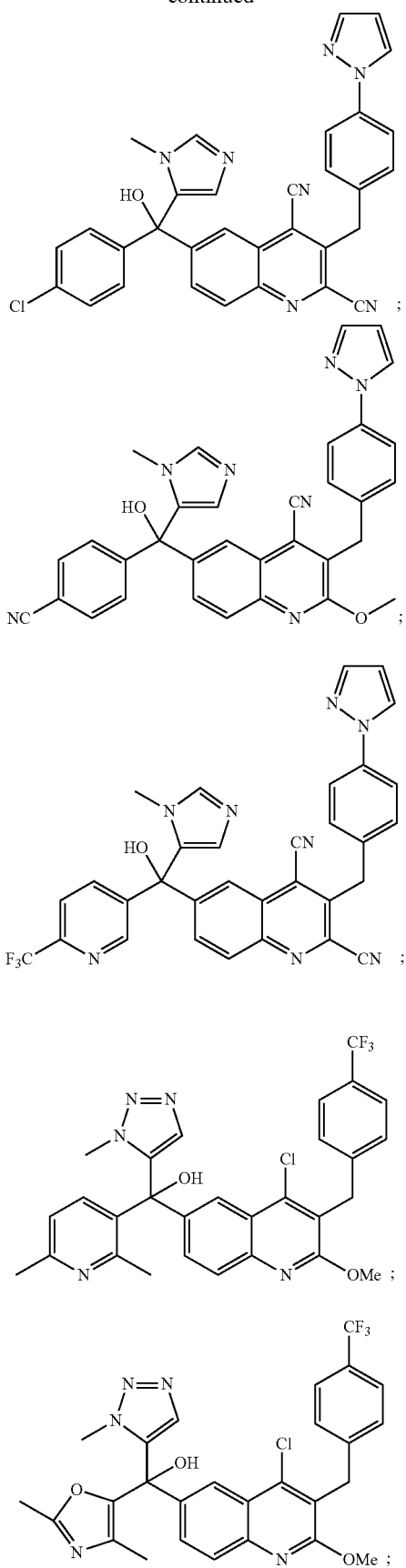
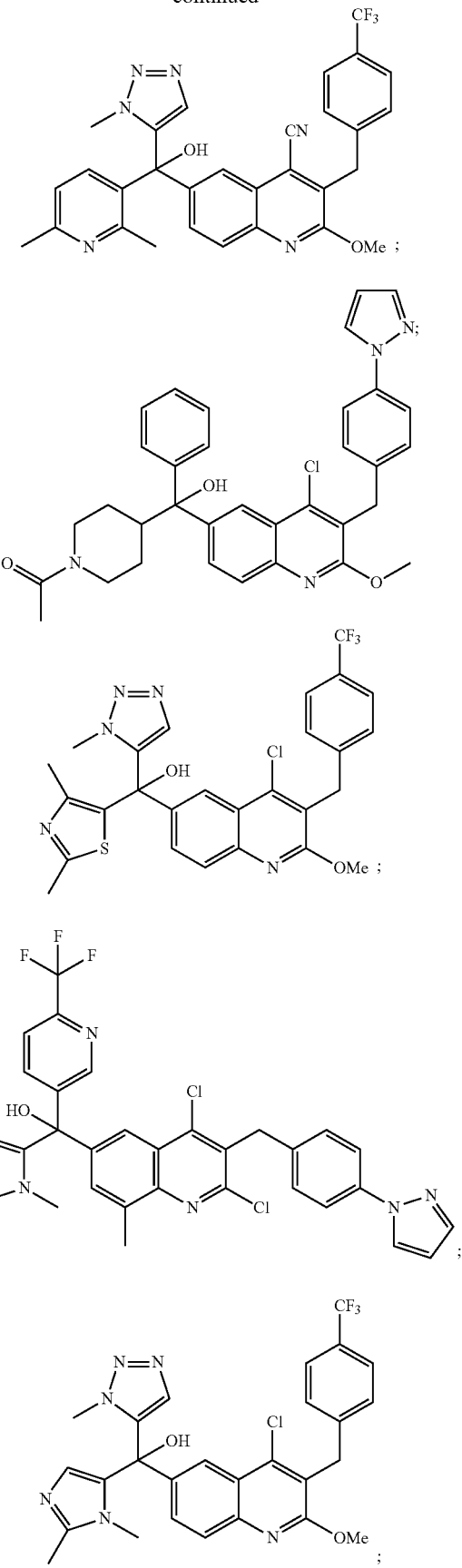

273
-continued
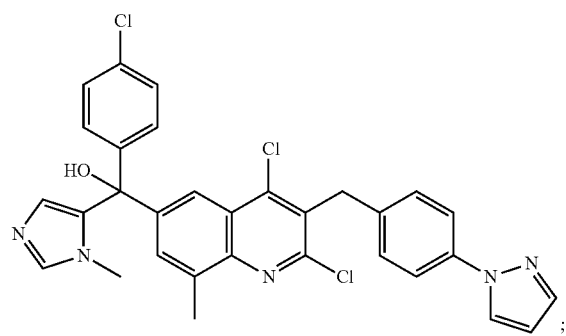
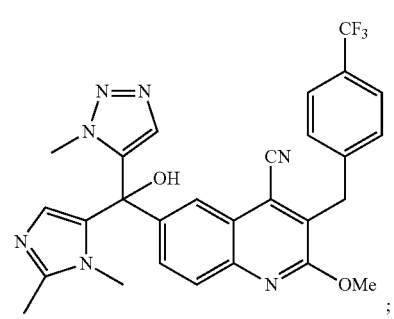
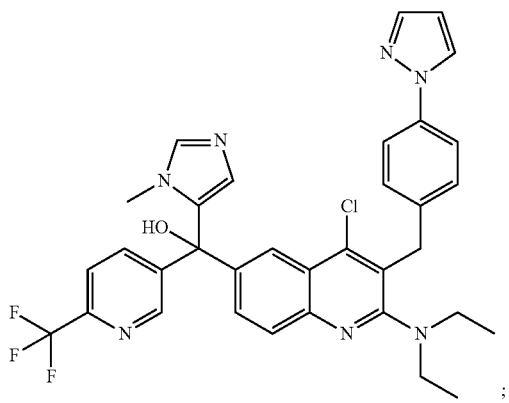
and pharmaceutically acceptable salts thereof.
8. A compound of claim 1 selected from the group consisting of:
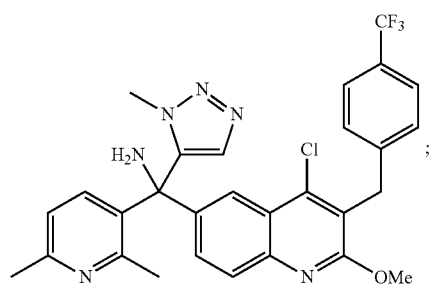
274
-continued
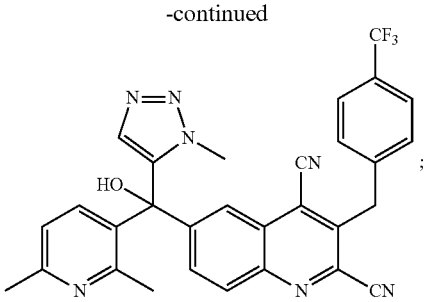
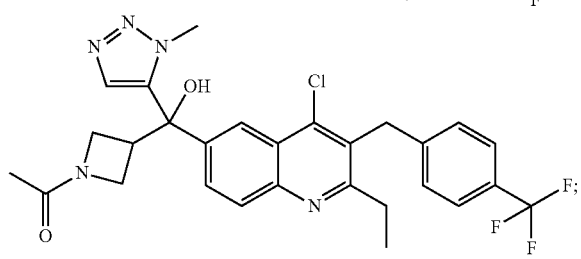
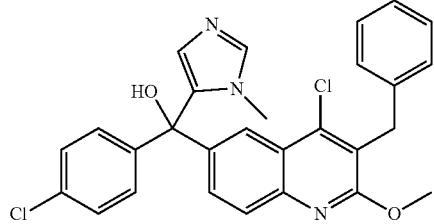
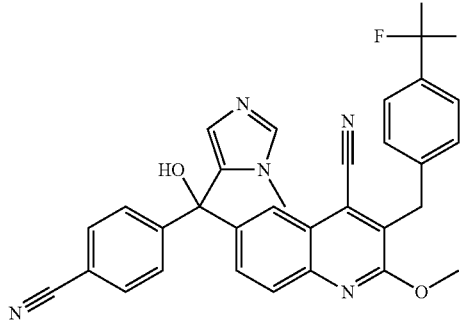
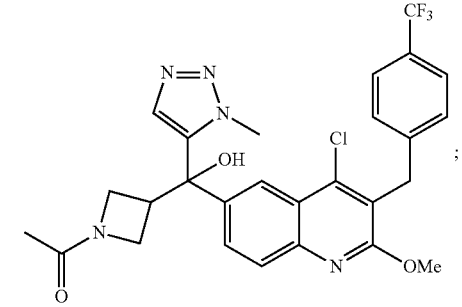

-continued

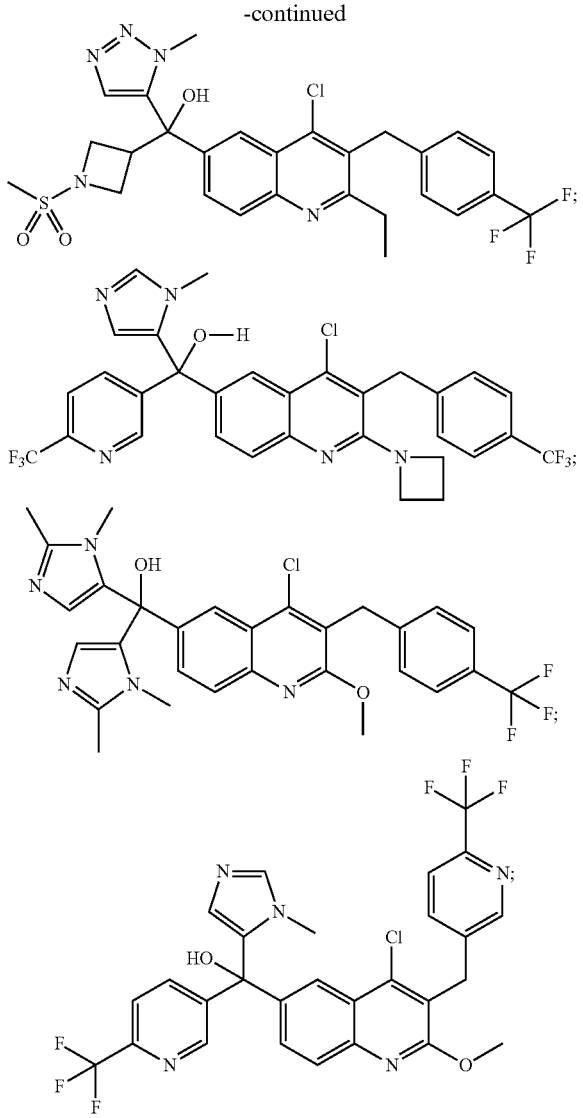

and pharmaceutically acceptable salts thereof.

9. A compound which is

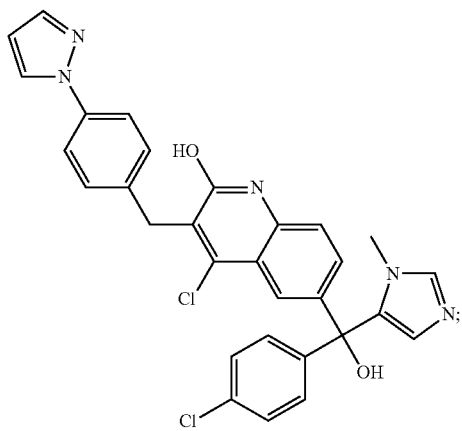 [SMILES: Cn1cncc1C(O)(c1ccc(Cl)cc1)c1ccc2nc(O)c(Cc3ccc(-n4cccn4)cc3)c(Cl)c2c1]

and pharmaceutically acceptable salts thereof.

10. A pharmaceutical composition, comprising a compound of claim 1 and a pharmaceutically acceptable carrier.

11. A pharmaceutical composition made by mixing a compound of claim 1 and a pharmaceutically acceptable carrier.

12. A process for making a pharmaceutical composition comprising mixing a compound of claim 1 and a pharmaceutically acceptable carrier.

13. A method for treating or ameliorating a RORγt mediated inflammatory syndrome, disorder or disease comprising administering to a subject in need thereof an effective amount of a compound of claim 1, wherein the disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis.

14. The method of claim 13, wherein the disease is psoriasis.

15. The method of claim 13, wherein the disease is rheumatoid arthritis.

16. The method of claim 13, wherein the disease is ulcerative colitis.

17. The method of claim 13, wherein the disease is Crohn's disease.

18. The method of claim 13, wherein the disease is multiple sclerosis.

19. The method of claim 13, wherein the disease is neutrophilic asthma.

20. The method of claim 13, wherein the disease is steroid resistant asthma.

21. The method of claim 13, wherein the disease is psoriatic arthritis.

22. The method of claim 13, wherein the disease is ankylosing spondylitis.

23. The method of claim 13, wherein the disease is systemic lupus erythematosus.

24. The method of claim 13, wherein the disease is chronic obstructive pulmonary disorder.

25. A method of treating or ameliorating a syndrome, disorder or disease, in a subject in need thereof comprising administering to the subject an effective amount of a compound of claim 1 or composition or medicament thereof in a combination therapy with one or more anti- inflammatory agents, or immunosuppressive agents, wherein said syndrome, disorder or disease is selected from the group consisting of: rheumatoid arthritis, and psoriasis.

26. A method for treating or ameliorating a RORγt mediated inflammatory syndrome, disorder or disease comprising administering to a subject in need thereof an effective amount of a compound of claim 7, wherein the disease is selected from the group consisting of: rheumatoid arthritis and psoriasis.

27. A method of inhibiting production of interleukin-17, comprising administering to a subject in need thereof an effective amount of a compound of claim 1.

* * * * *

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct      60
gccgccagct gcaccccact cctggaccac cccctgctga aaggacagg gagccaaggc     120
cggcagagcc aaggctcagt catgagaaca caaattgaag tgatcccttg caaaatctgt     180
ggggacaagt cgtctgggat ccactacggg gttatcacct gtgagggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcagggc caaggagca gatacccctca cctacacctt ggggctccca     540
gacgggcagc tgcccctggg ctcctcgcct gacctgcctg aggcttctgc ctgtccccct     600
ggcctcctga agcctcagg ctctgggccc tcatattcca caacttggc caaggcaggg     660
ctcaatgggg cctcatgcca ccttgaatac agccctgagc gggggcaaggc tgagggcaga     720
gagagcttct atagcacagg cagccagctg accctgacc gatgtggact tcgttttgag     780
gaacacaggc atcctgggct tggggaactg ggacagggcc cagacagcta cggcagcccc     840
agtttccgca gcacaccgga ggcaccctat gcctccctga cagagataga gcacctggtg     900
cagagcgtct gcaagtccta cagggagaca tgccagctgc ggctggagga cctgctgcgg     960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt ttgaaggcaa atacggtggc atggagctgt ccgagccctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga aagtagaaca gctgcagtac aatctggagc tggccttttca tcatcatctc    1440
tgcaagactc atcgccaaag catcctggca aagctgccac ccaaggggaa gcttcggagc    1500
ctgtgtagcc agcatgtgga aaggctgcag atcttccagc acctccaccc catcgtggtc    1560
caagccgctt tccctccact ctacaaggag ctcttcagca ctgaaaccga gtcacctgtg    1620
gggctgtcca gtgacctgg aagagggact ccttgcctct ccctatggcc tgctggccca    1680
cctccctgga ccccgttcca ccctcaccct tttccttttcc catgaaccct ggagggtggt    1740
ccccaccagc tctttggaag tgagcagatg ctgcggctgg ctttctgtca gcaggccggc    1800
ctggcagtgg gacaatcgcc agagggtggg gctggcagaa caccatctcc agcctcagct    1860
ttgacctgtc tcatttccca tattccttca cacccagctt ctggaaggca tggggtggct    1920
gggatttaag gacttctggg ggaccaagac atcctcaaga aaacagggc atccagggct    1980
ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctgggtct    2220
aaccaaaaat ggatgggatg aggatgagag gctggagata attgttttat gggatttggg    2280
tgtgggacta gggtacaatg aaggccaaga gcatctcaga catagagtta aaactcaaac    2340
```

```
ctcttatgtg cactttaaag atagacttta ggggctggca caaatctgat cagagacaca   2400
tatccataca caggtgaaac acatacagac tcaacagcaa tcatgcagtt ccagagacac   2460
atgaacctga cacaatctct cttatccttg aggccacagc ttggaggagc ctagaggcct   2520
caggggaaag tcccaatcct gagggaccct cccaaacatt tccatggtgc tccagtccac   2580
tgatcttggg tctggggtga tccaaatacc accccagctc agctgtcttc taccactag   2640 aagacccaag agaagcagaa gtcgctcgca ctggtcagtc ggaaggcaag atcagatcct   2700
ggaggacttt cctggcctgc ccgccagccc tgctcttgtt gtggagaagg aagcagatgt   2760
gatcacatca ccccgtcatt gggcaccgct gactccagca tggaggacac cagggagcag   2820
ggcctgggcc tgtttcccca gctgtgatct tgcccagaac ctctcttggc ttcataaaca   2880
gctgtgaacc ctcccctgag ggattaacag caatgatggg cagtcgtgga gttggggggg   2940 ttggggggtgg gattgtgtcc tctaagggga cgggttcatc tgagtaaaca taaacccccaa   3000 cttgtgccat tctttataaa atgatttta aggcaaaaaa aaaaaaaaa aaaa           3054

<210> SEQ ID NO 2
<211> LENGTH: 786
<212> TYPE: DNA
<213> ORGANISM: Homo sapiens

<400> SEQUENCE: 2
agcacaccgg aggcacccta tgcctccctg acagagatag agcacctggt gcagagcgtc     60
tgcaagtcct acaggagac atgccagctg cggctggagg acctgctgcg gcagcgctcc     120
aacatcttct cccgggagga agtgactggc taccagagga gtccatgtg ggagatgtgg     180 gaacggtgtg cccaccacct caccgaggcc attcagtacg tggtggagtt cgccaagagg     240
ctctcaggct ttatggagct ctgccagaat gaccagattt gcttctcaa agcaggagca     300 atggaagtgg tgctggttag gatgtgccgg gcctacaatg ctgacaaccg cacggtcttt     360
tttgaaggca aatacggtgg catggagctg ttccgagcct tgggctgcag cgagctcatc     420
agctccatct ttgacttctc ccactcccta agtgccttgc acttttccga ggatgagatt     480
gccctctaca cagcccttgt tctcatcaat gcccatcggc cagggctcca agagaaaagg     540
aaagtagaac agctgcagta caatctggag ctggcctttc atcatcatct ctgcaagact     600
catcgccaaa gcatcctggc aaagctgcca cccaagggga gcttcggag cctgtgtagc     660 cagcatgtgg aaaggctgca gatcttccag cacctccacc ccatcgtggt ccaagccgct     720
ttccctccac tctacaagga gctcttcagc actgaaaccg agtcacctgt ggggctgtcc     780
aagtga                                                                 786

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
```

-continued

```
<220> FEATURE:
<223> OTHER INFORMATION: Construct used in the Thermofluor assay

<400> SEQUENCE: 4

Met Ala His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
        50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
                100                 105                 110

Asp Gln Ile Val Leu Leu Lys Ala Gly Ala Met Glu Val Val Leu Val
            115                 120                 125

Arg Met Cys Arg Ala Tyr Asn Ala Asp Asn Arg Thr Val Phe Phe Glu
        130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
                180                 185                 190

Ala His Arg Pro Gly Leu Gln Glu Lys Arg Lys Val Glu Gln Leu Gln
            195                 200                 205

Tyr Asn Leu Glu Leu Ala Phe His His His Leu Cys Lys Thr His Arg
        210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
            260                 265                 270

Thr Glu Thr Glu Ser Pro Val Gly Leu Ser Lys
        275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain
```

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7

```
agcacaccgg aggcacccta tgcctccctg acagagatag agcacctggt gcagagcgtc      60
tgcaagtcct acagggagac atgccagctg cggctggagg acctgctgcg gcagcgctcc     120
aacatcttct cccggagga agtgactggc taccagagga agtccatgtg ggagatgtgg      180
gaacggtgtg cccaccacct caccgaggcc attcagtacg tggtggagtt cgccaagagg     240
ctctcaggct ttatggagct ctgccagaat gaccagattg tgcttctcaa agcaggagca     300
atggaagtgg tgctggttag gatgtgccgg gcctacaatg ctgacaaccg cacggtcttt     360
tttgaaggca atacggtgg catggagctg ttccgagcct tgggctgcag cgagctcatc      420
agctccatct ttgacttctc ccactcccta agtgccttgc acttttccga ggatgagatt     480
gccctctaca cagcccttgt tctcatcaat gcccatcggc cagggctcca agagaaaagg     540
aaagtagaac agctgcagta caatctggag ctggccttc atcatcatct ctgcaagact      600
catcgccaaa gcatcctggc aaagctgcca cccaagggga agcttcggag cctgtgtagc     660
cagcatgtgg aaaggctgca gatcttccag cacctccacc ccatcgtggt ccaagccgct     720
ttccctccac tcttcaagga gctcttcagc actgaaaccg agtcacctgt ggggctgtcc     780
aagtga                                                                786
```

<210> SEQ ID NO 8
<211> LENGTH: 261
<212> TYPE: PRT
<213> ORGANISM: Homo sapiens

<400> SEQUENCE: 8

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

```
Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
            260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240
```

Phe Pro Pro Leu Phe Lys Glu Leu Phe Ser Thr Glu Thr Glu Ser Pro
        245                 250                 255

Val Gly Leu Ser Lys
   260